(12) United States Patent
Vogelstein et al.

(10) Patent No.: US 6,333,152 B1
(45) Date of Patent: Dec. 25, 2001

(54) GENE EXPRESSION PROFILES IN NORMAL AND CANCER CELLS

(75) Inventors: Bert Vogelstein, Baltimore; Kenneth W. Kinzler, BelAir; Lin Zhang; Wei Zhou, both of Baltimore, all of MD (US)

(73) Assignee: The JohnsHopkins University, Baltimore, MD (US)

( * ) Notice: Subject to any disclaimer, the term of this patent is extended or adjusted under 35 U.S.C. 154(b) by 0 days.

(21) Appl. No.: 09/081,646

(22) Filed: May 20, 1998

(51) Int. Cl.$^7$ .............................. C12Q 1/68; C12P 19/34; C07H 21/02; C07H 21/04
(52) U.S. Cl. ......................... 435/6; 435/91.2; 536/23.1; 536/24.3; 536/24.31; 536/24.32; 536/24.33
(58) Field of Search .................... 435/6, 91.2; 536/23.1, 536/24.3, 24.31, 24.32

(56) References Cited

FOREIGN PATENT DOCUMENTS

| 0 294 362 A | 9/1988 | (EP) . |
| 95/11923 A | 5/1995 | (EP) . |
| 0 761 822 A | 3/1997 | (EP) . |
| 95/19369 A | 7/1995 | (WO) . |
| 95/21944 A | 8/1995 | (WO) . |
| 97/14812 A | 4/1997 | (WO) . |

OTHER PUBLICATIONS

Hillier et al (Genbank Locus R00299, Mar. 31, 1995).*
Auffray et al (Genbank Locus F02405, Feb. 2, 1995).*
Hillier et al (Genbank Locus R46506, May 10, 1995).*
Marra et al (Genbank Locus AA042077, Sep. 3, 1996).*
Hillier et al (Genbank Locus R33101, Apr. 28, 1995).*
Adams et al (Genbank Locus T30327, Sep. 6, 1995).*
Hillier et al (Genbank Locus T71394, Mar. 15, 1995).*
Iadonato et al (Genbank Locus HSAC002113, May 13, 1997).*
Hillier et al (Genbank Locus R05854, Apr. 3, 1995).*
Schena et al, "Quantitative monitoring of gene expression patterns with a complementary DNA microarray", Science 270:467–470, Oct. 1995.*

Sugio K. et al. "Differential expression of c–myc gene and c–fos gene in premalignant and malignant tissue" Cancer Research, vol. 38, No. 17, 1988 pp. 4855–4861.

Van Belzen N. et al. "Detection of different gene expression in differentiating colon caricoma cells by differential display" Journal of Pathology, vol. 178, No. Suppl., 1996, p. 2A.

Velculescu V.E. et al. "Serial Analysis of Gene Expression" Science, vol. 270, Oct. 20, 1995, pp. 484–487.

Schweinfest C.W. et al. "Substraction hybridization cDNA libraries from colon carinoma and hepatic cancer" Genetic Analysis Techniques and Applications, vol. 7, 1990, pp. 64–70.

Gress T.M. et al. "A pancreatic cancer–specific expression profile" Oncogene, vol. 13, 1996, pp. 1819–1830.

Gress T. et al. "Identification of genes with pancreatic cancer specific expression by use of cDNA representational difference analysis" Gastroenterology, vol. 110, No. 4 Suppl. 1996.

Zhang L. et al. "Gene expression profiles in normal and cancer cells." Science, vol. 276, 1997, pp. 1268–1272.

Van Belzen N. et al. "A novel gene which is up–regulated during coloon epithelial cell diffeerentiation and down–regulated in colorectal neoplasms" Laboratory Investigation, vol. 77, pp. 85–92.

* cited by examiner

Primary Examiner—Jeffrey Fredman
(74) Attorney, Agent, or Firm—Bannee & Witcoff

(57) ABSTRACT

As a step towards understanding the complex differences between normal and cancer cells, gene expression patterns were examined in gastrointestinal tumors. More than 300,000 transcripts derived from at least 45,000 different genes were analyzed. Although extensive similarity was noted between the expression profiles, more than 500 transcripts that were expressed at significantly different levels in normal and neoplastic cells were identified. These data provide insights into the extent of expression differences underlying malignancy and reveal genes that are useful as diagnostic or prognostic markers.

19 Claims, 2 Drawing Sheets

GENE EXPRESSION PROFILES IN NORMAL AND CANCER CELLS

This invention was made with support from the National Institutes of Health, Grant No. GM07309, CA57345, and CA62924. The U.S. government therefore retains certain rights in the invention.

TECHNICAL FIELD OF THE INVENTION

This invention is related to the diagnosis of cancer, and tools for carrying out such diagnosis.

BACKGROUND OF THE INVENTION

Much of cancer research over the past 50 years has been devoted to the analyses of genes that are expressed differently in tumor cells compared to their normal counterparts. Although hundreds of studies have pointed out differences in the expression of one or a few genes, no comprehensive study of gene expression in the cancer cell has been reported. It is therefore not known how many genes are expressed differentially in tumor versus normal cells, whether the bulk of these differences are cell autonomous rather than being dependent on the tumor microenvironment, and whether most differences are cell-type specific or tumor specific. Thus there is a need in the art for information on the molecular changes that occur in cells during cancer development and progression.

SUMMARY OF THE INVENTION

According to one embodiment of the invention, a method is provided for diagnosing colon cancer in a sample suspected of being neoplastic. The method comprises the steps of:

comparing the level of at least one transcript in a first sample of a tissue to a second sample, wherein the first sample is of a colonic tissue suspected of being neoplastic and the second sample is of a normal human colonic tissue, and wherein the transcript is identified by a tag selected from the group consisting of those shown in Table 3;

identifying the first sample as neoplastic when the level of the at least one transcript is found to be lower in the first sample than in the second sample.

According to another embodiment of the invention, another method is provided for diagnosing colon cancer in a sample suspected of being neoplastic. The method comprises the steps of:

comparing the level of at least one transcript in a first sample of a tissue to a second sample, wherein the first sample is of a colonic tissue suspected of being neoplastic and the second sample is of a normal human colonic tissue, and wherein the transcript is identified by a tag selected from the group consisting of those shown in Table 2;

identifying the first sample as neoplastic when the level of the at least one transcript is found to be higher in the first sample than in the second sample.

In another embodiment of the invention an isolated and purified human nucleic acid molecule is provided. The molecule comprises a SAGE tag selected from SEQ ID NOS:1–734.

In yet another aspect of the invention an isolated nucleotide probe is provided. The probe comprises at least 12 nucleotides of a human nucleic acid molecule, wherein the human nucleic acid molecule comprises a SAGE tag selected from SEQ ID NOS: 1–734.

According to another aspect of the invention a method is provided for diagnosing pancreatic cancer in a sample suspected of being neoplastic. The method comprises the steps of:

comparing the level of at least one transcript in a first sample of a tissue to a second sample, wherein the first sample is of a pancreatic tissue suspected of being neoplastic and the second sample is of a normal human colon tissue, wherein said transcript is identified by a tag selected from the group consisting of those shown Table 4;

identifying the first sample as neoplastic when the level of the at least one transcript is found to be higher in the first sample than in the second sample.

According to still another embodiment of the invention a method of diagnosing cancer in a sample suspected of being neoplastic is provided. The method comprises the steps of:

comparing the level of at least one transcript in a first sample of a tissue to a second sample, wherein the first sample is of a tissue suspected of being neoplastic and the second sample is of a normal human tissue, wherein said transcript is identified by a tag selected from the group consisting of those shown Table 5;

identifying the first sample as neoplastic when the level of the at least one transcript is found to be higher in the first sample than in the second sample.

According to another embodiment of the invention a method is provided to aid in the determination of a prognosis for a colon cancer patient. The method comprises the steps of:

comparing the level of at least one transcript in a first sample of a tissue to a second sample, wherein the first sample is of a neoplastic colonic tissue and the second sample is of a normal human colonic tissue, and wherein the transcript is identified by a tag selected from the group consisting of those shown in Table 3;

determining a poorer prognosis if the level of the at least one transcript is found to be lower in the first sample than in the second sample.

According to another aspect of the invention a method to aid in determining a prognosis for a patient with colon cancer is provided. The method comprises the steps of:

comparing the level of at least one transcript in a first tissue sample to a second sample, wherein the first sample is of a colonic cancer tissue and the second sample is of a normal human colonic tissue, and wherein the transcript is identified by a tag selected from the group consisting of those shown in Table 2;

determining a poorer prognosis if the level of the at least one transcript is found to be higher in the first sample than in the second sample.

In yet another embodiment of the invention a method is provided for diagnosing colon cancer in a sample suspected of being neoplastic. The method comprises the steps of:

comparing the level of expression of at least one protein in a first sample of a tissue to a second sample, wherein the first sample is of a colonic tissue suspected of being neoplastic and the second sample is of a normal human colonic tissue, and wherein the protein is encoded by a transcript identified by a tag selected from the group consisting of those shown in Table 3;

identifying the first sample as neoplastic when the level of expression of the protein is found to be lower in the first sample than in the second sample.

In another aspect of the invention a method of diagnosing colon cancer in a sample suspected of being neoplastic is provided. The method comprises the steps of:

comparing the level of expression of at least one protein in a first sample of a tissue to a second sample, wherein the first sample is of a colonic tissue suspected of being neoplastic and the second sample is of a normal human colonic tissue, and wherein the protein is encoded by a transcript identified by a tag selected from the group consisting of those shown in Table 2;

identifying the first sample as neoplastic when expression of the protein is found to be higher in the first sample than in the second sample.

According to another embodiment of the invention a method is provided to aid in determining a prognosis of a patient having pancreatic cancer. The method comprises the steps of:

comparing the level of at least one transcript in a first sample of a tissue to a second sample, wherein the first sample is of a neoplastic pancreatic tissue and the second sample is of a normal human colon tissue, wherein said transcript is identified by a tag selected from the group consisting of those shown Table 4;

determining a poorer prognosis if transcription is found to be higher in the first sample than in the second sample.

In yet another aspect of the invention a method to aid in providing a prognosis for a cancer patient is provided. The method comprises the steps of:

comparing the level of at least one transcript in a first sample of a tissue to a second sample, wherein the first sample is of a neoplastic tissue and the second sample is of a normal human tissue of the same tissue type, wherein said transcript is identified by a tag selected from the group consisting of those shown Table 5;

determining a poorer prognosis if transcription is found to be higher in the first sample than in the second sample.

According to still another aspect of the invention, a method is provided for diagnosing pancreatic cancer in a sample suspected of being neoplastic. The method comprises the steps of:

comparing the level of expression of at least one protein encoded by a transcript in a first sample of a tissue to a second sample, wherein the first sample is of a pancreatic tissue suspected of being neoplastic and the second sample is of a normal human colon tissue, wherein said protein is encoded by a transcript identified by a tag selected from the group consisting of those shown Table 4;

identifying the first sample as neoplastic when expression of the protein is found to be higher in the first sample than in the second sample.

According to yet another aspect of the invention a method is provided for diagnosing cancer in a sample suspected of being neoplastic. The method comprises the steps of:

comparing the level of expression of at least one protein in a first sample of a tissue to a second sample, wherein the first sample is of a tissue suspected of being neoplastic and the second ample is of a normal human tissue, wherein said protein is encoded by a transcript identified by a tag selected from the group consisting of those shown Table 5;

identifying the first sample as neoplastic when expression of the protein is found to be higher in the first sample than in the second sample.

In still another embodiment of the invention a method is provided to aid in the determination of a prognosis of a colon cancer patient. The method comprises the steps of:

comparing the level of expression of at least one protein in a first sample of a tissue to a second sample, wherein the first sample is of a neoplastic colonic tissue and the second sample is of a normal human colonic tissue, and wherein the protein is encoded by a transcript identified by a tag selected from the group consisting of those shown in Table 3;

determining a poorer prognosis if the level of expression is found to be lower in the first sample than in the second sample.

In still another embodiment of the invention a method is provided to aid in determining a prognosis for a patient with colon cancer. The method comprises the steps of:

comparing the level of expression of at least one protein in a first tissue sample to a second sample, wherein the first sample is of a colonic cancer tissue and the second sample is of a normal human colonic tissue, and wherein the protein is encoded by a transcript identified by a tag selected from the group consisting of those shown in Table 2;

determining a poorer prognosis if the level of expression is found to be higher in the first sample than in the second sample.

In still another aspect of the invention a method is provided to aid in determining a prognosis of a patient having pancreatic cancer. The method comprises the steps of:

comparing the level of expression of at least one protein in a first sample of a tissue to a second sample, wherein the first sample is of a neoplastic pancreatic tissue and the second sample is of a normal human colon tissue, wherein said protein is encoded by a transcript identified by a tag selected from the group consisting of those shown Table 4;

determining a poorer prognosis if the level of expression is found to be higher in the first sample than in the second sample.

According to even a further aspect of the invention a method is provided to aid in providing a prognosis for a cancer patient. The method comprises the steps of:

comparing the level of expression of at least one protein in a first sample of a tissue to a second sample, wherein the first sample is of a neoplastic tissue and the second sample is of a normal human tissue of the same tissue type, wherein said protein is encoded by a transcript identified by a tag selected from the group consisting of those shown Table 5;

determining a poorer prognosis if the level of expression is found to be higher in the first sample than in the second sample.

In still another embodiment of the invention a method of treating a cancer cell is provided. The method comprises the step of:

administering to a cancer cell an antibody which specifically binds to a protein encoded by a transcript identified by a tag selected from the group consisting of those shown in Tables 2, 4, and 5, wherein the antibody is linked to a cytotoxic agent.

In another aspect of the invention an antibody linked to a cytotoxic agent is provided. The antibody specifically binds to a protein encoded by a transcript identified by a tag selected from the group consisting of those shown in Tables 2, 4, and 5.

According to another aspect of the invention, a method of detecting colon cancer in a patient is provided. The method comprises the steps of:

comparing the level of at least one protein or transcript in a first body sample to a second body sample, wherein the first sample is a body sample of the patient and the second sample is of a normal human, wherein the protein is encoded by a transcript and the transcript is identified by a tag selected from the group consisting of those shown in Table 2, wherein the first and second body sample is a sample selected from the group consisting of blood, urine, feces, sputum, and serum;

identifying neoplasia when the level of the at least one protein or transcript is found to be higher in the first sample than in the second sample.

In another aspect of the invention a method of detecting pancreatic cancer in a patient is provided. The method comprises the steps of:

comparing the level of at least one protein or transcript encoded by a transcript in a first sample of a tissue to a second sample, wherein the first sample is of the patient and the second sample is of a normal human, wherein said protein is encoded by a transcript and the transcript is identified by a tag selected from the group consisting of those shown Table 4, wherein the first and second sample is a sample selected from the group consisting of blood, urine, feces, sputum, and serum;

identifying neoplasia when the level of the at least one protein or transcript is found to be higher in the first sample than in the second sample.

Also provided by the present invention is a method of detecting cancer in a patient. The method comprises the steps of:

comparing the level of at least one protein or transcript in a first sample to a second sample, wherein the first sample is of patient and the second sample is of a normal human, wherein said protein is encoded by a transcript and the transcript is identified by a tag selected from the group consisting of those shown Table 5, wherein the first and second body sample is a sample selected from the group consisting of blood, urine, feces, sputum, and serum;

identifying neoplasia when the level of the at least one protein or transcript is found to be higher in the first sample than in the second sample.

Additionally provided by the present invention is a method to aid in the determination of a prognosis for a colon cancer patient. The method comprises the steps of:

comparing the level of at least one protein or transcript in a first sample to a second sample, wherein the first sample is of a colon cancer patient and the second sample is of a normal human, wherein the protein is encoded by a transcript and the transcript is identified by a tag selected from the group consisting of those shown in Table 3, wherein the first and second body sample is a sample selected from the group consisting of blood, urine, feces, sputum, and serum;

determining a poorer prognosis if the level of the at least one protein or transcript is found to be lower in the first sample than in the second sample.

Provided by another embodiment of the invention is a method to aid in determining a prognosis for a patient with colon cancer. The method comprises the steps of.

comparing the level of at least one protein or transcript in a first sample to a second sample, wherein the first sample is of a colonic cancer patient and the second sample is of a normal human, wherein the protein is encoded by a transcript and the transcript is identified by a tag selected from the group consisting of those shown in Table 2, wherein the first and second sample is a sample selected from the group consisting of blood, urine, feces, sputum, and serum;

determining a poorer prognosis if the level of the at least one protein or transcript is found to be higher in the first sample than in the second sample.

According to still another aspect of the invention, a method to aid in determining a prognosis of a patient having pancreatic cancer is provided. The method comprises the steps of:

comparing the level of at least one protein or transcript in a first sample to a second sample, wherein the first sample is of a pancreatic cancer patient and the second sample is of a normal human, wherein said protein is encoded by a transcript and the transcript is identified by a tag selected from the group consisting of those shown Table 4, wherein said first and second sample is a sample selected from the group consisting of blood, urine, feces, sputum, and serum;

determining a poorer prognosis if the level of the at least one protein or transcript is found to be higher in the first sample than in the second sample.

Also provided by the present invention is a method to aid in providing a prognosis for a cancer patient. The method comprises the steps of:

comparing the level of expression of at least one protein or transcript in a first sample to a second sample, wherein the first sample is of a cancer patient and the second sample is of a normal human, wherein said protein is encoded by a transcript and the transcript is identified by a tag selected from the group consisting of those shown Table 5, wherein the first and second sample is a sample selected from the group consisting of blood, urine, feces, sputum, and serum;

determining a poorer prognosis if the level of the at least one protein or transcript is found to be higher in the first sample than in the second sample.

The present invention further includes antisense oligonucleotides complementary in whole or in part to SEQ ID NOS: 1–734.

This invention also provides a method for screening for candidate agents that modulate the expression of a polynucleotide selected from the group consisting of the polynucleotides in, SEQ ID NOS:1–870 or their respective complements, by contacting a test agent with a pancreatic or colon cell and monitoring expression of the polynucleotide, wherein the test agent which modifies the expression of the polynucleotide is a candidate agent.

The present invention provides the art with new methods and reagents for diagnosing and prognosing cancers. In addition, some of the newly disclosed genes may play an important role in the development of cancers.

BRIEF DESCRIPTION OF THE DRAWINGS

FIG. 1. Comparison of expression patterns in colorectal cancers and normal colon epithelium.

FIG. 2. Northern blot analysis of genes differentially expressed in gastrointestinal neoplasia. Northern blot analysis was performed on total RNA (5 μg isolated from primary CR carcinomas (T) and matching normal colon epithelium (N), or pancreatic carcinomas. The top panel in each case show an example of the ethidium bromide stained gels prior to transfer. The number of SAGE tags observed in the original analysis is indicated to the right of each blot. FIG. 2A) H204104, Guanylin (M95714); H259108, (see Table 2); H1000193, (see Table 2); H998030, (see Table 2). (FIG. 2B) H294155, RIG-E (U42376); H560056, TIMP-1 (S68252). (FIG. 2C) H802810, EST338411 (W52120); H85882, 1–8D (X57351); H618841, GA733-1 (X13425).

Figure 1A:
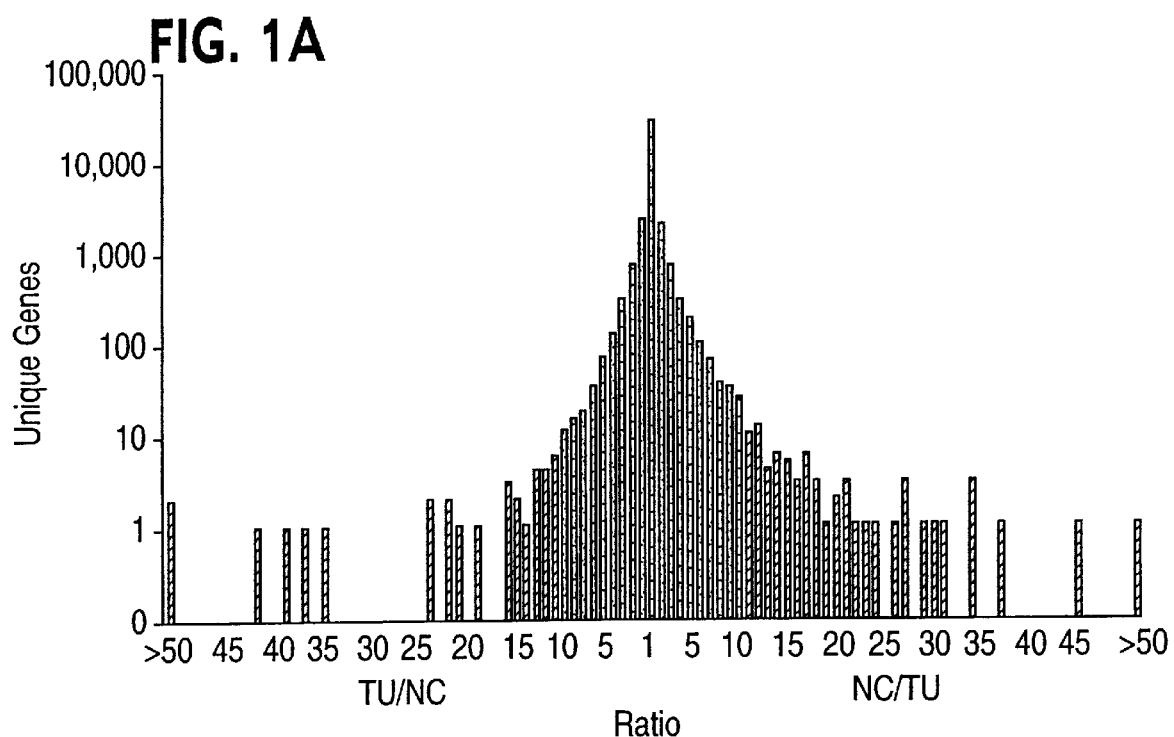
(FIG. 1A) A semilogarithmic plot reveals 51 tags that were decreased more than 10 fold in primary CR cancer cells whereas 32 tags were increased more than 10 fold. 62,168 and 60,878 tags derived from normal colon epithelium and primary CR cancers, respectively, were used for this analysis. The relative expression of each transcript was determined by dividing the number of tags observed in tumor and normal tissue as indicated. To avoid division by 0, a tag value of 1 was used for any tag that was not detectable in one of the samples. These ratios were then rounded to the nearest integer and their distribution plotted on the abscissa. The number of genes displaying each ratio was plotted on the ordinate. Tu: CR tumors; NC: Normal colon.
Figure 1B:
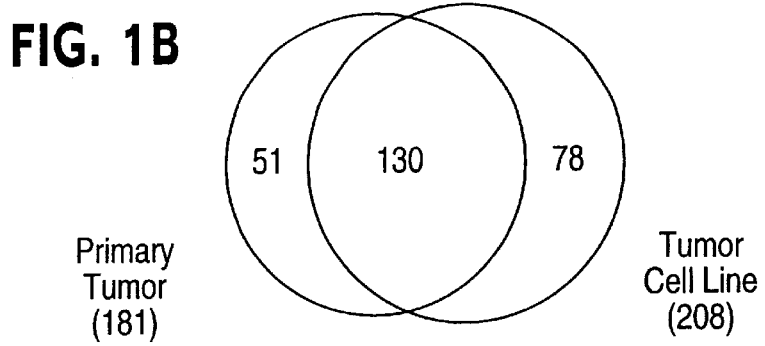
(FIG. 1B and FIG. 1C). Differentially expressed genes in colorectal cancers. The number of transcripts found to be differentially expressed (P<0.01) are presented as Venn diagrams. Diagrams of transcripts that were decreased (FIG. 1B) or increased (FIG. 1C) in CR cancers compared to normal colon epithelium. Comparisons were between primary tumors and cells in culture as indicated.
Figure 1C:
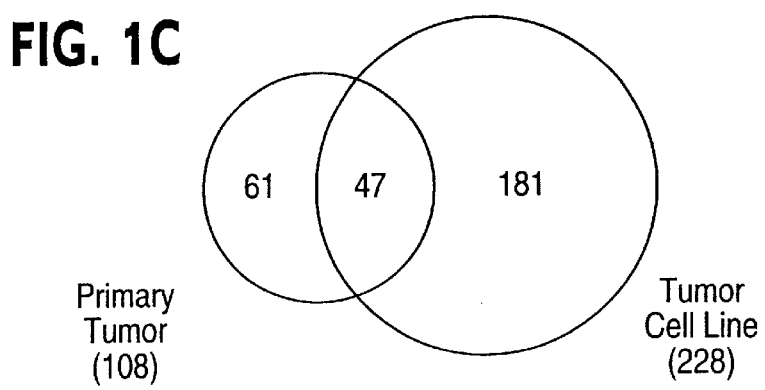
Figure 2A:
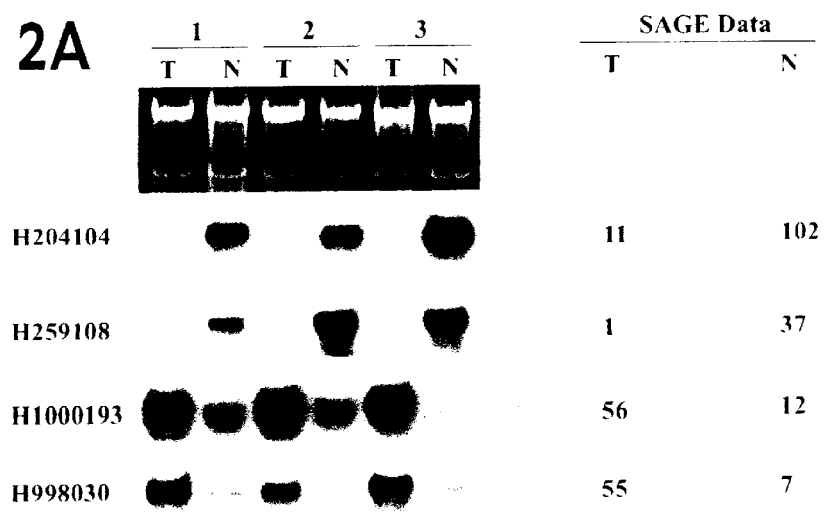
(FIG. 2A) Examples of transcripts that were decreased or increased in CR cancers.
Figure 2B:
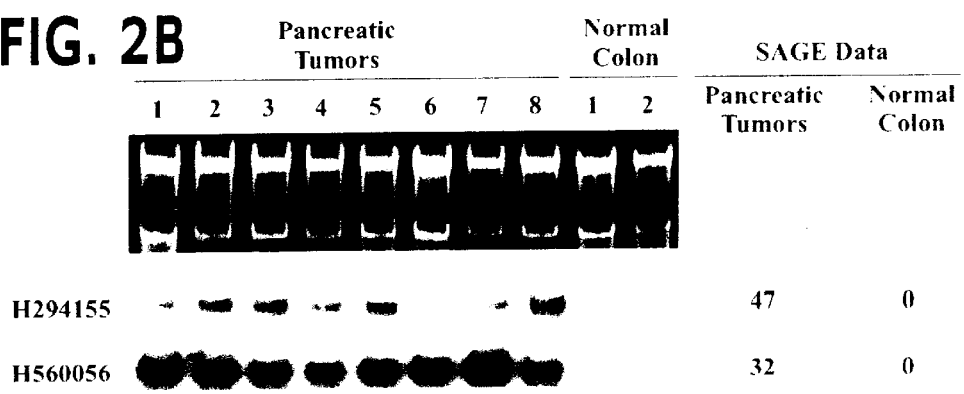
(FIG. 2B) Examples of transcripts increased in pancreatic cancers (10).
Figure 2C:
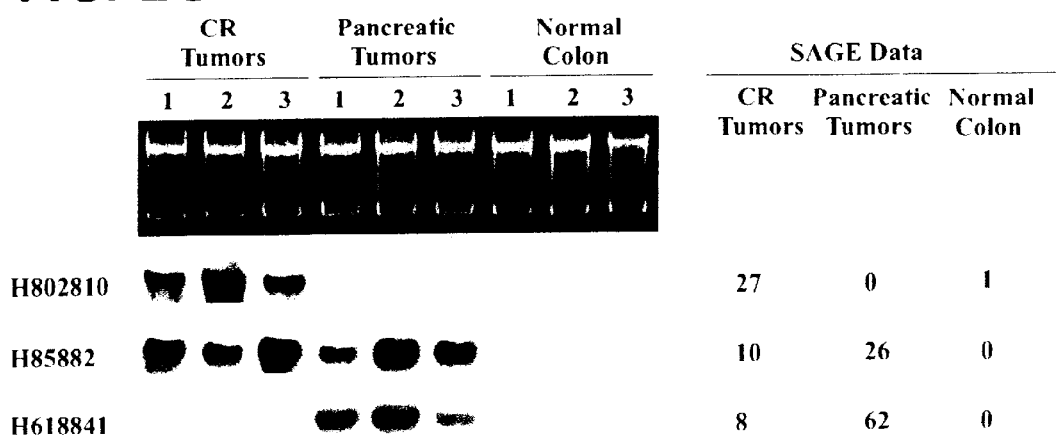
(FIG. 2C) Examples of transcripts elevated in cancer which were or were not cancer type specific. Probes used for Northern blot analysis were as follows (Human SAGE Tag unique identifier, gene name, (GenBank accession number))

Tables 2–5. Transcripts Differentially Expressed in Human Cancer. Tag sequence represents the NlaIII site plus the adjacent 11 bp SAGE tag. Tag number indicates a SAGE UID (unique identifier). NC, TU, CL, PT, PC, refers to the number of the indicated tag observed in RNA isolated from normal colorectal epithelium, primary colorectal cancers, colorectal cancer cell lines, primary pancreatic cancers, or pancreatic cancer cell lines, respectively. The Accession and Gene Name refer to representative GenBank entries that contain the tag sequence.

Table 2 Transcripts increased in colorectal cancer.

Table 3 Transcripts decreased in colorectal cancer.

Table 4 Transcripts increased in pancreatic cancer.

Table 5 Transcripts increased in pancreatic and colorectal cancer.

DETAILED DESCRIPTION

The inventors have discovered sets of human genes which are either upregulated or downregulated in cancer cells, as compared to normal cells. Specifically, certain genes have been found to be upregulated or downregulated in colorectal and/or pancreatic cancer cells, when compared to normal colon cells. These sets of differentially regulated genes can be used as diagnostic markers, either individually or in sets of, for example, 2, 5, 10, 20, or 30.

Genes whose expression was detected to be increased in colorectal cancer are shown in Table 2. Genes whose expression was detected to be decreased in colorectal cancer are shown in Table 3. Genes whose expression was detected as increased in pancreatic cancer are shown in Table 4. Genes whose expression was detected as increased in both pancreatic cancer and colorectal cancer are shown in Table 5. These latter genes likely play a role in neoplastic development generally.

Tag sequences, as provided herein, uniquely identify genes. This is due to their length, and their specific location (3') in a gene from which they are drawn. The full length genes can be identified by matching the tag to a gene data base member, or by using the tag sequences as probes to physically isolate previously unidentified genes from cDNA libraries. The methods by which genes are isolated from libraries using DNA probes are well known in the art. See, for example, Veculescu et al., Science 270: 484 (1995), and Sambrook et al. (1989), MOLECULAR CLONING: A LABORATORY MANUAL, 2nd ed. (Cold Spring Harbor Press, Cold Spring Harbor, N.Y.). Once a gene or transcript has been identified, either by matching to a data base entry, or by physically hybridizing to a cDNA molecule, the position of the hybridizing or matching region in the transcript can be determined. If the tag sequence is not in the 3' end, immediately adjacent to the restriction enzyme used to generate the SAGE tags, then a spurious match may have been made. Confirmation of the identity of a SAGE tag can be made by comparing transcription levels of the tag to that of the identified gene in certain cell types.

In addition to the sequences shown in, SEQ ID NOS:1–870, or their complements, this invention also provides the anti-sense polynucleotide stand, e.g. antisense RNA to these sequences or their complements. One can obtain an antisense RNA using the sequences provided in SEQ ID NOS:1–734 and the methodology described in Vander Krol et al. (1988) Bio Techniques 6:958.

The invention also encompasses polynucleotides which differ from that of the polynucleotides described above, but which produce the same phenotypic effect, such as the allele. These altered, but phenotypically equivalent polynucleotides are referred to "equivalent nucleic acids." This invention also encompasses polynucleotides characterized by changes in non-coding regions that do not alter the phenotype of the polypeptide produced therefrom when compared to the polynucleotide herein. This invention further encompasses polynucleotides, which hybridize to the polynucleotides of the subject invention under conditions of moderate or high stringency.

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples. Briefly, this invention further provides a method for detecting a single-stranded polynucleotide identified by SEQ ID NOS:1–870 or its complement, by contacting target single-stranded polynucleotides with a labeled, single-stranded polynucleotide (a probe) which is at least 10 nucleotides of the complement of SEQ ID NOS:1–870 (or the corresponding complement) under conditions permitting hybridization (preferably moderately stringent hybridization conditions) of complementary single-stranded polynucleotides, or more preferably, under highly stringent hybridization conditions. Hybridized polynucleotide pairs are separated from un-hybridized, single-stranded polynucleotides. The hybridized polynucleotide pairs are detected using methods well known to those of skill in the art and set forth, for example, in Sambrook et al. (1989) supra.

The polynucleotides of this invention can be isolated using the technique described in the experimental section or replicated using PCR. The PCR technology is the subject matter of U.S. Pat. Nos. 4,683,195, 4,800,159, 4,754,065, and 4,683,202 and described in PCR: The Polymerase Chain Reaction (Mullis et al. eds, Birkhauser Press, Boston (1994)) or MacPherson et al. (1991) and (1994), supra, and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable host cell. The DNA can be inserted by any appropriate method, e.g., by the use of an appropriate gene delivery vector or by electroporation. When the cell replicates and the DNA is transcribed into RNA; the RNA can then be isolated using methods well known to those of skill in the art, for example, as set forth in Sambrook et al. (1989) supra. For instance, mRNA can be isolated using various lytic enzymes or chemical solutions according to the procedures set forth in Sambrook et al. (1989), supra or extracted by nucleic-acid-binding resins following the accompanying instructions provided by manufactures.

Polynucleotides having at least 10 nucleotides and exhibiting sequence complementarity or homology to SEQ ID NOS: 1–734 find utility as hybridization probes. In some aspects, the full coding sequence of the transcript, i.e., for SEQ ID NOS: 1–734, are known. Accordingly, any portion of the known sequences available in Gendank, or homologous sequences, can be used in the methods of this invention.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region of comparable size contained in the previously identified sequences identified by SEQ ID NOS:1–734, which correspond to previously characterized genes or SEQ ID NOS:1–734, which correspond to known ESTs. More preferably, the probe is 85% identical to the corresponding gene sequence after alignment of the homologous region; even more preferably, it exhibits 90% identity.

These probes can be used in radioassays (e.g. Southern and Northern blot analysis) to detect, prognose, diagnose or monitor various pancreatic or colon cells or tissue containing these cells. The probes also can be attached to a solid support or an array such as a chip for use in high throughput screening assays for the detection of expression of the gene corresponding to one or more polynucleotide(s) of this invention. Accordingly, this invention also provides at least one of the transcripts identified as SEQ ID NOS:1–734, or its complement, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between about 10 and about 100 nucleotides, or even full length according to the complementary sequences one wishes to detect.

Nucleotide probes having complementary sequences over stretches greater than 10 nucleotides in length are generally preferred, so as to increase stability and selectivity of the hybrid, and thereby improving the specificity of particular hybrid molecules obtained. More preferably, one can design polynucleotides having gene-complementary stretches of more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. A preferred probe is about 50–75 or more preferably, 50–100, nucleotides in length.

The polynucleotides of the present invention can serve as primers for the detection of genes or gene transcripts that are expressed in pancreatic or colon cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase.

A preferred amplification method is PCR. However, PCR conditions used for each reaction are empirically determined. A number of parameters influence the success of a reaction. Among them are annealing temperature and time, extension time, $Mg^{2+}$ ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

The invention further provides the isolated polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)), which contains maps, functional properties, commercial suppliers and a reference to Gen-EMBL accession numbers for various suitable vectors. Preferable, these vectors are capable of transcribing RNA in vitro or in vivo.

Fragment of the sequences shown in SEQ ID NOS:1–734 or their respective complements also are encompassed by this invention, preferably at least 10 nucleotides and more preferably having at least 18 nucleotides. Larger polynucleotides, e.g., cDNA or genomic DNA, which hybridize under moderate or stringent conditions to the polynucleotide sequences shown in SEQ ID NOS:1–734, or their respective complements, also are encompassed by this invention.

In one embodiment, these fragments are polynucleotides that encode polypeptides or proteins having diagnostic and therapeutic utilities as described herein as well as probes to identify transcripts of the protein which may or may not be present. These nucleic acid fragments can by prepared, for example, by restriction enzyme digestion of the polynucleotide of SEQ ID NOS:1–734, or their complements, and then labeled with a detectable marker. Alternatively, random fragments can be generated using nick translation of the molecule. For methodology for the preparation and labeling of such fragments, see Sambrook et al., (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook et al. (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, an animal cell (rat or mouse), a human cell, or a procaryotic cell such as a bacterial cell, containing a polynucleotide encoding a protein or polypeptide or antibody.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A.D. et al. (1989) BioTechniques 7:980–990). The methodology of using replication-incompetent retroviruses for retroviral-mediated gene transfer of gene markers is well established (Correll et al. (1989) PNAS USA 86:8912; Bordignon (1989) PNAS USA 86:8912–52; Culver, K. (1991) PNAS USA 88:3155; and Rill, D.R. (1991) Blood 79(10):2694–700. Clinical investigations have shown that there are few or no adverse effects associated with the viral vectors, see Anderson (1992) Science 256:808–13.

Compositions containing the polynucleotides of this invention, in isolated form or contained within a vector or host cell are further provided herein. When these compositions are to be used pharmaceutically, they are combined with a pharmaceutically acceptable carrier.

This invention further encompasses genes, either genomic or cDNA, which code for a polypeptide or protein in the cell of interest. The genes specifically hybridize under moderate or stringent conditions to a polynucleotide identified by SEQ ID NOS:1–870 or their respective complements. The process of identification of larger fragment or the full-length coding sequence to which the partial sequence depicted in SEQ ID NOS:1–870 hybridizes preferably involves the use of the methods and reagents provided in this invention, either singularly or in combination.

Five methods are disclosed herein which allows one of skill in the art to isolate the gene or cDNA corresponding to the transcripts of the invention.

RACE-PCR Technique

One method to isolate the gene or cDNA which code for a polypeptide or protein and which corresponds to a transcript of this invention, involves the 5'-RACE-PCR technique. In this technique, the poly-A mRNA that contains the coding sequence of particular interest is first identified by hybridization to a sequence disclosed herein and then reverse transcribed with a 3'-primer comprising the sequence disclosed herein. The newly synthesized cDNA strand is then tagged with an anchor primer of a known sequence, which preferably contains a convenient cloning restriction site attached at the 5' end. The tagged cDNA is then amplified with the 3'-primer (or a nested primer sharing sequence homology to the internal sequences of the coding region) and the 5'-anchor primer. The amplification may be conducted under conditions of various levels of stringency to optimize the amplification specificity. 5'-RACE-PCR can be readily performed using commercial kits (available from, e.g., BRL Life Technologies Inc, Clotech) according to the manufacturer's instructions.

Identification of Known Genes or ESTs

In addition, databases exist that reduce the complexity of ESTs by assembling contiguous EST sequences into tentative genes. For example, TIGR has assembled human ESTs into a datable called THC for tentative human consensus sequences. The THC database allows for a more definitive assignment compared to ESTs alone. Software programs exist (give examples) that allow for assembling ESTs into contiguous sequences from any organism.

Isolation of cDNAs from a Library by Probing with the SAGE Transcript or Tag

Alternatively, mRNA from a sample preparation was used to construct cDNA library in the ZAP Express vector following the procedure described in Velculescu et al. (1997) Science 270:484. The ZAP Express cDNA synthesis kit (Stratagene) was used accordingly to the manufacturer's protocol. Plates containing 250 to 2000 plaques are hybridized as described in Rupert et al. (1988) Mol. Cell. Bio. 8:3104 to oligonucleotide probes with the same conditions previously described for standard probes except that the hybridization temperature is reduced to room temperature. Washes are performed in 6X standard-saline-citrate 0.1% SDS for 30 minutes at room temperature. The probes are labeled with 32P-ATP through use of T4 polynucleotide kinase.

TABLE 2

Transcripts increased in colon cancer
Transcripts increased in only colon primary tumors compared to normal colon (61 genes)

| SEQ ID NO: | Tag Sequence | Tag_Number | NC | TU | CL | PT | PC | Accession | Gene Name |
|---|---|---|---|---|---|---|---|---|---|
| 1 | CATGCACCTAATTGG | H285759 | 612 | 755 | 411 | 161 | 333 | F15516 | *H. sapiens* mitochondrial EST sequence (1-t-12) from |
| 2 | CATGTGATTTCACTT | H933704 | 452 | 595 | 235 | 80 | 314 | U35430 | Human cytochrome c oxidase subunit III (COIII) pse |
| 3 | CATGCCTGTAATCCC | H388150 | 433 | 549 | 380 | 443 | 197 | Z70701 | *H. sapiens* mRNA (fetal brain cDNA c2_11). |
|   |   |   |   |   |   |   |   | X71347 | *H. sapiens* HNF1-C mRNA. |
|   |   |   |   |   |   |   |   | X71346 | *H. sapiens* HNF1-B mRNA. |
| 4 | CATGCACTACTCACC | H291282 | 293 | 527 | 78 | 14 | 83 | U09500 | Human mitochondrion cytochrome b gene, partial cds |
| 5 | CATGGTGAAACCCCA(G) | H753750 | 392 | 517 | 389 | 453 | 194 | X66785 | *H. sapiens* mRNA for transacylase (DBT). |
|   |   |   |   |   |   |   |   | X17648 | Human mRNA for granulocyte-macrophage colony-stimu |
|   |   |   |   |   |   |   |   | U09087 | Human thymopoietin beta mRNA, complete cds. |
|   |   |   |   |   |   |   |   | U09088 | Human thymopoietin gamma mRNA, complete cds. |
|   |   |   |   |   |   |   |   | U20770 | Human metastasis suppressor (KAI1) mRNA, complete |
| 6 | CATGGGCTTTAGGGA | H687915 | 37 | 372 | 6 | 29 | 11 | W15552 | zb91h11.s1 Soares parathyroid tumor NbHPA *Homo sap* |
|   |   |   |   |   |   |   |   | W32091 | zc05d03.s1 Soares parathyroid tumor NbHPA *Homo sap* |
|   |   |   |   |   |   |   |   | R62866 | yi11d07.r1 *Homo sapiens* cDNA clone 138925 5'. |
| 7 | CATGACTTTCCAAA | H130369 | 32 | 272 | 32 | 23 | 20 | X89839 | *H. sapiens* mitochondrial DNA for loop attachment se |
| 8 | CATGTGGTGTATGCA | H965434 | 53 | 271 | 6 | 30 | 5 | T11555 | A1486F *Homo sapiens* cDNA clone A1486 similar to Mi |
| 9 | CATGAGGGTGTTTTC | H175872 | 26 | 218 | 7 | 20 | 10 | T15773 | IB1870 *Homo sapiens* cDNA 3'end similar to Human mi |
| 10 | CATGAGGTCAGGAGA(T) | H177315 | 93 | 213 | 113 | 148 | 58 | X12544 | Human mRNA for HLA class II DR-beta (HLA-DR B). |
|   |   |   |   |   |   |   |   | S73483 | phosphorylase kinase catalytic subunit PHKG2 homol |
| 11 | CATGTTGGCCAGGCT | H1025322 | 124 | 194 | 63 | 111 | 51 | X74301 | *H. sapiens* mRNA for MHC class II transactivator. |
|   |   |   |   |   |   |   |   | U28687 | Human zinc finger containing protein ZNF157 (ZNF 15 |
|   |   |   |   |   |   |   |   | U29119 | Human leiomyoma LM-196.4 ectopic sequence from HMG |
|   |   |   |   |   |   |   |   | U56236 | Human Fc alpha receptor b mRNA, complete cds. |
| 12 | CATGATCACGCCCTC | H214616 | 97 | 186 | 17 | 41 | 49 | W03751 | za62h11.r1 Soares fetal liver spleen 1NFLS *Homo sa* |
|   |   |   |   |   |   |   |   | W03770 | za63f10.r1 Soares fetal liver spleen 1NFLS *Homo sa* |
|   |   |   |   |   |   |   |   | W04748 | za42f09.r1 Soares fetal liver spleen 1NFLS *Homo sa* |
| 13 | CATGGGGGTCAGGGG | H699691 | 37 | 170 | 11 | 16 | 9 | T12078 | A730R *Homo sapiens* cDNA clone A730 similar to Mito |
|   |   |   |   |   |   |   |   | W45641 | zc26a12.s1 Soares senescent fibroblasts NbHSF Homo |
| 14 | CATGGCTAGGTTTAT | H641789 | 38 | 144 | 13 | 25 | 13 | D51017 | Human fetal brain cDNA 3'-end GEN-007C04. |
|   |   |   |   |   |   |   |   | D53694 | Human fetal brain cDNA 3'-end GEN-117E01. |
| 15 | CATGCCCCGTACATC | H350996 | 56 | 132 | 35 | 0 | 18 |   | Unknown |
| 16 | CATGAGTAGGTGGCC | H183018 | 18 | 131 | 2 | 17 | 7 | D51021 | Human fetal brain cDNA 3'-end GEN-007D07. |
|   |   |   |   |   |   |   |   | D51052 | Human fetal brain cDNA 3'-end GEN-009C05. |
|   |   |   |   |   |   |   |   | D52836 | Human fetal brain cDNA 3'-end GEN-089E01. |
| 17 | CATGCCTGTAGTCCC | H388278 | 79 | 124 | 61 | 71 | 23 | D83195 | Human DNA for Deoxyribonuclease I precursor. |
| 18 | CATGAGACCCACAAC | H136465 | 64 | 121 | 28 | 24 | 15 | D54113 | Human fetal brain cDNA 5'-end GEN-129B05. |
| 19 | CATGCATTTGTAATA | H327364 | 49 | 107 | 35 | 7 | 40 | F15796 | *H. sapiens* mitochondrial EST sequence (102-25) from |
| 20 | CATGTCCCCGTACCT | H874182 | 28 | 78 | 14 | 0 | 13 |   |   |
| 21 | CATGGCCAACCTCCT | H606582 | 23 | 73 | 8 | 6 | 19 | Z59183 | *H.sapiens* CpG island DNA genomic Mse1 fragment, c1 |
|   |   |   |   |   |   |   |   | D52905 | Human fetal brain cDNA 5'-end GEN-091D11. |
| 22 | CATGGCCATCCCCTT | H609624 | 29 | 73 | 7 | 14 | 16 | F16449 | *H. sapiens* mitochondrial EST sequence (129-09) from |
| 23 | CATGTTGGTCAGGCT | H1027370 | 35 | 67 | 18 | 35 | 14 | U06452 | Human melanoma antigen recognized by T-cells (MART |
| 24 | CATGTCCTATTAAG | H881603 | 20 | 49 | 17 | 15 | 26 |   |   |
| 25 | CATGTTACTTATACT | H991026 | 2 | 47 | 2 | 1 | 4 | D51004 | Human fetal brain cDNA 3'-end GEN-006D02. |
|   |   |   |   |   |   |   |   | L49057 | *Homo sapiens* retinal fovea EST HFD010904 seqnence |
|   |   |   |   |   |   |   |   | D51071 | Human fetal brain cDNA 3'-end GEN-010E01. |
| 26 | CATGATGGCAGGAGT | H238755 | 13 | 45 | 1 | 4 | 2 |   |   |
| 27 | CATGCTAAGGCGAGG | H461411 | 5 | 44 | 2 | 3 | 3 |   |   |
| 28 | CATGGGTGAGACACT | H713234 | 7 | 44 | 20 | 13 | 15 | J03592 | Human ADP/ATP translocase mRNA, 3' end, clone pHAT |

TABLE 2-continued

Transcripts increased in colon cancer
Transcripts increased in only colon primary tumors compared to normal colon (61 genes)

| SEQ ID NO: | Tag Sequence | Tag Number | NC | TU | CL | PT | PC | Accession | Gene Name |
|---|---|---|---|---|---|---|---|---|---|
| 29 | CATGACCTGTATCCC | H97078 | 6 | 42 | 17 | 100 | 32 | X57352 | Human 1-8U gene from interferon-inducible gene fam |
| 30 | CATGCCAGTCCGCCT | H339302 | 0 | 39 | 0 | 1 | 0 | H01571 | yj33e06.r1 Homo sapiens cDNA clone 150562 5' simil |
|  |  |  |  |  |  |  |  | H03072 | yj46g12.r1 Homo sapiens cDNA clone 151846 5' simil |
| 31 | CATGTAATTTTTGCC | H802810 | 1 | 37 | 0 | 1 | 0 | T25155 | EST730 Homo sapiens cDNA clone 34C11. |
| 32 | CATGTTAGCTTGTTT | H993264 | 6 | 37 | 2 | 3 | 5 | D50972 | Human fetal brain cDNA 3'-end GEN-004A05. |
|  |  |  |  |  |  |  |  | D51211 | Human fetal brain cDNA 3'-end GEN-017E08. |
|  |  |  |  |  |  |  |  | D52162 | Human fetal brain cDNA 3'-end GEN-069F04. |
|  |  |  |  |  |  |  |  | T23865 | seq2012 Homo sapiens cDNA clone Cot1374Ft-4HB3MA-3 |
| 33 | CATGGCCACCCCCTG | H607576 | 0 | 35 | 1 | 0 | 0 | M32053 | Human H19 RNA gene, complete cds. |
| 34 | CATGTAATAAAGGTG | H798764 | 13 | 35 | 19 | 33 | 51 | X67247 | H. sapiens rpS8 gene for ribosomal protein S8. |
| 35 | CATGTACTGCTCGGA | H817627 | 13 | 35 | 5 | 1 | 14 | T11939 | A953F Homo sapiens cDNA clone A953 similar to Mito |
| 36 | CATGGTGAAACCCA | H753749 | 9 | 31 | 22 | 30 | 4 | T95857 | ye42f01.s1 Homo sapiens cDNA clone 120409 3' simil |
|  |  |  |  |  |  |  |  | W03237 | za35b09.r1 Soares fetal liver spleen 1NFLS Homo sa |
|  |  |  |  |  |  |  |  | W03326 | za63g03.r1 Soares fetal liver spleen 1NFLS Homo sa |
| 37 | CATGGAAACTGAACA | H526210 | 6 | 26 | 17 | 5 | 3 | X54195 | Human line-1 element DNA, host sequence flanking t |
|  |  |  |  |  |  |  |  | U29607 | Human methionine aminopeptidase mRNA, complete cds |
|  |  |  |  |  |  |  |  | H95100 | yw57b10.r1 Homo sapiens cDNA clone 256315 5' simil |
| 38 | CATGACTTTTTAAAA | H131009 | 1 | 22 | 4 | 1 | 0 |  |  |
| 39 | CATGGACTGCGTGCC | H555450 | 0 | 21 | 7 | 9 | 12 | D29062 | Human keratinocyte cDNA, clone 067. |
|  |  |  |  |  |  |  |  | D29563 | Human keratinocyte cDNA, clone 713. |
| 40 | CATGTCAGTGGTAGT | H863923 | 4 | 21 | 2 | 2 | 1 | T03196 | FB3B5 Homo sapiens cDNA clone FB3B5 3'end. |
| 41 | CATGAAACTGTGGTT | H7916 | 2 | 20 | 2 | 2 | 1 | Z57093 | H. sapiens CpG DNA, clone 164a10, reverse read cpg1 |
|  |  |  |  |  |  |  |  | Z60184 | H. sapiens CpG island DNA genomic Mse1 fragment, c1 |
|  |  |  |  |  |  |  |  | Z63649 | H. sapiens CpG island DNA genomic Mse1 fragment, c1 |
|  |  |  |  |  |  |  |  | W31349 | zb95d06.s1 Soares parathyroid tumor NbHPA Homo sap |
| 42 | CATGGGGGGGGGGGT | H699051 | 0 | 19 | 0 | 0 | 0 |  |  |
| 43 | CATGGTGCCCGTGCC |  | 2 | 19 | 1 | 0 | 0 | W31448 | zb96h01.s1 Soares parathyroid tumor NbHPA Homo sap |
|  |  |  |  |  |  |  |  | W47282 | zc40b06.r1 Soares senescent fibroblasts NbHSF Homo |
| 44 | CATGGGGGGTAACTA | H699144 | 3 | 19 | 15 | 12 | 5 | X71428 | H. sapiens fus mRNA |
|  |  |  |  |  |  |  |  | S62140 | TLS = translocated in liposarcoma [human, mRNA, 1824 |
|  |  |  |  |  |  |  |  | W31782 | zb96a06.r1 Soares parathyroid tumor NbHPA Homo sap |
| 45 | CATGTCCTGCCCCAT | H883029 | 3 | 19 | 14 | 27 | 16 | M24398 | Human parathymosin mRNA, complete cds. |
| 46 | CATGAAGTGGCAAGA | H47683 | 0 | 16 | 0 | 0 | 0 |  |  |
| 47 | CATGGGTATTAACCA | H708358 | 0 | 16 | 0 | 0 | 0 | U33317 | Human defensin 6 (HD-6) gene, complete cds. |
|  |  |  |  |  |  |  |  | M98331 | Homo sapiens defensin 6 mRNA, complete cds. |
| 48 | CATGGGCTACACCTT | H684312 | 2 | 16 | 0 | 2 | 1 | D32027 | Human mRNA for T cell receptor V beta 14 CDR3, par |
|  |  |  |  |  |  |  | 2 | 16 | 0 | 2 | 1 | T11701 | A1225F Homo sapiens cDNA clone A1225 similar to Mi |
| 49 | CATGAGGGTGTTTCC | H175870 | 1 | 15 | 0 | 0 | 0 | D51783 | Human fetal brain cDNA 5'-end GEN-051G02. |
| 50 | CATGCAAGGACCAGC | H272467 | 0 | 13 | 0 | 2 | 0 | D13138 | Human mRNA for dipeptidase. |
|  |  |  |  |  |  |  |  |  | Homo sapiens (clones MDP4, MDP7) microsomal dipept |
|  |  |  |  |  |  |  |  |  | RDP = renal dipeptidase [human, kidney, Genomic, 357 |
| 51 | CATGTGGAAATGACC | H950498 | 0 | 13 | 0 | 167 | 0 | M10629 | Human alpha-1 collagen gene, 3' end with polyA sit |
| 52 | CATGATCCGCCTGCC | H219514 | 1 | 13 | 3 | 4 | 1 | H11641 | ym17e04.s1 Homo sapiens cDNA clone 47962 3' simila |
|  |  |  |  |  |  |  |  | R95667 | yq51a09.s1 Homo sapiens cDNA clone 199288 3' simil |
| 53 | CATGTCCCGTACAC | H875282 | 1 | 13 | 0 | 0 | 1 |  |  |

TABLE 2-continued

Transcripts increased in colon cancer
Transcripts increased in only colon primary tumors compared to normal colon (61 genes)

| SEQ ID NO: | Tag Sequence | Tag_Number | NC | TU | CL | PT | PC | Accession | Gene Name |
|---|---|---|---|---|---|---|---|---|---|
| 54 | CATGATGTAAAAAAT | H241665 | 0 | 11 | 0 | 12 | 14 | M74090 | Human TB2 gene mRNA, 3' end. |
|  |  |  |  |  |  |  |  | J03801 | Human lysozyme mRNA, complete cds with an Alu repe |
|  |  |  |  |  |  |  |  | M19045 | Human lysozyme mRNA, complete cds. |
| 55 | CATGCCAGCCCCGTC | H337244 | 0 | 11 | 0 | 0 | 0 |  |  |
| 56 | CATGACCATTCTGCT | H85882 | 0 | 10 | 1 | 26 | 3 | X57351 | Human 1-8D gene from interferon-inducible gene fam |
|  |  |  |  |  |  |  |  | X02490 | Human interferon-inducible mRNA (cDNA 1-8). |
| 57 | CATGAGGACCATCGC | H165175 | 0 | 10 | 0 | 0 | 0 |  |  |
| 58 | CATGATGTGAAGAGT(A) | H243747 | 0 | 10 | 0 | 165 | 0 | J03040 | Human SPARC/osteonectin mRNA, complete cds. |
| 59 | CATGCAGTTGGTTGT | H310975 | 0 | 10 | 6 | 7 | 4 | U55217 | Human RNA fragment from patients with Crohn's dise |
| 60 | CATGGCCCTCTGCCA | H613862 | 0 | 10 | 2 | 15 | 7 |  |  |
| 61 | CATGTTAGATAAGCA | H992010 | 0 | 10 | 3 | 3 | 6 | M94083 | Human chaperonin-like protein (HTR3) mRNA, complet |
|  |  |  |  |  |  |  |  | L27706 | Human chaperonin protein (Tcp20) gene complete cds |

NC: Normal Colon
TU: Colon Primary Tumor
CL: Colon Cancer Cell Line
PT: Pancreatic Primary Tumor
PC: Pancreatic Cancer Cell Line

TABLE 2

Transcripts increased in colon cancer
Transcripts increased in both colon primary tumors and colon cancer cell lines compared to normal colon (47 genes)

| SEQ ID NO: | Tag Sequence | Tag_Number | NC | CT | CL | PT | PC | Accession | Gene Name |
|---|---|---|---|---|---|---|---|---|---|
| 62 | CATGGCAGCCATCCG | H599350 | 87 | 180 | 230 | 72 | 138 | U14969 | Human ribosomal protein L28 mRNA, complete cds. |
| 63 | CATGATGGCTGGTAT | H239533 | 52 | 153 | 318 | 80 | 294 | X17206 | Human mRNA for LLRep3. |
| 64 | CATGCCCGTCCGGAA | H355689 | 87 | 142 | 246 | 178 | 250 | X64707 | H. sapiens BBC1 mRNA |
| 65 | CATGAGGCTACGGAA | H171113 | 44 | 117 | 167 | 86 | 147 | X56932 | H. sapiens mRNA for 23 kD highly basic protein |
| 66 | CATGAGCACCTCCAG | H148949 | 42 | 116 | 197 | 103 | 190 | Z11692 | H. sapiens mRNA for elongation factor 2. |
| 67 | CATGCTGGGTTAATA | H502724 | 29 | 115 | 160 | 75 | 134 | M81757 | H. sapiens S19 ribosomal protein mRNA, complete cds |
| 68 | CATGGGATTTGGCCT | H671654 | 55 | 108 | 222 | 73 | 185 | M17887 | Human acidic ribosomal phosphoprotein P2 mRNA, com |
| 69 | CATGTACCATCAATA | H807748 | 46 | 107 | 98 | 64 | 189 | X53778 | H. sapiens hng mRNA for uracil DNA glycosylase. |
|  |  |  |  |  |  |  |  | J02642 | Human glyceraldehyde 3-phosphate dehydrogenase mRN |
| 70 | CATGTGGGCAAAGCC | H959498 | 51 | 103 | 156 | 45 | 152 | Z11531 | H. sapiens mRNA for elongation-factor-1-gamma. |
|  |  |  |  |  |  |  |  | M55409 | Human pancreatic tumor-related protein mRNA, 3' en |
| 71 | CATGAATCCTGTGGA | H55227 | 30 | 95 | 102 | 48 | 156 | Z28407 | H. sapiens mRNA for ribosomal protein L8. |
| 72 | CATGGGACCACTGAA | H660601 | 36 | 92 | 114 | 43 | 63 | X73460 | H. sapiens mRNA for ribosomal protein L3. |
| 73 | CATGAGGGCTTCCAA | H174037 | 47 | 91 | 167 | 91 | 155 | M73791 | Human novel gene mRNA, complete cds. |
|  |  |  |  |  |  |  |  | M64241 | Human Wilm's tumor-related protein (QM) mRNA, comp |
|  |  |  |  |  |  |  |  | S35960 | laminin receptor homolog {3' region} [human, mRNA |
| 74 | CATGAAGGTGGAGGA | H44683 | 48 | 91 | 182 | 113 | 215 | X80822 | H. sapiens mRNA for ORF. |
| 75 | CATGTGCACGTTTTC | H935680 | 45 | 87 | 105 | 61 | 122 | X03342 | Human mRNA for ribosomal protein L32 |
| 76 | CATGTCAGATCTTTG | H861056 | 37 | 81 | 93 | 50 | 92 | M58458 | Human ribosomal protein S4 (RPS4X) isoform mRNA, c |
|  |  |  |  |  |  |  |  | M22146 | Human scar protein mRNA, complete cds. |
| 77 | CATGTGGTGTTGAGG | H965603 | 42 | 79 | 83 | 55 | 250 | X69150 | H. sapiens mRNA for ribosomal protein S18. |
|  |  |  |  |  |  |  |  | L06432 | Homo sapiens 18S ribosomal protein (HKE3) mRNA seq |
| 78 | CATGCCTAGCTGGAT | H379369 | 28 | 77 | 80 | 46 | 143 | Y00052 | Human mRNA for T-cell cyclophilin. |
| 79 | CATGCTTGGGTTTTG | 518912 | 0 | 73 | 42 | 0 | 0 | X07868 | Human DNA for insulin-like growth factor II (IGP-2); |
| 80 | CATGCTCCTCACCTG | H482584 | 12 | 72 | 41 | 34 | 50 | U16811 | Human Bak mRNA, complete cds. |
| 81 | CATGCTGTTGGTGAT | H507577 | 17 | 65 | 116 | 48 | 103 | D14530 | Human homolog of yeast ribosomal protein S28, comp |

TABLE 2-continued

Transcripts increased in colon cancer
Transcripts increased in both colon primary tumors and colon cancer cell lines compared to normal colon (47 genes)

| SEQ ID NO: | Tag Sequence | Tag_Number | NC | CT | CL | PT | PC | Accession | Gene Name |
|---|---|---|---|---|---|---|---|---|---|
| 82 | CATGCGCCGGAACAC | H416261 | 28 | 62 | 183 | 55 | 94 | X73974 | *H. sapiens* HRPL4 mRNA. |
| 83 | CATGCAATAAATGTT | H274492 | 9 | 60 | 73 | 55 | 119 | D23661 | Human mRNA for ribosomal protein L37, complete cds |
| 84 | CATGACATCATCGAT | H79065 | 15 | 57 | 82 | 42 | 118 | L06505 | Human ribosomal protein L12 mRNA, complete cds. |
| 85 | CATGTTCAATAAAAA | H1000193 | 12 | 56 | 154 | 49 | 99 | M17886 | Human acidic ribosomal phosphoprotein P1 mRNA, com |
| 86 | CATGGAACACATCCA | H528694 | 24 | 56 | 71 | 24 | 146 | X63527 | *H. sapiens* mRNA for ribosomal protein L19. |
| 87 | CATGTTATGGGATCT | H998030 | 7 | 55 | 78 | 35 | 77 | M24194 | Human MHC protein homologous to chicken B complex |
| 88 | CATGGCATAATAGGT |  | 18 | 53 | 50 | 19 | 61 | U14967 | Human ribosomal protein L21 mRNA, complete cds. |
| 89 | CATGATTCTCCAGTA | H253260 | 23 | 50 | 103 | 49 | 120 | X55954 | Human mRNA for HL23 ribosomal protein homologue. |
|  |  |  |  |  |  |  |  | X52839 | Human mRNA for ribosomal protein L17. |
| 90 | CATGACTCCAAAAAA | H119809 | 15 | 49 | 64 | 21 | 64 | H38868 | yp61a04.r1 *Homo sapiens* cDNA clone 191886 5' simil |
|  |  |  |  |  |  |  |  | H71935 | ys15f12.r1 *Homo sapiens* cDNA clone 214895 5'. |
|  |  |  |  |  |  |  |  | Z43914 | *H. sapiens* partial cDNA sequence; clone c-1od03. |
|  |  |  |  |  |  |  |  | T48545 | hbc3221 *Homo sapiens* cDNA clone hbc3221 5'end. |
| 91 | CATGCTGTTGATTGC | H507455 | 9 | 44 | 54 | 22 | 40 | X04347 | Human liver mRNA fragment DNA binding protein UPI |
| 92 | CATGTACAAAATCGA | 802871 | 0 | 42 | 20 | 0 | 0 | X00910 | Human mRNA for IGF-II precursor (insulin-like grow |
| 93 | CATGGAAAAATGGTT | H524524 | 14 | 41 | 81 | 15 | 57 | X61156 | *H. sapiens* mRNA for laminin-binding protein. |
|  |  |  |  |  |  |  |  | J03799 | Human colin carcinoma laminin-binding protein mRNA |
| 94 | CATGAAGAAGATAGA | H33331 | 9 | 39 | 69 | 30 | 56 | U02032 | Human ribosomal protein L23a mRNA, partial cds. |
| 95 | CATGCCTTCGAGATC | H390692 | 12 | 36 | 51 | 25 | 86 | U14970 | Human ribosomal protein S5 mRNA, complete cds. |
| 96 | CATGACTGGGTCTAT | H125661 | 5 | 29 | 25 | 25 | 38 | X58965 | *H. sapiens* RNA for nm23-H2 gene. |
|  |  |  |  |  |  |  |  | M36981 | Human putative NDP kinase (nm23-H2S) mRNA, complet |
|  |  |  |  |  |  |  |  | L16785 | *Homo sapiens* c-myc transcription factor (puf) mRNA |
| 97 | CATGCAGCTCACTGA | H302367 | 9 | 29 | 40 | 27 | 31 | L10376 | Human (clone CTG-B33) mRNA sequence. |
|  |  |  |  |  |  |  |  | S80520 | CAG-isl 7 {trinucleotide repeat-containing sequenc |
| 98 | CATGGTGTGTTTGTA | H769020 | 0 | 24 | 15 | 22 | 8 | M77349 | Human transforming growth factor-beta induced gene |
| 99 | CATGGTGCGCTGAGC | H760291 | 0 | 22 | 17 | 44 | 18 | X58536 | Human mRNA for HLA class I locus C heavy chain. |
| 100 | CATGGTTCACATTAG | H774461 | 3 | 22 | 25 | 141 | 10 | X00497 | Human mRNA for HLA-DR antigens associated invarian |
| 101 | CATGTGAAATAAAAC | H918273 | 2 | 18 | 37 | 8 | 22 | X16934 | Human hB23 gene for B23 nucleophosmin. |
| 102 | CATGAAAAGAAACTT | H2056 | 1 | 16 | 27 | 11 | 25 | Y00345 | Human mRNA for polyA binding protein. |
| 103 | CATGTGCTGCCTGTT | H948604 | 1 | 15 | 16 | 11 | 3 | X81005 | *H. sapiens* HCG IV mRNA. |
|  |  |  |  |  |  |  |  | D28137 | Human mRNA for BST-2, complete cds. |
|  |  |  |  |  |  |  |  | W46476 | Soares senescent fibroblasts NbHSF *Homo sapiens* cDNA clone 324128 3'. |
| 104 | CATGCTGATGGCAGA | H495251 | 0 | 14 | 15 | 8 | 6 |  |  |
|  |  |  |  |  |  |  |  | X72718 | *H. sapiens* DNA for orphan TCR V-beta segment (allel |
|  |  |  |  |  |  |  |  | H121311 | Soares fetal heart NbHH19W *Homo sapiens* cDNA clone 342926 3'. |
| 105 | CATGACTCGCTCTGT | H121311 | 0 | 12 | 16 | 5 | 7 |  |  |
|  |  |  |  |  |  |  |  | AA305589 | EST176663 Colon carcinoma (Caco-2) cell line II *Homo sapiens* cDNA 5' end |
| 106 | CATGGCCCAAGGACC | H610466 | 0 | 12 | 19 | 82 | 17 | X53416 | Human mRNA for actin-binding protein (filamin) (AB |
| 107 | CATGATCTTGTTACT | H229106 | 0 | 11 | 28 | 67 | 0 | X02761 | Human mRNA for fibronectin (FN precursor). |
| 108 | CATGAAGCTGCTGGA | H40571 | 0 | 10 | 17 | 6 | 6 | Z26305 | *H. sapiens* isoform 1 gene for L-type calcium channe |

NC: Normal Colon
TU: Colon Primary Tumor
CL: Colon Cancer Cell Line
PT: Pancreatic Primary Tumor
PC: Pancreatic Cancer Cell Line

TABLE 2

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 109 | CATGTGTGTTGAGAG | H978825 | 71 | 79 | 487 | 136 | 412 | X16869 | Human mRNA for elongation factor 1-alpha |
| 110 | CATGGCCGAGGAAGG | H615043 | 72 | 66 | 265 | 105 | 125 | X53505 | Human ribosomal protein S12. |
| 111 | CATGCAAACCATCCA | H263478 | 137 | 83 | 245 | 36 | 502 | X12883 | Human cytokeratin 18. |
| 112 | CATGCACAAACGGTA | H278636 | 63 | 53 | 201 | 74 | 179 | L19739 | Homo sapiens metallopanstimulin (MPS1) |
| 113 | CATGAAAAAAAAAAAA | H1 | 31 | 48 | 186 | 66 | 102 | X83412 | H.sapiens B1 mRNA for mucin. |
| | | | | | | | | Z32564 | H.sapiens FRGAMMA mRNA (819bp) for folate receptor |
| | | | | | | | | X76180 | H.sapiens mRNA for lung amiloride sensitive Na+ ch |
| | | | | | | | | U08470 | Human FR-gamma' mRNA, complete cds. |
| | | | | | | | | U08471 | Human folate receptor 3 mRNA, complete cds. |
| 114 | CATGTTGGTCCTCTG | H1027448 | 115 | 128 | 179 | 104 | 358 | S64930 | Human L41 ribosomal protein |
| 115 | CATGTCTCCATACCC | H906438 | 0 | 0 | 176 | 48 | 0 | T91925 | ye02f02.r1 Homo sapiens cDNA clone 116571 5'. |
| 116 | CATGAAGACAGTGGC | H33979 | 59 | 61 | 172 | 55 | 252 | X66699 | H.sapiens ribosomal protein L37a. |
| 117 | CATGCCGTCCAAGGG | H374027 | 50 | 39 | 138 | 60 | 108 | M60854 | Human ribosomal protein S16 |
| 118 | CATGGGGAAAATGC | H696375 | 90 | 90 | 136 | 293 | 231 | M92381 | Human thymosin beta 10 |
| 119 | CATGAAGGAGATGGG | H41531 | 30 | 37 | 133 | 38 | 161 | X69181 | H.sapiens mRNA for ribosomal protein L31. |
| 120 | CATGAGGGAGTTTC | H567488 | 38 | 53 | 112 | 65 | 142 | U14968 | Human ribosomal protein L27a |
| 121 | CATGGCGCTGGTTCCA | H424694 | 42 | 64 | 111 | 53 | 49 | X79234 | H.sapiens ribosomal protein L11. |
| 122 | CATGGCCGTGTCCGC | H618199 | 56 | 39 | 109 | 28 | 120 | J03537 | Human ribosomal protein S6 |
| 123 | CATGACCACACGAG | H549145 | 32 | 59 | 105 | 44 | 70 | U58682 | Human ribosomal protein 528 mRNA, complete cds |
| 124 | CATGTCACCCACACC | H857362 | 36 | 48 | 103 | 44 | 65 | X52839 | Human mRNA for ribosomal protein L17 |
| 125 | CATGCGCCGCGGCT | H416106 | 39 | 43 | 90 | 52 | 184 | U12465 | Human ribosomal protein L35 |
| 126 | CATGCTCAACATCTC | H475448 | 27 | 41 | 89 | 27 | 145 | M17885 | Human M2-type pyruvate kinase mRNA, complete cds. |
| 127 | CATGTTGGCCCCACCC | H955718 | 20 | 30 | 80 | 46 | 55 | M23725 | Human acidic ribosomal phosphoprotein P0 |
| | | | | | | | | M6252 | Human TCB gene encoding cytosolic thyroid hormone- |
| 128 | CATGCCCTGGGTTCT | H359102 | 34 | 49 | 78 | 92 | 145 | M11147 | Human ferritin L chain |
| 129 | CATGAGCATCTCCAG | H150997 | 0 | 0 | 77 | 0 | 0 | H09058 | y196f1.1.r1 Homo sapiens cDNA clone 45943 5'. |
| | | | | | | | | Z44640 | H. sapiens partial cDNA sequence; clone c-26b05. |
| | | | | | | | | N75111 | y29e01.r1 Homo sapiens cDNA clone 284472 5'. |
| 130 | CATGGCCTGTATGAG | H621369 | 24 | 32 | 77 | 33 | 99 | M31520 | Human ribosomal protein S24 mRNA. |
| 131 | CATGAGCTCTCCCTG | H161624 | 33 | 39 | 76 | 21 | 67 | X53777 | Human L23 mRNA for putative ribosomal protein. |
| 132 | CATGCCAGGAGGAAT | H338081 | 27 | 12 | 74 | 23 | 87 | AA223340 | gb|AA223340|AA23340 Homo sapiens cDNA clone 650651 3' similar to gb:Y00371_rna1 HEAT SHOCK COGNATE 71 KD PROTEIN (HUMAN) |
| 133 | CATGGGCAAGCCCCA | H672342 | 30 | 55 | 72 | 27 | 61 | U12404 | Human Csa-19 |
| 134 | CATGAGGAAAGCTGC | H163999 | 31 | 42 | 70 | 32 | 146 | F16378 | H.sapiens EST sequence (135-18) from skeletal muscle |
| 135 | CATGAACGCGGCCAA | H26261 | 29 | 46 | 69 | 54 | 79 | Z23063 | Homo sapiens macrophage migration inhibitory factor |
| 136 | CATGCCAGAACAGAC | H335945 | 23 | 39 | 66 | 42 | 148 | X79238 | H.sapiens ribosomal protein L30. |
| 137 | CATGGCCGCCATCTC | H615736 | 7 | 10 | 65 | 10 | 22 | U55017 | Human transketolase (TKT) |
| 138 | CATGGTGTTAACCAG | H769045 | 16 | 19 | 65 | 17 | 76 | L25899 | H.sapiens ribosomal protein L10 |
| 139 | CATGGCCTCGGAAAT | H383489 | 9 | 13 | 64 | 23 | 46 | Z26876 | H.sapiens ribosomal protein L38. |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 140 | CATGAGGTCCTAGCC | H177610 | 15 | 27 | 63 | 43 | 41 | X06547 | Human class Pi glutathione S-transferase |
| 141 | CATGGTTCCCTGGCC | H775658 | 31 | 26 | 63 | 32 | 96 | X65923 | H.sapiens fau mRNA. |
| 142 | CATGTAAGGAGCTGA | H796831 | 32 | 58 | 62 | 42 | 68 | X77770 | H.sapiens RPS26 |
| 143 | CATGAACTAAAAAAA | H28673 | 7 | 14 | 60 | 17 | 39 | W52460 | zc5411.r1 Soares senescent fibroblasts NbHSF Homo sapiens cDNA clone 309077 3'. |
| 144 | CATGATTTGTCCCAG | H260949 | 17 | 13 | 57 | 9 | 91 | N92893 | zb71h03.s1 Homo sapiens cDNA clone 309077 3'. |
| 145 | CATGATAATTCTTTG | H200576 | 13 | 27 | 53 | 30 | 69 | X14957 | Human hmg1 mRNA for high mobility group protein 1. |
| 146 | CATGCCCAGCCAGT | H348756 | 18 | 23 | 53 | 5 | 85 | U14973 | Human ribosomal protein S29 |
| 147 | CATGGGAGTGGACAT | H667269 | 15 | 13 | 49 | 13 | 45 | U14999 | Human XP1PO ribosomal protein S3 (rpS3) |
| 148 | CATGTAAAAAAAAAA | H786433 | 13 | 8 | 48 | 10 | 26 | L11566 | Homo sapiens ribosomal protein L18 (RPL18) |
| 149 | CATGGTGTTGCACAA | H769605 | 19 | 21 | 48 | 21 | 47 | H08238 | yl87a01.r1 Homo sapiens cDNA clone 44932 5'. |
| 150 | CATGGCCAGCCCAGC | H608595 | 6 | 21 | 47 | 11 | 15 | X79239 | H.sapiens ribosomal protein S13. |
| | | | | | | | | U31657 | Human unknown protein mRNA, partial cds. |
| | | | | | | | | H41030 | yn92a10.r1 Homo sapiens cDNA clone 175866 5'. |
| 151 | CATGGGCTCCCACTG | H685384 | 14 | 24 | 47 | 23 | 15 | M16660 | Human 90-kDa heat-shock protein |
| 152 | CATGTCAACTTCTGG | H853983 | 0 | 0 | 46 | 2 | 0 | N57419 | yw82e04.r1 Homo sapiens cDNA clone 258750 5' simil |
| 153 | CATGATGCTGCCAA | H583573 | 6 | 12 | 46 | 27 | 18 | X59357 | Human mRNA for Epstein-Barr virus small RNAs (EBER) |
| | | | | | | | | L21756 | Homo sapiens acute myeloid leukemia associated protein |
| | | | | | | | | D17652 | Human mRNA for HBpl5/L22, complete cds. |
| 154 | CATGAATAGGTCCAA | H51925 | 13 | 31 | 46 | 47 | 53 | M64716 | Human ribosomal protein S25 |
| 155 | CATGGCTTTTAAGGA | H655115 | 8 | 26 | 45 | 22 | 63 | L06498 | Homo sapiens ribosomal protein S20 (RPS20) |
| 156 | CATGAATGCAGGCAG | H58533 | 2 | 12 | 44 | 6 | 27 | M61831 | Human S-adenosylhomocysteine hydrolase (AHCY) |
| 157 | CATGCCCAGCTGGA | H610939 | 8 | 18 | 43 | 0 | 22 | Z21507 | Human elongation factor 1 delta (EF 1 delta) |
| 158 | CATGGCCGCGTTCG | H678334 | 6 | 6 | 42 | 0 | 18 | M13932 | Human ribosomal protein S17 mRNA |
| 159 | CATGTAGGGAATAA | H928269 | 14 | 26 | 42 | 15 | 42 | M10036 | Human triosephosphate isomerase |
| 160 | CATGTGTACCTGTAA | H968173 | 14 | 24 | 42 | 35 | 49 | K00558 | human alpha-tubulin |
| 161 | CATGGGCAAGAAGAA | H672265 | 8 | 7 | 41 | 12 | 87 | L19527 | Homo sapiens ribosomal protein L27 (RPL27) |
| 162 | CATGAACTAACAAAA | H28737 | 6 | 14 | 40 | 14 | 15 | X63237 | H.sapiens Uba80 mRNA for ubiquitin. |
| 163 | CATGTATACGCTCAG | H837237 | 0 | 0 | 38 | 0 | 9 | | Unknown |
| 164 | CATGTACAAGAGGAA | H803369 | 7 | 17 | 38 | 14 | 42 | X69391 | H.sapiens ribosomal protein L6. |
| 165 | CATGGTTAACGTCCC | H770486 | 8 | 17 | 38 | 12 | 25 | H11182 | ym14a02.r1 Homo sapiens cDNA clone 47866 5' |
| | | | | | | | | T40302 | ya31g04.r5 Homo sapiens cDNA clone 62262 5' |
| | | | | | | | | T89480 | yd98a05.r1 Homo sapiens cDNA clone 116240 5' |
| 166 | CATGGAGACTCCTGC | H558943 | 13 | 12 | 38 | 32 | 10 | H01362 | yi99c06.r1 Homo sapiens cDNA clone 147370 5' |
| 167 | CATGATCCACATCGC | H217399 | 3 | 10 | 37 | 10 | 14 | H94371 | yw54e05.r1 Homo sapiens cDNA clone 256064 5'. |
| | | | | | | | | T49412 | ya75b09.r1 Homo sapiens cDNA clone 67481 5'. |
| | | | | | | | | T51058 | yb55a12.r1 HomosapiensDNAclone 750705'. |
| 168 | CATGGAAGCTTTGCA | H534522 | 11 | 13 | 37 | 14 | 25 | X07270 | Human heat shock protein hsp86. |
| 169 | CATGCTGGCGAGCGC | H501287 | 2 | 9 | 36 | 3 | 18 | M91670 | Human ubiquitin carrier protein (E2-EPF) |
| 170 | CATGCTGAGACAAAG | H493633 | 13 | 8 | 36 | 8 | 26 | X74070 | H.sapiens transcription factor BTF 3. |
| 171 | CATGAACGACCTCGT | H24951 | 7 | 13 | 35 | 22 | 40 | V00599 | Human beta-tubulin |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 172 | CATGGCATAGGCTGC | H602783 | 9 | 16 | 35 | 2 | 17 | X84694 L38995 S75463 | *H.sapiens* mRNA for elongations factor Tu-mitochondria *Homo sapiens* nuclear-encoded mitochondrial elongatation factor P43 = mitochondrial elongation factor homolog [human |
| 173 | CATGCATCTTCACCA | H319302 | 12 | 14 | 35 | 9 | 16 | H48893 | yq80b12.r1 *Homo sapiens* cDNA clone 202079 5' |
| 174 | CATGCCTGCTGGGC | H621035 | 10 | 5 | 32 | 18 | 107 | X71973 | *H.sapiens* GPx-4 mRNA for phospholipid hydroperoxidase |
| 175 | CATGACAGGCTACGG | H76231 | 0 | 5 | 31 | 64 | 0 | M95787 | Human 22kDa smooth muscle protein (SM22) |
| 176 | CATGGAAATGTAAGA | H528067 | 5 | 12 | 31 | 14 | 25 | H80294 R74294 | yu59g01.s1 *Homo sapiens* cDNA clone 230448 3'. yi57f06.r1 *Homo sapiens* cDNA clone 143363 5' |
| 177 | CATGGAAGCCAGCCA | H533798 | 1 | 3 | 30 | 9 | 11 | L36055 | Human 4E-binding protein 1 |
| 178 | CATGTTACCATATCA | H988366 | 10 | 28 | 30 | 19 | 86 | F17005 | *H.sapiens* EST sequence (011-T1-18) from skeletal muscle |
| 179 | CATGTTGCTCACAAA | H1023249 | 1 | 2 | 29 | 1 | 2 | H10519 | y190g04.r1 *Homo sapiens* cDNA clone 45563 5'. |
| 180 | CATGTCCCGCTCGA | H874103 | 0 | 6 | 29 | 0 | 0 | | Unknown |
| 181 | CATGATTAACAAAGC | H246019 | 8 | 9 | 29 | 25 | 26 | X04409 | Human coupling protein G(s) alpha-subunit |
| 182 | CATGCAGATCTTTGT | H298495 | 2 | 7 | 28 | 8 | 24 | X56998 | Human UbA52 adrenal mRNA for ubiquitin-52 amino acid |
| 183 | CATGGTTCGTGCAA | H777109 | 9 | 28 | 28 | 17 | 46 | F19234 | *H.sapiens* EST sequence (005-X3-16) from skeletal m |
| 184 | CATGGACGTGTGGGC | H552683 | 3 | 4 | 27 | 2 | 16 | X52317 | Human histone H2A.Z. |
| 185 | CATGCTAAAAAAAAA | H458753 | 4 | 8 | 27 | 19 | 8 | M33680 | Human 26-kDa cell surface protein TAPA-1 |
| 186 | CATGGGGTTTTTATT | H704500 | 4 | 1 | 27 | 6 | 18 | L28809 | *Homo sapiens* dbpB-like protein |
| 187 | CATGCCGATCACCGG | H363799 | 7 | 9 | 27 | 7 | 15 | M29536 | Human translational initiation factor 2 beta subunit |
| 188 | CATGGCACAAGAAGA | H594051 | 6 | 9 | 26 | 7 | 29 | W07137 D20503 N91592 | za92a1 1.r1 Soares fetal lung NbHL19W *Homo sapiens* Human HL60 3'directed MboI cDNA, HUMGS01477, clone Soares fetal lung NbHL19W *Homo sapiens* cDNA clone 303055 3'. |
| | | | | | | | | H83884 | yx84c07.s1 *Homo sapiens* cDNA clone 249420 3' similar to contains Alu repetitive element;. |
| 189 | CATGTCTCTACCCAC | H908373 | 7 | 11 | 26 | 11 | 13 | Z22572 L09209 L19597 S60099 | *H.sapiens* CDEI binding protein mRNA. *Homo sapiens* amyloid protein homologue mRNA, compl Human binding protein mRNA, partial cds. APPH = amyloid precursor protein homolog [human, pla |
| 190 | CATGGTTTCCCAAG | H783697 | 1 | 0 | 25 | 3 | 0 | W07587 N28502 N35630 | zb06f02.r1 Soares fetal lung NbHL19W *Homo sapiens* yx36f06.r1 *Homo sapiens* cDNA clone 263843 5' yx62a03.r1 *Homo sapiens* cDNA clone 266284 5' |
| 191 | CATGCCTGTCCAGCC | H388426 | 2 | 3 | 25 | 3 | 13 | Z40265 W02723 N24893 N32178 | *H. sapiens* partial cDNA sequence; clone c-1xe03. zc65.o03.s1 Soares fetal heart NbHH19W *Homo sapiens* yx99h09.s1 *Homo sapiens* cDNA clone 269921 3'. yy25b09.s1 *Homo sapiens* cDNA clone 272249 3'. |
| 192 | CATGTCATCATCTGA | H865503 | 5 | 15 | 25 | 5 | 7 | H21873 H26394 H69857 H70714 | yl34b10.s1 *Homo sapiens* cDNA clone 160123 3' simil yl48e12.s1 *Homo sapiens* cDNA clone 161518 3' simil yr88d02.s1 *Homo sapiens* cDNA clone 212355 3' simil yu69b1#.s1 *Homo sapiens* cDNA clone 239037 3' simil |
| 193 | CATGCCCTGCCTTGT | H358783 | 5 | 8 | 25 | 16 | 31 | X55110 | Human mRNA for neurite outgrowth-promoting protein |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 194 | CATGGCCGGGCCCTC | H617048 | 1 | 1 | 24 | 0 | 1 | X03168 | Human mRNA for S-protein. |
| 195 | CATGTTGCTCAAAAA | H1023233 | 2 | 1 | 24 | 2 | 2 | AA143561 | zo32d09.s1 Stratagene colon (#937204) *Homo sapiens* cDNA clone 588593 3' similar to contains LTR7,t1 LTR7 repetitive element |
| | | | | | | | | AA152342 | z001g11.s1 Stratagene colon (#937204) *Homo sapiens* cDNA clone 566468 3' similar to contains LTR7,t3 LTR7 repetitive element; |
| | | | | | | | | AA115727 | z186h11.s1 Stratagene colon (#937204) *Homo sapiens* cDNA clone 511557 3' similar to contains LTR7,t1 LTR7 repetitive element |
| 196 | CATGCAAAATCAGGA | H262987 | 6 | 2 | 24 | 5 | 15 | R76502 | yi61f09.r1 *Homo sapiens* cDNA clone 143753 5'. |
| | | | | | | | | T32681 | EST52915 *Homo sapiens* cDNA clone 5' end similar to None. |
| | | | | | | | | T34662 | EST72468 *Homo sapiens* cDNA clone 5' end similar to None. |
| 197 | CATGGAAGATGTGGG | H533435 | 1 | 5 | 23 | 4 | 7 | H04634 | yj49h03.r1 *Homo sapiens* cDNA clone 152117 5'. |
| | | | | | | | | F00364 | *H. sapiens* partial cDNA sequence; clone 76D12; ver |
| 198 | CATGGTGCTCATTCA | H761150 | 0 | 8 | 23 | 6 | 4 | H01503 | yj21c05.s1 *Homo sapiens* cDNA clone 149384 3'. |
| | | | | | | | | H84813 | yv86c02.s1 *Homo sapiens* cDNA clone 249602 3' simil |
| | | | | | | | | H84956 | yy88f07.s1 *Homo sapiens* cDNA clone 249829 3' simil |
| 199 | CATGGCTTTACTTTG | H654464 | 4 | 5 | 23 | 9 | 5 | L38961 | *Homo sapiens* putative transmembrane protein (B5) |
| 200 | CATGTTTTCTGAAAA | H1046401 | 6 | 13 | 23 | 10 | 10 | J04026 | Human thioredoxin (TXN) mRNA |
| 201 | CATGTTGCTCACACA | H1023250 | 1 | 4 | 22 | 0 | 4 | D11078 | Human RGH2 gene. |
| 202 | CATGGATTTCTCAGC | H589267 | 0 | 0 | 22 | 0 | 19 | X53279 | Human mRNA for placental-like alkaline phosphatase |
| 203 | CATGAGGAGGGAGGC | H166539 | 2 | 3 | 22 | 2 | 4 | M77836 | Human pyrroline 5-carboxylate reductase mRNA, |
| 204 | CATGGCTTAACCTGG | H651359 | 3 | 4 | 22 | 2 | 4 | X07674 | Human glutamate dehydrogenase |
| 205 | CATGCTCTTCGAGAA | H490889 | 4 | 8 | 22 | 27 | 19 | Y00433 | Human mRNA for glutathione peroxidase |
| 206 | CATGAGAACAAAACC | H132098 | 1 | 7 | 21 | 9 | 6 | X67951 | *H.sapiens* mRNA for proliferation-associated gene |
| 207 | CATGCCCAGGGAGAA | H346761 | 3 | 3 | 21 | 2 | 24 | U38846 | Human stimulator of TAR RNA binding (SRB) |
| 208 | CATGCACTTCAAGGG | H294155 | 0 | 3 | 20 | 47 | 107 | D16933 | Human HepG2 3' region cDNA, clone hmd4f1 1. |
| 209 | CATGGCCGAGAGAGG | H631331 | 2 | 2 | 20 | 4 | 1 | U42376 | Human retinoic acid induced RIG-E |
| 210 | CATGTTACCTCCTTC | H989024 | 4 | 7 | 20 | 3 | 22 | | Unknown |
| 211 | CATGACTCTGCCAAG | H122449 | 4 | 7 | 20 | 3 | 7 | F17524 | *H.sapiens* EST sequence (012-T2-32) from skeletal m |
| 212 | CATGTCAGATGCGT | H861095 | 1 | 6 | 19 | 12 | 7 | | Unknown |
| 213 | CATGGGCCTTTTTTT | H679936 | 3 | 3 | 19 | 5 | 7 | W52942 | zc03h05.r1 Soares parathyroid tumor NbHPA Homo sap |
| 214 | CATGTGGACGCGCTG | H951912 | 0 | 5 | 19 | 0 | 3 | R21316 | yg48h11.r1 *Homo sapiens* cDNA clone 35917 5' simila |
| 215 | CATGCCTGCTCCCTG | H386904 | 0 | 5 | 19 | 6 | 0 | X00566 | Human lipoprotein apoAI |
| 216 | CATGGCCACACCCCA(C) | H607318 | 2 | 6 | 18 | 18 | 5 | M80244 | Human E16 mRNA |
| 217 | CATGATTATTTTTCT | H249854 | 0 | 3 | 18 | 5 | 15 | H27927 | y158c11.s1 *Homo sapiens* cDNA clone 162452 3' simil |
| 218 | CATGAACCCTGGGA | H529899 | 2 | 7 | 18 | 5 | 20 | X57959 | *H.sapiens* ribosomal protein L7. |
| | | | | | | | 15 | AA299898 | EST12509 Uterus tumor I *Homo sapiens* cDNA 5' end |
| 219 | CATGGGCTGATGTGG | H686319 | 3 | 5 | 18 | 8 | 17 | U09510 | Human glycyl-tRNA synthetase. |
| 220 | CATGTCAATAAAGAA | H855049 | 3 | 10 | 18 | 4 | 4 | X76013 | *H.sapiens* QRSHs mRNA for glutaminyl-tRNA synthetas |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 221 | CATGAAAAGTGAAGAT | H11785 | 0 | 7 | 17 | 0 | 5 | W16529 | zb10a11.r1 Soares fetal lung NbHL19W *Homo sapiens* |
| | | | | | | | | W35192 | zc70b05.r1 Soares fetal heart NbHH19W *Homo sapiens* |
| | | | | | | | | W52451 | zc45d09.r1 Soares senescent fibroblasts NbHSF Homo |
| 222 | CATGCACGCGCTCAA | H288373 | 0 | 1 | 17 | 0 | 3 | D38251 | Human mRNA for RPBS (XAP4) |
| 223 | CATGAACTAATACTA | H28872 | 1 | 6 | 17 | 13 | 31 | D52570 | Human fetal brain cDNA 5′-end GEN-081G12. |
| | | | | | | | | D52758 | Human fetal brain cDNA 5′-end GEN-087A08. |
| | | | | | | | | D55953 | Human fetal brain cDNA 5′-end GEN407H12. |
| 224 | CATGCTGTACCTGGA | H504187 | 1 | 0 | 17 | 12 | 6 | M22490 | Human bone morphogenetic protein-2B (BMP-2B) |
| 225 | CATGCGACCCCACGC | H398663 | 2 | 6 | 17 | 48 | 0 | M12529 | Human apolipoprotein E |
| 226 | CATGTAGAAAAATAA | H819213 | 0 | 1 | 16 | 2 | 7 | X16539 | *H.sapiens* RNA for neuroleukin gene. |
| | | | | | | | | M27691 | Human transactivator protein (CREB) mRNA, complete |
| 227 | CATGATCTTGAAAGG | H228867 | 0 | 0 | 16 | 5 | 3 | M86667 | *H.sapiens* NAP (nucleosome assembly protein) |
| 228 | CATGCAGCTGGCCAT | H302741 | 0 | 1 | 16 | 14 | 0 | X53743 | *H.sapiens* mRNA for fibulin-1 C. |
| 229 | CATGATCTTGAAAGG | H228867 | 0 | 0 | 16 | 5 | 3 | Z26328 | *H. sapiens* partial cDNA sequence; clone HEC59 |
| 230 | CATGATCTTGAAAGG | H228867 | 0 | 0 | 16 | 5 | 3 | Z26328 | *H. sapiens* partial cDNA sequence; clone HEC059 |
| 231 | CATGGTTGGAGGTGCG | H762554 | 2 | 10 | 16 | 3 | 5 | U22055 | Human 100 kDa coactivator mRNA |
| 232 | CATGGTTGGACCCCAA | H762197 | 1 | 5 | 15 | 7 | 10 | R91724 | yp98e02.r1 *Homo sapiens* cDNA clone 195482 5′ simil |
| | | | | | | | | W51770 | zc48a02.r1 Soares senescent fibroblasts NbHSF Homo |
| | | | | | | | | N42086 | yy05b03.r1 *Homo sapiens* cDNA clone 270317 5′ |
| 233 | CATGGAGCAGCTGGA | H561787 | 0 | 5 | 15 | 2 | 4 | R80990 | yi94c02.r1 *Homo sapiens* cDNA clone 146882 5′ |
| | | | | | | | | R95056 | yq44f01.r1 *Homo sapiens* cDNA clone 198649 5′ simil |
| 234 | CATGCGGGAGGGCT | H663002 | 1 | 6 | 15 | 8 | 7 | F16507 | *H.sapiens* EST sequence (147-09) from skeletal musc |
| | | | | | | | | T50201 | yb77h05.r1 *Homo sapiens* cDNA clone 77241 5′ simila |
| 235 | CATGATTGGCTTAAA | H256497 | 1 | 8 | 15 | 0 | 16 | S85655 | Human prohibitin |
| 236 | CATGAAAAATTTAA | H524541 | 0 | 3 | 15 | 4 | 0 | M38188 | Human unknown protein from clone pHGR74 mRNA, comp |
| 237 | CATGGATCACAGTTT | H577840 | 0 | 5 | 15 | 5 | 0 | Y00711 | Human lactate dehydrogenase B (LDH-B). |
| 238 | CATGAGCCTTTGTTG | H155632 | 1 | 2 | 15 | 23 | 5 | D83174 | Human collagen binding protein 2. |
| 239 | CATGTCTGCACCTCC | H910430 | 1 | 0 | 15 | 0 | 2 | X70940 | *H.sapiens* elongation factor 1 alpha-2. |
| 240 | CATGAACAGAAGCAA | H18469 | 0 | 2 | 15 | 3 | 11 | T30623 | EST19638 *Homo sapiens* cDNA 5′ end similar to None. |
| | | | | | | | | C01011 | HUMGS0004747, Human Gene Signature, 3′-directed cDNA sequence. |
| | | | | | | | | AA111865 | zm62d06.s1 Stratagene fibroblast (#937212) *Homo sapiens* cDNA clone 530219 3′ |
| 241 | CATGTGTTCAGGACC | H980130 | 1 | 1 | 14 | 5 | 11 | W56516 | zd16c08.r1 Soares fetal heart NbHH19W *Homo sapiens* |
| | | | | | | | | H30299 | yo77d04.r1 *Homo sapiens* cDNA clone 183943 5′ simil |
| | | | | | | | | H50265 | yo28c02.r1 *Homo sapiens* cDNA clone 179234 5. |
| 242 | CATGTAGAATAATGGC | H822331 | 1 | 4 | 14 | 6 | 14 | W01702 | za37a06.r1 Soares fetal liver spleen 1NFLS Homo sa |
| | | | | | | | | W04495 | za58b10.r1 Soares fetal liver spleen 1NFLS Homo sa |
| | | | | | | | | W23528 | zc71g11.s1 Soares fetal heart NbHH19W *Homo sapiens* |
| 243 | CATGCTTAATCCTGA | H508767 | 0 | 6 | 14 | 6 | 12 | D11838 | Human HepG2 3′-directed MboI cDNA, clone hm02e09. |
| 244 | CATGGGCAGGAGGACC | H673954 | 0 | 6 | 14 | 5 | 11 | X75598 | *H.sapiens* nm23H1 gene. |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 245 | CATGTTGACTGAAGCC | H925194 | 0 | 5 | 14 | 3 | 0 | T35470<br>T35536<br>T35545 | EST85850 *Homo sapiens* cDNA 5′ end similar to None.<br>EST86951 *Homo sapiens* cDNA 5′ end similar to None.<br>EST87066 *Homo sapiens* cDNA 5′ end similar to None. |
| 246 | CATGGATAGTTGTGG | H576495 | 0 | 1 | 14 | 2 | 1 | H01694<br>N78851<br>N78931 | yj33g11.s1 *Homo sapiens* cDNA clone 150596 3′.<br>zb17d08.s1 *Homo sapiens* cDNA clone 302319 3′.<br>za92h06.s1 *Homo sapiens* cDNA clone 300059 3′. |
| 247 | CATGGTTGGTGGACAC | H765573 | 1 | 4 | 13 | 6 | 13 | H90469<br>R76765<br>T35045 | yo01e06.r1 *Homo sapiens* cDNA clone 241474 5′ simil<br>yi63g01.r1 *Homo sapiens* cDNA clone 143952 5′ simil<br>EST79335 *Homo sapiens* cDNA similar to None. |
| 248 | CATGTGGGTACCTT | H961304 | 0 | 6 | 13 | 2 | 9 | H51447<br>W46469<br>W51800<br>R33196 | yo31a05.r1 *Homo sapiens* cDNA clone 179504 5′.<br>zc32c05.r1 Soares senescent fibroblasts NbHSF Homo<br>zc48e04.r1 Soares senescent fibroblasts NbHSF Homo<br>yh77f08.r1 *Homo sapiens* cDNA clone 135783 5′. |
| 249 | CATGTTCATTATAAT | H1003313 | 1 | 10 | 13 | 8 | 10 | J04799 | Human prothymosin-alpha |
| 250 | CATGCTTCTGTGTAC(T) | H515821 | 0 | 5 | 13 | 8 | 12 | D80012 | Human KIAA0190 protein |
| 251 | CATGACTGGCGAAGT | H125315 | 1 | 5 | 13 | 2 | 5 | U02389 | Human hLON ATP-dependent protease mRNA |
| 252 | CATGGAAAGAGCTGA | H526495 | 1 | 3 | 13 | 1 | 6 | T29819 | EST96617 *Homo sapiens* cDNA 5′ end similar to ATP-d |
| 253 | CATGCAAACTCTATGG | H269775 | 0 | 1 | 13 | 1 | 5 | X14850 | Human histone H2A.X. |
| 254 | CATGAAATTTGGTGC | H16303 | 0 | 0 | 13 | 0 | 2 | J04088 | Human DNA topoisomerase II (top2) mRNA |
| | | | | | | | | K01891 | Human beta globin retrovirus-like repetitive element |
| | | | | | | | | H88396 | EST28e05 *Homo sapiens* cDNA clone 28e05 |
| 255 | CATGCTGCACTTACT | H496114 | 1 | 2 | 13 | 1 | 8 | X74796 | *H.sapiens* p85Mcm mRNA. |
| | | | | | | | | D28480 | Human mRNA for hMCM2, complete cds. |
| | | | | | | | | D55716 | Human B lymphoma mRNA for P1cdc47, complete cds. |
| 256 | CATGAATATTGAGAA | H53129 | 0 | 5 | 13 | 6 | 11 | T30327<br>T34394<br>T47475<br>T50289 | EST14849 *Homo sapiens* cDNA 5′ end similar to None.<br>EST66942 *Homo sapiens* cDNA 5′ end similar to None.<br>yb14c03.r1 *Homo sapiens* CDNA clone 71140 5′.<br>yb14h08.r1 *Homo sapiens* cDNA clone 71199 5′. |
| 257 | CATGTCGCCGGGCGC | H890535 | 0 | 1 | 13 | 2 | 1 | | Unknown |
| 258 | CATGGGGCAGCCG | H697495 | 0 | 2 | 13 | 2 | 7 | | Unknown |
| 259 | CATGCCAAGAAAGAA | H329737 | 0 | 6 | 12 | 4 | 4 | H59914 | Human inducible poly(A)-binding protein |
| 260 | CATGTTTTTGATAAA | H1048113 | 0 | 5 | 12 | 4 | 12 | U33818 | Human HepG2 3′ region cDNA, clone hmd2c11. |
| 261 | CATGTGTGGAGAGCC | H977034 | 0 | 0 | 12 | 0 | 0 | D16891 | Human apolipoprotein A-II |
| 262 | CATGCCCACGGTTAG | H345789 | 0 | 5 | 12 | 5 | 4 | M29882 | *H.sapiens* mitoxantrone-resistance associated mRNA. |
| 263 | CATGAATTCTCCTAA | H63325 | 0 | 1 | 12 | 1 | 1 | Z49216 | Unknown |
| 264 | CATGACCTCCGGGC | H548203 | 0 | 0 | 12 | 0 | 0 | | Unknown |
| 265 | CATGTGAATCTGGGT | H921067 | 0 | 2 | 11 | 0 | 8 | M93651 | Human set gene |
| 266 | CATGTCCTTCTCCAC | H884181 | 0 | 5 | 11 | 7 | 8 | X15804 | Human alpha-actinin. |
| 267 | CATGTATCTGTCTAC | H843485 | 0 | 4 | 11 | 14 | 3 | T19569 | 609F *Homo sapiens* cDNA clone 609 similar to SET protein |
| 268 | CATGACGTTCTCTTC | H114144 | 0 | 0 | 11 | 2 | 17 | Z36249 | HHEA18W *H. sapiens* partial cDNA sequence; clone HEA18W; |

TABLE 2-continued

Transcripts increased in colon cancer
Transcripts increased in only colon cancer
cell lines compared to normal colon (182 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 269 | CATGCCCTGAGTCAG | H358581 | 0 | 0 | 11 | 0 | 0 | AA207189 | zq73e07.r1 Stratagene neuroepithelium (#937231) *Homo sapiens* cDNA clone 647268 5' similar to TR:E16910 E16910 ENDONUCLEASE.; |
| 270 | CATGGAATTCCTCGA | H540023 | 0 | 3 | 11 | 3 | 1 | N80776 AA02580 AA279492 | za98h04.s1 *Homo sapiens* cDNA clone 300631 3' ze90d01.s1 Soares fetal heart NbHH19W *Homo sapiens* cDNA clone 366241 3' zs85h05.s1 Soares NbHTGBC *Homo sapiens* cDNA clone 704313 3' |
| 271 | CATGGACGCCGAACT | H550274 | 0 | 1 | 11 | 6 | 0 | | Unknown |
| 272 | CATGGGCGGACTGGGG | H631275 | 0 | 0 | 11 | 1 | 0 | AA098867 | zk84f04.s1 Soares pregnant uterus NbHPU *Homo sapiens* cDNA clone 489535 3' similar to SW:A5_XENLA P28824 A5 PROTEIN PRECURSOR; |
| 273 | CATGGGAACACACAG | H656453 | 0 | 1 | 11 | 0 | 2 | R48460 AA173819 | yj67c12.r1 *Homo sapiens* cDNA clone 153814 5' zp01c02.r1 Stratagene ovarian cancer (#937219) *Homo sapiens* cDNA clones 595106 5' |
| 274 | CATGTTGCGGAGCCC | H1022502 | 0 | 2 | 11 | 2 | 1 | L19183 | HUMMAC30X Human MAC30 mRNA, 3' end. |
| 275 | CATGGCAGACATTGA | H598335 | 0 | 7 | 10 | 4 | 9 | H41078 | yr24a07.s1 *Homo sapiens* cDNA clone 191060 3' simil |
| 276 | CATGCACTTGAAAA | H294401 | 0 | 1 | 10 | 5 | 0 | H04630 | yj49g03.r1 *Homo sapiens* cDNA clone 1521 16 5' |
| 277 | CATGGGTTGGCAGG | H719435 | 0 | 0 | 10 | 24 | 0 | R77027 | yi66e12.r1 *Homo sapiens* cDNA clone 144238 5' |
| 278 | CATGTTCCTCGGGC | H1007018 | 0 | 1 | 10 | 4 | 12 | R32331 | yh68g02.s1 *Homo sapiens* cDNA clone 134930 3' simil |
| 279 | CATGCTGCCGAGCT | -497192 | 0 | 8 | 10 | 1 | 10 | T86566 | yd77g07.r1 *Homo sapiens* cDNA clone 114300 5' simil |
| 280 | CATGGTGAAAAAA | H753665 | 0 | 2 | 10 | 3 | 7 | S77357 | transcript ch111 [human, RF1,RF48 stomach cancer c |
| 281 | CATGCTGTGCAGCA | H506149 | 0 | 6 | 10 | 6 | 1 | M34338 | Human spermidine synthase |
| 282 | CATGTAGTTTGTGG | -835515 | 0 | 1 | 10 | 0 | 2 | U03911 | Human mutator gene (hMSH2) |
| 283 | CATGTATGTAGTAGTG | H242380 | 0 | 5 | 10 | 9 | 7 | D55671 | Human heterogeneous nuclear ribonucleoprotein |
| 284 | CATGGACCCACTACC | H545906 | 0 | 1 | 10 | 3 | 1 | J03569 | Human lymphocyte activation antigen 4F2 large subunit |
| 285 | CATGAAATAGGTTTT | H12992 | 0 | 1 | 10 | 6 | 3 | D53402 | Human fetal brain cDNA 5'-end GEN-108D03. |
| | | | | | | | | T61971 | yb96f02.r1 *Homo sapiens* cDNA clone 79035 5' |
| | | | | | | | | D61243 | Human fetal brain cDNA 5'-end GEN-171G06. |
| | | | | | | | | N77240 | yv44d02.r1 *Homo sapiens* cDNA clone 245571 5' |
| 286 | CATGCCGGGCGTGGT | H371131 | 0 | 0 | 10 | 1 | 2 | T35761 | EST90898 *Homo sapiens* cDNA 5' end similar to EST c |
| 287 | CATGGACTGAGCTTG | H555168 | 0 | 8 | 10 | 3 | 3 | T31901 | EST40719 *Homo sapiens* cDNA 5' end similar to None. |
| 288 | CATGAAACGCCCAAT | H6481 | 0 | 2 | 10 | 1 | 3 | X98264 | HSMPP4I H.sapiens mRNA for M-phase phosphoprotein, mpp4, 1523bp |
| 289 | CATGATGAGGCGGG | H223027 | 0 | 4 | 10 | 7 | 1 | | Unknown |
| 290 | CATGGCCCACATCCG(A) | H610614 | 0 | 9 | 10 | 6 | 2 | D87433 | Human mRNA for KIAA0246 gene, partial cds |

TABLE 3

Transcripts decreased in colon cancer
Transcripts decreased in only colon primary tumors
compared to normal colon (51 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag sequence | Tag_Number | NC | CT | CL | PT | PC | Accession | Gene Name |
|---|---|---|---|---|---|---|---|---|---|
| 291 | CATGGCTTTATTTGT | H654591 | 184 | 110 | 185 | 203 | 111 | X00351 | Human mRNA for beta-actin. |
| 292 | CATGCTAGCCTCACG | H468434 | 170 | 61 | 130 | 80 | 75 | X04098 | Human mRNA for cytoskeletal gamma-actin. |
| 293 | CATGCAAACCATCCA | H263478 | 137 | 83 | 245 | 36 | 502 | X12883 | Human mRNA for cytokeratin 18. |
| 294 | CATGCTTCCAGCTAA | H513181 | 64 | 23 | 36 | 53 | 104 | D00017 | Human lipocortin II mRNA. |
| 295 | CATGCCCAGTTGCT | H348922 | 61 | 27 | 38 | 37 | 46 | X04106 | Human mRNA for calcium dependent protease (small subunit) |
| 296 | CATGGATGAACCCCC | H581974 | 53 | 4 | 42 | 6 | 32 | Z65513 | H.sapiens CpG island DNA genomic Mse1 fragment, c1 |
| 297 | CATGCTGTACAGACA | H504098 | 50 | 22 | 26 | 6 | 32 | W61077 | zd30d02.r1 Soares fetal heart NbHH19W Homo sapiens |
| 298 | CATGCGGACTCACTG | H427848 | 47 | 15 | 26 | 18 | 4 | D60944 | Human fetal brain cDNA 5'-end GEN-141D02. |
| 299 | CATGCCCCGCGGAA | H349801 | 47 | 10 | 21 | 15 | 8 | — | Unknown |
| 300 | CATGCCTGGAAGAGG | H387107 | 46 | 19 | 39 | 47 | 14 | J02783 | Human thyroid hormone binding protein (p55) mRNA, |
| 301 | CATGGCCTGGCCATC | H621140 | 46 | 19 | 24 | 16 | 20 | N33042 | yy05d05.s1 Homo sapiens cDNA clone 270345 3' |
| 302 | CATGAGCAGGAGCAG | H150053 | 43 | 12 | 26 | 24 | 20 | W07627 | zb06a05.r1 Soares fetal lung NbHL19W Homo sapiens |
| 303 | CATGAACGTGCAGGG | H28235 | 42 | 6 | 57 | 2 | 10 | X01630 | Human mRNA for argininosuccinate synthetase. |
| 304 | CATGCCGCCCTGCA | H615802 | 40 | 12 | 16 | 17 | 8 | D43682 | Human mRNA for very-long-chain acyl-CoA dehydrogen |
| 305 | CATGGTGGGGAGAGGA | H960651 | 40 | 5 | 36 | 10 | 5 | D29146 | Human keratinocyte cDNA, clone 173. |
| 306 | CATGGCTGCCCTTGA | H648575 | 38 | 10 | 20 | 6 | 39 | K00557 | human alpha-tubulin mRNA, 3' end. |
| 307 | CATGTGGCCATCTGC | H955615 | 37 | 5 | 15 | 19 | 18 | AA341633 | AA341633 EST47188 Fetal kidney II Homo sapiens cDNA 5' end |
| 308 | CATGCGTTCCTGCGG | H456167 | 35 | 4 | 36 | 8 | 0 | X77956 | H.sapiens Id1 mRNA. |
| 309 | CATGTGCATCTGGTG | H937452 | 33 | 9 | 14 | 13 | 10 | X87949 | H.sapiens mRNA for BiP protein. |
| 310 | CATGGTGACCTCCTT | H755160 | 33 | 7 | 12 | 6 | 31 | J04823 | Human cytochrome c oxidase subunit VIII (COX8) mRNA |
| 311 | CATGTAGCTCTATGG | H826831 | 33 | 5 | 18 | 9 | 13 | U16798 | Human Na,K-ATPase alpha-1 subunit mRNA, complete c |
| 312 | CATGGTGCGCTAGGG | H760267 | 29 | 7 | 26 | 19 | 27 | R50350 | gb\|R50350\|R50350 yj59c04.s1 Homo sapiens cDNA clone 153030 3'. yj59c04.r1 Homo sapiens cDNA clone 153030 5'. |
| | | | | | | | | R50013 | |
| | | | | | | | | C02981 | Human Heart cDNA, clone 3NHC0642. |
| 313 | CATGGGGCGCTGTGG | H694767 | 28 | 6 | 20 | 6 | 26 | T31329 | EST30445 Homo sapiens cDNA 5' end similar to ubiquinol cytochrome-c reductase, 6.4 kDa. |
| 314 | CATGCCTCCAGTAC | H382130 | 27 | 6 | 12 | 3 | 19 | — | Unknown |
| 315 | CATGCCTGTGACAGC | H388627 | 27 | 3 | 14 | 8 | 7 | H63643 | yr34d11.r1 Homo sapiens cDNA clone 207189 5' simil |
| 316 | CATGTCACAGTGCCT | H856806 | 24 | 5 | 8 | 17 | 11 | W60924 | zd27c08.r1 Soares fetal heart NbHH19W Homo sapiens |
| 317 | CATGAATAAAGGCTA | H49320 | 23 | 5 | 7 | 11 | 13 | L25081 | Human GTPase (rhoC) mRNA, complete cds. |
| 318 | CATGTTGTTGTTGAA | H1031929 | 23 | 5 | 13 | 15 | 25 | D45887 | Human mRNA for calmodulin, complete cds |
| 319 | CATGAAGGTAGCAGA | H44179 | 23 | 4 | 10 | 16 | 12 | N62815 | yy6b11.s1 Homo sapiens cDNA clone 278493 3'. |
| 320 | CATGGTGTTGGGGGT | H769707 | 21 | 2 | 5 | 14 | 10 | R68653 | yi14506.s1 Homo sapiens cDNA clone 139187 3'. |
| 321 | CATGTGCAGCGCCTG | H936344 | 21 | 1 | 5 | 7 | 13 | X90858 | H.sapiens mRNA for uridine phosphorylase. |
| 322 | CATGATGGCACGGAG | H238697 | 20 | 2 | 4 | 6 | 3 | H19458 | yn54c02.s1 Homo sapiens cDNA clone 172226 3' simil |
| 323 | CATGCCAGACACCC | H608326 | 20 | 1 | 6 | 1 | 9 | T30468 | EST17149 Homo sapiens cDNA 5' end similar to None. |
| 324 | CATGCTTCTTGCCCC | H515990 | 20 | 0 | 17 | 3 | 0 | V00491 | Human gene for alpha 1 globin. |
| 325 | CATGACCCACGTCAG | H86453 | 19 | 2 | 7 | 22 | 9 | X51345 | Human jun-B mRNA for JUN-B protein. |

TABLE 3-continued

Transcripts decreased in colon cancer
Transcripts decreased in only colon primary tumors
compared to normal colon (51 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag sequence | Tag_Number | NC | CT | CL | PT | PC | Accession | Gene Name |
|---|---|---|---|---|---|---|---|---|---|
| 326 | CATGGGCTGCCTGCC | H686458 | 18 | 3 | 4 | 5 | 8 | R72429 R48449 R52128 | yj90e08.s1 *Homo sapiens* cDNA clone 156038 3'. yj67b10.s1 *Homo sapiens* cDNA clone 153787 3'. yj72b03.s1 *Homo sapiens* cDNA clone 154253 3'. |
| 327 | CATGAGGGCCGGTG | H567660 | 18 | 2 | 14 | 6 | 16 | X12910 | Human Na+,K+ ATPase gene exons 1–3 (alpha III is |
| 328 | CATGATGAATCCGG | H581847 | 17 | 1 | 3 | 2 | 2 | | Unknown |
| 329 | CATGAGCCCGACCAC | H153109 | 16 | 2 | 11 | 7 | 5 | X81006 | *H.sapiens* HCG I mRNA. |
| 330 | CATGGTTCAGCTGTC | H774780 | 16 | 2 | 12 | 3 | 12 | L08666 | *Homo sapiens* porin (por) mRNA, complete cds and tr |
| 331 | CATGCCTCGCTCAGT | H383443 | 16 | 1 | 8 | 6 | 7 | U04627 | Human 78 kDa gastrin-binding protein mRNA, complet |
| 332 | CATGCAAATAAAAGT | H265219 | 15 | 1 | 8 | 9 | 0 | U17077 | Human BENE mRNA, partial cds. |
| 333 | CATGTGCCGCCCGCA | H940378 | 15 | 1 | 8 | 0 | 3 | U28369 | Human semaphorin V mRNA, complete cds. |
| 334 | CATGGCAGTGGCCTC | H601752 | 15 | 0 | 6 | 4 | 3 | D12038 | Human HepG2 3'-directed MboI cDNA, clone s150. |
| 335 | CATGCTGGGCCTGAA | H502137 | 14 | 0 | 3 | 3 | 18 | U77396 | Human TNF-alpha inducible responsive element mRNA, |
| 336 | CATGCCCATTGGAG | H611305 | 13 | 1 | 6 | 13 | 17 | Z29093 | *H.sapiens* EDDR1 gene for receptor tyrosine kinase. |
| 337 | CATGAAGAAAACCTC | H32792 | 12 | 0 | 2 | 2 | 0 | T94990 N69310 N98502 | ye38a04.s1 *Homo sapiens* cDNA clone 119982 3'. za25g05.s1 *Homo sapiens* cDNA clone 293624 3'. zb86e03.s1 Soares senescent fibroblasts NbHSF *Homo sapiens* cDNA clone 310492 3' |
| 338 | CATGAATGATTTCT | H538878 | 12 | 0 | 6 | 6 | 14 | F18838 | *H.sapiens* EST sequence (007-X1-01) from skeletal m |
| 339 | CATGGCCTGGTCCTT | H621272 | 12 | 0 | 3 | 3 | 8 | AA226928 | z21b10.s1 Stratagene NT2 neuronal precursor 937240 *Homo sapiens* cDNA clone 664027 3' |
| 340 | CCATGGCCCACACAG | H610579 | 11 | 0 | 1 | 1 | 0 | M60047 | Human heparin binding protein (HBp17) mRNA |
| 341 | CATGGATTCCAGTT | H671052 | 11 | 0 | 4 | 3 | 2 | W52456 | zc45e09.r1 Soares senescent fibroblasts NbHSF Homo |

TABLE 3

Transcripts decreased in colon cancer

Transcripts decreased in both colon primary tumors and colon cancer cell lines compared to normal colon (130 genes)

NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 342 | CATGCCTCCAGCTAC | H382109 | 803 | 191 | 304 | 136 | 663 | X12882 | Human mRNA for cytokeratin 8. |
| 343 | CATGCTAAGACTTCA | H460926 | 708 | 282 | 402 | 142 | 497 | F15636 | H.sapiens mitochondrial EST sequence (002T15) |
| 344 | CATGCCCAGGTCAC | H610997 | 705 | 58 | 2 | 2 | 1 | | Unknown |
| 345 | CATGACCCTTGGCCA | H90022 | 512 | 348 | 93 | 43 | 235 | F16940 | H.sapiens mitochondrial EST sequence (009-T1-21) f |
| 346 | CATGACATTGGGTGA | H81583 | 504 | 92 | 4 | 0 | 0 | M10050 | Human liver fatty acid binding protein (FABP) mRNA |
| 347 | CATGGCGAAACCCTG | H622680 | 486 | 108 | 27 | 30 | 13 | S61953 | c-erbB3 = receptor tyrosine kinase {alternatively sp |
| 348 | CATGAGCCCTACAAA | H153361 | 367 | 242 | 132 | 71 | 204 | F15506 | H.sapiens mitochondrial EST sequence (1-t-02) from |
| 349 | CATGGACCCAAGATA | H545828 | 276 | 131 | 0 | 7 | 0 | T39321 | ya04c01.r2 Homo sapiens cDNA clone 60480 5'. |
| | | | | | | | | H24673 | yl41a01.s1 Homo sapiens cDNA clone 160776 3'; |
| | | | | | | | | D25586 | HUMGS02706 Human colon 3'directed MboI cDNA, HUMGS02706, clone cm1673. |
| 350 | CATGGCCGGGTGGGC | H617195 | 256 | 88 | 148 | 144 | 178 | T96160 | ye09b02.s1 Homo sapiens cDNA clone 117195 3'. |
| 351 | CATGTTGGGGTTTCC | H1026814 | 202 | 75 | 84 | 235 | 369 | X64364 | H.sapiens mRNA for M6 antigen. |
| 352 | CATGCTCCACCGAA (or G) | H479577 | 201 | 120 | 0 | 11 | 3 | M11146 | Human ferritin H chain mRNA, complete cds. |
| 353 | CATGGCAGGGGCCTCA | H600670 | 196 | 68 | 6 | 32 | 19 | L15203 | Human secretory protein (P1.B) mRNA, complete cds. |
| 354 | CATGATCGTGGCGGG | H224923 | 194 | 24 | 97 | 40 | 39 | X93036 | H.sapiens mRNA for MAT8 protein. |
| | | | | | | | | H93844 | yv07h09.r1 Homo sapiens cDNA clone 242081 5' similar to SP:A39484 A39484 ANDROGEN-WITHDRAWAL APOPTOSIS PROTEIN RVP1, |
| 355 | CATGCAAGCATCCCC | H271574 | 190 | 99 | 101 | 30 | 139 | F17001 | H.sapiens mitochondrial EST sequence (011-T1-13)f |
| 356 | CATGGACATCAAGTC | H544012 | 189 | 33 | 76 | 57 | 219 | Y00503 | Human mRNA forkeratin 19. |
| 357 | CATGGTTGTGGTTAA | H782013 | 178 | 110 | 14 | 340 | 139 | W16632 | zb05a11.r1 Soares fetal lung NbHL19W Homo sapiens cDNA clone 301148 5' similar to gb:V00567 BETA-2-MICROGLOBULIN PRECURSOR (HUMAN); |
| | | | | | | | | AA143804 | zo31h04.s1 Stratagene colon (#937204) Homo sapiens cDNA clone 588535 3' |
| | | | | | | | | AA133597 | 97 zl92h02.s1 Stratagene colon (#937204) Homo sapiens cDNA clone 512115 3 |
| 358 | CTAGTGCTCCTACCC | H947654 | 174 | 27 | 1 | 0 | 0 | T53199 | ya86c05.s1 Homo sapiens cDNA clone 68552 3'. |
| 359 | CATGCACCCCTGATG | H284132 | 172 | 33 | 26 | 3 | 6 | R00081 | ye73c04.s1 Homo sapiens cDNA clone 123366 3'. |
| 360 | CATGCCGCTGCACTC | H368200 | 163 | 40 | 4 | 10 | 4 | M16364 | Human creatine kinase-B mRNA, complete cds. |
| | | | | | | | | R09410 | yf22e12.s1 Homo sapiens cDNA clone 127630 3' similar to contains Alu repetitive element |
| | | | | | | | | C01918 | HUMGS0003915, Human Gene Signature, 3'-directed cDNA sequence. |
| | | | | | | | | R92735 | yq04h09.s1 Homo sapiens cDNA clone 196001 3' similar to contains Alu repetitive element |
| | | | | | | | | W90374 | zh78e12.s1 Soares fetal liver spleen INFLS S1 Homo sapiens cDNA clone 418222 3' similar to contains Alu repetitive element |
| 361 | CATGCTGGCCCTCGG | H501111 | 163 | 20 | 0 | 26 | 1 | X52003 | H.sapiens pS2 protein gene. |
| 362 | CATGCCCCCTGATC | H350116 | 160 | 40 | 24 | 88 | 181 | M18981 | Human prolactin receptor-associated protein (PRA) |

TABLE 3-continued

Transcripts decreased in colon cancer
Transcripts decreased in both colon primary tumors and colon cancer
cell lines compared to normal colon (130 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 363 | CATGTTCACTGTGAG | H1001401 | 160 | 34 | 13 | 74 | 71 | M64303 | Human galactoside-binding protein mRNA. |
| 364 | CATGATTGGAGTGCT | H256186 | 155 | 34 | 1 | 11 | 6 | X16455 | Human mRNA for carcinoembryonic antigen pCEA80-11. |
| 365 | CATGTGACCTGTGT | H493039 | 149 | 44 | 32 | 98 | 37 | U14943 | Human MHC antigen (HLA-B) mRNA, complete cds. |
| 366 | CATGAGCAGATCAGG | H149715 | 145 | 50 | 88 | 156 | 130 | M81457 | Human calpactin 1 light chain mRNA, complete cds. |
| 367 | CATGGGAAAACAGAA | H655433 | 126 | 37 | 0 | 24 | 16 | C21047 | HUMGS0002546, Human Gene Signature, 3'-directed cDNA sequence |
|  |  |  |  |  |  |  |  | AA132779 | zo21h08.s1 Stratagene colon (#937204) Homo sapiens cDNA clone 587583 3' similar to SW:LEG4_RAT P38552 GALECTIN-4 |
|  |  |  |  |  |  |  |  | AA054072 | zl68h06.s1 Stratagene colon (#937208) Homo sapiens cDNA clone 509819 3' |
|  |  |  |  |  |  |  |  | AA132736 | zo18g08.s1 Stratagene colon (#937204) Homo sapiens cDNA clone 587294 3' similar to SW:LEG4_RAT P38552 GALECTIN-4 |
| 368 | CATGTCACCGGTCAG | H857781 | 122 | 7 | 7 | 30 | 7 | X04412 | Human mRNA for plasma gelsolin. |
| 369 | CATGTGCAGCACGAG | H936217 | 122 | 26 | 32 | 84 | 2 | X77658 | H. sapiens mRNA for HLA-B*7301. |
| 370 | CATGGGAAACTGTGAA | H657337 | 115 | 7 | 1 | 14 | 21 | AA146606 | zo35c09.s1 Stratagene colon (#937204) Homo sapiens cDNA clone 588880 3' |
|  |  |  |  |  |  |  |  | AA146775 | zo35g09.s1 Stratagene colon (#937204) Homo sapiens cDNA clone 588928 3' |
|  |  |  |  |  |  |  |  | AA161043 | zo74g11.s1 Stratagene pancreas (#937208) Homo sapiens cDNA clone 592676 3' |
|  |  |  |  |  |  |  |  | AA088704 | zl83f08.s1 Stratagene colon (#937208) Homo sapiens cDNA clone 511239 3' |
| 371 | CATGCGAGGGGCCAG | H404117 | 114 | 32 | 54 | 60 | 40 | H00427 | yj23g11.r1 Homo sapiens cDNA clone 149636 5'. |
|  |  |  |  |  |  |  |  | AA158715 | zo63d03.s1 Stratagene pancreas (#937208) Homo sapiens cDNA clone 591557 3' |
|  |  |  |  |  |  |  |  | T08562 | EST06454 Homo sapiens cDNA clone HIBBG31 3' end. |
|  |  |  |  |  |  |  |  | AA078845 | zm21a12.s1 Stratagene pancreas (#937208) Homo sapiens cDNA clone 526270 3' |
| 372 | CATGTAAATTGCAAA | H790417 | 113 | 6 | 1 | 0 | 0 | X73502 | H. Sapiens mRNA for cytokeratin 20. |
| 373 | CATGGGCTGGGGGCC | H686762 | 113 | 36 | 48 | 45 | 43 | J03191 | Human profilin mRNA, complete cds. |
| 374 | CATGGTGCTGAATGG | H761359 | 109 | 20 | 30 | 67 | 111 | U02629 | Human smooth muscle myosin alkali light chain mRNA |
| 375 | CATGGTGCACTGAGC | H758243 | 107 | 13 | 36 | 34 | 82 | X07059 | Human M4-50 mRNA for HLA class I antigen. |
| 376 | CATGTTTAACGGCCG | H1032614 | 107 | 31 | 14 | 3 | 37 | F15592 | H.sapiens mitochondrial EST sequence (001T24) from |
| 377 | CATGCCCTCCCGAAG | H357729 | 106 | 17 | 7 | 3 | 6 | AA053660 | zl74e07.s1 Stratagene colon (#937204) Homo sapiens cDNA clone 510372 3' similar to contains Alu repetitive element |
|  |  |  |  |  |  |  |  | D25711 | HUMGS04077 Human colon 3'directed MboI cDNA, clone cm1210 |
| 378 | CATGAGGTGGCAAGA | H178755 | 105 | 15 | 22 | 14 | 27 | Z56800 | H.sapiens CpG DNA, clone 140c4, reverse read cpg14(Mitochondria EST |

TABLE 3-continued

Transcripts decreased in colon cancer
Transcripts decreased in both colon primary tumors and colon cancer
cell lines compared to normal colon (130 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 379 | CATGATACTCCACTC | H204104 | 102 | 11 | 0 | 0 | 0 | M95174 | Human guanylin mRNA, complete cds. |
| 380 | CATGCTCGCGCTGGG | H484987 | 101 | 25 | 5 | 4 | 16 | | Unknown |
| 381 | CATGGGGGCAGGGCC | H697514 | 82 | 32 | 28 | 37 | 65 | R90863 | yn01b01.r1 *Homo sapiens* cDNA clone 167113 5' similar to SP-ZK783.1 CE00760:. |
| | | | | | | | | T24702 | EST277 *Homo sapiens* cDNA clone 10H4. |
| 382 | CATGGAAGCAGGACC | H533666 | 80 | 33 | 42 | 28 | 87 | X95404 | *H.sapiens* mRNA for non-muscle type cofilin. |
| 383 | CATGCCAGGGGAGAA | H338569 | 75 | 22 | 28 | 30 | 16 | X67325 | *H.sapiens* p27 mRNA. |
| 384 | CATGACACAGCAAGA | H70211 | 74 | 31 | 30 | 10 | 31 | F16604 | *H.sapiens* mitochondrial EST sequence (009T28) from |
| 385 | CATGAGAATAGCTTG | H134304 | 69 | 29 | 1 | 3 | 0 | N69361 | za16e03.s1 *Homo sapiens* cDNA clone 292684 3' similar to contains Alu repetitive element;contains element L1 repetitive element |
| | | | | | | | | AA015918 | ze30s10.s1 Soares retina N2b4HR *Homo sapiens* cDNA clone 360475 3' similar to contains Alu repetitive element |
| | | | | | | | | H26689 | yl14h01.s1 *Homo sapiens* cDNA clone 158257 3' similar to contains Alu repetitive element;contains TAR1 repetitive element;. |
| 386 | CATGCGCTGTGGGGT | H424875 | 68 | 9 | 6 | 5 | 23 | AA256365 | zr79h11.s1 Soares NhHMPu S1 *Homo sapiens* cDNA clone 681957 3' similar to WP:C33A12.7 CE05353 |
| | | | | | | | | W47357 | zc39e11.s1 Soares senescent fibroblasts NbHSF *Homo sapiens* cDNA clone 324716 3' |
| | | | | | | | | W19276 | zb90f03.s1 Soares senescent fibroblasts NbHSF *Homo sapiens* cDNA clone 310877 3' |
| | | | | | | | | R07159 | yf13h12.s1 *Homo sapiens* cDNA clone 126791 3'. |
| 387 | CATGCATAGGTTTAG | H314109 | 68 | 5 | 0 | 0 | 0 | L02785 | *Homo sapiens* colon mucosa-associated (DRA) mRNA |
| 388 | CATGGCCGACCAGGT | H614731 | 65 | 19 | 0 | 3 | 6 | U11862 | Human clone HP-DAO1 diamine oxidase |
| 389 | CATGAGCTCTTGGAG | H161769 | 64 | 11 | 1 | 1 | 2 | N93240 | zb68b06.s1 *Homo sapiens* cDNA clone 308723 3'. |
| | | | | | | | | T16906 | NIB1986 Normalized infant brain, Bento Soares *Homo sapiens* cDNA 3'end. |
| | | | | | | | | H78256 | yu22h07.s1 *Homo sapiens* cDNA clone 234589 3' similar to SP:SBP_MOUSE P17563 SELENIUM-BINDING |
| | | | | | | | | T32362 | EST47523 *Homo sapiens* cDNA 3' end similar to similar to Selenium-binding protein,liver. |
| 390 | CATGCCCAACGCGCT | H344474 | 57 | 1 | 0 | 3 | 0 | V00493 | Human messenger RNA for alpha globin. |
| 391 | CATGACGCGGCGCG | H555054 | 55 | 21 | 2 | 7 | 14 | | Unknown |
| 392 | CATGACCCCCCCGCC | H87386 | 54 | 16 | 15 | 15 | 3 | X51346 | Human jun-D mRNA for JUN-D protein. |
| 393 | CATGATGCGGGAGAA | H236169 | 52 | 6 | 10 | 11 | 7 | R34039 | yh83f04.r1 Homosapiens cDNA clone 136351 5'. |
| | | | | | | | | H03961 | yj44e07.s1 *Homo sapiens* cDNA clone 151620 3'. |
| | | | | | | | | R33498 | yh83f04.s1 *Homo sapiens* cDNA clone 136351 3'. |
| 394 | CATGTCAGCTGCAAC | H862097 | 51 | 6 | 0 | 0 | 0 | AA053043 | zi71e06.r1 Stratagene colon (#937204) *Homo sapiens* cDNA clone 510082 5' |
| 395 | CATGGTAAGTGTACT | H723890 | 50 | 14 | 15 | 1 | 30 | F17394 | *H.sapiens* mitochondrial EST sequence (007T13) from |

TABLE 3-continued

Transcripts decreased in colon cancer

Transcripts decreased in both colon primary tumors and colon cancer cell lines compared to normal colon (130 genes)

NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 396 | CATGTGTGGGTGCTG | H977640 | 49 | 20 | 17 | 21 | 8 | Z13009 | H.sapiens mRNA for E-cadherin. |
| 397 | CATGGCTGTGCCTGG | H650847 | 48 | 17 | 15 | 8 | 31 | X15505 | Human mRNA for pancreatic trypsinogen III. |
| 398 | CATGTGAGTGACAGA | H929299 | 48 | 4 | 0 | 0 | 0 | H14641 | yl26g02.s1 Homo sapiens cDNA clone 159410 3' |
| 399 | CATGGGCTGGGCCTG | H686744 | 47 | 11 | 13 | 32 | 8 | M20469 | Human brain-type clathrin light-chain b mRNA, |
| 400 | CATGTAATCCCAGCA | H800074 | 46 | 15 | 5 | 8 | 11 | N50873 | yy92c07.s1 Homo sapiens cDNA clone 281004 3' similar to contains Alu repetitive element;contains element MER32 repetitive element |
| 401 | CATGGACCAGTGGCT | H545514 | 45 | 1 | 0 | 0 | 1 | U79725 | Human A33 antigen precursor mRNA, complete cds |
| 402 | CATGGGCACCGTGCT | H673210 | 44 | 10 | 1 | 14 | 14 |  | Unknown |
| 403 | CATGAAGGACCTTTT | H41344 | 43 | 17 | 14 | 22 | 24 | H11216 | ym14f06.r1 Homo sapiens cDNA clone 47991 5'. |
|  |  |  |  |  |  |  |  | H52178 | yh85h08.s1 Homo sapiens cDNA clone 231135 3'. |
|  |  |  |  |  |  |  |  | T40539 | ya05b02.s1 Homo sapiens cDNA clone 60555 3'. |
| 404 | CATGGCAGCTCCTGT | H599903 | 43 | 8 | 17 | 24 | 13 | AA303091 | EST12940 Uterus tumor I Homo sapiens cDNA 3' end |
|  |  |  |  |  |  |  |  | W02429 | za52d02.r1 Soares fetal liver spleen 1NFLS Homo sapiens cDNA clone 296163 5'. |
|  |  |  |  |  |  |  |  | N20325 | yx44c11.s1 Homo sapiens cDNA clone 264596 3'; |
|  |  |  |  |  |  |  |  | N45127 | yz13c12.s1 Homo sapiens cDNA clone 282934 3'. |
|  |  |  |  |  |  |  |  | N90407 | zb38c11.s1 Soares parathyroid tumor NbHPA Homo sapiens cDNA clone 305876 3'. |
| 405 | CATGTGTCCTGGTTC | H972720 | 43 | 12 | 14 | 25 | 5 | U03106 | Human wild-type p53 activated fragment-1 (WAF1) mR |
| 406 | CATGACAAACCCCCA | H65878 | 42 | 16 | 7 | 12 | 11 | W37827 | zc11f01.s1 Soares parathyroid tumor NbHPA Homo sapiens cDNA clone 322009 3' |
|  |  |  |  |  |  |  |  | W15332 | gb|W15332|W15332 zc16d10.s1 Soares parathyroid tumor NbHPA Homo sapiens cDNA clone 322483 3'. |
|  |  |  |  |  |  |  |  | W32410 | zc04g10.s1 Soares parathyroid tumor NbHPA Homo sapiens cDNA clone 321378 3' |
| 407 | CATGTAGGATGGGGG | H828331 | 41 | 6 | 11 | 6 | 9 | N32312 | yw82c01.s1 Homo sapiens cDNA clone 258720 3'. |
| 408 | CATGACTGTGGCGGC | H126619 | 41 | 7 | 1 | 4 | 35 | U51478 | Human sodium/potassium-transporting ATPase beta-3 |
| 409 | CATGGTAGCAGGTGT | H730287 | 40 | 7 | 13 | 17 | 24 | AA180815 | Unknown |
|  |  |  |  |  |  |  |  |  | zp44f11.s1 Stratagene muscle 937209 Homo sapiens cDNA clone 612333 3' similar to contains Alu repetitive element; |
|  |  |  |  |  |  |  |  | R34696 | yh87e04.s1 Homo sapiens cDNA clone 136734 3' similar to contains Alu repetitive element; |
|  |  |  |  |  |  |  |  | R34696 | yh87e04.s1 Homo sapiens cDNA clone 136734 3' similar to contains Alu repetitive element; |
|  |  |  |  |  |  |  |  | AA194497 | zq06e03.s1 Stratagene muscle 937209 Homo sapiens cDNA clone 628924 3' similar to contains Alu repetitive element |

TABLE 3-continued

Transcripts decreased in colon cancer

Transcripts decreased in both colon primary tumors and colon cancer
cell lines compared to normal colon (130 genes)

NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 410 | CATGAATCACAAATA | H53508 | 40 | 12 | 0 | 3 | 0 | T11144 | hbc760 *Homo sapiens* cDNA clone hbc760 3′end similar to nonspacific crossreacting antigen. |
| 411 | CATGAGGATGGTCCC | H167606 | 40 | 11 | 4 | 4 | 5 | AA058357 | zi67e01.s1 Stratagene colon (#937204) *Homo sapiens* cDNA clone 509688 3′ similar to TR:G189087 |
|  |  |  |  |  |  |  |  | C05803 | similar to none |
|  |  |  |  |  |  |  |  | AA143765 | zo31e02.s1 Stratagene colon (#937204) *Homo sapiens* cDNA clone 588506 3′ |
|  |  |  |  |  |  |  |  | AA179299 | zp45b09.s1 Stratagene HeLa ce11 s3 937216 *Homo sapiens* cDNA clone 612377 3′ |
| 412 | CATGCCAAAGCTATA | H328308 | 38 | 11 | 6 | 2 | 18 | M35252 | Human CO-029. |
| 413 | CATGCGGGAGTCGGG | H434907 | 38 | 8 | 6 | 0 | 0 | R87448 | ym89c10.s1 *Homo sapiens* cDNA clone 166098 3′. |
| 414 | CATGGCCGTGGAGAG | H618121 | 38 | 9 | 5 | 17 | 26 | X79882 | *H.sapiens* 1rp mRNA. |
| 415 | CATGCCCCGAAGCC | H349706 | 37 | 6 | 0 | 0 | 0 |  | Unknown |
| 416 | CATGATTTCAAGATG | H259108 | 37 | 1 | 0 | 0 | 0 | J03037 | Human carbonic anhydrase II mRNA, complete cds. |
| 417 | CATGGCCCAGTGGCT | H611050 | 37 | 3 | 0 | 2 | 10 |  | Unknown |
| 418 | CATGATGGTGGGGGA | H241323 | 36 | 2 | 6 | 25 | 2 | M92843 | *H.sapiens* zinc finger transcriptional regulator mRNA |
| 419 | CATGCCTGCCCCCCT | H386390 | 35 | 12 | 7 | 7 | 5 | X60188 | Human ERK1 mRNA for protein serine/threonine kinase |
| 420 | CTAGTGGAAAGTGAA | H950457 | 34 | 1 | 1 | 12 | 0 | V01512 | Human cellular oncogene c-fos (complete sequence). |
| 421 | CATGGTCATCACCAC | H740629 | 34 | 0 | 0 | 0 | 0 | U34279 | Human uroguanylin mRNA, complete cds. |
| 422 | CATGCTTATGGTCCC | H511670 | 34 | 1 | 0 | 3 | 1 | AA287021 | zs57c03.s1 Soares NbHTGBC *Homo sapiens* cDNA clone 701572 3′ |
| 423 | CATGCTGGGCCTCTG | H502136 | 34 | 3 | 4 | 11 | 5 | T55226 | yb47a01.s1 *Homo sapiens* cDNA clone 74280 3′ containing L1 repetitive element |
|  |  |  |  |  |  |  |  | R37446 | yf56e10.s1 *Homo sapiens* cDNA clone 26129 3′ similar to gb:X07173 INTER-ALPHA-TRYPSIN INHIBITOR COMPLEX COMPONENT II |
|  |  |  |  |  |  |  |  | AA406180 | zu65c08.s1 Soares testis NHT *Homo sapiens* cDNA clone 742862 3′ |
| 424 | CATGGCCCAGGGCCC | H610982 | 33 | 3 | 0 | 0 | 2 | R09752 | Unknown |
| 425 | CATGTTTTACTGAT | H1047673 | 33 | 7 | 0 | 4 | 2 | R81530 | yj02b10.r1 *Homo sapiens* cDNA clone 147547 5′; |
|  |  |  |  |  |  |  |  | T32348 | EST47211 *Homo sapiens* cDNA 3′ end similar to None.. |
|  |  |  |  |  |  |  |  | W57810 | zd17g02.s1 Soares fetal heart NbHH19W *Homo sapiens* cDNA clone 340946 3′ |
|  |  |  |  |  |  |  |  | AA398527 | zi47e12.s1 Soares ovary tumor NbHOT *Homo sapiens* cDNA clone 725518 3′ |
| 426 | CATGCCTGCTTGTCG | H387054 | 32 | 2 | 1 | 6 | 32 | X63187 | *H.sapiens* HE4 mRNA for extracellular proteinase inhibitor homologue |
| 427 | CATGACCTGGGGAGG | H96931 | 32 | 6 | 4 | 8 | 6 |  | Unknown |
| 428 | CATGCCTTCAAATCA | H390158 | 31 | 1 | 0 | 0 | 0 | R46266 | g52g07.s1 *Homo sapiens* cDNA clone 36232 3′ similar to gb:M33987 CARBONIC ANHYDRASE I |

TABLE 3-continued

Transcripts decreased in colon cancer

Transcripts decreased in both colon primary tumors and colon cancer cell lines compared to normal colon (130 genes)

NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 429 | CATGTTCGGAGCTGTT | H893564 | 30 | 1 | 4 | 7 | 1 | H98618 AA171705 | yx12a06.s1 *Homo sapiens* cDNA clone 261490 3′; zo97h01.s1 Stratagene ovarian cancer (#937219) *Homo sapiens* cDNA clone 594865 3′ |
| 430 | CATGGGAGGTGGGGC | H666539 | 30 | 6 | 5 | 32 | 22 | H99212 | yx15g08.s1 *Homo sapiens* cDNA clone 261854 3′; |
| 431 | CATGTTCCACTAACC | H1003970 | 30 | 7 | 3 | 16 | 17 | AA029975 | zk10e12.s1 Soares pregnant uterus NbHPU *Homo sapiens* cDNA clone 470158 3′ |
|  |  |  |  |  |  |  |  | M75161 | H.sapiens granulin mRNA, complete cds. |
|  |  |  |  |  |  |  |  | T30344 | gb|U53204|HSU53204 Human plectin (PLEC1) mRNA, complete cds. |
| 432 | CATGGTCTGGGGGAT | H752297 | 29 | 1 | 3 | 9 | 3 | T60135 | yc22a06.s1 *Homo sapiens* cDNA clone 81394 3′. |
|  |  |  |  |  |  |  |  | T30403 | gb|U67963|HSU67963 Human lysophospholipase homolog (HU-K5) mRNA |
| 433 | CATGTTAACCCCTCC | H984414 | 29 | 5 | 0 | 18 | 0 | R23595 | yh39a12.r1 *Homo sapiens* cDNA clone 132094 5′ similar to gb:D26129 RIBONUCLEASE PANCREATIC PRECURSOR (HUMAN) |
|  |  |  |  |  |  |  |  | R69445 | yj83c08.s1 *Homo sapiens* cDNA clone 155342 3′ similar to gb:D26129 RIBONUCLEASE PANCREATIC PRECURSOR (HUMAN); |
|  |  |  |  |  |  |  |  | R79191 | yi84h01.s1 *Homo sapiens* cDNA clone 145969 3′ similar to gb:D26129 RIBONUCLEASE PANCREATIC PRECURSOR (HUMAN); |
|  |  |  |  |  |  |  |  | R49965 | yj56c03.s1 *Homo sapiens* cDNA clone 152740 3′ similar to gb:D26129 RIBONUCLEASE PANCREATIC PRECURSOR (HUMAN); |
| 434 | CATGATGACGCTCAC | H231029 | 28 | 5 | 5 | 4 | 6 | AA410947 | zv35h12.r1 Soares ovary tumor NbHOT *Homo sapiens* cDNA clone 755687 5′ similar to TR:G459890 G459890 OVEREXPRESSED IN TESTICULAR TUMORS |
|  |  |  |  |  |  |  |  | H02520 | yj40c11.r1 *Homo sapiens* cDNA clone 151220 5′. |
|  |  |  |  |  |  |  |  | AA130551 | zo12g08.r1 Stratagene colon (#937204) *Homo sapiens* cDNA clone 586718 5′ similar to TR:G459890 G459890 OVEREXPRESSED IN TESTICULAR TUMORS. |
| 435 | CATGCACCTGTCATC | H286420 | 28 | 5 | 0 | 5 | 4 | W68230 | zd33c10.s1 Soares fetal heart NbHH19W *Homo sapiens* cDNA clone 342450 3′ similar to contains Alu repetitive element |
|  |  |  |  |  |  |  |  | R89822 | yp90a02.s1 *Homo sapiens* cDNA clone 194666 3′ similar to contains Alu repetitive element; |
|  |  |  |  |  |  |  |  | AA053322 | zk69e08.s1 Soares pregnant uterus NbHPU *Homo sapiens* cDNA clone 488102 3′ similar to contains element MER6 repetitive element |
| 436 | CATGGATCCCAACTG | H578824 | 27 | 1 | 1 | 24 | 17 | V00594 | Human mRNA for metallothionein from cadmium-treated cells |

TABLE 3-continued

Transcripts decreased in colon cancer

Transcripts decreased in both colon primary tumors and colon cancer cell lines compared to normal colon (130 genes)

NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 437 | CATGCTTAGAGGGGT | H510123 | 27 | 1 | 5 | 9 | 6 | H43742 | yp21d05.r1 *Homo sapiens* cDNA clone 188073 5' similar to gb|J05021 EZRIN |
| 438 | CATGATGGCCCATAC | H238925 | 27 | 4 | 3 | 1 | 0 | | emb|Y09616|HSICE *H.sapiens* mRNA for putative carboxylesterase |
| 439 | CATGGCAAGAAAGTG | H591884 | 27 | 1 | 0 | 2 | 0 | V00497 | Human messenger RNA for beta-globin. |
| 440 | CATGTACCTCTGATT | H810468 | 27 | 5 | 7 | 11 | 12 | X65614 | *H.sapiens* mRNA for calcium-binding protein S100P. |
| 441 | CATGATGATGGCACC | H233106 | 26 | 0 | 2 | 0 | 2 | | |
| 442 | CATGTTCTGTAGCCC | H1014566 | 25 | 5 | 0 | 4 | 0 | | emb|Z69881|HSSERCA3M *H.sapiens* mRNA for adenosine triphosphatase, calcium |
| 443 | CATGCCTGTCTGCCA | H388582 | 24 | 1 | 2 | 1 | 3 | T99568 | ye65c02.r1 *Homo sapiens* cDNA clone 122594 5' |
| 444 | CATGTATGATGAGCA | H844682 | 23 | 4 | 0 | 1 | 0 | T87539 | yd89f09.s1 *Homo sapiens* cDNA clone 115433 3'; gb|AA347726|AA347126 EST54132 Fetal heart II *Homo sapiens* cDNA 5' end similar to transmembrane secretory component |
| 445 | CATGCTGGCAAAGGT | H500747 | 23 | 0 | 0 | 0 | 0 | | *Homo sapiens* bone-derived growth factor (BPGF-1) m |
| 446 | CATGCTTGATTCCCA | H517078 | 23 | 4 | 4 | 17 | 7 | L42379 | *H.sapiens* CL 100 mRNA for protein tyrosine phosphatase |
| 447 | CATGCTTGACATACC | H516402 | 22 | 0 | 0 | 7 | 2 | X68277 | Human N-benzoyl-L-tyrosyl-p-amino-benzoic acid hydrolase alpha subunit (PPH alpha) mRNA, complete cds |
| 448 | CATGGCTGGCACATT | H649492 | 22 | 5 | 0 | 0 | 0 | M82962 | |
| 449 | CATGTCTGAATTATG | H909556 | 21 | 1 | 1 | 1 | 1 | X16354 | Human mRNA for transmembrane carcinoembryonic antigen (CEA) |
| 450 | CATGGGAAGAGCACT | H657554 | 21 | 1 | 1 | 3 | 3 | X74570 | *H.sapiens* mRNA for Gal-beta(1-3/1-4)GlcNAcalpha-2,3-sialyltransferase |
| 451 | CATGGCTCTTCCCCA | H646998 | 20 | 2 | 0 | 1 | 0 | R87768 | yo45d01.s1 *Homo sapiens* cDNA clone 180865 3' similar to contains PTR5 repetitive element |
|  |  |  |  |  |  |  |  | R85880 | yo36g07.s1 *Homo sapiens* cDNA clone 180060 3' similar to contains PTR5 repetitive element |
| 452 | CATGAAAATCTGGCAC | H14245 | 20 | 2 | 0 | 4 | 3 | L20826 | Human I-plastin mRNA, complete cds. |
| 453 | CATGTAATTTGCATT | H802708 | 19 | 2 | 0 | 1 | 7 | Z50751 | HSB4BMR *H.sapiens* mRNA for B4B |
|  |  |  |  |  |  |  |  | U77085 | Human epithelial membrane protein (CL-20) mRNA, complete cds |
|  |  |  |  |  |  |  |  | Y07909 | HSPAPR *H.sapiens* mRNA for Progression Associated Protein |
| 454 | CATGGTGTGGGGCGCC | H764570 | 18 | 1 | 1 | 8 | 2 | R48529 | yj64g10.r1 *Homo sapiens* cDNA clone 153570 5' |
| 455 | CATGTTATGGTGTGA | H998127 | 17 | 0 | 0 | 1 | 0 | T27534 | EST10a24 Clontech adult human fat cell library HL1108A *Homo sapiens* cDNA clone 10a24. |
| 456 | CATGGGAGAAAACAGC | H663571 | 17 | 1 | 2 | 4 | 0 | T86124 | yd84b04.s1 *Homo sapiens* cDNA clone 114895 3' |
|  |  |  |  |  |  |  |  | AA131008 | zo15g05.s1 Stratagene colon (#937204) *Homo sapiens* cDNA clone 587000 3' |
|  |  |  |  |  |  |  |  | R49945 | yj58g11.s1 *Homo sapiens* cDNA clone 152996 3' |
| 457 | CATGCCAACACCAGC | H328787 | 17 | 1 | 0 | 0 | 0 | T57044 | ya84h01.s1 *Homo sapiens* cDNA clone 68401 3' |
| 458 | CATGAGGTGACTGGG | H178299 | 17 | 0 | 0 | 0 | 0 | | |

TABLE 3-continued

Transcripts decreased in colon cancer
Transcripts decreased in both colon primary tumors and colon cancer
cell lines compared to normal colon (130 genes)
NC: Normal Colon
TU: Colon Primary Tumor
CL: Colon Cancer Cell Line
PT: Pancreatic Primary Tumor
PC: Pancreatic Cancer Cell Line

| SEQ ID NO: | Tag Sequence | Tag_Number | NC | TU | CL | PT | PC | Accession | Gene Name |
|---|---|---|---|---|---|---|---|---|---|
| 459 | CATGGCCATCCTCCA | H609654 | 16 | 0 | 0 | 0 | 0 |  | gb|R73013|R73013 yj94a09.r1 *Homo sapiens* cDNA clone 156376 5'. |
| 460 | CATGTTTCTCGTCGC | H1039799 | 15 | 1 | 0 | 4 | 4 | M69013 | Human guanine nucleotide-binding regulatory protein |
| 461 | CATGTCAGAGCGCTG | H860776 | 15 | 1 | 1 | 1 | 0 |  | Unknown |
| 462 | CATGTTCCGCGTTCC | H1006014 | 14 | 1 | 0 | 0 | 2 | N58523 | yv72h06.s1 Soares fetal liver spleen 1NFLS *Homo sapiens* cDNA clone 248315 3' similar to contains element PTR7 repetitive element |
| 463 | CATGTACGGTGTGGG | H814011 | 14 | 1 | 0 | 0 | 0 |  | Unknown |
| 464 | CATGCTCAGAACTFG | H477216 | 14 | 0 | 1 | 4 | 13 |  | Unknown |
| 465 | CATGGGACTAAATGA | H662543 | 13 | 1 | 0 | 1 | 0 | M29540 | Human carcinoembryonic antigen mRNA (CEA), complete cds. |
| 466 | CATGGCTTGGGGATF | H653988 | 12 | 0 | 0 | 0 | 1 | D25786 | HUMGS04154 Human colon 3'directed MboI cDNA, HUMGS04154, clone cm0215. |
|  |  |  |  |  |  |  |  | T73613 | yc36e02.r1 *Homo sapiens* cDNA clone 82778 5' similar to gb:L07765 LIVER CARBOXYLESTERASE PRECURSOR |
| 467 | CATGACCCAACTGCC | H86138 | 12 | 0 | 0 | 0 | 1 |  | Unknown |
| 468 | CATGCTGAACCTCCC | H491894 | 12 | 0 | 0 | 2 | 2 |  | gb|T95615|T95615 ye40e03.s1 *Homo sapiens* cDNA clone 120220 3'. |
| 469 | CATGCAAGAGTTTCT | H271102 | 11 | 0 | 0 | 2 | 0 | AA226797 | zr19h11.s1 Stratagene NT2 neuronal precursor 937230 *Homo sapiens* cDNA clone 663837 3' |
|  |  |  |  |  |  |  |  | AA218730 | zq97h01.s1 Stratagene NT2 neuronal precursor 937230 *Homo sapiens* cDNA clone 649969 3' |
| 470 | CATGGTCCGAGTGCA | H743610 | 11 | 0 | 0 | 8 | 5 | H38178 | yp57f10.r1 *Homo sapiens* cDNA clone 191563 5' similar to gb:M90657 TUMOR-ASSOCIATED ANTIGEN L6 (HUMAN); |
| 471 | CATGTTTGGTTTCAC | H1043445 | 11 | 0 | 0 | 0 | 0 |  | Unknown |

TABLE 3

Transcripts decreased in colon cancer
Transcripts decreased in only colon cancer
cell lines compared to normal colon (78 genes)

| SEQ ID NO: | Tag sequence | Tag_Number | NC | TU | CL | PT | PC | Accession | Gene Name |
|---|---|---|---|---|---|---|---|---|---|
| 472 | CATGCACCTAATTGG | H285759 | 612 | 755 | 411 | 161 | 333 | F15516 | *H. sapiens* mitochondrial EST sequence (1-t-12) |
| 473 | CATGATTTGAGAAGC | H260227 | 603 | 566 | 158 | 249 | 173 | F12396 | *H. sapiens* partial cDNA sequence; clone c-39e04. |
| 474 | CATGTGATTTCACTT | H933704 | 452 | 595 | 235 | 80 | 314 | L08441 | Human autonomously replicating sequence (ARS) mRNA |
| 475 | CATGTTCATACACCT | H1002566 | 444 | 357 | 114 | 64 | 191 | F15553 | *H. sapiens* mitochondrial EST sequence (001T14) |
| 476 | CATGCCACTGCACTC | H335432 | 385 | 402 | 223 | 278 | 132 | X51525 | Human cortex mRNA containing an Alu repetitive element |
| 477 | CATGACTAACACCCT | H114966 | 369 | 446 | 171 | 76 | 161 | F16402 | *H. sapiens* mitochondrial EST sequence (141-20) |
| 478 | CATGCACTACTCACC | H291282 | 293 | 527 | 78 | 14 | 83 | U09500 | Human mitochondrion cytochrome b gene, partial cds |
| 479 | CATGAAAACATTCTC | H1272 | 200 | 169 | 98 | 17 | 223 | F15744 | *H. sapiens* mitochondrial EST sequence (101-03) |
| 480 | CATGCTCATAAGGAA | H478249 | 184 | 127 | 70 | 21 | 75 | F15511 | *H. sapiens* mitochondrial EST sequence (1-t-07) |
| 481 | CATGTCGAAGCCCCC | H885334 | 147 | 183 | 94 | 49 | 57 | F18587 | *H. sapiens* mitochondrial EST sequence (022T19) |
| 482 | CATGACGCAGGGAGA | H103075 | 145 | 160 | 91 | 69 | 47 | H03983 | yj47a08.s1 *Homo sapiens* cDNA clone 151862 3'. |
| 483 | CATGTTGGCCAGGCT | H1025322 | 124 | 194 | 63 | 111 | 51 | X74301 | *H. sapiens* mRNA for MHC class II transactivator. |
| 484 | CATGTTGGTGAAGGA | H1027595 | 98 | 106 | 17 | 183 | 107 | M17733 | Human thymosin beta-4 mRNA, complete cds. |
| 485 | CATGATCACGCCCTC | H214616 | 97 | 186 | 17 | 41 | 49 | U46913 | Human EST overexpressed in pancreatic cancer (xs31) |
| 486 | CATGTGCCTGCACCA | H941638 | 67 | 48 | 25 | 75 | 34 | X05607 | Human mRNA for cysteine proteinase inhibitor precursor |
| 487 | CATGAGACCCACAAC | H136465 | 64 | 121 | 28 | 24 | 15 | D54113 | Human fetal brain cDNA 5'-end GEN-129B05. |
| 488 | CATGAGTTTGTTAGT | H196339 | 60 | 33 | 17 | 13 | 15 | X14758 | Human mRNA for adenocarcinoma-associated antigen |
| 489 | CATGGGAACAAACAG | H656389 | 56 | 41 | 4 | 31 | 3 | L33930 | *Homo sapiens* CD24 signal transducer mRNA |
| 490 | CATGTGGTGTATGCA | H965434 | 53 | 271 | 6 | 30 | 5 | D50954 | Human fetal brain cDNA 3'-end GEN-002A10. |
| 491 | CATGGAAATACAGTT | H527436 | 49 | 35 | 10 | 100 | 36 | M11233 | Human cathepsin D mRNA, complete cds. |
| 492 | CATGGTGGCTCACGC | H763719 | 49 | 37 | 21 | 27 | 15 | U25801 | Human Tax1 binding protein mRNA, partial cds. |
| 493 | CATGGTGGTGCACAC | H765509 | 45 | 26 | 18 | 23 | 15 | U31215 | Human metabotropic glutamate receptor 1 alpha |
| 494 | CATGGGGTTGGCTTG | H704160 | 44 | 56 | 2 | 6 | 1 | S79597 | tRNASer(UNC) [human, muscle, MERRF/MELAS overlap s |
| 495 | CATGGTGGCGGGTGC | H763567 | 42 | 32 | 15 | 20 | 5 | T48809 | yb05c03.r1 *Homo sapiens* cDNA clone 70276 5' contai |
| 496 | CATGTAGACTAGCAA | H821029 | 39 | 23 | 1 | 23 | 10 | M69023 | Human globin gene. |
| 497 | CATGGCTAGGTTTAT | H641789 | 38 | 144 | 13 | 25 | 13 | D51017 | Human fetal brain cDNA 3'-end GEN-007C04. |
| 498 | CATGGGCTTTAGGGA | H687915 | 37 | 372 | 6 | 29 | 11 | W15552 | zb91h11.s1 Soares parathyroid tumor NbHPA Homo sap |
| 499 | CATGGGGGTCAGGG | H699691 | 37 | 170 | 11 | 16 | 9 | F16326 | *H. sapiens* mitochondrial EST sequence (132-20) from skeletal muscle |
| 500 | CATGATTTTCTAAAA | H261569 | 33 | 13 | 11 | 8 | 2 | AA315049 | EST186995 HCC cell line (matastasis to liver in mouse) II *Homo sapiens* cDNA 5' end |
| 501 | CATGCACTTGCCCT | H294488 | 33 | 18 | 11 | 17 | 36 | F01150 | *H. sapiens* partial cDNA sequence; clone A6A03; ver |
| 502 | CATGCCTGCTGCAGG | H386963 | 32 | 13 | 0 | 6 | 2 | N29971 | yw53h01.s1 *Homo sapiens* cDNA clone 255985 3'. |
| 503 | CATGAGAACCTTCCA | H132598 | 32 | 14 | 3 | 16 | 12 | K02883 | Human MHC class I HLA-A2 gene, complete cds. |
| 504 | CATGCTCTGCCCTC | H489822 | 32 | 32 | 7 | 20 | 5 | R09140 | yf25f1 2.s1 *Homo sapiens* cDNA clone 127919 3'. |
| | | | | | | | | R76005 | y122c10.s1 *Homo sapiens* cDNA clone 158994 3'. |
| | | | | | | | | T33596 | EST58371 *Homo sapiens* cDNA 3' end similar to None. |
| 505 | CATGGCCATCCCCTT | H609624 | 29 | 73 | 7 | 14 | 16 | F16449 | *H. sapiens* mitochondrial EST sequence (129-09) |
| 506 | CATGGCCCAGCGGCC | H610922 | 28 | 9 | 1 | 1 | 7 | AA292959 | zt54f10.s1 Soares ovary tumor NbHOT *Homo sapiens* cDNA clone 726187 3' |
| 507 | CATGTGGCGCGTGTC | H956860 | 26 | 8 | 1 | 1 | 2 | AA292466 | zt31c11.r1 Soares ovary tumor NbHOT *Homo sapiens* cDNA clone 723956 5' similar to TR:G205858 G205858 RAT ORF |

TABLE 3-continued

Transcripts decreased in colon cancer
Transcripts decreased in only colon cancer
cell lines compared to normal colon (78 genes)

| SEQ ID NO: | Tag sequence | Tag_Number | NC | TU | CL | PT | PC | Accession | Gene Name |
|---|---|---|---|---|---|---|---|---|---|
| | | | | | | | | N92384 | zb62d07.s1 Soares fetal lung NbHL19W Homo sapiens cDNA clone 308173 3' similar to PIR:A39484 A39484 androgen-withdrawl apoptosis protein RVP1, prostatic - rat |
| | | | | | | | | N80203 | zb19c06.s1 Homo sapiens cDNA clone 302506 3' similar to PIR:A39484 A39484 androgen-withdrawal apoptosis protein RVP1, prostatic - rat; |
| | | | | | | | | AA039323 | zk39d06.s1 Soares pregnant uterus NbHPU Homo sapiens cDNA clone 485195 3' similar to PIR:A39484 A39484 androgen-withdrawal apoptosis protein RVP1 |
| 508 | CATGAGGGTGTTTTC | H175872 | 26 | 218 | 7 | 20 | 10 | U21468 | Human partial cDNA sequence with CCA repeat region |
| 509 | CATGCCTGGGAAGTG | H387596 | 25 | 10 | 0 | 45 | 17 | M34088 | Human episialin variant A mRNA, 3' end. |
| 510 | CATGAGTCTGCTGGA | H188027 | 24 | 9 | 1 | 0 | 0 | | Unknown |
| 511 | CATGCCCGCCTCTTC | H353760 | 24 | 11 | 2 | 3 | 4 | T10098 | seq816 Homo sapiens cDNA clone b4HB3MA-COT8-HAP-Ft |
| 512 | CATGAAAAGAGTGGT | H2235 | 22 | 9 | 2 | 0 | 7 | X83228 | H. sapiens mRNA for LI-cadherin. |
| 513 | CATGGCCACGTGGAG | H607977 | 21 | 7 | 1 | 2 | 2 | L27415 | Homo sapiens huntingtin (HD) gene, exon 66. |
| 514 | CATGAGGATGTGGG | H167659 | 21 | 5 | 4 | 1 | 3 | C00470 | dbj|C00470|C00470 HUMGS0007620, Human Gene Signature, 3'-directed cDNA sequence. |
| | | | | | | | | N63531 | yy62g08.s1 Homo sapiens cDNA clone 278174 3'. |
| | | | | | | | | AA165679 | zo80f04.s1 Stratagene ovarian cancer (#937219) Homo sapiens cDNA clone 593215 3' |
| 515 | CATGTATAGTCCTCT | H838494 | 20 | 7 | 1 | 3 | 4 | AA411012 | zv40a02.s1 Soares ovary tumor NbHOT Homo sapiens cDNA clone 756074 3' |
| | | | | | | | | AA133595 | z192g08.s1 Stratagene colon (#937204) Homo sapiens cDNA clone 512126 3' |
| | | | | | | | | AA292774 | zt56b12.s1 Soares ovary tumor NbHOT Homo sapiens cDNA clone 726335 3' |
| 516 | CATGGGTCCTCTCTT | H710520 | 20 | 7 | 2 | 2 | 2 | R53216 | yj73h02.r1 Homo sapiens cDNA clone 154419 5' simil |
| 517 | CATGATGGGCTTGAT | H240121 | 19 | 4 | 0 | 3 | 3 | D20113 | Human HL60 3'directed MboI cDNA, HUMGS01086, clone |
| 518 | CATGCTGCCCCCCAT | H496981 | 19 | 5 | 0 | 1 | 4 | | Unknown |
| 519 | CATGTTCTCTACACA | H1013522 | 19 | 4 | 1 | 8 | 2 | U35048 | Human TSC-22 protein mRNA, complete cds. |
| 520 | CATGAAGAAGCAGGG | H33355 | 18 | 4 | 2 | 2 | 8 | R81767 | yj05g03.r1 Homo sapiens cDNA clone 147892 5'. |
| 521 | CATGAGTAGGTGGCC | H183018 | 18 | 131 | 2 | 17 | 7 | D51021 | Human fetal brain cDNA 3'-end GEN-007D07. |
| 522 | CATGACAGTGTGTGT | H77551 | 18 | 5 | 3 | 0 | 8 | D26146 | Human DNA for putative protein kinase. |
| 523 | CATGGGAAAAGTGGT | H655547 | 18 | 13 | 3 | 70 | 1 | M11465 | Human alpha-1-antitrypsin mRNA, complete cds. |
| 524 | CATGAAGAAAGCTC | H32926 | 17 | 4 | 0 | 5 | 1 | R78188 | yi81g01.r1 Homo sapiens cDNA clone 145680 5'. |
| 525 | CATGACACCCATCAC | H70965 | 17 | 4 | 0 | 0 | 0 | M22406 | Human intestinal mucin mRNA, partial cds, clone SM |
| 526 | CATGAGATCCCAAGG | H144707 | 17 | 18 | 0 | 0 | 0 | T24507 | EST082 Homo sapiens cDNA clone 3E6.. |
| | | | | | | | | N79237 | za63a11.s1 Homo sapiens cDNA clone 297212 3' similar to PIR:S49589 549589 cortical granule lectin - African clawed frog ;. |
| | | | | | | | | T31354 | \E5T30893 Homo sapiens cDNA 5' end similar to None.. |
| 527 | CATGAATAGTTTCCC | H52214 | 16 | 4 | 0 | 0 | 0 | H54696 | yq92e02.s1 Homo sapiens cDNA clone 203258 3' simil |
| 528 | CATGCAGAAAGCATC | H295060 | 16 | 9 | 0 | 0 | 0 | M22430 | Human RASF-A PLA2 mRNA, complete cds. |
| 529 | CATGGCTTTGCTTTG | H654976 | 16 | 4 | 2 | 8 | 1 | AA374631 | EST86866 HSC172 cells I Homo sapiens cDNA 5' end |
| | | | | | | | | AA137163 | zn93g08.r1 Stratagene lung carcinoma 937218 Homo sapiens cDNA clone 565790 5' |
| | | | | | | | | AA029320 | zk10f05.s1 Soares pregnant uterus NbHPU Homo sapiens cDNA clone 470145 3' |
| 530 | CATGTGCTGCATTGA | H948543 | 15 | 2 | 0 | 1 | 0 | D25681 | Human colon 3'directed MboI cDNA, HUMGS04047, clon |
| | | | | | | | | AA253331 | zr72g02.s1 Soares NhHMPu S1 Homo sapiens cDNA clone 668978 3' |
| | | | | | | | | H05110 | y175f07.s1 Homo sapiens cDNA clone 43778 3'. |

TABLE 3-continued

Transcripts decreased in colon cancer
Transcripts decreased in only colon cancer
cell lines compared to normal colon (78 genes)

| SEQ ID NO: | Tag sequence | Tag_Number | NC | TU | CL | PT | PC | Accession | Gene Name |
|---|---|---|---|---|---|---|---|---|---|
| 531 | CATGCCATCGTCCTT | H341720 | 15 | 8 | 1 | 1 | 10 | | Unknown |
| 532 | CATGGAACAGCTCAC | H529013 | 14 | 23 | 0 | 0 | 0 | AA297150 | EST112734 Colon I *Homo sapiens* cDNA 5' end |
| 533 | CATGGGGCTACGTCC | H695406 | 14 | 4 | 0 | 1 | 0 | M25629 | Human kallikrein mRNA, complete cds, clone clone p |
| 534 | CATGCCCGGCTCCTC | H354776 | 14 | 7 | 1 | 5 | 2 | H18836 | ym45d10.s1 *Homo sapiens* cDNA clone 51262 3'. |
| | | | | | | | | AA026974 | zk01e10.s1 Soares pregnant uterus NbHPU *Homo sapiens* cDNA clone 469290 3' |
| | | | | | | | | AA405031 | zu12c12.r1 Soares testis NHT *Homo sapiens* cDNA clone 731638 5' similar to gb:M61900 Human prostaglandin D synthase gene, complete cds. (HUMAN); |
| 535 | CATGAGGTACTACTA | H176584 | 13 | 9 | 0 | 9 | 8 | U66894 | gb|U66894|HSU66894 Human epithelium-restricted Ets protein ESX mRNA, |
| | | | | | | | | U73843 | Human epithelial-specific transcription factor ESE-1b (ESE-1) mRNA, complete cds |
| 536 | CATGCAAATAAATTA | H265232 | 13 | 3 | 0 | 1 | 0 | D25996 | Human Colon 3'directed MboI cDNA, HUMG506772 |
| 537 | CATGCTGTAAAAAAA | H503809 | 13 | 6 | 0 | 1 | 1 | | Unknown |
| 538 | CATGGTTCAATCCCT | H774358 | 13 | 3 | 0 | 2 | 0 | AA071520 | ze88g07.s1 Soares fetal heart NbHH19W *Homo sapiens* cDNA clone 366108 3' |
| | | | | | | | | N90742 | za90h10.s1 Soares fetal lung NbHL19W *Homo sapiens* cDNA clone 299875 3'. |
| | | | | | | | | AA086292 | zn52h06.s1 Stratagene muscle 937209 *Homo sapiens* cDNA clone 561851 3'. |
| 539 | CATGAATAAAGCCTT | H49304 | 12 | 4 | 0 | 0 | 0 | D11499 | Human HepG2 3'-directed MboI cDNA, clone a-35. |
| 540 | CATGGGAAGGTTTAC | H658173 | 12 | 2 | 0 | 1 | 0 | T16031 | IB2474 *Homo sapiens* cDNA 3'end. |
| 541 | CATGGGATGGCTTAT | H670333 | 12 | 1 | 0 | 6 | 1 | T74426 | yc82e01.r1 *Homo sapiens* cDNA clone 22306 5'. |
| 542 | CATGGGTGGCCCGGG | H715099 | 12 | 2 | 0 | 3 | 2 | N73771 | za61h02.s1 *Homo sapiens* cDNA clone 297075 3'. |
| | | | | | | | | W90388 | zh75f08.s1 Soares fetal liver spleen 1NFLS S1 *Homo sapiens* cDNA clone 417927 3' |
| | | | | | | | | F03786 | *H. sapiens* partial cDNA sequence; clone c-29h08. |
| 543 | CATGTACTGTACTTC | H817952 | 12 | 2 | 0 | 0 | 0 | U1463 | Human 11 beta-hydroxysteroid dehydrogenase type II |
| 544 | CATGCCCTTGCACTC | H360008 | 11 | 6 | 0 | 3 | 3 | T41121 | ya31a06.s5 *Homo sapiens* cDNA clone 62194 3' contains Alu repetitive element,. |
| 545 | CATGCGGTGGGACCA | H440966 | 11 | 4 | 0 | 2 | 0 | | Unknown |
| 546 | CATGGCCCCCAACCA | H611590 | 11 | 2 | 0 | 0 | 0 | | Unknown |
| 547 | CATGGCCGGCGCTC | H616862 | 11 | 2 | 0 | 0 | 0 | Z58486 | Unknown |
| 548 | CATGGGAGGCGCTCA | H666014 | 11 | 1 | 0 | 0 | 0 | | Unknown |
| 549 | CATGTCCCCGTTACA | H874226 | 11 | 11 | 0 | 0 | 0 | W68073 | zd42c12.s1 Soares fetal heart NbHH19W *Homo sapiens* cDNA clone 343318 3' similar to contains Alu repetitive element; |

NC: Normal Colon
TU: Colon Primary Tumor
CL: Colon Cancer Cell Line
PT: Pancreatic Primary Tumor
PC: Pancreatic Cancer Cell Line

TABLE 4

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 550 | CATGAAAGCAAACCA | H9222 | 0 | 6 | 1 | 3 | 11 | Examples | R38305 | yh95b04.s1 *Homo sapiens* cDNA clone 137455 3' |
|  |  |  |  |  |  |  |  |  | AA126719 | zk95b03.s1 Soares pregnant uterus NbHPU *Homo sapiens* cDNA clone 490541 3' |
|  |  |  |  |  |  |  |  |  | AA044296 | zk51c03.s1 Soares pregnant uterus NbHPU *Homo sapiens* cDNA clone 486340 3' |
|  |  |  |  |  |  |  |  |  | AA131586 | zl33c08.s1 Soares pregnant uterus NbHPU *Homo sapiens* cDNA clone 503726 3'. |
| 551 | CATGAAAGCAGTTTA | H9408 | 1 | 5 | 2 | 21 | 3 | Examples | AA157983 | zo71h12.s1 Stratagene pancreas (#937208) *Homo sapiens* cDNA clone 592391 3' |
|  |  |  |  |  |  |  |  |  | AA292929 | zt54c04.s1 Soares ovary tumor NbHOT *Homo sapiens* cDNA clone 726174 3' |
|  |  |  |  |  |  |  |  |  | AA159306 | zo78c07.s1 Stratagene pancreas (#937208) Homo zo78c07.s1 Stratagene pancreas (#937208) Homo |
|  |  |  |  |  |  |  |  |  | R54012 | yj70h01.s1 *Homo sapiens* cDNA clone 154129 3' |
|  |  |  |  |  |  |  |  |  | T62936 | yb99t08.s1 *Homo sapiens* cDNA clone 79335 3' |
| 552 | CATGAAAGCGGGGCT | H9898 | 0 | 0 | 0 | 0 | 13 | Examples | X52426 | H. sapiens mRNA for cytokeratin 13 |
| 553 | CATGAAATCCTGGGT | H13803 | 0 | 1 | 1 | 16 | 2 | Examples | X51698 | H.sapiens spasmolytic polypeptide (SP) mRNA. |
| 554 | CATGAAATGGACAAC | H14865 | 0 | 0 | 1 | 0 | 13 | Examples | N70419 | za61d12.s1 *Homo sapiens* cDNA clone 297047 3' |
|  |  |  |  |  |  |  |  |  | AA411599 | zv16g01.r1 Soares NhHMPu S1 *Homo sapiens* cDNA clone 753840 3' |
|  |  |  |  |  |  |  |  |  | AA410508 | zv16g01.s1 Soares NhHMPu S1 *Homo sapiens* cDNA clone 753840 |
| 555 | CATGAACCAGTTTGT | H21247 | 1 | 1 | 6 | 8 | 13 | Examples | AA115723 | zl86g12.s1 Stratagene colon (#937204) *Homo sapiens* cDNA clone 511558 3' |
|  |  |  |  |  |  |  |  |  | AA132875 | zo19c04.s1 Stratagene colon (#937204) *Homo sapiens* cDNA clone 587358 3' |
|  |  |  |  |  |  |  |  |  | AA147677 | zo44a06.s1 Stratagene endothelial cell 937223 *Homo sapiens* cDNA clone 589714 3' |
|  |  |  |  |  |  |  |  |  | AA206883 | zq81h12.s1 Stratagene hNT neuron (#937233) *Homo sapiens* cDNA clone 648071 3' |
| 556 | CATGAACTCTTGAAG | H30689 | 3 | 7 | 13 | 13 | 17 | Examples | R51318 | yg72f03.s1 *Homo sapiens* cDNA clone 38681 3' |
|  |  |  |  |  |  |  |  |  | T35270 | EST82235 *Homo sapiens* cDNA 3' end similar to None |
|  |  |  |  |  |  |  |  |  | AA412071 | zt65h12.s1 Soares testis NHT *Homo sapiens* cDNA clone 727271 3' |
| 557 | CATGAACTGCTTCAA | H31221 | 7 | 6 | 8 | 6 | 130 | Examples | N63154 | yz37h12.s1 *Homo sapiens* cDNA clone 285263 3' |
|  |  |  |  |  |  |  |  |  | T87236 | yc81h04.s1 *Homo sapiens* cDNA clone 22603 3' |
|  |  |  |  |  |  |  |  |  | AA150720 | zl46f04.s1 Soares pregnant uterus NbHPU *Homo sapiens* cDNA clone 504991 3' |
| 558 | CATGAACTTGGCCAT | H32405 | 0 | 0 | 0 | 8 | 11 | Examples | AA045773 | zl68b12.s1 Stratagene colon (#937204) *Homo sapiens* |
|  |  |  |  |  |  |  |  |  | X07819 | Human pump-1 mRNA homolog. to metalloproteinase, |
|  |  |  |  |  |  |  |  |  | L22523 | Human matrilysin gene, exon 5 |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 559 | CATGAAGATCCCCGC | H36183 | 5 | 10 | 14 | 12 | 23 | Examples | R72650 W70287 | yj95e05.s1 *Homo sapiens* cDNA clone 156512 3' zd58e02.s1 Soares fetal heart NbHH19W *Homo sapiens* cDNA clone 344858 3' similar to SW:CUTA_ECOLI P36654 PERIPLASMIC DIVALENT CATION TOLERANCE PROTEIN CUTA |
|  |  |  |  |  |  |  |  |  | R72650 | yj95e05.s1 *Homo sapiens* cDNA clone 156512 3' similar to SP:CYCY_ECOLI P36654 C-TYPE CYTOCHROME BIOGENESIS PROTEIN CYCY |
|  |  |  |  |  |  |  |  |  | AA181976 | zp61a11.s1 Stratagene endothelial cell 937223 *Homo sapiens* cDNA clone 624668 3' similar to SW:CUTA_ECOLI P36654 PERIPLASMIC DIVALENT CATION TOLERANCE PROTEIN CUTA |
| 560 | CATGAAGGGAGGGTC | H43180 | 6 | 3 | 8 | 15 | 41 | Examples | U46751 | Human phosphotyrosine independent ligand p62 for the Lck SH2 domain mRNA, complete cds |
| 561 | CATGAAGTTGCTATT | H48756 | 10 | 9 | 18 | 31 | 27 | Examples | J03077 M86181 D00422 J03015 | Human co-beta glucosidase (proactivator) mRNA Human prosaposin (PSAP) gene Human sphingolipid activator proteins, mRNA *Homo sapiens* sphingolipid activator protein 1 mRNA |
|  |  |  |  |  |  |  |  |  | M60255 | Human mutant cerebroside sulfate activator protein |
| 562 | CATGAATGAAAAAAA | H57345 | 0 | 1 | 5 | 2 | 10 | No Match |  |  |
| 563 | CATGACAAACTGTGG | H66031 | 17 | 4 | 24 | 5 | 60 | Examples | N22375 AA084643 | yw37d01.s1 *Homo sapiens* cDNA clone 254401 3' zn20e01.s1 Stratagene neuroepithelium NT2RAMI 937234 *Homo sapiens* cDNA clone 547992 3' |
|  |  |  |  |  |  |  |  |  | AA279290 AA046253 | zs84a06.s1 Soares NbHTGBC *Homo sapiens* cDNA clone 704146 3' zf12a02.s1 Soares fetal heart NbHH19W *Homo sapiens* cDNA clone 376682 3' |
| 564 | CATGACAACTCAATA | H67396 | 2 | 7 | 7 | 16 | 37 | Examples | Z58016 AA151668 | *H.sapiens* CpG DNA, clone 26c7, zo29c02.s1 Stratagene colon (#937204) *Homo sapiens* cDNA clone 588290 3' similar to SW:B13_MOUSE P28662 BRAIN PROTEIN I3 |
|  |  |  |  |  |  |  |  |  | W02958 | za07e06.r1 Soares melanocyte 2NbHM *Homo sapiens* cDNA clone 291874 5' |
| 565 | CATGACACCCTGTGC | H71151 | 0 | 1 | 0 | 2 | 14 | Examples | AA1556464 | zo70e05.s1 Stratagene pancreas (#937208) *Homo sapiens* cDNA clone 592256 3' |
|  |  |  |  |  |  |  |  |  | AA025673 | ze90h09.s1 Soares fetal heart NbHH19W *Homo sapiens* cDNA clone 366305 3' |
| 566 | CATGACCATTGGATT | H85924 | 0 | 8 | 5 | 13 | 4 | Examples | N70895 X02491 J04164 | za89h12.s1 *Homo sapiens* cDNA clone 299783 3' Human interferon-inducible mRNA (cDNA 9-27) Human interferon-inducible protein 9-27 mRNA |
|  |  |  |  |  |  |  |  |  | X84958 | *H.sapiens* mRNA for interferon-induced 17kDa membra |
| 567 | CATGACCCTTTAACA | H90050 | 1 | 4 | 2 | 13 | 7 | Examples | X56841 X64879 | *H.sapiens* HLA-E gene. *H.sapiens* mRNA for HLA-E heavy chain (exons 4-7) |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 568 | CATGACGCCGTGGT | H91579 | 49 | 22 | 45 | 70 | 94 | Examples | M21186 M61107 | Human neutrophil cytochrome b light chain p22A Human p22-phox (CYBA) gene, exons 3 and 4 |
| 569 | CATGACCTGTGACCA | H97158 | 0 | 3 | 0 | 28 | 17 | Examples | D00244 K02286 M15476 X02419 | Human Pro-urokinase gene, Human urokinase gene, 3′ end Human pro-urokinase mRNA, complete cds Human uPA gene for urokinase-plasminogen activator |
| 570 | CATGACGCCCTGCTC | H103912 | 0 | 1 | 0 | 11 | 2 | Examples | L08835 M87313 | Human myotonic dystrophy kinase (DM kinase) gene Homo sapiens myotonin protein kinase (DM) mRNA |
| 571 | CATGACGTGGTGATG | H113380 | 2 | 4 | 4 | 5 | 20 | Examples | H44451 AA157329 | yo75f06.s1 Homosapiens cDNA clone 183779 3′ z042f07.s1 Stratagene endothelial cell 937223 Homo sapiens cDNA clone 589573 3′ similar to SW:L10K_RATQ05310 LEYDIG CELL TUMOR 10 KD PROTEIN |
| | | | | | | | | | W46455 | zc32g06.s1 Soares senescent fibroblasts NbHSF Homo sapiens cDNA clone 324058 3′ similar to SW:L10K_RAT Q05310 LEYDIG CELL TUMOR 10 KD PROTEIN |
| 572 | CATGACTCAGCCCGG | H119383 | 0 | 0 | 3 | 21 | 3 | Examples | M92357 | Homo sapiens B94 protein mRNA, complete cds. |
| 573 | CATGACTGAGGAAAG | H123521 | 0 | 0 | 0 | 53 | 22 | Examples | X64875 M31159 | H.sapiens mRNA for insulin-like growth factor binding protein 3 Human growth hormone-dependent insulin-like growth factor binding protein 3 |
| | | | | | | | | | M35878 S56205 | Human insulin like growth factor-binding protein-3 insulin-like growth factor binding protein 3 {3′ region} |
| 574 | CATGACTGCCCGCTG | H124264 | 1 | 0 | 0 | 22 | 9 | Examples | U65932 U65937 | Human extracellular matrix protein 1 (ECM1) mRNA Human extracellular matrix protein 1 (ECM1) gene, exon 9 |
| 575 | CATGACTGTATTTTC | H126208 | 3 | 4 | 9 | 2 | 22 | Examples | AA148916 | zo03f09.s1 Stratagene colon (#937204) Homo sapiens cDNA clone 566633 3′ |
| | | | | | | | | | AA129137 | zo12a11.s1 Stratagene colon (#937204) Homo sapiens cDNA clone 586652 3′ |
| | | | | | | | | | AA115437 | zl85g09.s1 Stratagene colon (#937204) Homo sapiens cDNA clone 511456 3′ |
| | | | | | | | | | AA126967 | zl87e07.s1 Stratagene colon (#937204) Homo sapiens cDNA clone 511620 3′ |
| 576 | CATGAGCACTGCAGC | H149395 | 1 | 2 | 6 | 3 | 16 | Examples | R24613 | yh36c03.r1 Homo sapiens cDNA clone 131812 |
| 577 | CATGAGCAGGAGCGT | H150055 | 1 | 0 | 0 | 0 | 15 | Examples | H43243 | yp05e05.r1 Homo sapiens cDNA clone 186560 5′ |
| 578 | CATGAGCTGTATTCT | H162622 | 0 | 2 | 0 | 1 | 11 | Examples | X54942 | H.sapiens ckshs2 mRNA for Cks1 protein homologue |
| 579 | CATGAGGATGACCCC | H167446 | 1 | 7 | 12 | 10 | 13 | Examples | AA044081 | zk50g07.s1 Soares pregnant uterus NbHPU Homo sapiens cDNA clone 486300 3′ |
| | | | | | | | | | AA044211 | zk50g07.r1 Soares pregnant uterus NbHPU Homo sapiens cDNA clone 486300 5′ similar to PIR:A40533 A40533 cAMP-dependent protein kinase major membrane substrate |
| 580 | CATGAGGTCTTCAAT | H178129 | 4 | 2 | 0 | 60 | 2 | Examples | X14787 | Class A, Human mRNA for thrombospondin. |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 581 | CATGAGGGTGCGGGGG | H178603 | 0 | 2 | 2 | 1 | 11 | Examples | R27738 H00276 | yh64f11.s1 *Homo sapiens* cDNA clone 134541 3' yj22f12.s1 *Homo sapiens* cDNA clone 149519 3' similar to SP:ZK637.5 CE00436 ARSA |
| 582 | CATGAGTATCTGGGA | H183787 | 3 | 3 | 1 | 15 | 73 | Examples | AA076235 H13159 AA146632 | zm19d07.s1 Stratagene pancreas (#937208) *Homo sapiens* cDNA clone 526093 3' yj16c04.s1 *Homo sapiens* cDNA clone 148902 3' zo71e11.s1 Stratagene pancreas (#937208) *Homo sapiens* cDNA clone 592364 3' |
| 583 | CATGATACTTTAATT | H204740 | 1 | 0 | 3 | 18 | 9 | Examples | X80062 U01691 X12454 M18366 M21731 J03745 | *H.sapiens* SA mRNA. Human annexin V (ANX5) gene Human mRNA for vascular anticoagulant Human placental anticoagulant protein (PAP) mRNA Human lipocortin-V mRNA, complete cds Human endonexin II mRNA, complete cds |
| 584 | CATGATCAAGAATCC | H213518 | 2 | 1 | 5 | 25 | 1 | Examples | J03909 aa383911 | GAMMA-INTERFERON-INDUCIBLE PROTEIN IP-30 PRECURSOR (HUMAN) EST93784 Thymus II *Homo sapiens* cDNA 3' end similar to interferon, gamma transducer 1 |
| 585 | CATGATCAAGGGTGT | H213679 | 12 | 9 | 25 | 12 | 156 | Examples | U09953 U21138 D14531 | Human ribosomal protein L9 mRNA Human ribosomal protein L9 mRNA, complete cds Human mRNA for human homologue of rat ribosomal protein |
| 586 | CATGATCAAGTTCGA | H213751 | 0 | 2 | 8 | 3 | 10 | Examples | AA063259 | zm03a05.s1 Stratagene corneal stroma (#937222) *Homo sapiens* cDNA clone 513008 3' |
| 587 | CATGATCCGGCGCCA | H219750 | 16 | 7 | 14 | 12 | 40 | Examples | L42856 | RNA polymerase II transcription factor SIII p18 subunit mRNA |
| 588 | CATGATGAAACTTCG | H229502 | 1 | 0 | 0 | 17 | 4 | Examples | Z59242 | *H.sapiens* CpG DNA, clone 13a10, reverse read cpg1 |
| 589 | CATGATGCGAAAGGC | H235531 | 2 | 3 | 12 | 3 | 22 | Examples | Z25820 | *H.sapiens* mRNA for mitochondrial dodecenoyl-CoA dehydrogenase |
| | | | | | | | | | L24774 | *Homo sapiens* delta3, delta2-CoA-isomerase mRNA |
| 590 | CATGATGTCTTCGTT | H243676 | 0 | 0 | 1 | 0 | 14 | Examples | M84711 | 40S RIBOSOMAL PROTEIN S3A (HUMAN) |
| 591 | CATGATGTCTTTTCT | H243710 | 1 | 2 | 1 | 14 | 2 | Examples | M62403 U20982 | Human insulin-like growth factor binding protein 4 Human insulin-like growth factor binding protein-4 (IGFBP4) gene, promoter and complete cds |
| 592 | CATGATGTGTAACGA | H244487 | 0 | 4 | 5 | 44 | 94 | Examples | Z33457 | *H.sapiens* mts1 gene. |
| | | | | | | | | | M80563 | Human CAPL protein mRNA, complete cds |
| 593 | CATGCAACTTAAAGC | H270083 | 0 | 1 | 2 | 10 | 1 | Examples | N23307 | yx70o09.s1 *Homo sapiens* cDNA clone 267065 3' similar to gb:L12350 THROMBOSPONDIN 2 PRECURSOR (HUMAN) |
| 594 | CATGCACCTGTCCTT | H286424 | 0 | 4 | 2 | 10 | 1 | Examples | AA285023 | zt25e11.s1 Soares ovary tumor NbHOT *Homo sapiens* cDNA clone 714188 3' similar to gb:M33680 CD81 ANTIGEN (HUMAN) |
| | | | | | | | | | M33680 | CD81 antigen |
| 595 | CATGCACTCAATAAA | H291889 | 0 | 0 | 2 | 3 | 19 | Examples | D78203 | Neurosin |
| | | | | | | | | | U62801 | protease M |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 596 | CATGCAGCCTGGGGC | H300971 | 0 | 0 | 0 | 0 | 10 | Examples | AA149942 | zo68d04.s1 Stratagene pancreas (#937208) *Homo sapiens* cDNA clone 592039 3' similar to TR:E218488 E218488 TRYPTASE |
| 597 | CATGCAGCGCGCCCT | H301462 | 4 | 11 | 12 | 10 | 21 | Examples | AA187553 | zp66b09.s1 Stratagene endothelial cell 937223 *Homo sapiens* cDNA clone 625145 5' similar to gb:M16937 HOMEOBOX PROTEIN HOX-B7 (HUMAN);contains element MER22 repetitive element |
|  |  |  |  |  |  |  |  |  | M16937 | Homeobox protein HOX-B7 |
| 598 | CATGCAGGTTGTCCT | H307126 | 0 | 0 | 4 | 0 | 10 | No Match | U14972 | Human ribosomal protein S10 mRNA |
| 599 | CATGCAGTCTCTCAA | H309109 | 2 | 6 | 6 | 2 | 17 | Examples | U27293 | Human leukotriene A4 hydrolase gene |
| 600 | CATGCATCCCGTGAC | H316857 | 0 | 3 | 3 | 3 | 13 | Examples | J02959 | Human leukotriene A-4 hydrolase mRNA, complete cds |
| 601 | CATGCATTCCTCCTT | H325080 | 0 | 2 | 5 | 13 | 3 | Examples | X82434 | *H.sapiens* mRNA for emerin |
| 602 | CATGCCACCCCACC | H333138 | 3 | 7 | 17 | 18 | 2 | Examples | M88338 | Human serum constituent protein (MSE55) mRNA |
| 603 | CATGCCAGTGGCCCG | H339606 | 23 | 11 | 37 | 22 | 56 | Examples | U14971 | Human ribosomal protein S9 mRNA |
| 604 | CATGCCATTTCTGG | H344031 | 0 | 2 | 6 | 1 | 10 | Examples | L01697 | Homosapiens alpha-1 type XV collagen mRNA |
| 605 | CATGCCCAAGCTAGC | H344691 | 19 | 8 | 8 | 18 | 44 | Examples | X54079 | Human mRNA for heat shock protein HSP27. |
|  |  |  |  |  |  |  |  |  | Z23090 | *H.sapiens* mRNA for 28 kDa heat shock protein |
|  |  |  |  |  |  |  |  |  | X16477 | Human mRNA fragment for estrogen-regulated 24k protein |
|  |  |  |  |  |  |  |  |  | S74571 | estrogen receptor-related protein = 27-kDa heat shock protein |
| 606 | CATGCCCATCCGAAA | H347489 | 20 | 15 | 43 | 19 | 61 | Examples | X69392 | *H.sapiens* mRNA for ribosomal protein L26. |
|  |  |  |  |  |  |  |  |  | L07287 | Human ribosomal protein L26 (RPL26) gene |
| 607 | CATGCCCCTGCAGA | H350099 | 0 | 1 | 6 | 14 | 25 | Examples | U40434 | Human mesothelin or CAK1 antigen precursor mRNA |
|  |  |  |  |  |  |  |  |  | D49441 | Human mRNA for pre-pro-megakaryocyte potentiating factor, complete cds. |
| 608 | CATGCCCGCATAGAT | H353481 | 0 | 0 | 0 | 8 | 11 | Examples | U12819 | Human p16-INK4 (p16) gene |
|  |  |  |  |  |  |  |  |  | U38945 | Human hypothetical 18.1 kDa protein (CDKN2A) mRNA |
|  |  |  |  |  |  |  |  |  | S69804 | MTS1 = multiple tumor suppressor 1/cyclin-dependent kinase 4 inhibitor p16 |
|  |  |  |  |  |  |  |  |  | S69822 | CDK4I = cyclin-dependent kinase 4 inhibitor |
|  |  |  |  |  |  |  |  |  | S78535 | tumor suppressor gene, P16/MTS1/CDKN2 = cell cycle cycle negative regulator beta form |
| 609 | CATGCCCTCCTCTGGGG | H357867 | 8 | 2 | 5 | 14 | 34 | Examples | Z47319 | *H.sapiens* mRNA for expressed sequence tag (clone 21f67l19) |
|  |  |  |  |  |  |  |  |  | AA398406 | zt60h12.s1 Soares testis NHT *Homo sapiens* cDNA clone 726791 3' |
| 610 | CATGCCGGCCCTACC | H370034 | 4 | 4 | 1 | 14 | 19 | Examples | U21049 | Human DD96 mRNA |
| 611 | CATGCCTGGTTCCAA | H387925 | 0 | 2 | 1 | 30 | 99 | Examples | X03212 | KERATIN, TYPE II CYTOSKELETAL 7 |
|  |  |  |  |  |  |  |  |  | AA187637 | zp73f01.s1 Stratagene HeLa cell s3 937216 *Homo sapiens* cDNA clone 625849 3' |
| 612 | CATGCCTTTGAACAG | H392709 | 5 | 3 | 6 | 2 | 23 | Examples | AA176457 | zp35g11.s1 Stratagene muscle 937209 *Homo sapiens* cDNA clone 611492 3' similar to TR:G663269 G663269 BOLA |
|  |  |  |  |  |  |  |  |  | AA176541 | zp35e11.s1 Stratagene muscle 937209 *Homo sapiens* cDNA clone 611468 3' similar to TR:G663269 G663269 BOLA. |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 613 | CATGGCGCCGACGATG | H415844 | 21 | 13 | 45 | 75 | 7 | Examples | X02492 | Human interferon-inducible mRNA fragment |
| 614 | CATGCTCAACAGCAA | H475429 | 2 | 5 | 10 | 6 | 17 | Examples | T53402 | ya88g05.s1 Homo sapiens cDNA clone 68792 3' |
|  |  |  |  |  |  |  |  |  | W69493 | zd47g08.s1 Soares fetal heart NbHH19W Homo sapiens cDNA clone 343838 3' similar to PIR:S24168 S24168 hypothetical protein - human |
| 615 | CATGCTCAACCCCCC | H475478 | 1 | 4 | 2 | 23 | 1 | Examples | X13916 | Human mRNA for LDL-receptor related protein |
| 616 | CATGCTGAGAAACTG | H493576 | 2 | 3 | 1 | 8 | 18 | Examples | X80335 | H.sapiens (24) Ferritin H pseudogene. |
| 617 | CATGCTGAGTCTCCC | H494454 | 1 | 4 | 4 | 21 | 13 | Examples | X04828 | Human mRNA for G(i) protein alpha-subunit |
| 618 | CATGCTGCTAIACGA | H498887 | 16 | 30 | 28 | 30 | 44 | Examples | U14966 | Human ribosomal protein L5 mRNA |
| 619 | CATGCTGCTGAGTGA | H499247 | 1 | 3 | 4 | 13 | 13 | Examples | T90665 | yd41g08.s1 Homo sapiens cDNA clone 110846 3' |
|  |  |  |  |  |  |  |  |  | AA338799 | EST43791 Fetal brain I Homo sapiens cDNA 3' end similar to steroid hormone receptor hERR1 |
| 620 | CATGCTGGCGCCGAT | H501337 | 0 | 0 | 4 | 0 | 10 | Examples | H97236 | yv98b06.s1 Homo sapiens cDNA clone 250739 3' |
| 621 | CATGCTTCCAGCTAA | H513181 | 64 | 23 | 36 | 53 | 104 | Examples | C14084 | Human fetal brain cDNA 3'-end GEN-018D10 |
| 622 | CATGCTTCCTTGCCT | H514022 | 0 | 3 | 4 | 89 | 7 | Examples | D00017 | Human lipocortin II mRNA |
|  |  |  |  |  |  |  |  |  | Z19574 | H.sapiens gene for cytokeratin 17. |
|  |  |  |  |  |  |  |  |  | X62571 | H.sapiens mRNA for kenatin-related protein |
| 623 | CATGCTTTCTTCCCT | H522198 | 0 | 2 | 1 | 16 | 4 | Examples | X05803 | Human radiated keratinocyte mRNA 266 |
| 624 | CATGGAAAAAAAAAA | H524289 | 7 | 14 | 21 | 26 | 37 | Examples | X79067 | H.sapiens ERF-1 mRNA 3' end. |
|  |  |  |  |  |  |  |  |  | X51779 | Human mRNA containing an Alu repeat |
| 625 | CATGGAAAACAAGATG | H525348 | 4 | 7 | 14 | 8 | 22 | Examples | X82240 | H.sapiens mRNA for Tcell leukemia/lymphoma 1 |
|  |  |  |  |  |  |  |  |  | V00572 | Human mRNA encoding phosphoglycerate kinase. |
|  |  |  |  |  |  |  |  |  | D29018 | Human keratinocyte cDNA, clone 001 |
| 626 | CATGGAAATACAGTT | H527436 | 49 | 35 | 10 | ## | 36 | Examples | L00160 | Human phosphoglycerate kinase (pgk) mRNA |
|  |  |  |  |  |  |  |  |  | X05344 | Human mRNA for cathepsin D |
|  |  |  |  |  |  |  |  |  | M11233 | Human cathepsin D mRNA, complete cds |
| 627 | CATGGAAATGATGAG | H527929 | 4 | 7 | 5 | 14 | 26 | Examples | T90296 | yd42l03.s1 Homo sapiens cDNA clone 110909 3' similar to SP:R151.9 CE00827 |
|  |  |  |  |  |  |  |  |  | AA320942 | EST23523 Adipose tissue, brown Homo sapiens cDNA 3' end |
| 628 | CATGGAAGATGTGTG | H533436 | 3 | 7 | 16 | 6 | 28 | Examples | AA181811 | zp64f07.s1 Stratagene endothelial cell 937223 Homo sapiens cDNA clone 624997 3' |
|  |  |  |  |  |  |  |  |  | AA148508 | zl06c06.s1 Soares pregnant uterus NbHPU Homo sapiens cDNA clone 491530 3' similar to WP:ZK652.2 CE00448 |
| 629 | CATGGAATTTATAA | H540621 | 6 | 3 | 10 | 9 | 28 | Examples | L21950 | Human peripheral benzodiazepine receptor related mRNA |
|  |  |  |  |  |  |  |  |  | M36035 | Human peripheral benzodiazepine receptor (hpbs) mRNA |
| 630 | CATGGACAAAAAAAA | H540673 | 1 | 2 | 10 | 3 | 17 | No Match |  |  |
| 631 | CATGGACCACCTTTA | H545152 | 0 | 1 | 0 | 11 | 2 | Examples | U19718 | Human microfibril-associated glycoprotein (MFAP2). |
| 632 | CATGGACCAGGCCCT | H545430 | 0 | 3 | 0 | 20 | 18 | Examples | M75165 | H.sapiens epithelial tropomyosin (TM1) mRNA |
|  |  |  |  |  |  |  |  |  | M12125 | Human fibroblast muscle-type tropomyosin mRNA |
|  |  |  |  |  |  |  |  |  | M74817 | Human tropomyosin-1 (TM-beta) mRNA, complete cds |
| 633 | CATGGACCCCAAGGC | H546059 | 2 | 5 | 9 | 16 | 10 | Examples | M74092 | Human cyclin mRNA |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 634 | CATGGACCCTGCCCT | H546710 | 31 | 36 | 20 | 71 | 65 | Examples | L37033 | *Homo sapiens* FK-506 binding protein homologue |
| 635 | CATGGACCTATCTCT | H548062 | 0 | 1 | 0 | 13 | 1 | Examples | N90046 | zb37g02.s1 Soares parathyroid tumor NbHPA *Homo sapiens* cDNA clone 305810 3' |
|  |  |  |  |  |  |  |  |  | AA115048 | zl06a10.s1 Soares pregnant uterus NbHPU *Homo sapiens* cDNA clone 491514 3' |
| 636 | CATGGACGGCGCAGG | H551315 | 3 | 4 | 5 | 32 | 3 | Examples | M63193 | Human platelet-derived endothelial cell growth factor |
| 637 | CATGGACTCTCTGTT | H554876 | 1 | 4 | 3 | 0 | 14 | Examples | M61764 | Human gamma-tubulin mRNA, |
| 638 | CATGGAGAGCTTTGC | H559615 | 0 | 0 | 0 | 2 | 10 | Examples | D17793 | Human mRNA (HA1753) for ORF |
| 639 | CATGGAGAGTGTCTG | H560056 | 0 | 5 | 8 | 32 | 11 | Examples | S68252 | TIMP-1 = metalloproteinase inhibitor |
|  |  |  |  |  |  |  |  |  | X02598 | EPA glycoprotein (erythroid-potentiating activity) |
|  |  |  |  |  |  |  |  |  | X03124 | tissue inhibitor of metalloproteinase 2 |
| 640 | CATGGAGCAGGATGA | H561807 | 0 | 0 | 0 | 1 | 12 | No Match | AA214523 | zr89c01.s1 Soares NbHTGBC *Homo sapiens* cDNA clone 682848 3' |
| 641 | CATGGAGGGAGTTCC | H567486 | 1 | 1 | 0 | 4 | 13 | Examples | N30324 | yw75d01.s1 Soares *Homo sapiens* cDNA clone 258049 3' |
| 642 | CATGGAGTCCGGAGC | H570787 | 0 | 0 | 2 | 1 | 10 | Examples | X70070 | H.sapiens mRNA for neurotensin receptor. |
| 643 | CATGGAGTTATGTTG | H572656 | 0 | 0 | 3 | 0 | 10 | Examples | H57673 | yr27a10.s1 Soares *Homo sapiens* cDNA clone 206490 3' |
|  |  |  |  |  |  |  |  |  | W94333 | ze12c08.s1 Soares fetal heart NbHH19W *Homo sapiens* cDNA clone 358766 3' similar to SW:YA94_SCHPO Q09783 HYPOTHETICAL 11.4 KD PROTEIN C13G6.04 IN CHROMOSOME I |
| 644 | CATGGAGTTCGACCT | H572806 | 7 | 3 | 7 | 15 | 29 | No Match | AA046631 | zk72006.s1 Soares pregnant uterus NbHPU *Homo sapiens* cDNA clone 483363 3' |
| 645 | CATGGATTAAGTGAG | H585913 | 3 | 5 | 2 | 2 | 19 | Examples | R91942 | y406g03.s1 *Homo sapiens* cDNA clone 196180 3' |
|  |  |  |  |  |  |  |  |  | AA040439 | zk46c12.s1 Soares pregnant uterus NbHPU *Homo sapiens* cDNA clone 485878 3' |
| 646 | CATGGATTGAACCTC | H587800 | 1 | 0 | 5 | 1 | 12 | Examples | U60205 | methyl sterol oxidase (ERG25) |
| 647 | CATGGCAAAAAAAAA | H589825 | 17 | 13 | 29 | 73 | 38 | No Match |  |  |
| 648 | CATGGCATTTAAATA | H605956 | 2 | 10 | 8 | 3 | 55 | Examples | X60489 | Human mRNA for elongation factor-1-beta, |
|  |  |  |  |  |  |  |  |  | X60656 | H.sapiens mRNA for elongation factor 1-beta |
| 649 | CATGGCCAACAACGA | H606471 | 0 | 0 | 0 | 12 | 1 | Examples | U08021 | Human nicotinamide N-methyltransferase (NNMT) mRNA, 0 |
| 650 | CATGGCCCCCAATAA | H611597 | 1 | 4 | 1 | 47 | 9 | Examples | X15256 | Human mRNA for 14kDa beta-galactoside-binding lectin |
|  |  |  |  |  |  |  |  |  | X14829 | Human mRNA for beta-galactoside-binding lectin |
|  |  |  |  |  |  |  |  |  | J04456 | Human 14 kd lectin mRNA, complete cds |
|  |  |  |  |  |  |  |  |  | S44881 | HL14 = beta-galactoside binding protein |
| 651 | CATGGCCGCTACTTC | H616224 | 0 | 0 | 1 | 3 | 16 | Examples | AA054483 | zk82d04.s1 Soares pregnant uterus NbHPU *Homo sapiens* cDNA clone 489319 5' similar to contains Alu repetitive element |
| 652 | CATGGCCGTCGGAGG | H617891 | 8 | 5 | 2 | 44 | 3 | Examples | AA243725 | zr68g12.s1 Soares NhHMPu S1 *Homo sapiens* cDNA clone 668614 3' similar to gb:X02492 INTERFERON-INDUCED PROTEIN 6-16 PRECURSOR (HUMAN) |
| 653 | CATGGCCTACCCGAG | H618841 | 0 | 4 | 4 | 23 | 39 | Examples | X13425 | Human mRNA fbr pancreatic carcinoma marker GA733-1, 0 |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 654 | CATGGCGGGGTGGAG | H633577 | 3 | 8 | 5 | 27 | 6 | Examples | AA136985 | zl02b03.s1 Soares pregnant uterus NbHPU *Homo sapiens* cDNA clone 491117 3' |
| 655 | CATGGCTCAGCTGGA | H643707 | 12 | 29 | 24 | 35 | 35 | Examples | AA053346 | zl70h04.s1 Stratagene colon (#937204) *Homo sapiens* cDNA clone 510007 3' similar to gb:Z21507 ELONGATION FACTOR 1-DELTA |
| 656 | CATGGCTTTTCAGAC | H655177 | 1 | 6 | 7 | 13 | 10 | Examples | U43368 | Human VEGF related factor isoform VRF186 precursor, 0 |
| | | | | | | | | | U52819 | Human vascular endothelial growth factor B 186 |
| 657 | CATGGGAAAAAAAAA | H655361 | 11 | 8 | 30 | 16 | 38 | Examples | M38259 | Human cytochrome c oxidase subunit VIb |
| | | | | | | | | | M60748 | Human histone H1 (H1F4) gene, complete cds |
| | | | | | | | | | M73239 | Human (clone SF1) hepatocyte growth factor (HGF) |
| | | | | | | | | | M73240 | Human (clone SF2) hepatocyte growth factor (HGF) |
| 658 | CATGGGAAAAGTTGGT | H655547 | 18 | 13 | 3 | 70 | 1 | Examples | X02920 | Human mRNA for alpha 1-antitrypsin carboxyterminal, 0 |
| | | | | | | | | | X01683 | Human mRNA for alpha 1-antitrypsin |
| | | | | | | | | | V00496 | Human messenger RNA for alpha-1-antitrypsin |
| | | | | | | | | | J00067 | Human alpha-1 antitrypsin gene, 3' end |
| 659 | CATGGGAAGGGAGGC | H658059 | 0 | 0 | 4 | 6 | 16 | Examples | AA127040 | zl22b01.s1 Soares pregnant uterus NbHPU *Homo sapiens* cDNA clone 502633 3' |
| | | | | | | | | | W81387 | zd86f06.s1 Soares fetal heart NbHH19W *Homo sapiens* cDNA clone 347555 3' |
| 660 | CATGGGAGTCATTGT | H666943 | 6 | 5 | 6 | 10 | 32 | Examples | H45477 | yo72h08.s1 *Homo sapiens* cDNA clone 183519 3' |
| 661 | CATGGGAGTGTGCGT | H667367 | 0 | 0 | 1 | 1 | 10 | Examples | D26598 | Human mRNA for proteasome subunit HsC10-II, 0 |
| | | | | | | | | | N74310 | za78co1.s1 *Homo sapiens* cDNA clone 298656 3' |
| | | | | | | | | | H92750 | yt92e01.s1 *Homo sapiens* cDNA clone 231768 3' |
| | | | | | | | | | T24084 | seq2272 *Homo sapiens* cDNA clone ssb4H3MA(extended-ft-6) 3' |
| 662 | CATGGGATTGTCTGG | H671455 | 3 | 7 | 13 | 5 | 21 | Examples | X17567 | *H.sapiens* RNA for snRNP protein B |
| | | | | | | | | | M34081 | Human small nuclear ribonucleoprotein particle SmB |
| 663 | CATGGGCCCCTCACC | H677330 | 0 | 0 | 2 | 9 | 22 | Examples | M69054 | Human insulin-like growth factor binding protein 6, 0 |
| | | | | | | | | | M62402 | Human insulin-like growth factor binding protein 6 |
| 664 | CATGGGCCCTCTGAG | H677753 | 0 | 1 | 4 | 7 | 14 | Examples | N74323 | za78d08.s1 *Homo sapiens* cDNA clone 298671 3' |
| | | | | | | | | | H46766 | yo18t08.s1 *Homo sapiens* cDNA clone 178311 3' |
| | | | | | | | | | H41102 | yn88a08.s1 *Homo sapiens* cDNA clone 175478 3' |
| 665 | CATGGGCTGTCTGG | H686815 | 0 | 1 | 3 | 13 | 22 | Examples | AA074777 | zm84b09.s1 Stratagene ovarian cancer (#937219) *Homo sapiens* cDNA clone 544601 3' |
| | | | | | | | | | AA062735 | zm04a04.s1 Stratagene corneal stroma (#937222) *Homo sapiens* cDNA clone 513102 3' |
| | | | | | | | | | AA112905 | zm63f12.s1 Stratagene fibroblast (#937212) *Homo sapiens* cDNA clone 530351 3' |
| 666 | CATGGGGAAGCAGAT | H688713 | 25 | 7 | 9 | 0 | 72 | No Match | | |
| 667 | CATGGGGAGGGGTGG | H690863 | 2 | 3 | 1 | 16 | 2 | No Match | | |
| 668 | CATGGGGAGGTAGCA | H690890 | 1 | 0 | 1 | 14 | 1 | No Match | | |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 669 | CATGGGCATCTCTT | H693112 | 1 | 1 | 3 | 39 | 2 | Examples | V00523 X00274 K01171 J00202 | Human mRNA for histocompatibility antigen HLA-DR Human gene for HLA-DR alpha heavy chain a class II Human HLA-DR alpha-chain mRNA human hla-dr heavy chain gene; 3' flank |
| 670 | CATGGGTGGGAGAT | H715401 | 1 | 4 | 10 | 10 | 14 | Examples | U18009 T33413 T33339 | Human chromosome 17q21 mRNA clone LF113. EST57778 Homo sapiens cDNA 3' end similar to None EST57474 Homo sapiens cDNA 3' end similar to None |
| 671 | CATGGTACTGTAGCA | H728778 | 3 | 3 | 1 | 16 | 30 | Examples | M59911 | Human integrin alpha-3 chain mRNA |
| 672 | CATGGTACTGTGGCT | H728810 | 23 | 10 | 16 | 15 | 50 | Examples | X87689 | H.sapiens mRNA for putative p64 CLCP protein |
| 673 | CATGGTCAAAATTTC | H737344 | 0 | 0 | 0 | 10 | 1 | Examples | L12350 | Human thrombospondin 2 (THBS2) mRNA |
| 674 | CATGGTCTGGGGCTT | H752296 | 25 | 35 | 45 | 76 | 29 | Examples | D21261 | Human mRNA (HA1756) for ORF |
| | | | | | | | | | D29543 | Human keratinocyte cDNA, clone 686 |
| 675 | CATGGTCTGTGAGAG | H752521 | 0 | 5 | 7 | 12 | 2 | Examples | H51290 N20338 AA158271 | yp07a05.s1 Homo sapiens cDNA clone 186704 3' yx44g12.s1 Homo sapiens cDNA clone 264646 3' zo76e09.st Stratagene pancreas (#937208) Homo sapiens cDNA clone 592840 3' |
| 676 | CATGGTCTGTGCAGG | H752531 | 0 | 0 | 0 | 1 | 13 | No Match | | |
| 677 | CATGGTCTTGAAGCC | H753162 | 0 | 1 | 2 | 1 | 10 | No Match | | |
| 678 | CATGGTGAATGACGG | H754323 | 25 | 14 | 42 | 15 | 89 | Examples | X87373 | Class C, H.sapiens RPS3a gene |
| 679 | CATGGTCGAATTTTC | H754567 | 0 | 2 | 8 | 1 | 10 | Examples | X08058 | GLUTATHIONE S-TRANSFERASE P (HUMAN) |
| 680 | CATGGTGCGGAGGAC | H760361 | 0 | 3 | 2 | 11 | 25 | Examples | X51439 | Human mRNA for serum amyloid A (SAA) protein |
| 681 | CATGGTGCTGGAGAA | H761481 | 2 | 9 | 9 | 13 | 26 | Examples | U15008 | Human SnRNP core protein Sm D2 mRNA |
| 682 | CATGGTGGAGGGCAC | H762533 | 1 | 1 | 3 | 6 | 34 | Examples | U62800 | Cystatin M (CST6) |
| 683 | CATGGTGTACAGGA | H765003 | 14 | 17 | 15 | 39 | 30 | Examples | H46430 AA047563 | yo12h12.s1 Homo sapiens cDNA clone 177767 3' zf13a06.s1 Soares fetal heart NbHH19W Homo sapiens cDNA clone 376786 3' |
| 684 | CATGGTTCACTGCAG | H774629 | 0 | 2 | 1 | 13 | 3 | Examples | AA130701 | zo13f02.s1 Stratagene colon (#937204) Homo sapiens cDNA clone 586779 3' |
| | | | | | | | | | X59288 M24283 J03132 | H.sapiens gene for intercellular adhesion molecule Human major group rhinovirus receptor (HRV) mRNA Human intercellular adhesion molecule-1 (ICAM-1) |
| 685 | CATGGTTGTCTTTGG | H781823 | 1 | 1 | 6 | 30 | 24 | Examples | M55100 | Human cell surface glycoprotein P3.58 mRNA |
| 686 | CATGGTTGTGGTTAA | H782013 | ## | ## | 14 | ## | 139 | Examples | K02765 | Human complement component C3 mRNA, alpha and beta |
| 687 | CATGGTTTAAATCGA | H782391 | 1 | 6 | 12 | 4 | 14 | Examples | M17987 | Human beta-2-microglobulin gene |
| 688 | CATGTAAGGCTTAAC | H797169 | 0 | 0 | 6 | 1 | 12 | Examples | D00760 | Human mRNA for proteasome subunit HC3 |
| | | | | | | | | | X57025 | INSULIN-LIKE GROWTH FACTOR IA PRECURSOR (HUMAN) |
| 689 | CATGTAAITITGGAA | H802793 | 0 | 2 | 5 | 2 | 10 | No Match | | |
| 690 | CATGTAATTTTGGAT | H802793 | | | | | | No Match | | |
| 691 | CATGTACAITTTCAT | H806901 | 1 | 4 | 2 | 3 | 14 | Examples | X85373 | H.sapiens mRNA for Sm protein G |
| 692 | CATGTACCCGTACA | H808370 | 0 | 1 | 4 | 0 | 10 | No Match | | |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 693 | CATGTACCCTTCTAT | H808925 | 0 | 0 | 0 | 17 | 7 | No Match | J02931 | Human placental tissue factor (two forms) mRNA |
| 694 | CATGTAGGAAAGTAA | H827437 | 1 | 0 | 5 | 5 | 24 | Examples | M16553 | Human tissue factor mRNA, complete cds |
|  |  |  |  |  |  |  |  |  | M27436 | Human tissue factor gene, complete cds |
| 695 | CATGTAGGTTGTCTA | H831416 | 49 | 61 | 61 | 89 | 130 | Examples | X64899 | H.sapiens mRNA homologous to mouse P21 mRNA. |
|  |  |  |  |  |  |  |  |  | X16064 | Human mRNA for translationally controlled tumor protein |
|  |  |  |  |  |  |  |  |  | L13806 | Homo sapiens (clone 04) translationally controlled tumor protein |
| 696 | CATGTATATTTTCTC | H839672 | 1 | 0 | 3 | 8 | 16 | Examples | M98479 | Human transglutaminase mRNA |
| 697 | CATGTATTTTCTgCC | H851834 | 0 | 1 | 2 | 16 | 3 | Examples | D12149 | Human HepG2 3'-directed MboI cDNA, clone s247 |
| 698 | CATGTCACAAGCAAA | H856209 | 10 | 28 | 27 | 24 | 48 | Examples | X80909 | H.sapiens alpha NAC mRNA |
| 699 | CATGTCCAAATCGAT | H868569 | 0 | 1 | 0 | 43 | 17 | Examples | X56134 | Human mRNA for vimentin. |
|  |  |  |  |  |  |  |  |  | Z19554 | H.sapiens vimentin gene |
|  |  |  |  |  |  |  |  |  | M14144 | Human vimentin gene, complete cds |
| 700 | CATGTCCACTGGCCT | H870310 | 0 | 0 | 1 | 12 | 2 | Examples | M25246 | Human vimentin (HuVim3) mRNA, 3' end |
|  |  |  |  |  |  |  |  |  | N92906 | zb57a08.s1 Homo sapiens cDNA clone 307670 3' |
|  |  |  |  |  |  |  |  |  | T17488 | NIB978 Normalized infant brain, Bento Soares Homo sapiens cDNA 3'end |
|  |  |  |  |  |  |  |  |  | A349906 | EST56900 Infant brain Homo sapiens cDNA 3' end |
| 701 | CATGTCCATCTGTTG | H871920 | 6 | 6 | 10 | 25 | 5 | Examples | X67016 | H.sapiens mRNA for amphiglycan |
|  |  |  |  |  |  |  |  |  | D13292 | Human mRNA for ryudocan core protein |
| 702 | CATGTCGTCTTTATC | H899060 | 2 | 5 | 15 | 1 | 69 | Examples | M77233 | Human ribosomal protein S7 mRNA |
| 703 | CATGTCTCTGATGCT | H908858 | 1 | 5 | 2 | 46 | 19 | Examples | S48568 | tissue inhibitor of metalloproteinase 2 (3'-end region) |
| 704 | CATGTCTTGTAACTG | H916232 | 0 | 4 | 3 | 1 | 13 | Examples | N71680 | yz93b03.s1 Homo sapiens cDNA clone 290573 3' |
| 705 | CATGTCTTGTGCATA | H916372 | 14 | 22 | 15 | 20 | 45 | Examples | X03083 | Human mRNA for lactate dehydrogenase-A |
|  |  |  |  |  |  |  |  |  | X02152 | Human lactate dehydrogenase-A |
|  |  |  |  |  |  |  |  |  | X02153 | Human pseudogene for lactate dehydrogenase-A |
| 706 | CATGTGAAGTCACTG | H920392 | 1 | 1 | 6 | 0 | 16 | No Match |  |  |
| 707 | CATGTGAAGTTATAC | H920525 | 0 | 1 | 3 | 6 | 11 | Examples | X07979 | CTGTGG, Class A, Human mRNA for fibronectin receptor beta subunit. |
| 708 | CATGTGATGTCTGGT | H932731 | 0 | 8 | 3 | 11 | 12 | Examples | AA027860 | zk05h07.s1 Soares pregnant uterus NbHPU Homo sapiens cDNA clone 469693 3' |
| 709 | CATGTGCCATCTGTA | H938876 | 1 | 3 | 7 | 3 | 16 | Examples | M25753 | G2/MITOTIC-SPECIFIC CYCLIN B1 (HUMAN) |
|  |  |  |  |  |  |  |  |  | T60151 | yc22c04.s1 Homo sapiens cDNA clone 81414 3' |
|  |  |  |  |  |  |  |  |  | R67969 | yi29g08.s1 Homo sapiens cDNA clone 140702 3' |
| 710 | CATGTGCCCTCAAAA | H939841 | 11 | 13 | 3 | 13 | 43 | Examples | AA169614 | zo91f03.s1 Stratagene ovarian cancer (#937219) Homo sapiens cDNA clone 594269 3' similar to SW:NGAL_HUMAN P80188 NEUTROPHIL GELATINASE-ASSOCIATED LIPOCALIN PRECURSOR |
| 711 | CATGTGCCCTCAGAA | H939849 | 3 | 4 | 0 | 11 | 19 | Examples | N79823 | zb15d08.s1 Homo sapiens cDNA clone 302127 3' similar to SW:NGAL_HUMAN P80188 NEUTROPHIL GELATINASE-ASSOCIATED LIPOCALIN PRECURSOR |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 712 | CATGTGCCCTCAGGA | H939851 | 13 | 31 | 10 | 25 | 83 | Examples | AA075896 | zm90h04.s1 Stratagene ovarian cancer (#937219) *Homo sapiens* cDNA clone 545239 3' similar to SW:NGAL_HUMAN P80188 NEUTROPHIL GELATINASE-ASSOCIATED LIPOCALIN PRECURSOR |
| 713 | CATGTGCCCTCAGGC | H920392 | 0 | 3 | 1 | 2 | 12 | No Match Examples | AA100279 | zl81e07.s1 Stratagene colon (#937204) *Homo sapiens* cDNA clone 511044 3' |
| 714 | CATGTGCCTTACTTT | H941856 | 2 | 5 | 2 | 17 | 3 | No Match |  |  |
| 715 | CATGTGCGCTGGCCC | H944038 | 2 | 6 | 6 | 4 | 16 | Examples | AA029262 | zk10a01.s1 Soares pregnant uterus NbHPU *Homo sapiens* cDNA clone 470088 3' |
| 716 | CATGTGCTTCATCTG | H949560 |  |  |  |  |  |  | N54281 | yv66e10.s1 Soares fetal liver spleen 1NFLS *Homo sapiens* cDNA clone 247722 3' |
|  |  |  |  |  |  |  |  |  | AA114075 | zn76c02.s1 Stratagene N12 neuronal precursor 937230 *Homo sapiens* cDNA clone 564098 3' |
| 717 | CATGTGGAGTGGAGG | H953251 | 18 | 15 | 7 | 22 | 48 | Examples | L76200 | *Homo sapiens* guanylate kinase (GUK1) mRNA |
| 718 | CATGTGGCCCCAGGT | H955723 | 0 | 3 | 3 | 37 | 4 | Examples | X00570 | Human mRNA for precursor of apolipoprotein CI |
| 719 | CATGTGGGTGAGCCA | H962086 | 13 | 15 | 13 | 76 | 27 | Examples | L16510 | *Homo sapiens* cathepsin B mRNA |
|  |  |  |  |  |  |  |  |  | M14221 | Human cathepsin B proteinase mRNA, complete cds |
| 720 | CATGTGTGAGCCCCT | H975446 | 3 | 3 | 3 | 22 | 8 | Examples | L35240 | Human enigma gene |
| 721 | CATGTGTGCTAAATG | H976644 | 8 | 21 | 26 | 18 | 50 | Examples | L38941 | *Homo sapiens* ribosomal protein L34 (RPL34) mRNA |
| 722 | CATGTGTGTGTTTGT | H978687 | 6 | 7 | 16 | 25 | 15 | Examples | X03473 | Human gene for histone H1(0) |
| 723 | CATGTTATGGATCTC | H997944 | 0 | 1 | 1 | 21 | 1 | Examples | AA034505 | zk23g08.s1 Soares pregnant uterus NbHPU *Homo sapiens* cDNA clone 471422 3' |
|  |  |  |  |  |  |  |  |  | AA235464 | zt31b06.s1 Soares ovary tumor NbHOT *Homo sapiens* cDNA clone 723923 3' |
|  |  |  |  |  |  |  |  |  | AA037024 | zk30c10.s1 Soares pregnant uterus NbHPU *Homo sapiens* cDNA clone 472050 3' |
| 724 | CATGTTCATTGTAGA | H1003443 | 0 | 7 | 0 | 10 | 3 | Examples | H53629 | yu38d04.s1 *Homo sapiens* cDNA clone 236071 3' |
|  |  |  |  |  |  |  |  |  | T06706 | EST04595 *Homo sapiens* cDNA clone HFBDX32 |
|  |  |  |  |  |  |  |  |  | T16635 | NIB1599 Normalized infant brain, Bento Soares *Homo sapiens* cDNA 3'end similar to EST04595 *H. sapiens* cDNA clone HFBDX32 |
| 725 | CATGTTCTGTGAATC | H1014660 | 3 | 4 | 3 | 24 | 5 | Examples | AA026678 | ze97h02.s1 Soares fetal heart NbHH19W *Homo sapiens* cDNA clone 366963 3' |
|  |  |  |  |  |  |  |  |  | AA280283 | zt05a03.s1 Soares NbHTGBC *Homo sapiens* cDNA clone 712204 3' |
|  |  |  |  |  |  |  |  |  | H10141 | ym05a09.s1 *Homo sapiens* cDNA clone 46675 3' |
| 726 | CATGTTGCCCCGTG | H1021276 | 0 | 0 | 0 | 8 | 17 | Examples | X66029 | *H.sapiens* mRNA for tyrosine kinase receptor. |
| 727 | CATGTTGCTGACTTT | H1023520 | 1 | 5 | 1 | 33 | 1 | Examples | X15880 | Human mRNA for collagen VI alpha-1 |
|  |  |  |  |  |  |  |  |  | X72414 | *H.sapiens* gene for glutaminyl-tRNA synthetase |

TABLE 4-continued

Transcripts increased in pancreatic cancer
SAGE Tags elevated only in Pancreatic Tumor
NC: Normal Colon
Tu: Colon Tumor
CC: Colon Cancer Cell Line
PT: Pancreatic Tumor
PC: Pancreatic Cell Line

| SEQ ID NO: | Tag_Sequence | Tag_Number | NC | Tu | CC | PT | PC | | Accession | Gene Name |
|---|---|---|---|---|---|---|---|---|---|---|
| 728 | CATGTTTGGAGATCTC | H1024568 | 4 | 11 | 16 | 10 | 24 | Examples | AA044568 | zk73h10.s1 Soares pregnant uterus NbHPU *Homo sapiens* cDNA clone 488515 3' |
|  |  |  |  |  |  |  |  |  | N71899 | yz36b07.s1 *Homo sapiens* cDNA clone 285109 3' |
|  |  |  |  |  |  |  |  |  | AA400793 | z71g03.s1 Soares testis NHT *Homo sapiens* cDNA clone 727828 3' |
| 729 | CATGTTTGGGGTTTCC | H1026814 | ## | 75 | 84 | ## | 369 | Examples | X80336 | *H.sapiens* (5) Ferritin H pseudogene. |
|  |  |  |  |  |  |  |  |  | X00318 | Human mRNA for apoferritin H chain type |
|  |  |  |  |  |  |  |  |  | X03488 | Human apoferritin H gene exons 2-4 |
|  |  |  |  |  |  |  |  |  | M97164 | Human ferritin heavy chain mRNA, complete cds |
|  |  |  |  |  |  |  |  |  | L20941 | Human ferritin heavy chain mRNA, complete cds |
| 730 | CATGTTTGGTGAAGGA | H1027595 | 98 | ## | 17 | ## | 107 | Examples | X02493 | Human interferon-inducible mRNA (cDNA 6-26). |
|  |  |  |  |  |  |  |  |  | M11948 | Human promyelocytic leukemia cell mRNA |
|  |  |  |  |  |  |  |  |  | M17733 | Human thymosin beta-4 mRNA, complete cds |
| 731 | CATGTTTCCCTCAAA | H1037777 | 0 | 1 | 0 | 13 | 1 | Examples | N78832 | zb17a08.s1 *Homo sapiens* cDNA clone 302294 3' |
|  |  |  |  |  |  |  |  |  | AA411095 | z33d02.s1 Soares ovary tumor NbHOT *Homo sapiens* cDNA clone 724131 3' |
|  |  |  |  |  |  |  |  |  | W81693 | zd84g11.s1 Soares fetal heart NbHH19W *Homo sapiens* cDNA clone 347396 3' |
| 732 | CATGTTTCCTTCCTT | H1038296 | 0 | 6 | 3 | 7 | 17 | Examples | M20471 | Human brain-type clathrin light-chain a mRNA |
|  |  |  |  |  |  |  |  |  | M20472 | Human lymphocyte clathrin light-chain A mRNA |
| 733 | CATGTTTGCACCTTT | H1041504 | 2 | 0 | 0 | 16 | 1 | Examples | X78947 | *H.sapiens* mRNA for connective tissue growth factor |
|  |  |  |  |  |  |  |  |  | U14750 | Human connective tissue growth factor mRNA |
| 734 | CATGTTTGTTAAAA | H1044225 |  |  |  |  |  |  | H06492 | yl78c08.s1 *Homo sapiens* cDNA clone 44273 3' |
|  |  |  |  |  |  |  |  |  | T35952 | EST94173 *Homo sapiens* cDNA 3' end similar to None |
|  |  |  |  |  |  |  |  |  | AA253218 | zr53g10.s1 Soares NhHMPu S1 *Homo sapiens* cDNA clone 667170 3' |

TABLE 5

Transcripts increased in pancreatic and colorectal cancer
SAGE tags that were elevated in both in coloreactal and pancreatic tumors,
and are likely to be specific for tumors in general.

| SEQ ID NO: | Tag_Sequence | | Tag_Number | Accession | Description |
|---|---|---|---|---|---|
| 735 | CATG TGGAAATGAC | C | −950498 | M10629 | Human alpha-1 collagen gene, 3' end with polyA sit |
| 736 | CATG CACTTCAAGG | G | −294155 | U42376 | Human retinoic acid induced RIG-E precursor (E) mR |
| | | | | U56145 | Human thymic shared antigen-1/stem cell antigen-2 |
| 737 | CATG ATGTGAAGAG | T(A) | −243747 | J03040 | Human SPARC/osteonectin mRNA, complete cds. |
| | | | | M25746 | Human osteonectin gene exon 10, complete cds. |
| 738 | CATG GCCCAAGGAC | C | −610466 | X53416 | Human mRNA for actin-binding protein (filamin) (AB |
| 739 | CATG ATCTTGTTAC | T | −229106 | X02761 | Human mRNA for fibronectin (FN precursor). |
| | | | | K00799 | H+G37uman fibronectin (fn) 3' coding region and flank, |
| 740 | CATG GTGCGCTGAG | C | −760291 | X58536 | Human HLA class I locus C heavy chain. |
| | | | | M26432 | Human MHC class I HLA-C.1 gene, complete cds. |
| 741 | CATG ACAGGCTACG | G | −76231 | M95787 | Human 22kDa smooth muscle protein (SM22) mRNA, com |
| | | | | M83106 | Human SM22 mRNA, 5' end. |
| 742 | CATG GTGTGTTTGT | A | −769020 | M77349 | Human transforming growth factor-beta induced gene |
| 743 | CATG GATTTCTCAG | C | −589267 | X53279 | Human mRNA for placental-like alkaline phosphatase |
| | | | | X55958 | H. sapiens mRNA for alkaline phosphatase. |
| | | | | J04948 | Human alkaline phosphatase (ALP-1) mRNA, complete |
| 744 | CATG ACCATTCTGC | T | −85882 | X57351 | Human 1-8D gene from interferon-inducible gene fam |
| | | | | X02490 | Human interferon-inducible mRNA (cDNA 1-8). |
| 745 | CATG TCCTTCTCCA | C | −884181 | X15804 | Human mRNA for alpha-actinin. |
| 746 | CATG CTTCTGTGTA | C, T | −515821 | D80012 | Human mRNA for KIAA0190 protein. |
| 747 | CATG ATGTAAAAAA | T | −241665 | M74090 | Human TB2 gene mRNA, 3' end. |
| | | | | J03801 | Human lysozyme mRNA, complete cds with an Alu repe |
| | | | | M19045 | Human lysozyme mRNA, complete cds. |
| 748 | CATG GGCAGAGGAC | C | −673954 | X17620 | Human mRNA for Nm23 protein, involved in developme |
| | | | | X75598 | H. sapiens nm23H1 gene. |
| 749 | CATG AATATTGAGA | A | −53129 | U62962 | Human Int-6 mRNA, complete cds. |
| 750 | CATG TTTTTGATAA | A | −1048113 | D16891 | Human HepG2 3' region cDNA, clone hmd2c11. |
| 751 | CATG CAGCTGGCCA | T | −302741 | X53743 | H. sapiens mRNA for fibulin-1 C. |
| 752 | CATG GTTCACATTA | G | −774461 | X00497 | Human mRNA for HLA-DR antigens associated invarian |
| | | | | M13560 | Human Ia-associated invariant gamma-chain gene, ex |
| 753 | CATG AAAAGAAACT | T | −2056 | Y00345 | Human mRNA for polyA binding protein. |
| 754 | CATG AATGCAGGCA | G | −58533 | M61831 | Human S-adenosylhomocysteine hydrolase (AHCY) mRNA |
| | | | | M61832 | Human S-adenosylhomocysteine hydrolase (AHCY) mRNA |
| 755 | CATG TGAAATAAAA | C | −918273 | X16934 | Human hB23 gene for B23 nucleophosmin. |
| | | | | M28699 | *Homo sapiens* nucleolar phosphoprotein B23 (NPM1) m |
| | | | | M23613 | Human nucleophosmin mRNA, complete cds. |
| | | | | M26697 | Human nucleolar protein (B23) mRNA, complete cds. |
| 756 | CATG TTATGGGATC | T | −998030 | M24194 | Human MHC protein homologous to chicken B complex |
| 757 | CATG CAATAAATGT | T | −274492 | D23661 | Human mRNA for ribosomal protein L37, complete cds |
| | | | | L11567 | *Homo sapiens* ribosomal protein L37 mRNA, complete |
| 758 | CATG AGCCTTTGTT | G | −155632 | D83174 | Human mRNA for collagen binding protein 2. |
| 759 | CATG ACCTGTATCC | C | −97078 | X57352 | Human 1-8U gene from interferon-inducible gene fam |
| 760 | CATG TTCAATAAAA | A | −1000193 | M17886 | Human acidic ribosomal phosphoprotein P1 mRNA, com |
| | | | | J05068 | H+G126uman transcobalamin I mRNA, complete cds. |
| 761 | CATG CGACCCCACG | C | −398663 | M12529 | Human apolipoprotein E mRNA, complete cds. |
| | | | | K00396 | Human apolipoprotein E (epsilon 2 and 3 alleles) m |
| 762 | CATG CAGATCTTTG | T | −298495 | X56998 | Human UbA52 adrenal mRNA for ubiquitin-52 amino ac |
| | | | | X56999 | Human UbA52 placental mRNA for ubiquitin-52 amino |
| 763 | CATG CTGGCGAGCG | C | −501287 | X07491 | Human DNA inserts showing sperm-specific hypomethy |
| | | | | M91670 | Human ubiquitin carrier protein (E2-EPF) mRNA, com |
| 764 | CATG ATTGGCTTAA | A | −256497 | L14272 | Human prohibitin (PHB) gene, exons 1–7. |
| | | | | S85655 | prohibitin [human, mRNA, 1043 nt]. |
| 765 | CATG GTGGTGGACA | C | −765573 | U62435 | Human nicotinic acetylcholine receptor alpha6 subu |
| | | | | U68041 | Human breast and ovarian cancer susceptibility pro |
| 766 | CATG TCCTGCCCCA | T | −883029 | M24398 | Human parathymosin mRNA, complete cds. |
| 767 | CATG ACTGGGTCTA | T | −125661 | X58965 | H. sapiens RNA for nm23-H2 gene. |
| | | | | M36981 | Human putative NDP kinase (nm-H2S) mRNA, complet |
| | | | | L16785 | *Homo sapiens* c-myc transcription factor (puf) mRNA |
| 768 | CATG AAGAAGATAG | A | −33331 | U02032 | Human ribosomal protein L23a mRNA, partial cds. |
| | | | | U37230 | Human ribosomal protein L23a mRNA, complete cds. |
| | | | | U43701 | Human ribosomal protein L23a mRNA, complete cds. |
| | | | | L13799 | *Homo sapiens* (clone 01) liver expressed protein mR |
| 769 | CATG ACATCATCGA | T | −79065 | L06505 | Human ribosomal protein L12 mRNA, complete cds. |
| 770 | CATG CTGTTGGTGA | T | −507577 | D14530 | Human homolog of yeast ribosomal protein S28, comp |
| 771 | CATG ATTATTTTTC | T | −249854 | X57959 | H. sapiens mRNA for ribosomal protein L7. |
| | | | | X57958 | H. sapiens mRNA for ribosomal protein L7. |
| | | | | X52967 | Human mRNA for ribosomal protein L7. |
| | | | | L16558 | Human ribosomal protein L7 (RPL7) mRNA, complete c |
| 772 | CATG GCTTTTAAGG | A | −655115 | L06498 | *Homo sapiens* ribosomal protein S20 (RPS20) mRNA, c |
| 773 | CATG GGCAAGAAGA | A | −672265 | L19527 | *Homo sapiens* ribosomal protein L27 (RPL27) mRNA, c |
| | | | | L25346 | *Homo sapiens* ribosomal protein L27 (homologue of r |

TABLE 5-continued

Transcripts increased in pancreatic and colorectal cancer
SAGE tags that were elevated in both in coloreactal and pancreatic tumors,
and are likely to be specific for tumors in general.

| SEQ ID NO: | Tag_Sequence | | Tag_Number | Accession | Description |
|---|---|---|---|---|---|
| 774 | CATG CTCTTCGAGA | A | −490889 | Y00433 | Human mRNA for glutathione peroxidase (EC 1.11.1.9 |
| | | | | Y00483 | Human gene for gluthathione peroxidase. |
| | | | | X13710 | *H. sapiens* unspliced mRNA for glutathione peroxidas |
| | | | | X13709 | Human gpxl mRNA for gluthatione peroxidase. |
| | | | | M21304 | Human glutathione peroxidase (GPX1) mRNA, complete |
| 775 | CATG CTGTTGATTG | C | −507455 | X04347 | Human liver mRNA fragment DNA binding protein UPI |
| | | | | U00947 | Human clone C4E 3.2 (CAC)n/(GTG)n repeat-containin |
| 776 | CATG CTGGGTTAAT | A | −502724 | M81757 | *H. sapiens* S19 ribosomal protein mRNA, complete cds |
| 777 | CATG ATGGCTGGTA | T | −239533 | X17206 | Human mRNA for LLRep3. |
| 778 | CATG GATGCTGCCA | A | −583573 | X59357 | Human mRNA for Epstein-Barr virus small RNAs (EBER |
| | | | | L21756 | *Homo sapiens* acute myeloid leukemia associated pro |
| | | | | D17652 | Human mRNA for HBp15/L22, complete cds. |
| | | | | S76343 | AML1 . . . EAP {translocation breakpoint} [human, chro |
| 779 | CATG CCTTCGAGAT | C | −390692 | U14970 | Human ribosomal protein S5 mRNA, complete cds. |
| 780 | CATG CTCCTCACCT | G | −482584 | U16811 | Human Bak mRNA, complete cds. |
| | | | | U23765 | Human Bak protein mRNA, complete cds. |
| 781 | CATG TGTGTTGAGA | G | −978825 | X16869 | Human mRNA for elongation factor 1-alpha (clone CE |
| | | | | X16872 | Human DNA for elongation factor 1-alpha (clone lam |
| | | | | X03558 | Human mRNA for elongation factor 1-alpha subunit ( |
| | | | | D17182 | Human HepG2 3' region MboI cDNA, clone hmd2h03m3. |
| | | | | D17245 | Human HepG2 3' region MboI cDNA, clone hmd4h05m3. |
| | | | | D17259 | Human HepG2 3' region MboI cDNA, clone hmd5d07m3. |
| | | | | D17276 | Human HepG2 3' region MboI cDNA, clone hmd6a12m3. |
| | | | | M27364 | Human elongation factor 1 alpha mRNA, 3' end. |
| | | | | M29548 | Human elongation factor 1-alpha (EF1A) mRNA, parti |
| | | | | L41490 | *Homo sapiens* oncogene PTI-1 mRNA, complete cds. |
| | | | | L41498 | *Homo sapiens* oncogene PTI-1 mRNA, complete cds. |
| 782 | CATG TTACCATATC | A | −988366 | U57846 | Human ribosomal protein L39 mRNA, complete cds. |
| 783 | CATG GCCTGCTGGG | C | −621035 | X71973 | *H. sapiens* GPx-4 mRNA for phospholipid hydroperoxid |
| 784 | CATG CCTCGGAAAA | T | −383489 | Z26876 | *H. sapiens* gene for ribosomal protein L38. |
| 785 | CATG TACAAGAGGA | A | −803369 | X69391 | *H. sapiens* mRNA for ribosomal protein L6. |
| | | | −803369 | D17554 | Human mRNA for DNA-binding protein, TAXREB107, com |
| | | | −803369 | S71022 | neoplasm-related C140 product [human, thyroid carc |
| 786 | CATG AACGACCTCG | T | −24951 | V00598 | Human beta-tubulin pseudogene. |
| | | | −24951 | V00599 | Human mRNA fragment encoding beta-tubulin. (from c |
| 787 | CATG CCCTGCCTTG | T | −358783 | X55110 | Human mRNA for neurite outgrowth-promoting protein |
| 788 | CATG CCCAGGGAGA | A | −346761 | U38846 | Human stimulator of TAR RNA binding (SRB) mRNA, co |
| | | | | D16933 | Human HepG2 3' region cDNA, clone hmd4f1 1. |
| 789 | CATG AGCACCTCCA | G | −148949 | Z11692 | *H. sapiens* mRNA for elongation factor 2. |
| 790 | CATG CGCCGGAACA | C | −416261 | X73974 | *H. sapiens* HRPL4 mRNA. |
| | | | | D23660 | Human mRNA for ribosomal protein, complete cds. |
| 791 | CATG CTAAAAAAAA | A | −458753 | M33680 | Human 26-kDa cell surface protein TAPA-1 mRNA, com |
| 792 | CATG GGCTGATGTG | G | −686319 | U09510 | Human glycyl-tRNA synthetase mRNA, complete cds. |
| | | | | U09587 | Human glycyl-tRNA synthetase mRNA, complete cds. |
| | | | | D30658 | Human T-cell mRNA for glycyl tRNA synthetase, comp |
| 793 | CATG ATTCTCCAGT | A | −253260 | X55954 | Human mRNA for HL23 ribosomal protein homologue. |
| | | | | X52839 | Human mRNA for ribosomal protein L17. |
| 794 | CATG GAAAAATGGT | T | −524524 | X61156 | *H. sapiens* mRNA for laminin-binding protein. |
| | | | | X15005 | Human mRNA for potential laminin-binding protein ( |
| | | | | U43901 | Human 37 kD laminin receptor precursor/p40 ribosom |
| | | | | J03799 | Human colin carcinoma laminin-binding protein mRNA |
| | | | | M14199 | Human laminin receptor (2H5 epitope) mRNA, 5' end. |
| 795 | CATG CAGCTCACTG | A | −302367 | D87735 | Human mRNA for ribosomal protein L14, complete cds |
| | | | | L10376 | Human (clone CTG-B33) mRNA sequence. |
| | | | | S80520 | CAG-isl 7 {trinucleotide repeat-containing sequenc |
| 796 | CATG ATAATTCTTT | G | −200576 | U14973 | Human ribosomal protein S29 mRNA, complete cds. |
| | | | | L31610 | *Homo sapiens* (clone cori-1c15) S29 ribosomal prote |
| 797 | CATG AATCCTGTGG | A | −55227 | Z28407 | *H. sapiens* mRNA for ribosomal protein L8. |
| 798 | CATG AATAGGTCCA | A | −51925 | M64716 | Human ribosomal protein S25 mRNA, complete cds. |
| 799 | CATG AAAAAAAAAA | A | −1 | X83412 | *H. sapiens* B1 mRNA for mucin. |
| | | | | Z32564 | *H. sapiens* FRGAMMA mRNA (819bp) for folate receptor |
| | | | | Z32633 | *H. sapiens* FRGAMMA' mRNA for folate receptor (817bp |
| | | | | X76180 | *H. sapiens* mRNA for lung amiloride sensitive Na+ ch |
| | | | | U08470 | Human FR-gamma' mRNA, complete cds |
| | | | | U08471 | Human folate receptor 3 mRNA, complete cds. |
| | | | | U48697 | Human mariner-like element-containing mRNA, clone |
| | | | | D28532 | Human mRNA for renal Na+-dependent phosphate cotra |
| | | | | M55914 | Human c-myc binding protein (MBP-1) mRNA, complete |
| | | | | L06175 | *Homo sapiens* P5-1 mRNA, complete cds. |
| | | | | S73775 | calmitine=mitochondrial calcium-binding protein [h |
| | | | | S77393 | transcript ch138 [human, RF1, RF48 stomach cancer c |
| | | | | X60036 | *H. sapiens* mRNA for mitochondrial phosphate carrier |

TABLE 5-continued

Transcripts increased in pancreatic and colorectal cancer
SAGE tags that were elevated in both in coloreactal and pancreatic tumors,
and are likely to be specific for tumors in general.

| SEQ ID NO: | Tag_Sequence | Tag_Number | Accession | Description |
|---|---|---|---|---|
| 800 | CATG CCAGAACAGA C | −335945 | X79238 | H. sapiens mRNA for ribosomal protein L30. |
|  |  |  | L16991 | Human thymidylate kinase (CDC8) mRNA, complete cds |
| 801 | CATG AAGGTGGAGG A | −44683 | X80822 | H. sapiens mRNA for ORF. |
| 802 | CATG CCTAGCTGGA T | −379369 | X52856 | Human cyclophilin-related processed pseudogene. |
|  |  |  | X52857 | Human cyclophilin-related processed pseudogene. |
|  |  |  | X52854 | Human cyclophilin-related processed pseudogene. |
|  |  |  | X52851 | Human cyclophilin gene for cyclophilin (EC 5.2.1.8 |
|  |  |  | Y00052 | Human mRNA for T-celt cyclophilin. |
| 803 | CATG GAACACATCC A | −528694 | X63527 | H. sapiens mRNA for ribosomal protein L19. |
|  |  |  | S56985 | ribosomal protein L19 (human, breast cancer cell 1 |
| 804 | CATG AAGGAGATGG G | −41531 | X69181 | H. sapiens mRNA for ribosomal protein L31. |
|  |  |  | X15940 | Human mRNA for ribosomal protein L31. |
| 805 | CATG AGGCTACGGA A | −171113 | Z29650 | H. sapiens SMCX mRNA. |
|  |  |  | D17233 | Human HepG2 3' region MboI cDNA, clone hmd4c12m3. |
| 806 | CATG AGGTCCTAGC C | −177610 | X08096 | Human GST pi gene for glutathione S-transferase pi |
|  |  |  | X06547 | Human mRNA for class Pi glutathione S-transferase |
|  |  |  | X15480 | Human mRNA for anionic glutathione-S-transferase ( |
|  |  |  | X08058 | Human glutathione S-transferase pi gene. |
|  |  |  | U12472 | Human glutathione S-transferase (GST phi) gene, co |
|  |  |  | U21689 | Human glutathione S-transferase-P1c gene, complete |
|  |  |  | U62589 | Human glutathione S-transferase P1c (GSTp1c) mRNA, |
|  |  |  | M69113 | Human fatty acid ethyl ester synthase-III mRNA seq |
|  |  |  | M24485 | Homo sapiens (clone pHGST-pi) glutathione S-transf |
| 807 | CATG TGGTGTTGAG G | −965603 | X69150 | H. sapiens mRNA for ribosomal protein S18. |
|  |  |  | M96153 | Homo sapiens apolipoprotein B gene sequence. |
|  |  |  | L06432 | Homo sapiens 18S ribosomal protein (HKE3) mRNA seq |
| 808 | CATG CTCAACATCT C | −475448 | M17885 | Human acidic ribosomal phosphoprotein P0 mRNA, com |
| 809 | CATG GTGTTAACCA G | −769045 | L25899 | Human ribosomal protein L10 mRNA, complete cds. |
| 810 | CATG AGGGCTTCCA A | −174037 | X58125 | Human (D9S55) DNA segment containing (TG)24 repeat |
|  |  |  | D17268 | Human HepG2 3' region MboI cDNA, clone hmd5h09m3. |
|  |  |  | M73791 | Human novel gene mRNA, complete cds. |
|  |  |  | M64241 | Human Wilin's tumor-related protein (QM) mRNA, comp |
|  |  |  | S35960 | laminin receptor homolog {3' region} [human, mRNA |
| 811 | CATG GGATTTGGCC T | −671654 | M17887 | Human acidic ribosomalphosphoprotein P2 mRNA, com |
|  |  |  | M11147 | Human ferritin L chain mRNA, complete cds. |
|  |  |  | M12938 | Human ferritin light subunit mRNA, partial cds. |
|  |  |  | M10119 | Human ferritin light subunit mRNA, complete cds. |
| 812 | CATG ATTAACAAAG C | −246019 | X04409 | Human mRNA for coupling protein G(s) alpha-subunit |
|  |  |  | X04408 | Human mRNA for coupling protein G(s) alpha subunit |
|  |  |  | X56009 | Human GSA mRNA for alpha subunit of GsGTP binding |
|  |  |  | X07036 | Human mRNA stimulatory GTP-binding protein alpha s |
|  |  |  | M21142 | Human guanine nucleotide-binding protein alpha-sub |
|  |  |  | M14631 | Human guanine nucleotide-binding protein G-s, alph |
| 813 | CATG TGTACCTGTA A | −968173 | Z36832 | H. sapiens (xs31) mRNA, 835bp. |
|  |  |  | K00558 | #NAME? |
| 814 | CATG TGGCCCCACC C | −955718 | X56494 | H. sapiens M gene for M1-type and M2-type pyruvate |
|  |  |  | M23725 | Human M2-type pyruvate kinase mRNA, complete cds. |
|  |  |  | M26252 | Human TCB gene encoding cytosolic thyroid hormone- |
| 815 | CATG TAATAAAGGT G | −798764 | X67247 | H. sapiens rpS8 gene for ribosomal protein S8. |
| 816 | CATG GCATAATAGG T | −602315 | X89401 | H. sapiens mRNA for large subunit of ribosomal prot |
|  |  |  | U14967 | Human ribosomal protein L21 mRNA, complete cds. |
|  |  |  | U25789 | Human ribosomal protein L21 mRNA, complete cds. |
|  |  |  | L38826 | Homo sapiens L21 ribosomal protein gene, partial c |
| 817 | CATG TACCATCAAT A | −807748 | X53778 | H. sapiens hng mRNA for uracil DNA glycosylase. |
|  |  |  | U34995 | Human normal keratinocyte substraction library mRN |
|  |  |  | J02642 | Human glyceraldehyde 3-phosphate dehydrogenase mRN |
|  |  |  | M36164 | Human glyceraldehyde-3-phosphate dehydrogenase mRN |
|  |  |  | M33197 | Human glyceraldehyde-3-phosphate dehydrogenase (GA |
| 818 | CATG ATTTGTCCCA G | −260949 | X14957 | Human hmgI mRNA for high mobility group protein I. |
|  |  |  | X14958 | Human hmgI mRNA for high mobility group protein Y. |
|  |  |  | M23614 | Human HMG-I protein isoform mRNA (HMG1 gene), clon |
|  |  |  | M23619 | Human HMG-I protein isoform mRNA (HMG1 gene), clon |
|  |  |  | L17131 | Human high mobility group protein (HMG-I(Y)) gene |
|  |  |  | M23615 | Human HMG-Y protein isoform mRNA (HMGI gene), clon |
|  |  |  | M23616 | Human HMG-Y protein isoform mRNA (HMGI gene), clon |
|  |  |  | M23617 | Human HMG-Y protein isoform mRNA (HMGI gene), clon |
|  |  |  | M23618 | Human HMG-Y protein isoform mRNA (HMGI gene), clon |
| 819 | CATG GAGGGAGTTT C | −567488 | U14968 | Human ribosomal protein L27a mRNA, complete cds. |
| 820 | CATG CGCCGCCGGC T | −416106 | U12465 | Human ribosomal protein L35 mRNA, complete cds. |
| 821 | CATG GTGAAACCCA ALL | −753749 | Z63072 | H. sapiens CpG island DNA genomic Mse1 fragment, cl |
|  |  |  | X16294 | Human repetitive DNA containing interspersed repea |

TABLE 5-continued

Transcripts increased in pancreatic and colorectal cancer
SAGE tags that were elevated in both in coloreactal and pancreatic tumors,
and are likely to be specific for tumors in general.

| SEQ ID NO: | Tag_Sequence | Tag_Number | Accession | Description |
| --- | --- | --- | --- | --- |
| 822 | CATG AAGACAGTGG C | −33979 | X66699 | *H. sapiens* mRNA for ribosomal protein L37a. |
| | | | L06499 | *Homo sapiens* ribosomal protein L37a (RPL37A) mRNA, |
| | | | L22154 | Human ribosomal protein L37a mRNA sequence. |
| 823 | CATG CCCCAGCCAG T | −348755 | X55715 | Human Hums3 mRNA for 40S ribosomal protein s3. |
| | | | U14990 | Human XP1PO ribosomal protein S3 (rpS3) mRNA, comp |
| | | | U14991 | Human XP2NE ribosomal protein S3 (rpS3) mRNA, comp |
| | | | U14992 | Human IMR-90 ribosomal protein S3 (rpS3) mRNA, com |
| | | | S42658 | S3 ribosomal protein [human, colon, mRNA, 826 nt]. |
| 824 | CATG TGGGCAAAGC C | −959498 | X63526 | *H. sapiens* mRNA for protein homologous to elongatio |
| | | | Z11531 | *H. sapiens* mRNA for elongation factor-1-gamma. |
| | | | M55409 | Human pancreatic tumor-related protein mRNA, 3' en |
| 825 | CATG TGAGGGAATA A | −928269 | M10036 | Human triosephosphate isomerase mRNA, complete cds |
| 826 | CATG GACGACACGA G | −549145 | U58682 | Human ribosomal protein S28 mRNA, complete cds. |
| | | | M58458 | Human ribosomal protein S4 (RPS4X) isoform mRNA, c |
| | | | M22146 | Human scar protein mRNA, complete cds. |
| 827 | CATG AACGCGGCCA A | −26261 | Z23063 | *Homo sapiens* macrophage migration inhibitory facto |
| | | | L10612 | Human glycosylation-inhibiting factor mRNA, comple |
| | | | M95775 | *Homo sapiens* macrophage migration inhibitory facto |
| | | | L19686 | *Homo sapiens* macrophage migration inhibitory facto |
| | | | M25639 | Human migration inhibitory factor (MIF) mRNA, comp |
| 828 | CATG TGCACGTTTT C | −935680 | X03342 | Human mRNA for ribosomal protein L32. |
| | | | K03002 | Human mRNA from chromosome 15 gene with homology t |
| 829 | CATG CACAAACGGT A | −278636 | U57847 | Human ribosomal protein S27 mRNA, complete cds. |
| | | | L19739 | *Homo sapiens* metallopanstimulin (MPSl) mRNA, compl |
| 830 | CATG GGAGTGGACA T | −667269 | L11566 | *Homo sapiens* ribosomal protein L18 (RPL18) mRNA, c |
| 831 | CATG GCCGAGGAAG G | −615043 | Z54999 | *H. sapiens* CpG island DNA genomic Mse1 fragment, cl |
| | | | Z57572 | *H. sapiens* CpG island DNA genomic Mse1 fragment, cl |
| | | | Z56073 | *H. sapiens* CpG island DNA genomic Mse1 fragment, cl |
| | | | X53505 | Human mRNA for ribosomal protein S12. |
| 832 | CATG GGGGAAATCG C | −696375 | M92381 | Human thymosin beta 10 mRNA, complete cds. |
| | | | M20259 | Human thymosin beta-10 mRNA, complete cds. |
| 833 | CATG GCAGCCATCC G | −599350 | U14969 | Human ribosomal protein L28 mRNA, complete cds. |
| | | | D17257 | Human HepG2 3' region MboI cDNA, clone hmdSd04m3. |
| 834 | CATG TAAGGAGCTG A | −796831 | X77770 | *H. sapiens* RP526 mRNA. |
| | | | X69654 | *H. sapiens* mRNA for ribosomal protein S26. |
| 835 | CATG GGCAAGCCCC A | −672342 | U12404 | Human Csa-19 mRNA, complete cds. |
| | | | X79239 | *H. sapiens* mRNA for ribosomal protein S13. |
| | | | L01124 | Human ribosomal protein S13 (RPS13) mRNA, complete |
| 836 | CATG GTTCCCTGGC C | −775658 | X65923 | *H. sapiens* fau mRNA. |
| | | | U02523 | Human FAU1P pseudogene, trinucleotide repeat regio |
| 837 | CATG CCGTCCAAGG G | −374027 | M60854 | Human ribosomal protein S16 mRNA, complete cds. |
| 838 | CATG TTGGTCCTCT G | −1027448 | Z12962 | *H. sapiens* mRNA for homologue to yeast ribosomal pr |
| | | | S64030 | L41 ribosomal protein homolog {clone 7B6} [human, |
| 839 | CATG CAAACCATCC A | −263478 | X12883 | Human mRNA for cytokeratin 18. |
| | | | X12876 | Human mRNA fragment for cytokeratin 18. |
| | | | X12881 | Human mRNA for cytokeratin 18. |
| | | | M24842 | Human keratin 18 (K18) gene, complete cds. |
| | | | M26325 | Human cytokeratin 18 mRNA, 3' end. |
| | | | M26326 | Human keratin 18 mRNA, complete cds. |
| | | | M26327 | Human cytokeratin 18 mRNA, 3' end. |
| 840 | CATG AGCTCTCCCT G | −161624 | X53777 | Human L23 mRNA for putative ribosomal protein. |
| 841 | CATG AGGTCAGGAG A(T) | −177315 | D86979 | Human male bone marrow myeloblast mRNA for KIAA022 |
| | | | X55923 | Human DNA for Alu element P1N6. |
| | | | X79699 | *H. sapiens* ALU repeat, 230bp. |
| | | | X12544 | Human mRNA for HLA class II DR-beta (HLA-DRB). |
| | | | Z77989 | *H. sapiens* flow-sorted chromosome 6 HindIII fragmen |
| | | | U11831 | Human clone 2102V-I chromosome 18p telomeric seque |
| | | | U12580 | Human Alu repeat sequence A3. |
| | | | U12582 | Human Alu repeat sequence B2. |
| | | | U12583 | Human Alu repeat sequence D1. |
| | | | U14694 | Human Alu-Sb2 repeat, clone HALUSB08. |
| | | | U14695 | Human Alu-Sb2 repeat, clone HALUSB15. |
| | | | U14696 | Human Alu-Sb2 repeat, clone HALUSB27. |
| | | | U14697 | Human Alu-Sb2 repeat, clone HUM-11. |
| | | | U14698 | Human Alu-Sb2 repeat, clone HSB-8P. |
| | | | U14699 | Human Alu-Sb2 repeat, clone HUM-9. |
| | | | U14700 | Human Alu-Sb2 repeat, clone HALUSB35. |
| | | | U14701 | Human Alu-Sb2 repeat, clone HSB-2P. |
| | | | U14704 | Human Alu-Sb2 repeat, clone HUM-3. |
| | | | U14706 | Human Alu-Sb2 repeat, clone HUM-10. |
| | | | U14707 | Human Alu-Sb2 repeat, clone HUM-7. |
| | | | J00120 | Human (Lawn) c-myc proto-oncogene, complete coding |
| | | | L34653 | *Homo sapiens* platelet/endothelial cell adhesion mo |

TABLE 5-continued

Transcripts increased in pancreatic and colorectal cancer
SAGE tags that were elevated in both in coloreactal and pancreatic tumors,
and are likely to be specific for tumors in general.

| SEQ ID NO: | Tag_Sequence | Tag_Number | Accession | Description |
|---|---|---|---|---|
| | | | M37521 | Human XV2c gene. |
| | | | S61789 | NFI=neurofibromatosis type 1 {deletion breakpoint, |
| | | | S73483 | phosphorylase kinase catalytic subunit PHKG2 homol |
| | | | S75201 | cholinesterase {Alu element} [human, Insertion Mut |
| | | | S75337 | {Y Alu polymorphism, YAP, polymorphic subfamily-3} |
| 842 | CATG GGGCTGGGGT C | −695980 | Z49148 | H. sapiens mRNA for ribosomal protein L29. |
| | | | U10248 | Human ribosomal protein L29 (humrp129) mRNA, compl |
| | | | U49083 | Human cell surface heparin binding protein HIP mRN |
| | | | D16992 | Human HepG2 partial cDNA, clone hmd2d02m5. |
| | | | D16911 | Human HepG2 3' region cDNA, clone hmd3b09. |
| | | | J03537 | Human ribosomal protein S6 mRNA, complete cds. |
| | | | M20020 | Human ribosomal protein 56 mRNA, complete cds. |
| 843 | CATG ACGTTCTCTT C | −114144 | | EST |
| 844 | CATG TCTCCATACC C | −906438 | | EST |
| 845 | CATG GACTGCGTGC C | −555450 | | EST |
| 846 | CATG CTTAATCCTG A | −508767 | | EST |
| 847 | CATG GGTTGGCAGG G | −719435 | | EST |
| 848 | CATG GCCCTCTGCC A | −613862 | | EST |
| 849 | CATG AACAGAAGCA A | −18469 | | EST |
| 850 | CATG CTGCCGAGCT C | −497192 | | EST |
| 851 | CATG TTCCTCGGGC A | −1007018 | | EST |
| 852 | CATG AACTAATACT A | −28872 | | EST |
| 853 | CATG TAGATAATGG C | −822331 | | EST |
| 854 | CATG GCCACACCCC A, C | −607318 | | EST |
| 855 | CATG GAACCCTGGG A | −529899 | | EST |
| 856 | CATG AACTAAAAAA A | −28673 | | EST |
| 857 | CATG GAAATGTAAG A | −528067 | | EST |
| 858 | CATG ACTCCAAAAA A | −119809 | | EST |
| 859 | CATG GTTCGTGCCA A | −777109 | | EST |
| 860 | CATG TTACCTCCTT C | −989024 | | EST |
| 861 | CATG GCACAAGAAG A | −594051 | | EST |
| 862 | CATG CCCTGGGTTC T | −359102 | | EST |
| 863 | CATG GCCTGTATGA G | −621369 | | EST |
| 864 | CATG CCCGTCCGGA A | −355689 | | EST |
| 865 | CATG AGGAAAGCTG C | −163999 | | EST |
| 866 | CATG TCAGATCTTT G | −861056 | | EST |
| 867 | CATG CCAGGAGGAA T | −338081 | | EST |
| 868 | CATG TCACCCACAC C | −857362 | | EST |
| 869 | CATG GTGTTGCACA A | −769605 | | EST |
| 870 | CATG GCCGTGTCCG C | −618199 | | EST |

What is claimed is:

1. An isolated and purified first human nucleic acid molecule which has the same nucleotide sequence as a second nucleic acid molecule found in a human, which first human nucleic acid molecule comprises a SAGE tag shown in SEQ ID NO:180, wherein the SAGE tag is located adjacent to a NlaIII restriction enzyme site, wherein there are no NlaIII restriction enzyme sites further 3' than said site.

2. An isolated and purified human cDNA molecule which has the same nucleotide base sequence as a mRNA molecule found in a human, wherein said human cDNA molecule comprises a SAGE tag as shown in SEQ ID NO:180 or 289, wherein the SAGE tag is located adjacent to a NlaIII restriction enzyme site, wherein there are no NlaIII restriction enzyme sites further 3' than said site.

3. An isolated, labeled, single-stranded nucleotide probe comprising at least 10 contiguous nucleotides which have the same nucleotide base sequence as a human nucleic acid molecule found in a human, wherein the human nucleic acid molecule comprises a SAGE tag selected from SEQ ID NO:60, 98, 106, 108, 180, 248, 256, 289, 574, and 736 or its complement, wherein the SAGE tag is located adjacent to a NlaIII restriction enzyme site, wherein there are no NlaIII restriction enzyme sites further 3' than said site.

4. The probe of claim 3 which comprises the selected SAGE tag.

5. A diagnostic reagent for evaluating neoplasia of a colorectal tissue, comprising at least 2 probes according to claim 3.

6. The diagnostic reagent of claim 5 which comprises at least 5 probes according to claim 16.

7. The diagnostic reagent of claim 5 which comprises 10 probes according to claim 3.

8. An isolated and purified nucleic acid molecule which consists of a SAGE tag selected from the group consisting of SEQ ID NOS:60, 98, 106, 108, 180, 248, 256, 289, 574, and 736.

9. The molecule of claim 2 which comprises the SAGE tag which is SEQ ID NO: 180.

10. The probe of claim 3 wherein the SAGE tag is SEQ ID NO:180.

11. The probe of claim 3 wherein the SAGE tag is SEQ ID NO:60.

12. The probe of claim 3 wherein the SAGE tag is SEQ ID NO:98.

13. The probe of claim 3 wherein the SAGE tag is SEQ ID NO:106.

14. The probe of claim 3 wherein the SAGE tag is SEQ ID NO:108.

15. The probe of claim 3 wherein the SAGE tag is SEQ ID NO:248.

16. The probe of claim 3 wherein the SAGE tag is SEQ ID NO:256.

17. The probe of claim 3 wherein the SAGE tag is SEQ ID NO:289.

18. The probe of claim 3 wherein the SAGE tag is SEQ ID NO:574.

19. The probe of claim 3 wherein the SAGE tag is SEQ ID NO:736.

* * * * *

UNITED STATES PATENT AND TRADEMARK OFFICE
CERTIFICATE OF CORRECTION

PATENT NO.     : 6,333,152 B1                                                   Page 1 of 1
DATED          : December 25, 2001
INVENTOR(S)    : Bert Vogelstein et al.

It is certified that error appears in the above-identified patent and that said Letters Patent is hereby corrected as shown below:

<u>Title page,</u>
Item [73], replace "JohnsHopkins" with -- Johns Hopkins --
Item [60], insert -- Provisional application No. 60/047,352, filed on May 21, 1997. --
Item [56], replace "0 294 362" with -- 0 284 362 --
Item [56], OTHER PUBLICATIONS, "Sugio K. et al." reference, replace "vol. 38" with -- vol. 48 --
Item [74], *Attorney, Agent, or Firm,* replace "Bannee" with -- Banner --

Signed and Sealed this

Fifteenth Day of October, 2002

*Attest:*

*Attesting Officer*

JAMES E. ROGAN
*Director of the United States Patent and Trademark Office*

SEQUENCE LISTING

<160> NUMBER OF SEQ ID NOS: 871

<210> SEQ ID NO 1
<211> LENGTH: 15
<212> TYPE: DNA
<213> ORGANISM: Homo sapiens

<400> SEQUENCE: 1
catgcaccta attgg                                                  15

<210> SEQ ID NO 2
<211> LENGTH: 15
<212> TYPE: DNA
<213> ORGANISM: Homo sapiens

<400> SEQUENCE: 2
catgtgattt cactt                                                  15

<210> SEQ ID NO 3
<211> LENGTH: 15

-continued

```
<212> TYPE: DNA
<213> ORGANISM: Homo sapiens

<400> SEQUENCE: 3
catgcctgta atccc                                              15

<210> SEQ ID NO 4
<211> LENGTH: 15
<212> TYPE: DNA
<213> ORGANISM: Homo sapiens

<400> SEQUENCE: 4
catgcactac tcacc                                              15

<210> SEQ ID NO 5
<211> LENGTH: 15
<212> TYPE: DNA
<213> ORGANISM: Homo sapiens

<400> SEQUENCE: 5
catggtgaaa ccccr                                              15

<210> SEQ ID NO 6
<211> LENGTH: 15
<212> TYPE: DNA
<213> ORGANISM: Homo sapiens

<400> SEQUENCE: 6
catgggcttt aggga                                              15

<210> SEQ ID NO 7
<211> LENGTH: 14
<212> TYPE: DNA
<213> ORGANISM: Homo sapiens

<400> SEQUENCE: 7
catgactttc caaa                                               14

<210> SEQ ID NO 8
<211> LENGTH: 15
<212> TYPE: DNA
<213> ORGANISM: Homo sapiens

<400> SEQUENCE: 8
catgtggtgt atgca                                              15

<210> SEQ ID NO 9
<211> LENGTH: 15
<212> TYPE: DNA
<213> ORGANISM: Homo sapiens

<400> SEQUENCE: 9
catgagggtg ttttc                                              15

<210> SEQ ID NO 10
<211> LENGTH: 15
<212> TYPE: DNA
<213> ORGANISM: Homo sapiens

<400> SEQUENCE: 10
catgaggtca ggagw                                              15

<210> SEQ ID NO 11
```

-continued

```
<211> LENGTH: 15
<212> TYPE: DNA
<213> ORGANISM: Homo sapiens

<400> SEQUENCE: 11
catgttggcc aggct                                                    15

<210> SEQ ID NO 12
<211> LENGTH: 15
<212> TYPE: DNA
<213> ORGANISM: Homo sapiens

<400> SEQUENCE: 12
catgatcacg ccctc                                                    15

<210> SEQ ID NO 13
<211> LENGTH: 15
<212> TYPE: DNA
<213> ORGANISM: Homo sapiens

<400> SEQUENCE: 13
catgggggtc agggg                                                    15

<210> SEQ ID NO 14
<211> LENGTH: 15
<212> TYPE: DNA
<213> ORGANISM: Homo sapiens

<400> SEQUENCE: 14
catggctagg tttat                                                    15

<210> SEQ ID NO 15
<211> LENGTH: 15
<212> TYPE: DNA
<213> ORGANISM: Homo sapiens

<400> SEQUENCE: 15
catgccccgt acatc                                                    15

<210> SEQ ID NO 16
<211> LENGTH: 15
<212> TYPE: DNA
<213> ORGANISM: Homo sapiens

<400> SEQUENCE: 16
catgagtagg tggcc                                                    15

<210> SEQ ID NO 17
<211> LENGTH: 15
<212> TYPE: DNA
<213> ORGANISM: Homo sapiens

<400> SEQUENCE: 17
catgcctgta gtccc                                                    15

<210> SEQ ID NO 18
<211> LENGTH: 15
<212> TYPE: DNA
<213> ORGANISM: Homo sapiens

<400> SEQUENCE: 18
catgagaccc acaac                                                    15
```

```
<210> SEQ ID NO 19
<211> LENGTH: 15
<212> TYPE: DNA
<213> ORGANISM: Homo sapiens

<400> SEQUENCE: 19
catgcatttg taata                                                    15

<210> SEQ ID NO 20
<211> LENGTH: 15
<212> TYPE: DNA
<213> ORGANISM: Homo sapiens

<400> SEQUENCE: 20
catgtccccg tacct                                                    15

<210> SEQ ID NO 21
<211> LENGTH: 15
<212> TYPE: DNA
<213> ORGANISM: Homo sapiens

<400> SEQUENCE: 21
catggccaac ctcct                                                    15

<210> SEQ ID NO 22
<211> LENGTH: 15
<212> TYPE: DNA
<213> ORGANISM: Homo sapiens

<400> SEQUENCE: 22
catggccatc ccctt                                                    15

<210> SEQ ID NO 23
<211> LENGTH: 15
<212> TYPE: DNA
<213> ORGANISM: Homo sapiens

<400> SEQUENCE: 23
catgttggtc aggct                                                    15

<210> SEQ ID NO 24
<211> LENGTH: 14
<212> TYPE: DNA
<213> ORGANISM: Homo sapiens

<400> SEQUENCE: 24
catgtcctat taag                                                     14

<210> SEQ ID NO 25
<211> LENGTH: 15
<212> TYPE: DNA
<213> ORGANISM: Homo sapiens

<400> SEQUENCE: 25
catgttactt atact                                                    15

<210> SEQ ID NO 26
<211> LENGTH: 15
<212> TYPE: DNA
<213> ORGANISM: Homo sapiens

<400> SEQUENCE: 26
catgatggca ggagt                                                    15
```

```
<210> SEQ ID NO 27
<211> LENGTH: 15
<212> TYPE: DNA
<213> ORGANISM: Homo sapiens

<400> SEQUENCE: 27
catgctaagg cgagg                                                        15

<210> SEQ ID NO 28
<211> LENGTH: 15
<212> TYPE: DNA
<213> ORGANISM: Homo sapiens

<400> SEQUENCE: 28
catgggtgag acact                                                        15

<210> SEQ ID NO 29
<211> LENGTH: 15
<212> TYPE: DNA
<213> ORGANISM: Homo sapiens

<400> SEQUENCE: 29
catgacctgt atccc                                                        15

<210> SEQ ID NO 30
<211> LENGTH: 15
<212> TYPE: DNA
<213> ORGANISM: Homo sapiens

<400> SEQUENCE: 30
catgccagtc cgcct                                                        15

<210> SEQ ID NO 31
<211> LENGTH: 15
<212> TYPE: DNA
<213> ORGANISM: Homo sapiens

<400> SEQUENCE: 31
catgtaattt ttgcc                                                        15

<210> SEQ ID NO 32
<211> LENGTH: 15
<212> TYPE: DNA
<213> ORGANISM: Homo sapiens

<400> SEQUENCE: 32
catgttagct tgttt                                                        15

<210> SEQ ID NO 33
<211> LENGTH: 15
<212> TYPE: DNA
<213> ORGANISM: Homo sapiens

<400> SEQUENCE: 33
catggccacc ccctg                                                        15

<210> SEQ ID NO 34
<211> LENGTH: 15
<212> TYPE: DNA
<213> ORGANISM: Homo sapiens

<400> SEQUENCE: 34
catgtaataa aggtg                                                        15
```

<210> SEQ ID NO 35
<211> LENGTH: 15
<212> TYPE: DNA
<213> ORGANISM: Homo sapiens

<400> SEQUENCE: 35
catgtactgc tcgga                                                            15

<210> SEQ ID NO 36
<211> LENGTH: 14
<212> TYPE: DNA
<213> ORGANISM: Homo sapiens

<400> SEQUENCE: 36
catggtgaaa ccca                                                             14

<210> SEQ ID NO 37
<211> LENGTH: 15
<212> TYPE: DNA
<213> ORGANISM: Homo sapiens

<400> SEQUENCE: 37
catggaaact gaaca                                                            15

<210> SEQ ID NO 38
<211> LENGTH: 15
<212> TYPE: DNA
<213> ORGANISM: Homo sapiens

<400> SEQUENCE: 38
catgactttt taaaa                                                            15

<210> SEQ ID NO 39
<211> LENGTH: 15
<212> TYPE: DNA
<213> ORGANISM: Homo sapiens

<400> SEQUENCE: 39
catggactgc gtgcc                                                            15

<210> SEQ ID NO 40
<211> LENGTH: 15
<212> TYPE: DNA
<213> ORGANISM: Homo sapiens

<400> SEQUENCE: 40
catgtcagtg gtagt                                                            15

<210> SEQ ID NO 41
<211> LENGTH: 15
<212> TYPE: DNA
<213> ORGANISM: Homo sapiens

<400> SEQUENCE: 41
catgaaactg tggtt                                                            15

<210> SEQ ID NO 42
<211> LENGTH: 15
<212> TYPE: DNA
<213> ORGANISM: Homo sapiens

<400> SEQUENCE: 42

```
catgggggggg ggggt                                           15

<210> SEQ ID NO 43
<211> LENGTH: 15
<212> TYPE: DNA
<213> ORGANISM: Homo sapiens

<400> SEQUENCE: 43
catggtgccc gtgcc                                            15

<210> SEQ ID NO 44
<211> LENGTH: 15
<212> TYPE: DNA
<213> ORGANISM: Homo sapiens

<400> SEQUENCE: 44 catgggggt aacta                                             15

<210> SEQ ID NO 45
<211> LENGTH: 15
<212> TYPE: DNA
<213> ORGANISM: Homo sapiens

<400> SEQUENCE: 45
catgtcctgc cccat                                            15

<210> SEQ ID NO 46
<211> LENGTH: 15
<212> TYPE: DNA
<213> ORGANISM: Homo sapiens

<400> SEQUENCE: 46
catgaagtgg caaga                                            15

<210> SEQ ID NO 47
<211> LENGTH: 15
<212> TYPE: DNA
<213> ORGANISM: Homo sapiens

<400> SEQUENCE: 47
catgggtatt aacca                                            15

<210> SEQ ID NO 48
<211> LENGTH: 15
<212> TYPE: DNA
<213> ORGANISM: Homo sapiens

<400> SEQUENCE: 48
catgggctac acctt                                            15

<210> SEQ ID NO 49
<211> LENGTH: 15
<212> TYPE: DNA
<213> ORGANISM: Homo sapiens

<400> SEQUENCE: 49
catgagggtg tttcc                                            15

<210> SEQ ID NO 50
<211> LENGTH: 15
<212> TYPE: DNA
<213> ORGANISM: Homo sapiens

<400> SEQUENCE: 50
```

-continued catgcaagga ccagc                                                15

<210> SEQ ID NO 51
<211> LENGTH: 15
<212> TYPE: DNA
<213> ORGANISM: Homo sapiens

<400> SEQUENCE: 51
catgtggaaa tgacc                                                15

<210> SEQ ID NO 52
<211> LENGTH: 15
<212> TYPE: DNA
<213> ORGANISM: Homo sapiens

<400> SEQUENCE: 52
catgatccgc ctgcc                                                15

<210> SEQ ID NO 53
<211> LENGTH: 14
<212> TYPE: DNA
<213> ORGANISM: Homo sapiens

<400> SEQUENCE: 53
catgtcccgt acac                                                 14

<210> SEQ ID NO 54
<211> LENGTH: 15
<212> TYPE: DNA
<213> ORGANISM: Homo sapiens

<400> SEQUENCE: 54
catgatgtaa aaaat                                                15

<210> SEQ ID NO 55
<211> LENGTH: 15
<212> TYPE: DNA
<213> ORGANISM: Homo sapiens

<400> SEQUENCE: 55
catgccagcc ccgtc                                                15

<210> SEQ ID NO 56
<211> LENGTH: 15
<212> TYPE: DNA
<213> ORGANISM: Homo sapiens

<400> SEQUENCE: 56
catgaccatt ctgct                                                15

<210> SEQ ID NO 57
<211> LENGTH: 15
<212> TYPE: DNA
<213> ORGANISM: Homo sapiens

<400> SEQUENCE: 57
catgaggacc atcgc                                                15

<210> SEQ ID NO 58
<211> LENGTH: 15
<212> TYPE: DNA
<213> ORGANISM: Homo sapiens -continued

```
<400> SEQUENCE: 58
catgatgtga agagw                                                    15

<210> SEQ ID NO 59
<211> LENGTH: 15
<212> TYPE: DNA
<213> ORGANISM: Homo sapiens

<400> SEQUENCE: 59
catgcagttg gttgt                                                    15

<210> SEQ ID NO 60
<211> LENGTH: 15
<212> TYPE: DNA
<213> ORGANISM: Homo sapiens

<400> SEQUENCE: 60
catggccctc tgcca                                                    15

<210> SEQ ID NO 61
<211> LENGTH: 15
<212> TYPE: DNA
<213> ORGANISM: Homo sapiens

<400> SEQUENCE: 61
catgttagat aagca                                                    15

<210> SEQ ID NO 62
<211> LENGTH: 15
<212> TYPE: DNA
<213> ORGANISM: Homo sapiens

<400> SEQUENCE: 62
catggcagcc atccg                                                    15

<210> SEQ ID NO 63
<211> LENGTH: 15
<212> TYPE: DNA
<213> ORGANISM: Homo sapiens

<400> SEQUENCE: 63
catgatggct ggtat                                                    15

<210> SEQ ID NO 64
<211> LENGTH: 15
<212> TYPE: DNA
<213> ORGANISM: Homo sapiens

<400> SEQUENCE: 64
catgcccgtc cggaa                                                    15

<210> SEQ ID NO 65
<211> LENGTH: 15
<212> TYPE: DNA
<213> ORGANISM: Homo sapiens

<400> SEQUENCE: 65
catgaggcta cggaa                                                    15

<210> SEQ ID NO 66
<211> LENGTH: 15
<212> TYPE: DNA
<213> ORGANISM: Homo sapiens
```

```
<400> SEQUENCE: 66
catgagcacc tccag                                                    15

<210> SEQ ID NO 67
<211> LENGTH: 15
<212> TYPE: DNA
<213> ORGANISM: Homo sapiens

<400> SEQUENCE: 67
catgctgggt taata                                                    15

<210> SEQ ID NO 68
<211> LENGTH: 15
<212> TYPE: DNA
<213> ORGANISM: Homo sapiens

<400> SEQUENCE: 68
catgggattt ggcct                                                    15

<210> SEQ ID NO 69
<211> LENGTH: 15
<212> TYPE: DNA
<213> ORGANISM: Homo sapiens

<400> SEQUENCE: 69
catgtaccat caata                                                    15

<210> SEQ ID NO 70
<211> LENGTH: 15
<212> TYPE: DNA
<213> ORGANISM: Homo sapiens

<400> SEQUENCE: 70
catgtgggca aagcc                                                    15

<210> SEQ ID NO 71
<211> LENGTH: 15
<212> TYPE: DNA
<213> ORGANISM: Homo sapiens

<400> SEQUENCE: 71
catgaatcct gtgga                                                    15

<210> SEQ ID NO 72
<211> LENGTH: 15
<212> TYPE: DNA
<213> ORGANISM: Homo sapiens

<400> SEQUENCE: 72
catgggacca ctgaa                                                    15

<210> SEQ ID NO 73
<211> LENGTH: 15
<212> TYPE: DNA
<213> ORGANISM: Homo sapiens

<400> SEQUENCE: 73
catgagggct tccaa                                                    15

<210> SEQ ID NO 74
<211> LENGTH: 15
<212> TYPE: DNA
```

```
<213> ORGANISM: Homo sapiens

<400> SEQUENCE: 74
catgaaggtg gagga                                                      15

<210> SEQ ID NO 75
<211> LENGTH: 15
<212> TYPE: DNA
<213> ORGANISM: Homo sapiens

<400> SEQUENCE: 75
catgtgcacg ttttc                                                      15

<210> SEQ ID NO 76
<211> LENGTH: 15
<212> TYPE: DNA
<213> ORGANISM: Homo sapiens

<400> SEQUENCE: 76
catgtcagat ctttg                                                      15

<210> SEQ ID NO 77
<211> LENGTH: 15
<212> TYPE: DNA
<213> ORGANISM: Homo sapiens

<400> SEQUENCE: 77
catgtggtgt tgagg                                                      15

<210> SEQ ID NO 78
<211> LENGTH: 15
<212> TYPE: DNA
<213> ORGANISM: Homo sapiens

<400> SEQUENCE: 78
catgcctagc tggat                                                      15

<210> SEQ ID NO 79
<211> LENGTH: 15
<212> TYPE: DNA
<213> ORGANISM: Homo sapiens

<400> SEQUENCE: 79
catgcttggg ttttg                                                      15

<210> SEQ ID NO 80
<211> LENGTH: 15
<212> TYPE: DNA
<213> ORGANISM: Homo sapiens

<400> SEQUENCE: 80
catgctcctc acctg                                                      15

<210> SEQ ID NO 81
<211> LENGTH: 15
<212> TYPE: DNA
<213> ORGANISM: Homo sapiens

<400> SEQUENCE: 81
catgctgttg gtgat                                                      15

<210> SEQ ID NO 82
<211> LENGTH: 15
```

```
<212> TYPE: DNA
<213> ORGANISM: Homo sapiens

<400> SEQUENCE: 82
catgcgccgg aacac                                                    15

<210> SEQ ID NO 83
<211> LENGTH: 15
<212> TYPE: DNA
<213> ORGANISM: Homo sapiens

<400> SEQUENCE: 83
catgcaataa atgtt                                                    15

<210> SEQ ID NO 84
<211> LENGTH: 15
<212> TYPE: DNA
<213> ORGANISM: Homo sapiens

<400> SEQUENCE: 84
catgacatca tcgat                                                    15

<210> SEQ ID NO 85
<211> LENGTH: 15
<212> TYPE: DNA
<213> ORGANISM: Homo sapiens

<400> SEQUENCE: 85
catgttcaat aaaaa                                                    15

<210> SEQ ID NO 86
<211> LENGTH: 15
<212> TYPE: DNA
<213> ORGANISM: Homo sapiens

<400> SEQUENCE: 86
catggaacac atcca                                                    15

<210> SEQ ID NO 87
<211> LENGTH: 15
<212> TYPE: DNA
<213> ORGANISM: Homo sapiens

<400> SEQUENCE: 87
catgttatgg gatct                                                    15

<210> SEQ ID NO 88
<211> LENGTH: 15
<212> TYPE: DNA
<213> ORGANISM: Homo sapiens

<400> SEQUENCE: 88
catggcataa taggt                                                    15

<210> SEQ ID NO 89
<211> LENGTH: 15
<212> TYPE: DNA
<213> ORGANISM: Homo sapiens

<400> SEQUENCE: 89
catgattctc cagta                                                    15

<210> SEQ ID NO 90
```

```
<211> LENGTH: 15
<212> TYPE: DNA
<213> ORGANISM: Homo sapiens

<400> SEQUENCE: 90
catgactcca aaaaa                                                          15

<210> SEQ ID NO 91
<211> LENGTH: 15
<212> TYPE: DNA
<213> ORGANISM: Homo sapiens

<400> SEQUENCE: 91
catgctgttg attgc                                                          15

<210> SEQ ID NO 92
<211> LENGTH: 15
<212> TYPE: DNA
<213> ORGANISM: Homo sapiens

<400> SEQUENCE: 92
catgtacaaa atcga                                                          15

<210> SEQ ID NO 93
<211> LENGTH: 15
<212> TYPE: DNA
<213> ORGANISM: Homo sapiens

<400> SEQUENCE: 93
catggaaaaa tggtt                                                          15

<210> SEQ ID NO 94
<211> LENGTH: 15
<212> TYPE: DNA
<213> ORGANISM: Homo sapiens

<400> SEQUENCE: 94
catgaagaag ataga                                                          15

<210> SEQ ID NO 95
<211> LENGTH: 15
<212> TYPE: DNA
<213> ORGANISM: Homo sapiens

<400> SEQUENCE: 95
catgccttcg agatc                                                          15

<210> SEQ ID NO 96
<211> LENGTH: 15
<212> TYPE: DNA
<213> ORGANISM: Homo sapiens

<400> SEQUENCE: 96
catgactggg tctat                                                          15

<210> SEQ ID NO 97
<211> LENGTH: 15
<212> TYPE: DNA
<213> ORGANISM: Homo sapiens

<400> SEQUENCE: 97
catgcagctc actga                                                          15
```

```
<210> SEQ ID NO 98
<211> LENGTH: 15
<212> TYPE: DNA
<213> ORGANISM: Homo sapiens

<400> SEQUENCE: 98
catggtgtgt ttgta                                               15

<210> SEQ ID NO 99
<211> LENGTH: 15
<212> TYPE: DNA
<213> ORGANISM: Homo sapiens

<400> SEQUENCE: 99
catggtgcgc tgagc                                               15

<210> SEQ ID NO 100
<211> LENGTH: 15
<212> TYPE: DNA
<213> ORGANISM: Homo sapiens

<400> SEQUENCE: 100
catggttcac attag                                               15

<210> SEQ ID NO 101
<211> LENGTH: 15
<212> TYPE: DNA
<213> ORGANISM: Homo sapiens

<400> SEQUENCE: 101
catgtgaaat aaaac                                               15

<210> SEQ ID NO 102
<211> LENGTH: 15
<212> TYPE: DNA
<213> ORGANISM: Homo sapiens

<400> SEQUENCE: 102
catgaaaaga aactt                                               15

<210> SEQ ID NO 103
<211> LENGTH: 15
<212> TYPE: DNA
<213> ORGANISM: Homo sapiens

<400> SEQUENCE: 103
catgtgctgc ctgtt                                               15

<210> SEQ ID NO 104
<211> LENGTH: 15
<212> TYPE: DNA
<213> ORGANISM: Homo sapiens

<400> SEQUENCE: 104
catgctgatg gcaga                                               15

<210> SEQ ID NO 105
<211> LENGTH: 15
<212> TYPE: DNA
<213> ORGANISM: Homo sapiens

<400> SEQUENCE: 105
catgactcgc tctgt                                               15
```

-continued

```
<210> SEQ ID NO 106
<211> LENGTH: 15
<212> TYPE: DNA
<213> ORGANISM: Homo sapiens

<400> SEQUENCE: 106
catggcccaa ggacc                                                15

<210> SEQ ID NO 107
<211> LENGTH: 15
<212> TYPE: DNA
<213> ORGANISM: Homo sapiens

<400> SEQUENCE: 107
catgatcttg ttact                                                15

<210> SEQ ID NO 108
<211> LENGTH: 15
<212> TYPE: DNA
<213> ORGANISM: Homo sapiens

<400> SEQUENCE: 108
catgaagctg ctgga                                                15

<210> SEQ ID NO 109
<211> LENGTH: 15
<212> TYPE: DNA
<213> ORGANISM: Homo sapiens

<400> SEQUENCE: 109
catgtgtgtt gagag                                                15

<210> SEQ ID NO 110
<211> LENGTH: 15
<212> TYPE: DNA
<213> ORGANISM: Homo sapiens

<400> SEQUENCE: 110
catggccgag gaagg                                                15

<210> SEQ ID NO 111
<211> LENGTH: 15
<212> TYPE: DNA
<213> ORGANISM: Homo sapiens

<400> SEQUENCE: 111
catgcaaacc atcca                                                15

<210> SEQ ID NO 112
<211> LENGTH: 15
<212> TYPE: DNA
<213> ORGANISM: Homo sapiens

<400> SEQUENCE: 112
catgcacaaa cggta                                                15

<210> SEQ ID NO 113
<211> LENGTH: 15
<212> TYPE: DNA
<213> ORGANISM: Homo sapiens

<400> SEQUENCE: 113
catgaaaaaa aaaaa                                                15
```

<210> SEQ ID NO 114
<211> LENGTH: 15
<212> TYPE: DNA
<213> ORGANISM: Homo sapiens

<400> SEQUENCE: 114
catgttggtc ctctg                                                15

<210> SEQ ID NO 115
<211> LENGTH: 15
<212> TYPE: DNA
<213> ORGANISM: Homo sapiens

<400> SEQUENCE: 115
catgtctcca taccc                                                15

<210> SEQ ID NO 116
<211> LENGTH: 15
<212> TYPE: DNA
<213> ORGANISM: Homo sapiens

<400> SEQUENCE: 116
catgaagaca gtggc                                                15

<210> SEQ ID NO 117
<211> LENGTH: 15
<212> TYPE: DNA
<213> ORGANISM: Homo sapiens

<400> SEQUENCE: 117
catgccgtcc aaggg                                                15

<210> SEQ ID NO 118
<211> LENGTH: 15
<212> TYPE: DNA
<213> ORGANISM: Homo sapiens

<400> SEQUENCE: 118
catgggggaa atcgc                                                15

<210> SEQ ID NO 119
<211> LENGTH: 15
<212> TYPE: DNA
<213> ORGANISM: Homo sapiens

<400> SEQUENCE: 119
catgaaggag atggg                                                15

<210> SEQ ID NO 120
<211> LENGTH: 15
<212> TYPE: DNA
<213> ORGANISM: Homo sapiens

<400> SEQUENCE: 120
catggaggga gtttc                                                15

<210> SEQ ID NO 121
<211> LENGTH: 15
<212> TYPE: DNA
<213> ORGANISM: Homo sapiens

<400> SEQUENCE: 121
catgcgctgg ttcca 15

<210> SEQ ID NO 122
<211> LENGTH: 15
<212> TYPE: DNA
<213> ORGANISM: Homo sapiens

<400> SEQUENCE: 122
catggccgtg tccgc 15

<210> SEQ ID NO 123
<211> LENGTH: 15
<212> TYPE: DNA
<213> ORGANISM: Homo sapiens

<400> SEQUENCE: 123
catggacgac acgag 15

<210> SEQ ID NO 124
<211> LENGTH: 15
<212> TYPE: DNA
<213> ORGANISM: Homo sapiens

<400> SEQUENCE: 124
catgtcaccc acacc 15

<210> SEQ ID NO 125
<211> LENGTH: 15
<212> TYPE: DNA
<213> ORGANISM: Homo sapiens

<400> SEQUENCE: 125
catgcgccgc cggct 15

<210> SEQ ID NO 126
<211> LENGTH: 15
<212> TYPE: DNA
<213> ORGANISM: Homo sapiens

<400> SEQUENCE: 126
catgctcaac atctc 15

<210> SEQ ID NO 127
<211> LENGTH: 15
<212> TYPE: DNA
<213> ORGANISM: Homo sapiens

<400> SEQUENCE: 127
catgtggccc caccc 15

<210> SEQ ID NO 128
<211> LENGTH: 15
<212> TYPE: DNA
<213> ORGANISM: Homo sapiens

<400> SEQUENCE: 128
catgccctgg gttct 15

<210> SEQ ID NO 129
<211> LENGTH: 15
<212> TYPE: DNA
<213> ORGANISM: Homo sapiens

<400> SEQUENCE: 129

```
catgagcatc tccag                                                    15

<210> SEQ ID NO 130
<211> LENGTH: 15
<212> TYPE: DNA
<213> ORGANISM: Homo sapiens

<400> SEQUENCE: 130
catggcctgt atgag                                                    15

<210> SEQ ID NO 131
<211> LENGTH: 15
<212> TYPE: DNA
<213> ORGANISM: Homo sapiens

<400> SEQUENCE: 131
catgagctct ccctg                                                    15

<210> SEQ ID NO 132
<211> LENGTH: 15
<212> TYPE: DNA
<213> ORGANISM: Homo sapiens

<400> SEQUENCE: 132
catgccagga ggaat                                                    15

<210> SEQ ID NO 133
<211> LENGTH: 15
<212> TYPE: DNA
<213> ORGANISM: Homo sapiens

<400> SEQUENCE: 133
catgggcaag cccca                                                    15

<210> SEQ ID NO 134
<211> LENGTH: 15
<212> TYPE: DNA
<213> ORGANISM: Homo sapiens

<400> SEQUENCE: 134
catgaggaaa gctgc                                                    15

<210> SEQ ID NO 135
<211> LENGTH: 15
<212> TYPE: DNA
<213> ORGANISM: Homo sapiens

<400> SEQUENCE: 135
catgaacgcg gccaa                                                    15

<210> SEQ ID NO 136
<211> LENGTH: 15
<212> TYPE: DNA
<213> ORGANISM: Homo sapiens

<400> SEQUENCE: 136
catgccagaa cagac                                                    15

<210> SEQ ID NO 137
<211> LENGTH: 15
<212> TYPE: DNA
<213> ORGANISM: Homo sapiens
```

```
<400> SEQUENCE: 137
catggccgcc atctc                                                        15

<210> SEQ ID NO 138
<211> LENGTH: 15
<212> TYPE: DNA
<213> ORGANISM: Homo sapiens

<400> SEQUENCE: 138
catggtgtta accag                                                        15

<210> SEQ ID NO 139
<211> LENGTH: 15
<212> TYPE: DNA
<213> ORGANISM: Homo sapiens

<400> SEQUENCE: 139
catgcctcgg aaaat                                                        15

<210> SEQ ID NO 140
<211> LENGTH: 15
<212> TYPE: DNA
<213> ORGANISM: Homo sapiens

<400> SEQUENCE: 140
catgaggtcc tagcc                                                        15

<210> SEQ ID NO 141
<211> LENGTH: 15
<212> TYPE: DNA
<213> ORGANISM: Homo sapiens

<400> SEQUENCE: 141
catggttccc tggcc                                                        15

<210> SEQ ID NO 142
<211> LENGTH: 15
<212> TYPE: DNA
<213> ORGANISM: Homo sapiens

<400> SEQUENCE: 142
catgtaagga gctga                                                        15

<210> SEQ ID NO 143
<211> LENGTH: 15
<212> TYPE: DNA
<213> ORGANISM: Homo sapiens

<400> SEQUENCE: 143
catgaactaa aaaaa                                                        15

<210> SEQ ID NO 144
<211> LENGTH: 15
<212> TYPE: DNA
<213> ORGANISM: Homo sapiens

<400> SEQUENCE: 144
catgatttgt cccag                                                        15

<210> SEQ ID NO 145
<211> LENGTH: 15
<212> TYPE: DNA
<213> ORGANISM: Homo sapiens
```

<400> SEQUENCE: 145
catgataatt ctttg                    15

<210> SEQ ID NO 146
<211> LENGTH: 15
<212> TYPE: DNA
<213> ORGANISM: Homo sapiens

<400> SEQUENCE: 146
catgccccag ccagt                    15

<210> SEQ ID NO 147
<211> LENGTH: 15
<212> TYPE: DNA
<213> ORGANISM: Homo sapiens

<400> SEQUENCE: 147
catgggagtg gacat                    15

<210> SEQ ID NO 148
<211> LENGTH: 15
<212> TYPE: DNA
<213> ORGANISM: Homo sapiens

<400> SEQUENCE: 148
catgtaaaaa aaaaa                    15

<210> SEQ ID NO 149
<211> LENGTH: 15
<212> TYPE: DNA
<213> ORGANISM: Homo sapiens

<400> SEQUENCE: 149
catggtgttg cacaa                    15

<210> SEQ ID NO 150
<211> LENGTH: 15
<212> TYPE: DNA
<213> ORGANISM: Homo sapiens

<400> SEQUENCE: 150
catggccagc ccagc                    15

<210> SEQ ID NO 151
<211> LENGTH: 15
<212> TYPE: DNA
<213> ORGANISM: Homo sapiens

<400> SEQUENCE: 151
catgggctcc cactg                    15

<210> SEQ ID NO 152
<211> LENGTH: 15
<212> TYPE: DNA
<213> ORGANISM: Homo sapiens

<400> SEQUENCE: 152
catgtcaact tctgg                    15

<210> SEQ ID NO 153
<211> LENGTH: 15
<212> TYPE: DNA

-continued

```
<213> ORGANISM: Homo sapiens

<400> SEQUENCE: 153
catggatgct gccaa                                                15

<210> SEQ ID NO 154
<211> LENGTH: 15
<212> TYPE: DNA
<213> ORGANISM: Homo sapiens

<400> SEQUENCE: 154
catgaatagg tccaa                                                15

<210> SEQ ID NO 155
<211> LENGTH: 15
<212> TYPE: DNA
<213> ORGANISM: Homo sapiens

<400> SEQUENCE: 155
catggctttt aagga                                                15

<210> SEQ ID NO 156
<211> LENGTH: 15
<212> TYPE: DNA
<213> ORGANISM: Homo sapiens

<400> SEQUENCE: 156
catgaatgca ggcag                                                15

<210> SEQ ID NO 157
<211> LENGTH: 15
<212> TYPE: DNA
<213> ORGANISM: Homo sapiens

<400> SEQUENCE: 157
catggcccag ctgga                                                15

<210> SEQ ID NO 158
<211> LENGTH: 15
<212> TYPE: DNA
<213> ORGANISM: Homo sapiens

<400> SEQUENCE: 158
catgggccgc gttcg                                                15

<210> SEQ ID NO 159
<211> LENGTH: 15
<212> TYPE: DNA
<213> ORGANISM: Homo sapiens

<400> SEQUENCE: 159
catgtgaggg aataa                                                15

<210> SEQ ID NO 160
<211> LENGTH: 15
<212> TYPE: DNA
<213> ORGANISM: Homo sapiens

<400> SEQUENCE: 160
catgtgtacc tgtaa                                                15

<210> SEQ ID NO 161
<211> LENGTH: 15
```

```
<212> TYPE: DNA
<213> ORGANISM: Homo sapiens

<400> SEQUENCE: 161
catgggcaag aagaa                                                  15

<210> SEQ ID NO 162
<211> LENGTH: 15
<212> TYPE: DNA
<213> ORGANISM: Homo sapiens

<400> SEQUENCE: 162
catgaactaa caaaa                                                  15

<210> SEQ ID NO 163
<211> LENGTH: 15
<212> TYPE: DNA
<213> ORGANISM: Homo sapiens

<400> SEQUENCE: 163
catgtatacg ctcag                                                  15

<210> SEQ ID NO 164
<211> LENGTH: 15
<212> TYPE: DNA
<213> ORGANISM: Homo sapiens

<400> SEQUENCE: 164
catgtacaag aggaa                                                  15

<210> SEQ ID NO 165
<211> LENGTH: 15
<212> TYPE: DNA
<213> ORGANISM: Homo sapiens

<400> SEQUENCE: 165
catggttaac gtccc                                                  15

<210> SEQ ID NO 166
<211> LENGTH: 15
<212> TYPE: DNA
<213> ORGANISM: Homo sapiens

<400> SEQUENCE: 166
catggagact cctgc                                                  15

<210> SEQ ID NO 167
<211> LENGTH: 15
<212> TYPE: DNA
<213> ORGANISM: Homo sapiens

<400> SEQUENCE: 167
catgatccac atcgc                                                  15

<210> SEQ ID NO 168
<211> LENGTH: 15
<212> TYPE: DNA
<213> ORGANISM: Homo sapiens

<400> SEQUENCE: 168
catggaagct ttgca                                                  15

<210> SEQ ID NO 169
```

```
<211> LENGTH: 15
<212> TYPE: DNA
<213> ORGANISM: Homo sapiens

<400> SEQUENCE: 169
catgctggcg agcgc                                                    15

<210> SEQ ID NO 170
<211> LENGTH: 15
<212> TYPE: DNA
<213> ORGANISM: Homo sapiens

<400> SEQUENCE: 170
catgctgaga caaag                                                    15

<210> SEQ ID NO 171
<211> LENGTH: 15
<212> TYPE: DNA
<213> ORGANISM: Homo sapiens

<400> SEQUENCE: 171
catgaacgac ctcgt                                                    15

<210> SEQ ID NO 172
<211> LENGTH: 15
<212> TYPE: DNA
<213> ORGANISM: Homo sapiens

<400> SEQUENCE: 172
catggcatag gctgc                                                    15

<210> SEQ ID NO 173
<211> LENGTH: 15
<212> TYPE: DNA
<213> ORGANISM: Homo sapiens

<400> SEQUENCE: 173
catgcatctt cacca                                                    15

<210> SEQ ID NO 174
<211> LENGTH: 15
<212> TYPE: DNA
<213> ORGANISM: Homo sapiens

<400> SEQUENCE: 174
catggcctgc tgggc                                                    15

<210> SEQ ID NO 175
<211> LENGTH: 15
<212> TYPE: DNA
<213> ORGANISM: Homo sapiens

<400> SEQUENCE: 175
catgacaggc tacgg                                                    15

<210> SEQ ID NO 176
<211> LENGTH: 15
<212> TYPE: DNA
<213> ORGANISM: Homo sapiens

<400> SEQUENCE: 176
catggaaatg taaga                                                    15
```

```
<210> SEQ ID NO 177
<211> LENGTH: 15
<212> TYPE: DNA
<213> ORGANISM: Homo sapiens

<400> SEQUENCE: 177
catggaagcc agcca                                              15

<210> SEQ ID NO 178
<211> LENGTH: 15
<212> TYPE: DNA
<213> ORGANISM: Homo sapiens

<400> SEQUENCE: 178
catgttacca tatca                                              15

<210> SEQ ID NO 179
<211> LENGTH: 15
<212> TYPE: DNA
<213> ORGANISM: Homo sapiens

<400> SEQUENCE: 179
catgttgctc acaaa                                              15

<210> SEQ ID NO 180
<211> LENGTH: 15
<212> TYPE: DNA
<213> ORGANISM: Homo sapiens

<400> SEQUENCE: 180
catgtccccg ctcga                                              15

<210> SEQ ID NO 181
<211> LENGTH: 15
<212> TYPE: DNA
<213> ORGANISM: Homo sapiens

<400> SEQUENCE: 181
catgattaac aaagc                                              15

<210> SEQ ID NO 182
<211> LENGTH: 15
<212> TYPE: DNA
<213> ORGANISM: Homo sapiens

<400> SEQUENCE: 182
catgcagatc tttgt                                              15

<210> SEQ ID NO 183
<211> LENGTH: 15
<212> TYPE: DNA
<213> ORGANISM: Homo sapiens

<400> SEQUENCE: 183
catggttcgt gccaa                                              15

<210> SEQ ID NO 184
<211> LENGTH: 15
<212> TYPE: DNA
<213> ORGANISM: Homo sapiens

<400> SEQUENCE: 184
catggacgtg tgggc                                              15
```

<210> SEQ ID NO 185
<211> LENGTH: 15
<212> TYPE: DNA
<213> ORGANISM: Homo sapiens

<400> SEQUENCE: 185
catgctaaaa aaaaa                                                          15

<210> SEQ ID NO 186
<211> LENGTH: 15
<212> TYPE: DNA
<213> ORGANISM: Homo sapiens

<400> SEQUENCE: 186
catggggttt ttatt                                                          15

<210> SEQ ID NO 187
<211> LENGTH: 15
<212> TYPE: DNA
<213> ORGANISM: Homo sapiens

<400> SEQUENCE: 187
catgccgatc accgg                                                          15

<210> SEQ ID NO 188
<211> LENGTH: 15
<212> TYPE: DNA
<213> ORGANISM: Homo sapiens

<400> SEQUENCE: 188
catggcacaa gaaga                                                          15

<210> SEQ ID NO 189
<211> LENGTH: 15
<212> TYPE: DNA
<213> ORGANISM: Homo sapiens

<400> SEQUENCE: 189
catgtctcta cccac                                                          15

<210> SEQ ID NO 190
<211> LENGTH: 15
<212> TYPE: DNA
<213> ORGANISM: Homo sapiens

<400> SEQUENCE: 190
catggtttcc ccaag                                                          15

<210> SEQ ID NO 191
<211> LENGTH: 15
<212> TYPE: DNA
<213> ORGANISM: Homo sapiens

<400> SEQUENCE: 191
catgcctgtc cagcc                                                          15

<210> SEQ ID NO 192
<211> LENGTH: 15
<212> TYPE: DNA
<213> ORGANISM: Homo sapiens

<400> SEQUENCE: 192
catgtcatca tctga                                                          15

-continued

<210> SEQ ID NO 193
<211> LENGTH: 15
<212> TYPE: DNA
<213> ORGANISM: Homo sapiens

<400> SEQUENCE: 193
catgccctgc cttgt 15

<210> SEQ ID NO 194
<211> LENGTH: 15
<212> TYPE: DNA
<213> ORGANISM: Homo sapiens

<400> SEQUENCE: 194
catggccggg ccctc 15

<210> SEQ ID NO 195
<211> LENGTH: 15
<212> TYPE: DNA
<213> ORGANISM: Homo sapiens

<400> SEQUENCE: 195
catgttgctc aaaaa 15

<210> SEQ ID NO 196
<211> LENGTH: 15
<212> TYPE: DNA
<213> ORGANISM: Homo sapiens

<400> SEQUENCE: 196
catgcaaaat cagga 15

<210> SEQ ID NO 197
<211> LENGTH: 15
<212> TYPE: DNA
<213> ORGANISM: Homo sapiens

<400> SEQUENCE: 197
catggaagat gtggg 15

<210> SEQ ID NO 198
<211> LENGTH: 15
<212> TYPE: DNA
<213> ORGANISM: Homo sapiens

<400> SEQUENCE: 198
catggtgctc attca 15

<210> SEQ ID NO 199
<211> LENGTH: 15
<212> TYPE: DNA
<213> ORGANISM: Homo sapiens

<400> SEQUENCE: 199
catggcttta ctttg 15

<210> SEQ ID NO 200
<211> LENGTH: 15
<212> TYPE: DNA
<213> ORGANISM: Homo sapiens

<400> SEQUENCE: 200

-continued catgttttct gaaaa 15

<210> SEQ ID NO 201
<211> LENGTH: 15
<212> TYPE: DNA
<213> ORGANISM: Homo sapiens

<400> SEQUENCE: 201
catgttgctc acaca 15

<210> SEQ ID NO 202
<211> LENGTH: 15
<212> TYPE: DNA
<213> ORGANISM: Homo sapiens

<400> SEQUENCE: 202
catggatttc tcagc 15

<210> SEQ ID NO 203
<211> LENGTH: 15
<212> TYPE: DNA
<213> ORGANISM: Homo sapiens

<400> SEQUENCE: 203
catgaggagg gaggc 15

<210> SEQ ID NO 204
<211> LENGTH: 15
<212> TYPE: DNA
<213> ORGANISM: Homo sapiens

<400> SEQUENCE: 204
catggcttaa cctgg 15

<210> SEQ ID NO 205
<211> LENGTH: 15
<212> TYPE: DNA
<213> ORGANISM: Homo sapiens

<400> SEQUENCE: 205
catgctcttc gagaa 15

<210> SEQ ID NO 206
<211> LENGTH: 15
<212> TYPE: DNA
<213> ORGANISM: Homo sapiens

<400> SEQUENCE: 206
catgagaaca aaacc 15

<210> SEQ ID NO 207
<211> LENGTH: 15
<212> TYPE: DNA
<213> ORGANISM: Homo sapiens

<400> SEQUENCE: 207
catgcccagg gagaa 15

<210> SEQ ID NO 208
<211> LENGTH: 15
<212> TYPE: DNA
<213> ORGANISM: Homo sapiens

<400> SEQUENCE: 208
catgcacttc aaggg 15

<210> SEQ ID NO 209
<211> LENGTH: 15
<212> TYPE: DNA
<213> ORGANISM: Homo sapiens

<400> SEQUENCE: 209
catggcggag agagg 15

<210> SEQ ID NO 210
<211> LENGTH: 15
<212> TYPE: DNA
<213> ORGANISM: Homo sapiens

<400> SEQUENCE: 210
catgttacct ccttc 15

<210> SEQ ID NO 211
<211> LENGTH: 15
<212> TYPE: DNA
<213> ORGANISM: Homo sapiens

<400> SEQUENCE: 211
catgactctg ccaag 15

<210> SEQ ID NO 212
<211> LENGTH: 15
<212> TYPE: DNA
<213> ORGANISM: Homo sapiens

<400> SEQUENCE: 212
catgtcagat ggcgt 15

<210> SEQ ID NO 213
<211> LENGTH: 15
<212> TYPE: DNA
<213> ORGANISM: Homo sapiens

<400> SEQUENCE: 213
catgggcctt ttttt 15

<210> SEQ ID NO 214
<211> LENGTH: 15
<212> TYPE: DNA
<213> ORGANISM: Homo sapiens

<400> SEQUENCE: 214
catgtggacg cgctg 15

<210> SEQ ID NO 215
<211> LENGTH: 15
<212> TYPE: DNA
<213> ORGANISM: Homo sapiens

<400> SEQUENCE: 215
catgcctgct ccctg 15

<210> SEQ ID NO 216
<211> LENGTH: 15
<212> TYPE: DNA
<213> ORGANISM: Homo sapiens

```
<400> SEQUENCE: 216
catggccaca ccccm                                               15

<210> SEQ ID NO 217
<211> LENGTH: 15
<212> TYPE: DNA
<213> ORGANISM: Homo sapiens

<400> SEQUENCE: 217
catgattatt tttct                                               15

<210> SEQ ID NO 218
<211> LENGTH: 15
<212> TYPE: DNA
<213> ORGANISM: Homo sapiens

<400> SEQUENCE: 218
catggaaccc tggga                                               15

<210> SEQ ID NO 219
<211> LENGTH: 15
<212> TYPE: DNA
<213> ORGANISM: Homo sapiens

<400> SEQUENCE: 219
catgggctga tgtgg                                               15

<210> SEQ ID NO 220
<211> LENGTH: 15
<212> TYPE: DNA
<213> ORGANISM: Homo sapiens

<400> SEQUENCE: 220
catgtcaata aagaa                                               15

<210> SEQ ID NO 221
<211> LENGTH: 15
<212> TYPE: DNA
<213> ORGANISM: Homo sapiens

<400> SEQUENCE: 221
catgaaagtg aagat                                               15

<210> SEQ ID NO 222
<211> LENGTH: 15
<212> TYPE: DNA
<213> ORGANISM: Homo sapiens

<400> SEQUENCE: 222
catgcacgcg ctcaa                                               15

<210> SEQ ID NO 223
<211> LENGTH: 15
<212> TYPE: DNA
<213> ORGANISM: Homo sapiens

<400> SEQUENCE: 223
catgaactaa tacta                                               15

<210> SEQ ID NO 224
<211> LENGTH: 15
<212> TYPE: DNA
<213> ORGANISM: Homo sapiens
```

```
<400> SEQUENCE: 224
catgctgtac ctgga                                                15

<210> SEQ ID NO 225
<211> LENGTH: 15
<212> TYPE: DNA
<213> ORGANISM: Homo sapiens

<400> SEQUENCE: 225
catgcgaccc cacgc                                                15

<210> SEQ ID NO 226
<211> LENGTH: 15
<212> TYPE: DNA
<213> ORGANISM: Homo sapiens

<400> SEQUENCE: 226
catgtagaaa aataa                                                15

<210> SEQ ID NO 227
<211> LENGTH: 15
<212> TYPE: DNA
<213> ORGANISM: Homo sapiens

<400> SEQUENCE: 227
catgatcttg aaagg                                                15

<210> SEQ ID NO 228
<211> LENGTH: 15
<212> TYPE: DNA
<213> ORGANISM: Homo sapiens

<400> SEQUENCE: 228
catgcagctg gccat                                                15

<210> SEQ ID NO 229
<211> LENGTH: 15
<212> TYPE: DNA
<213> ORGANISM: Homo sapiens

<400> SEQUENCE: 229
catgatcttg aaagg                                                15

<210> SEQ ID NO 230
<211> LENGTH: 15
<212> TYPE: DNA
<213> ORGANISM: Homo sapiens

<400> SEQUENCE: 230
catgatcttg aaagg                                                15

<210> SEQ ID NO 231
<211> LENGTH: 15
<212> TYPE: DNA
<213> ORGANISM: Homo sapiens

<400> SEQUENCE: 231
catggtggag gtgcg                                                15

<210> SEQ ID NO 232
<211> LENGTH: 15
<212> TYPE: DNA
```

-continued

```
<213> ORGANISM: Homo sapiens

<400> SEQUENCE: 232
catggtggac cccaa                                              15

<210> SEQ ID NO 233
<211> LENGTH: 15
<212> TYPE: DNA
<213> ORGANISM: Homo sapiens

<400> SEQUENCE: 233
catggagcag ctgga                                              15

<210> SEQ ID NO 234
<211> LENGTH: 15
<212> TYPE: DNA
<213> ORGANISM: Homo sapiens

<400> SEQUENCE: 234
catggcggga gggct                                              15

<210> SEQ ID NO 235
<211> LENGTH: 15
<212> TYPE: DNA
<213> ORGANISM: Homo sapiens

<400> SEQUENCE: 235
catgattggc ttaaa                                              15

<210> SEQ ID NO 236
<211> LENGTH: 15
<212> TYPE: DNA
<213> ORGANISM: Homo sapiens

<400> SEQUENCE: 236
catggaaaaa tttaa                                              15

<210> SEQ ID NO 237
<211> LENGTH: 15
<212> TYPE: DNA
<213> ORGANISM: Homo sapiens

<400> SEQUENCE: 237
catggatcac agttt                                              15

<210> SEQ ID NO 238
<211> LENGTH: 15
<212> TYPE: DNA
<213> ORGANISM: Homo sapiens

<400> SEQUENCE: 238
catgagcctt tgttg                                              15

<210> SEQ ID NO 239
<211> LENGTH: 15
<212> TYPE: DNA
<213> ORGANISM: Homo sapiens

<400> SEQUENCE: 239
catgtctgca cctcc                                              15

<210> SEQ ID NO 240
<211> LENGTH: 15
```

```
<212> TYPE: DNA
<213> ORGANISM: Homo sapiens

<400> SEQUENCE: 240
catgaacaga agcaa                                                15

<210> SEQ ID NO 241
<211> LENGTH: 15
<212> TYPE: DNA
<213> ORGANISM: Homo sapiens

<400> SEQUENCE: 241
catgtgttca ggacc                                                15

<210> SEQ ID NO 242
<211> LENGTH: 15
<212> TYPE: DNA
<213> ORGANISM: Homo sapiens

<400> SEQUENCE: 242
catgtagata atggc                                                15

<210> SEQ ID NO 243
<211> LENGTH: 15
<212> TYPE: DNA
<213> ORGANISM: Homo sapiens

<400> SEQUENCE: 243
catgcttaat cctga                                                15

<210> SEQ ID NO 244
<211> LENGTH: 15
<212> TYPE: DNA
<213> ORGANISM: Homo sapiens

<400> SEQUENCE: 244
catgggcaga ggacc                                                15

<210> SEQ ID NO 245
<211> LENGTH: 15
<212> TYPE: DNA
<213> ORGANISM: Homo sapiens

<400> SEQUENCE: 245
catgtgactg aagcc                                                15

<210> SEQ ID NO 246
<211> LENGTH: 15
<212> TYPE: DNA
<213> ORGANISM: Homo sapiens

<400> SEQUENCE: 246
catggatagt tgtgg                                                15

<210> SEQ ID NO 247
<211> LENGTH: 15
<212> TYPE: DNA
<213> ORGANISM: Homo sapiens

<400> SEQUENCE: 247
catggtggtg gacac                                                15

<210> SEQ ID NO 248
```

-continued

```
<211> LENGTH: 15
<212> TYPE: DNA
<213> ORGANISM: Homo sapiens

<400> SEQUENCE: 248
catgtggggt acctt                                                        15

<210> SEQ ID NO 249
<211> LENGTH: 15
<212> TYPE: DNA
<213> ORGANISM: Homo sapiens

<400> SEQUENCE: 249
catgttcatt ataat                                                        15

<210> SEQ ID NO 250
<211> LENGTH: 15
<212> TYPE: DNA
<213> ORGANISM: Homo sapiens

<400> SEQUENCE: 250
catgcttctg tgtay                                                        15

<210> SEQ ID NO 251
<211> LENGTH: 15
<212> TYPE: DNA
<213> ORGANISM: Homo sapiens

<400> SEQUENCE: 251
catgactggc gaagt                                                        15

<210> SEQ ID NO 252
<211> LENGTH: 15
<212> TYPE: DNA
<213> ORGANISM: Homo sapiens

<400> SEQUENCE: 252
catggaaaga gctga                                                        15

<210> SEQ ID NO 253
<211> LENGTH: 15
<212> TYPE: DNA
<213> ORGANISM: Homo sapiens

<400> SEQUENCE: 253
catgcaactc tatgg                                                        15

<210> SEQ ID NO 254
<211> LENGTH: 15
<212> TYPE: DNA
<213> ORGANISM: Homo sapiens

<400> SEQUENCE: 254
catgaaattt ggtgc                                                        15

<210> SEQ ID NO 255
<211> LENGTH: 15
<212> TYPE: DNA
<213> ORGANISM: Homo sapiens

<400> SEQUENCE: 255
catgctgcac ttact                                                        15
```

```
<210> SEQ ID NO 256
<211> LENGTH: 15
<212> TYPE: DNA
<213> ORGANISM: Homo sapiens

<400> SEQUENCE: 256
catgaatatt gagaa                                                        15

<210> SEQ ID NO 257
<211> LENGTH: 15
<212> TYPE: DNA
<213> ORGANISM: Homo sapiens

<400> SEQUENCE: 257
catgtcgccg ggcgc                                                        15

<210> SEQ ID NO 258
<211> LENGTH: 14
<212> TYPE: DNA
<213> ORGANISM: Homo sapiens

<400> SEQUENCE: 258
catgggggca gccg                                                         14

<210> SEQ ID NO 259
<211> LENGTH: 15
<212> TYPE: DNA
<213> ORGANISM: Homo sapiens

<400> SEQUENCE: 259
catgccaaga aagaa                                                        15

<210> SEQ ID NO 260
<211> LENGTH: 15
<212> TYPE: DNA
<213> ORGANISM: Homo sapiens

<400> SEQUENCE: 260 catgttttg ataaa                                                         15

<210> SEQ ID NO 261
<211> LENGTH: 15
<212> TYPE: DNA
<213> ORGANISM: Homo sapiens

<400> SEQUENCE: 261
catgtgtgga gagcc                                                        15

<210> SEQ ID NO 262
<211> LENGTH: 15
<212> TYPE: DNA
<213> ORGANISM: Homo sapiens

<400> SEQUENCE: 262
catgcccacg gttag                                                        15

<210> SEQ ID NO 263
<211> LENGTH: 15
<212> TYPE: DNA
<213> ORGANISM: Homo sapiens

<400> SEQUENCE: 263
catgaattct cctaa                                                        15
```

-continued

<210> SEQ ID NO 264
<211> LENGTH: 15
<212> TYPE: DNA
<213> ORGANISM: Homo sapiens

<400> SEQUENCE: 264
catggacctc cgggc                                                15

<210> SEQ ID NO 265
<211> LENGTH: 15
<212> TYPE: DNA
<213> ORGANISM: Homo sapiens

<400> SEQUENCE: 265
catgtgaatc tgggt                                                15

<210> SEQ ID NO 266
<211> LENGTH: 15
<212> TYPE: DNA
<213> ORGANISM: Homo sapiens

<400> SEQUENCE: 266
catgtccttc tccac                                                15

<210> SEQ ID NO 267
<211> LENGTH: 15
<212> TYPE: DNA
<213> ORGANISM: Homo sapiens

<400> SEQUENCE: 267
catgtatctg tctac                                                15

<210> SEQ ID NO 268
<211> LENGTH: 15
<212> TYPE: DNA
<213> ORGANISM: Homo sapiens

<400> SEQUENCE: 268
catgacgttc tcttc                                                15

<210> SEQ ID NO 269
<211> LENGTH: 15
<212> TYPE: DNA
<213> ORGANISM: Homo sapiens

<400> SEQUENCE: 269
catgccctga gtcag                                                15

<210> SEQ ID NO 270
<211> LENGTH: 15
<212> TYPE: DNA
<213> ORGANISM: Homo sapiens

<400> SEQUENCE: 270
catggaattc ctcga                                                15

<210> SEQ ID NO 271
<211> LENGTH: 15
<212> TYPE: DNA
<213> ORGANISM: Homo sapiens

<400> SEQUENCE: 271
catggacgcc gaact                                                15

<210> SEQ ID NO 272
<211> LENGTH: 15
<212> TYPE: DNA
<213> ORGANISM: Homo sapiens

<400> SEQUENCE: 272
catggcggac tgggg                                                      15

<210> SEQ ID NO 273
<211> LENGTH: 15
<212> TYPE: DNA
<213> ORGANISM: Homo sapiens

<400> SEQUENCE: 273
catgggaaca cacag                                                      15

<210> SEQ ID NO 274
<211> LENGTH: 15
<212> TYPE: DNA
<213> ORGANISM: Homo sapiens

<400> SEQUENCE: 274
catgttgcgg agccc                                                      15

<210> SEQ ID NO 275
<211> LENGTH: 15
<212> TYPE: DNA
<213> ORGANISM: Homo sapiens

<400> SEQUENCE: 275
catggcagac attga                                                      15

<210> SEQ ID NO 276
<211> LENGTH: 14
<212> TYPE: DNA
<213> ORGANISM: Homo sapiens

<400> SEQUENCE: 276
catgcacttg aaaa                                                       14

<210> SEQ ID NO 277
<211> LENGTH: 14
<212> TYPE: DNA
<213> ORGANISM: Homo sapiens

<400> SEQUENCE: 277
catgggttgg cagg                                                       14

<210> SEQ ID NO 278
<211> LENGTH: 14
<212> TYPE: DNA
<213> ORGANISM: Homo sapiens

<400> SEQUENCE: 278
catgttcctc gggc                                                       14

<210> SEQ ID NO 279
<211> LENGTH: 14
<212> TYPE: DNA
<213> ORGANISM: Homo sapiens

<400> SEQUENCE: 279

```
catgctgccg agct                                                 14

<210> SEQ ID NO 280
<211> LENGTH: 14
<212> TYPE: DNA
<213> ORGANISM: Homo sapiens

<400> SEQUENCE: 280
catggtgaaa aaaa                                                 14

<210> SEQ ID NO 281
<211> LENGTH: 14
<212> TYPE: DNA
<213> ORGANISM: Homo sapiens

<400> SEQUENCE: 281
catgctgtgc agca                                                 14

<210> SEQ ID NO 282
<211> LENGTH: 14
<212> TYPE: DNA
<213> ORGANISM: Homo sapiens

<400> SEQUENCE: 282
catgtagttt gtgg                                                 14

<210> SEQ ID NO 283
<211> LENGTH: 15
<212> TYPE: DNA
<213> ORGANISM: Homo sapiens

<400> SEQUENCE: 283
catgatgtag tagtg                                                15

<210> SEQ ID NO 284
<211> LENGTH: 15
<212> TYPE: DNA
<213> ORGANISM: Homo sapiens

<400> SEQUENCE: 284
catggaccca ctacc                                                15

<210> SEQ ID NO 285
<211> LENGTH: 15
<212> TYPE: DNA
<213> ORGANISM: Homo sapiens

<400> SEQUENCE: 285
catgaaatag gtttt                                                15

<210> SEQ ID NO 286
<211> LENGTH: 15
<212> TYPE: DNA
<213> ORGANISM: Homo sapiens

<400> SEQUENCE: 286
catgccgggc gtggt                                                15

<210> SEQ ID NO 287
<211> LENGTH: 15
<212> TYPE: DNA
<213> ORGANISM: Homo sapiens

<400> SEQUENCE: 287
```
catggactga gcttg 15

<210> SEQ ID NO 288
<211> LENGTH: 15
<212> TYPE: DNA
<213> ORGANISM: Homo sapiens

<400> SEQUENCE: 288
catgaaacgc ccaat 15

<210> SEQ ID NO 289
<211> LENGTH: 15
<212> TYPE: DNA
<213> ORGANISM: Homo sapiens

<400> SEQUENCE: 289
catgatgagg ccggg 15

<210> SEQ ID NO 290
<211> LENGTH: 15
<212> TYPE: DNA
<213> ORGANISM: Homo sapiens

<400> SEQUENCE: 290
catggcccac atccr 15

<210> SEQ ID NO 291
<211> LENGTH: 15
<212> TYPE: DNA
<213> ORGANISM: Homo sapiens

<400> SEQUENCE: 291
catggcttta tttgt 15

<210> SEQ ID NO 292
<211> LENGTH: 15
<212> TYPE: DNA
<213> ORGANISM: Homo sapiens

<400> SEQUENCE: 292
catgctagcc tcacg 15

<210> SEQ ID NO 293
<211> LENGTH: 15
<212> TYPE: DNA
<213> ORGANISM: Homo sapiens

<400> SEQUENCE: 293
catgcaaacc atcca 15

<210> SEQ ID NO 294
<211> LENGTH: 15
<212> TYPE: DNA
<213> ORGANISM: Homo sapiens

<400> SEQUENCE: 294
catgcttcca gctaa 15

<210> SEQ ID NO 295
<211> LENGTH: 15
<212> TYPE: DNA
<213> ORGANISM: Homo sapiens -continued

<400> SEQUENCE: 295
catgccccag ttgct                                                          15

<210> SEQ ID NO 296
<211> LENGTH: 15
<212> TYPE: DNA
<213> ORGANISM: Homo sapiens

<400> SEQUENCE: 296
catggatgac ccccc                                                          15

<210> SEQ ID NO 297
<211> LENGTH: 15
<212> TYPE: DNA
<213> ORGANISM: Homo sapiens

<400> SEQUENCE: 297
catgctgtac agaca                                                          15

<210> SEQ ID NO 298
<211> LENGTH: 15
<212> TYPE: DNA
<213> ORGANISM: Homo sapiens

<400> SEQUENCE: 298
catgcggact cactg                                                          15

<210> SEQ ID NO 299
<211> LENGTH: 15
<212> TYPE: DNA
<213> ORGANISM: Homo sapiens

<400> SEQUENCE: 299
catgcccccg cggaa                                                          15

<210> SEQ ID NO 300
<211> LENGTH: 15
<212> TYPE: DNA
<213> ORGANISM: Homo sapiens

<400> SEQUENCE: 300
catgcctgga agagg                                                          15

<210> SEQ ID NO 301
<211> LENGTH: 15
<212> TYPE: DNA
<213> ORGANISM: Homo sapiens

<400> SEQUENCE: 301
catggcctgg ccatc                                                          15

<210> SEQ ID NO 302
<211> LENGTH: 15
<212> TYPE: DNA
<213> ORGANISM: Homo sapiens

<400> SEQUENCE: 302
catgagcagg agcag                                                          15

<210> SEQ ID NO 303
<211> LENGTH: 15
<212> TYPE: DNA
<213> ORGANISM: Homo sapiens

```
<400> SEQUENCE: 303
catgaacgtg caggg                                                   15

<210> SEQ ID NO 304
<211> LENGTH: 15
<212> TYPE: DNA
<213> ORGANISM: Homo sapiens

<400> SEQUENCE: 304
catggccgcc ctgca                                                   15

<210> SEQ ID NO 305
<211> LENGTH: 15
<212> TYPE: DNA
<213> ORGANISM: Homo sapiens

<400> SEQUENCE: 305
catgtgggga gagga                                                   15

<210> SEQ ID NO 306
<211> LENGTH: 15
<212> TYPE: DNA
<213> ORGANISM: Homo sapiens

<400> SEQUENCE: 306
catggctgcc cttga                                                   15

<210> SEQ ID NO 307
<211> LENGTH: 15
<212> TYPE: DNA
<213> ORGANISM: Homo sapiens

<400> SEQUENCE: 307
catgtggcca tctgc                                                   15

<210> SEQ ID NO 308
<211> LENGTH: 15
<212> TYPE: DNA
<213> ORGANISM: Homo sapiens

<400> SEQUENCE: 308
catgcgttcc tgcgg                                                   15

<210> SEQ ID NO 309
<211> LENGTH: 15
<212> TYPE: DNA
<213> ORGANISM: Homo sapiens

<400> SEQUENCE: 309
catgtgcatc tggtg                                                   15

<210> SEQ ID NO 310
<211> LENGTH: 15
<212> TYPE: DNA
<213> ORGANISM: Homo sapiens

<400> SEQUENCE: 310
catggtgacc tcctt                                                   15

<210> SEQ ID NO 311
<211> LENGTH: 15
<212> TYPE: DNA
```

-continued

<213> ORGANISM: Homo sapiens

<400> SEQUENCE: 311
catgtagctc tatgg					15

<210> SEQ ID NO 312
<211> LENGTH: 15
<212> TYPE: DNA
<213> ORGANISM: Homo sapiens

<400> SEQUENCE: 312
catggtgcgc taggg					15

<210> SEQ ID NO 313
<211> LENGTH: 15
<212> TYPE: DNA
<213> ORGANISM: Homo sapiens

<400> SEQUENCE: 313
catggggcgc tgtgg					15

<210> SEQ ID NO 314
<211> LENGTH: 14
<212> TYPE: DNA
<213> ORGANISM: Homo sapiens

<400> SEQUENCE: 314
catgcctcca gtac					14

<210> SEQ ID NO 315
<211> LENGTH: 15
<212> TYPE: DNA
<213> ORGANISM: Homo sapiens

<400> SEQUENCE: 315
catgcctgtg acagc					15

<210> SEQ ID NO 316
<211> LENGTH: 15
<212> TYPE: DNA
<213> ORGANISM: Homo sapiens

<400> SEQUENCE: 316
catgtcacag tgcct					15

<210> SEQ ID NO 317
<211> LENGTH: 15
<212> TYPE: DNA
<213> ORGANISM: Homo sapiens

<400> SEQUENCE: 317
catgaataaa ggcta					15

<210> SEQ ID NO 318
<211> LENGTH: 15
<212> TYPE: DNA
<213> ORGANISM: Homo sapiens

<400> SEQUENCE: 318
catgttgttg ttgaa					15

<210> SEQ ID NO 319
<211> LENGTH: 15

-continued

```
<212> TYPE: DNA
<213> ORGANISM: Homo sapiens

<400> SEQUENCE: 319
catgaaggta gcaga                                                         15

<210> SEQ ID NO 320
<211> LENGTH: 15
<212> TYPE: DNA
<213> ORGANISM: Homo sapiens

<400> SEQUENCE: 320
catggtgttg ggggt                                                         15

<210> SEQ ID NO 321
<211> LENGTH: 15
<212> TYPE: DNA
<213> ORGANISM: Homo sapiens

<400> SEQUENCE: 321
catgtgcagc gcctg                                                         15

<210> SEQ ID NO 322
<211> LENGTH: 15
<212> TYPE: DNA
<213> ORGANISM: Homo sapiens

<400> SEQUENCE: 322
catgatggca cggag                                                         15

<210> SEQ ID NO 323
<211> LENGTH: 15
<212> TYPE: DNA
<213> ORGANISM: Homo sapiens

<400> SEQUENCE: 323
catggccaga caccc                                                         15

<210> SEQ ID NO 324
<211> LENGTH: 15
<212> TYPE: DNA
<213> ORGANISM: Homo sapiens

<400> SEQUENCE: 324
catgcttctt gcccc                                                         15

<210> SEQ ID NO 325
<211> LENGTH: 15
<212> TYPE: DNA
<213> ORGANISM: Homo sapiens

<400> SEQUENCE: 325
catgacccac gtcag                                                         15

<210> SEQ ID NO 326
<211> LENGTH: 15
<212> TYPE: DNA
<213> ORGANISM: Homo sapiens

<400> SEQUENCE: 326
catgggctgc ctgcc                                                         15

<210> SEQ ID NO 327
```

-continued

```
<211> LENGTH: 15
<212> TYPE: DNA
<213> ORGANISM: Homo sapiens

<400> SEQUENCE: 327
catggagggc cggtg                                                        15

<210> SEQ ID NO 328
<211> LENGTH: 15
<212> TYPE: DNA
<213> ORGANISM: Homo sapiens

<400> SEQUENCE: 328
catggatgaa tccgg                                                        15

<210> SEQ ID NO 329
<211> LENGTH: 15
<212> TYPE: DNA
<213> ORGANISM: Homo sapiens

<400> SEQUENCE: 329
catgagcccg accac                                                        15

<210> SEQ ID NO 330
<211> LENGTH: 15
<212> TYPE: DNA
<213> ORGANISM: Homo sapiens

<400> SEQUENCE: 330
catggttcag ctgtc                                                        15

<210> SEQ ID NO 331
<211> LENGTH: 15
<212> TYPE: DNA
<213> ORGANISM: Homo sapiens

<400> SEQUENCE: 331
catgcctcgc tcagt                                                        15

<210> SEQ ID NO 332
<211> LENGTH: 15
<212> TYPE: DNA
<213> ORGANISM: Homo sapiens

<400> SEQUENCE: 332
catgcaaata aaagt                                                        15

<210> SEQ ID NO 333
<211> LENGTH: 15
<212> TYPE: DNA
<213> ORGANISM: Homo sapiens

<400> SEQUENCE: 333
catgtgccgc ccgca                                                        15

<210> SEQ ID NO 334
<211> LENGTH: 15
<212> TYPE: DNA
<213> ORGANISM: Homo sapiens

<400> SEQUENCE: 334
catggcagtg gcctc                                                        15
```

```
<210> SEQ ID NO 335
<211> LENGTH: 15
<212> TYPE: DNA
<213> ORGANISM: Homo sapiens

<400> SEQUENCE: 335
catgctgggc ctgaa                                                    15

<210> SEQ ID NO 336
<211> LENGTH: 15
<212> TYPE: DNA
<213> ORGANISM: Homo sapiens

<400> SEQUENCE: 336
catggcccat tggag                                                    15

<210> SEQ ID NO 337
<211> LENGTH: 15
<212> TYPE: DNA
<213> ORGANISM: Homo sapiens

<400> SEQUENCE: 337
catgaagaaa acctc                                                    15

<210> SEQ ID NO 338
<211> LENGTH: 15
<212> TYPE: DNA
<213> ORGANISM: Homo sapiens

<400> SEQUENCE: 338
catggaatga tttct                                                    15

<210> SEQ ID NO 339
<211> LENGTH: 15
<212> TYPE: DNA
<213> ORGANISM: Homo sapiens

<400> SEQUENCE: 339
catggcctgg tcctt                                                    15

<210> SEQ ID NO 340
<211> LENGTH: 15
<212> TYPE: DNA
<213> ORGANISM: Homo sapiens

<400> SEQUENCE: 340
ccatggccca cacag                                                    15

<210> SEQ ID NO 341
<211> LENGTH: 15
<212> TYPE: DNA
<213> ORGANISM: Homo sapiens

<400> SEQUENCE: 341
catgggattc cagtt                                                    15

<210> SEQ ID NO 342
<211> LENGTH: 15
<212> TYPE: DNA
<213> ORGANISM: Homo sapiens

<400> SEQUENCE: 342
catgcctcca gctac                                                    15
```

<210> SEQ ID NO 343
<211> LENGTH: 15
<212> TYPE: DNA
<213> ORGANISM: Homo sapiens

<400> SEQUENCE: 343
catgctaaga cttca                                                15

<210> SEQ ID NO 344
<211> LENGTH: 15
<212> TYPE: DNA
<213> ORGANISM: Homo sapiens

<400> SEQUENCE: 344
catggcccag gtcac                                                15

<210> SEQ ID NO 345
<211> LENGTH: 15
<212> TYPE: DNA
<213> ORGANISM: Homo sapiens

<400> SEQUENCE: 345
catgaccctt ggcca                                                15

<210> SEQ ID NO 346
<211> LENGTH: 15
<212> TYPE: DNA
<213> ORGANISM: Homo sapiens

<400> SEQUENCE: 346
catgacattg ggtga                                                15

<210> SEQ ID NO 347
<211> LENGTH: 15
<212> TYPE: DNA
<213> ORGANISM: Homo sapiens

<400> SEQUENCE: 347
catggcgaaa ccctg                                                15

<210> SEQ ID NO 348
<211> LENGTH: 15
<212> TYPE: DNA
<213> ORGANISM: Homo sapiens

<400> SEQUENCE: 348
catgagccct acaaa                                                15

<210> SEQ ID NO 349
<211> LENGTH: 15
<212> TYPE: DNA
<213> ORGANISM: Homo sapiens

<400> SEQUENCE: 349
catggaccca agata                                                15

<210> SEQ ID NO 350
<211> LENGTH: 15
<212> TYPE: DNA
<213> ORGANISM: Homo sapiens

<400> SEQUENCE: 350
catggccggg tgggc                                                15

<210> SEQ ID NO 351
<211> LENGTH: 15
<212> TYPE: DNA
<213> ORGANISM: Homo sapiens

<400> SEQUENCE: 351
catgttgggg tttcc                                                      15

<210> SEQ ID NO 352
<211> LENGTH: 15
<212> TYPE: DNA
<213> ORGANISM: Homo sapiens

<400> SEQUENCE: 352
catgctccac ccgar                                                      15

<210> SEQ ID NO 353
<211> LENGTH: 15
<212> TYPE: DNA
<213> ORGANISM: Homo sapiens

<400> SEQUENCE: 353
catggcaggg cctca                                                      15

<210> SEQ ID NO 354
<211> LENGTH: 15
<212> TYPE: DNA
<213> ORGANISM: Homo sapiens

<400> SEQUENCE: 354
catgatcgtg gcggg                                                      15

<210> SEQ ID NO 355
<211> LENGTH: 15
<212> TYPE: DNA
<213> ORGANISM: Homo sapiens

<400> SEQUENCE: 355
catgcaagca tcccc                                                      15

<210> SEQ ID NO 356
<211> LENGTH: 15
<212> TYPE: DNA
<213> ORGANISM: Homo sapiens

<400> SEQUENCE: 356
catggacatc aagtc                                                      15

<210> SEQ ID NO 357
<211> LENGTH: 15
<212> TYPE: DNA
<213> ORGANISM: Homo sapiens

<400> SEQUENCE: 357
catggttgtg gttaa                                                      15

<210> SEQ ID NO 358
<211> LENGTH: 15
<212> TYPE: DNA
<213> ORGANISM: Homo sapiens

<400> SEQUENCE: 358
ctagtgctcc taccc 15

<210> SEQ ID NO 359
<211> LENGTH: 15
<212> TYPE: DNA
<213> ORGANISM: Homo sapiens

<400> SEQUENCE: 359
catgcacccc tgatg 15

<210> SEQ ID NO 360
<211> LENGTH: 15
<212> TYPE: DNA
<213> ORGANISM: Homo sapiens

<400> SEQUENCE: 360
catgccgctg cactc 15

<210> SEQ ID NO 361
<211> LENGTH: 15
<212> TYPE: DNA
<213> ORGANISM: Homo sapiens

<400> SEQUENCE: 361
catgctggcc ctcgg 15

<210> SEQ ID NO 362
<211> LENGTH: 15
<212> TYPE: DNA
<213> ORGANISM: Homo sapiens

<400> SEQUENCE: 362
catgccccct ggatc 15

<210> SEQ ID NO 363
<211> LENGTH: 15
<212> TYPE: DNA
<213> ORGANISM: Homo sapiens

<400> SEQUENCE: 363
catgttcact gtgag 15

<210> SEQ ID NO 364
<211> LENGTH: 15
<212> TYPE: DNA
<213> ORGANISM: Homo sapiens

<400> SEQUENCE: 364
catgattgga gtgct 15

<210> SEQ ID NO 365
<211> LENGTH: 15
<212> TYPE: DNA
<213> ORGANISM: Homo sapiens

<400> SEQUENCE: 365
catgctgacc tgtgt 15

<210> SEQ ID NO 366
<211> LENGTH: 15
<212> TYPE: DNA
<213> ORGANISM: Homo sapiens

<400> SEQUENCE: 366

-continued catgagcaga tcagg 15

<210> SEQ ID NO 367
<211> LENGTH: 15
<212> TYPE: DNA
<213> ORGANISM: Homo sapiens

<400> SEQUENCE: 367
catgggaaaa cagaa 15

<210> SEQ ID NO 368
<211> LENGTH: 15
<212> TYPE: DNA
<213> ORGANISM: Homo sapiens

<400> SEQUENCE: 368
catgtcaccg gtcag 15

<210> SEQ ID NO 369
<211> LENGTH: 15
<212> TYPE: DNA
<213> ORGANISM: Homo sapiens

<400> SEQUENCE: 369
catgtgcagc acgag 15

<210> SEQ ID NO 370
<211> LENGTH: 15
<212> TYPE: DNA
<213> ORGANISM: Homo sapiens

<400> SEQUENCE: 370
catgggaact gtgaa 15

<210> SEQ ID NO 371
<211> LENGTH: 15
<212> TYPE: DNA
<213> ORGANISM: Homo sapiens

<400> SEQUENCE: 371
catgcgaggg gccag 15

<210> SEQ ID NO 372
<211> LENGTH: 15
<212> TYPE: DNA
<213> ORGANISM: Homo sapiens

<400> SEQUENCE: 372
catgtaaatt gcaaa 15

<210> SEQ ID NO 373
<211> LENGTH: 15
<212> TYPE: DNA
<213> ORGANISM: Homo sapiens

<400> SEQUENCE: 373
catgggctgg gggcc 15

<210> SEQ ID NO 374
<211> LENGTH: 15
<212> TYPE: DNA
<213> ORGANISM: Homo sapiens -continued

```
<400> SEQUENCE: 374
catggtgctg aatgg                                            15

<210> SEQ ID NO 375
<211> LENGTH: 15
<212> TYPE: DNA
<213> ORGANISM: Homo sapiens

<400> SEQUENCE: 375
catggtgcac tgagc                                            15

<210> SEQ ID NO 376
<211> LENGTH: 15
<212> TYPE: DNA
<213> ORGANISM: Homo sapiens

<400> SEQUENCE: 376
catgtttaac ggccg                                            15

<210> SEQ ID NO 377
<211> LENGTH: 15
<212> TYPE: DNA
<213> ORGANISM: Homo sapiens

<400> SEQUENCE: 377
catgccctcc cgaag                                            15

<210> SEQ ID NO 378
<211> LENGTH: 15
<212> TYPE: DNA
<213> ORGANISM: Homo sapiens

<400> SEQUENCE: 378
catgaggtgg caaga                                            15

<210> SEQ ID NO 379
<211> LENGTH: 15
<212> TYPE: DNA
<213> ORGANISM: Homo sapiens

<400> SEQUENCE: 379
catgatactc cactc                                            15

<210> SEQ ID NO 380
<211> LENGTH: 15
<212> TYPE: DNA
<213> ORGANISM: Homo sapiens

<400> SEQUENCE: 380
catgctcgcg ctggg                                            15

<210> SEQ ID NO 381
<211> LENGTH: 15
<212> TYPE: DNA
<213> ORGANISM: Homo sapiens

<400> SEQUENCE: 381
catgggggca gggcc                                            15

<210> SEQ ID NO 382
<211> LENGTH: 15
<212> TYPE: DNA
<213> ORGANISM: Homo sapiens
```

```
<400> SEQUENCE: 382
catggaagca ggacc                                          15

<210> SEQ ID NO 383
<211> LENGTH: 15
<212> TYPE: DNA
<213> ORGANISM: Homo sapiens

<400> SEQUENCE: 383
catgccaggg gagaa                                          15

<210> SEQ ID NO 384
<211> LENGTH: 15
<212> TYPE: DNA
<213> ORGANISM: Homo sapiens

<400> SEQUENCE: 384
catgacacag caaga                                          15

<210> SEQ ID NO 385
<211> LENGTH: 15
<212> TYPE: DNA
<213> ORGANISM: Homo sapiens

<400> SEQUENCE: 385
catgagaata gcttg                                          15

<210> SEQ ID NO 386
<211> LENGTH: 15
<212> TYPE: DNA
<213> ORGANISM: Homo sapiens

<400> SEQUENCE: 386
catgcgctgt ggggt                                          15

<210> SEQ ID NO 387
<211> LENGTH: 15
<212> TYPE: DNA
<213> ORGANISM: Homo sapiens

<400> SEQUENCE: 387
catgcatagg tttag                                          15

<210> SEQ ID NO 388
<211> LENGTH: 15
<212> TYPE: DNA
<213> ORGANISM: Homo sapiens

<400> SEQUENCE: 388
catggccgac caggt                                          15

<210> SEQ ID NO 389
<211> LENGTH: 15
<212> TYPE: DNA
<213> ORGANISM: Homo sapiens

<400> SEQUENCE: 389
catgagctct tggag                                          15

<210> SEQ ID NO 390
<211> LENGTH: 15
<212> TYPE: DNA
```

```
<213> ORGANISM: Homo sapiens

<400> SEQUENCE: 390
catgcccaac gcgct                                                  15

<210> SEQ ID NO 391
<211> LENGTH: 15
<212> TYPE: DNA
<213> ORGANISM: Homo sapiens

<400> SEQUENCE: 391
catggacgcg gcgcg                                                  15

<210> SEQ ID NO 392
<211> LENGTH: 15
<212> TYPE: DNA
<213> ORGANISM: Homo sapiens

<400> SEQUENCE: 392
catgaccccc ccgcc                                                  15

<210> SEQ ID NO 393
<211> LENGTH: 15
<212> TYPE: DNA
<213> ORGANISM: Homo sapiens

<400> SEQUENCE: 393
catgatgcgg gagaa                                                  15

<210> SEQ ID NO 394
<211> LENGTH: 15
<212> TYPE: DNA
<213> ORGANISM: Homo sapiens

<400> SEQUENCE: 394
catgtcagct gcaac                                                  15

<210> SEQ ID NO 395
<211> LENGTH: 15
<212> TYPE: DNA
<213> ORGANISM: Homo sapiens

<400> SEQUENCE: 395
catggtaagt gtact                                                  15

<210> SEQ ID NO 396
<211> LENGTH: 15
<212> TYPE: DNA
<213> ORGANISM: Homo sapiens

<400> SEQUENCE: 396
catgtgtggg tgctg                                                  15

<210> SEQ ID NO 397
<211> LENGTH: 15
<212> TYPE: DNA
<213> ORGANISM: Homo sapiens

<400> SEQUENCE: 397
catggctgtg cctgg                                                  15

<210> SEQ ID NO 398
<211> LENGTH: 15
```

<212> TYPE: DNA
<213> ORGANISM: Homo sapiens

<400> SEQUENCE: 398
catgtgagtg acaga                                                    15

<210> SEQ ID NO 399
<211> LENGTH: 15
<212> TYPE: DNA
<213> ORGANISM: Homo sapiens

<400> SEQUENCE: 399
catgggctgg gcctg                                                    15

<210> SEQ ID NO 400
<211> LENGTH: 15
<212> TYPE: DNA
<213> ORGANISM: Homo sapiens

<400> SEQUENCE: 400
catgtaatcc cagca                                                    15

<210> SEQ ID NO 401
<211> LENGTH: 15
<212> TYPE: DNA
<213> ORGANISM: Homo sapiens

<400> SEQUENCE: 401
catggaccag tggct                                                    15

<210> SEQ ID NO 402
<211> LENGTH: 15
<212> TYPE: DNA
<213> ORGANISM: Homo sapiens

<400> SEQUENCE: 402
catgggcacc gtgct                                                    15

<210> SEQ ID NO 403
<211> LENGTH: 15
<212> TYPE: DNA
<213> ORGANISM: Homo sapiens

<400> SEQUENCE: 403
catgaaggac ctttt                                                    15

<210> SEQ ID NO 404
<211> LENGTH: 15
<212> TYPE: DNA
<213> ORGANISM: Homo sapiens

<400> SEQUENCE: 404
catggcagct cctgt                                                    15

<210> SEQ ID NO 405
<211> LENGTH: 15
<212> TYPE: DNA
<213> ORGANISM: Homo sapiens

<400> SEQUENCE: 405
catgtgtcct ggttc                                                    15

<210> SEQ ID NO 406

```
<211> LENGTH: 15
<212> TYPE: DNA
<213> ORGANISM: Homo sapiens

<400> SEQUENCE: 406
catgacaaac cccca                                                    15

<210> SEQ ID NO 407
<211> LENGTH: 15
<212> TYPE: DNA
<213> ORGANISM: Homo sapiens

<400> SEQUENCE: 407
catgtaggat ggggg                                                    15

<210> SEQ ID NO 408
<211> LENGTH: 15
<212> TYPE: DNA
<213> ORGANISM: Homo sapiens

<400> SEQUENCE: 408
catgactgtg gcggc                                                    15

<210> SEQ ID NO 409
<211> LENGTH: 15
<212> TYPE: DNA
<213> ORGANISM: Homo sapiens

<400> SEQUENCE: 409
catggtagca ggtgt                                                    15

<210> SEQ ID NO 410
<211> LENGTH: 15
<212> TYPE: DNA
<213> ORGANISM: Homo sapiens

<400> SEQUENCE: 410
catgaatcac aaata                                                    15

<210> SEQ ID NO 411
<211> LENGTH: 15
<212> TYPE: DNA
<213> ORGANISM: Homo sapiens

<400> SEQUENCE: 411
catgaggatg gtccc                                                    15

<210> SEQ ID NO 412
<211> LENGTH: 15
<212> TYPE: DNA
<213> ORGANISM: Homo sapiens

<400> SEQUENCE: 412
catgccaaag ctata                                                    15

<210> SEQ ID NO 413
<211> LENGTH: 15
<212> TYPE: DNA
<213> ORGANISM: Homo sapiens

<400> SEQUENCE: 413
catgcgggag tcggg                                                    15
```

```
<210> SEQ ID NO 414
<211> LENGTH: 15
<212> TYPE: DNA
<213> ORGANISM: Homo sapiens

<400> SEQUENCE: 414
catggccgtg gagag                                                        15

<210> SEQ ID NO 415
<211> LENGTH: 15
<212> TYPE: DNA
<213> ORGANISM: Homo sapiens

<400> SEQUENCE: 415
catgcccccg aagcc                                                        15

<210> SEQ ID NO 416
<211> LENGTH: 15
<212> TYPE: DNA
<213> ORGANISM: Homo sapiens

<400> SEQUENCE: 416
catgatttca agatg                                                        15

<210> SEQ ID NO 417
<211> LENGTH: 15
<212> TYPE: DNA
<213> ORGANISM: Homo sapiens

<400> SEQUENCE: 417
catggcccag tggct                                                        15

<210> SEQ ID NO 418
<211> LENGTH: 15
<212> TYPE: DNA
<213> ORGANISM: Homo sapiens

<400> SEQUENCE: 418
catgatggtg gggga                                                        15

<210> SEQ ID NO 419
<211> LENGTH: 15
<212> TYPE: DNA
<213> ORGANISM: Homo sapiens

<400> SEQUENCE: 419
catgcctgcc cccct                                                        15

<210> SEQ ID NO 420
<211> LENGTH: 15
<212> TYPE: DNA
<213> ORGANISM: Homo sapiens

<400> SEQUENCE: 420
ctagtggaaa gtgaa                                                        15

<210> SEQ ID NO 421
<211> LENGTH: 15
<212> TYPE: DNA
<213> ORGANISM: Homo sapiens

<400> SEQUENCE: 421
catggtcatc accac                                                        15
```

<210> SEQ ID NO 422
<211> LENGTH: 15
<212> TYPE: DNA
<213> ORGANISM: Homo sapiens

<400> SEQUENCE: 422
catgcttatg gtccc                                                    15

<210> SEQ ID NO 423
<211> LENGTH: 15
<212> TYPE: DNA
<213> ORGANISM: Homo sapiens

<400> SEQUENCE: 423
catgctgggc ctctg                                                    15

<210> SEQ ID NO 424
<211> LENGTH: 15
<212> TYPE: DNA
<213> ORGANISM: Homo sapiens

<400> SEQUENCE: 424
catggcccag ggccc                                                    15

<210> SEQ ID NO 425
<211> LENGTH: 15
<212> TYPE: DNA
<213> ORGANISM: Homo sapiens

<400> SEQUENCE: 425
catgttttta ctgat                                                    15

<210> SEQ ID NO 426
<211> LENGTH: 15
<212> TYPE: DNA
<213> ORGANISM: Homo sapiens

<400> SEQUENCE: 426
catgcctgct tgtcg                                                    15

<210> SEQ ID NO 427
<211> LENGTH: 15
<212> TYPE: DNA
<213> ORGANISM: Homo sapiens

<400> SEQUENCE: 427
catgacctgg ggagg                                                    15

<210> SEQ ID NO 428
<211> LENGTH: 15
<212> TYPE: DNA
<213> ORGANISM: Homo sapiens

<400> SEQUENCE: 428
catgccttca aatca                                                    15

<210> SEQ ID NO 429
<211> LENGTH: 15
<212> TYPE: DNA
<213> ORGANISM: Homo sapiens

<400> SEQUENCE: 429
catgtcggag ctgtt                                                    15

```
<210> SEQ ID NO 430
<211> LENGTH: 15
<212> TYPE: DNA
<213> ORGANISM: Homo sapiens

<400> SEQUENCE: 430
catgggaggt ggggc                                              15

<210> SEQ ID NO 431
<211> LENGTH: 15
<212> TYPE: DNA
<213> ORGANISM: Homo sapiens

<400> SEQUENCE: 431
catgttccac taacc                                              15

<210> SEQ ID NO 432
<211> LENGTH: 15
<212> TYPE: DNA
<213> ORGANISM: Homo sapiens

<400> SEQUENCE: 432
catggtctgg gggat                                              15

<210> SEQ ID NO 433
<211> LENGTH: 15
<212> TYPE: DNA
<213> ORGANISM: Homo sapiens

<400> SEQUENCE: 433
catgttaacc cctcc                                              15

<210> SEQ ID NO 434
<211> LENGTH: 15
<212> TYPE: DNA
<213> ORGANISM: Homo sapiens

<400> SEQUENCE: 434
catgatgacg ctcac                                              15

<210> SEQ ID NO 435
<211> LENGTH: 15
<212> TYPE: DNA
<213> ORGANISM: Homo sapiens

<400> SEQUENCE: 435
catgcacctg tcatc                                              15

<210> SEQ ID NO 436
<211> LENGTH: 15
<212> TYPE: DNA
<213> ORGANISM: Homo sapiens

<400> SEQUENCE: 436
catggatccc aactg                                              15

<210> SEQ ID NO 437
<211> LENGTH: 15
<212> TYPE: DNA
<213> ORGANISM: Homo sapiens

<400> SEQUENCE: 437
```

-continued catgcttaga ggggt                    15

<210> SEQ ID NO 438
<211> LENGTH: 15
<212> TYPE: DNA
<213> ORGANISM: Homo sapiens

<400> SEQUENCE: 438
catgatggcc catac                    15

<210> SEQ ID NO 439
<211> LENGTH: 15
<212> TYPE: DNA
<213> ORGANISM: Homo sapiens

<400> SEQUENCE: 439
catggcaaga aagtg                    15

<210> SEQ ID NO 440
<211> LENGTH: 15
<212> TYPE: DNA
<213> ORGANISM: Homo sapiens

<400> SEQUENCE: 440
catgtacctc tgatt                    15

<210> SEQ ID NO 441
<211> LENGTH: 15
<212> TYPE: DNA
<213> ORGANISM: Homo sapiens

<400> SEQUENCE: 441
catgatgatg gcacc                    15

<210> SEQ ID NO 442
<211> LENGTH: 15
<212> TYPE: DNA
<213> ORGANISM: Homo sapiens

<400> SEQUENCE: 442
catgttctgt agccc                    15

<210> SEQ ID NO 443
<211> LENGTH: 15
<212> TYPE: DNA
<213> ORGANISM: Homo sapiens

<400> SEQUENCE: 443
catgcctgtc tgcca                    15

<210> SEQ ID NO 444
<211> LENGTH: 15
<212> TYPE: DNA
<213> ORGANISM: Homo sapiens

<400> SEQUENCE: 444
catgtatgat gagca                    15

<210> SEQ ID NO 445
<211> LENGTH: 15
<212> TYPE: DNA
<213> ORGANISM: Homo sapiens

<400> SEQUENCE: 445
catgctggca aaggt         15

<210> SEQ ID NO 446
<211> LENGTH: 15
<212> TYPE: DNA
<213> ORGANISM: Homo sapiens

<400> SEQUENCE: 446
catgcttgat tccca         15

<210> SEQ ID NO 447
<211> LENGTH: 15
<212> TYPE: DNA
<213> ORGANISM: Homo sapiens

<400> SEQUENCE: 447
catgcttgac atacc         15

<210> SEQ ID NO 448
<211> LENGTH: 15
<212> TYPE: DNA
<213> ORGANISM: Homo sapiens

<400> SEQUENCE: 448
catggctggc acatt         15

<210> SEQ ID NO 449
<211> LENGTH: 15
<212> TYPE: DNA
<213> ORGANISM: Homo sapiens

<400> SEQUENCE: 449
catgtctgaa ttatg         15

<210> SEQ ID NO 450
<211> LENGTH: 15
<212> TYPE: DNA
<213> ORGANISM: Homo sapiens

<400> SEQUENCE: 450
catgggaaga gcact         15

<210> SEQ ID NO 451
<211> LENGTH: 15
<212> TYPE: DNA
<213> ORGANISM: Homo sapiens

<400> SEQUENCE: 451
catggctctt cccca         15

<210> SEQ ID NO 452
<211> LENGTH: 15
<212> TYPE: DNA
<213> ORGANISM: Homo sapiens

<400> SEQUENCE: 452
catgaaatct ggcac         15

<210> SEQ ID NO 453
<211> LENGTH: 15
<212> TYPE: DNA
<213> ORGANISM: Homo sapiens -continued

```
<400> SEQUENCE: 453
catgtaattt gcatt                                                    15

<210> SEQ ID NO 454
<211> LENGTH: 15
<212> TYPE: DNA
<213> ORGANISM: Homo sapiens

<400> SEQUENCE: 454
catggtgggg gcgcc                                                    15

<210> SEQ ID NO 455
<211> LENGTH: 15
<212> TYPE: DNA
<213> ORGANISM: Homo sapiens

<400> SEQUENCE: 455
catgttatgg tgtga                                                    15

<210> SEQ ID NO 456
<211> LENGTH: 15
<212> TYPE: DNA
<213> ORGANISM: Homo sapiens

<400> SEQUENCE: 456
catgggagaa acagc                                                    15

<210> SEQ ID NO 457
<211> LENGTH: 15
<212> TYPE: DNA
<213> ORGANISM: Homo sapiens

<400> SEQUENCE: 457
catgccaaca ccagc                                                    15

<210> SEQ ID NO 458
<211> LENGTH: 15
<212> TYPE: DNA
<213> ORGANISM: Homo sapiens

<400> SEQUENCE: 458
catgaggtga ctggg                                                    15

<210> SEQ ID NO 459
<211> LENGTH: 15
<212> TYPE: DNA
<213> ORGANISM: Homo sapiens

<400> SEQUENCE: 459
catggccatc ctcca                                                    15

<210> SEQ ID NO 460
<211> LENGTH: 15
<212> TYPE: DNA
<213> ORGANISM: Homo sapiens

<400> SEQUENCE: 460
catgtttctc gtcgc                                                    15

<210> SEQ ID NO 461
<211> LENGTH: 15
<212> TYPE: DNA
<213> ORGANISM: Homo sapiens
```

```
<400> SEQUENCE: 461
catgtcagag cgctg                                                    15

<210> SEQ ID NO 462
<211> LENGTH: 15
<212> TYPE: DNA
<213> ORGANISM: Homo sapiens

<400> SEQUENCE: 462
catgttccgc gttcc                                                    15

<210> SEQ ID NO 463
<211> LENGTH: 15
<212> TYPE: DNA
<213> ORGANISM: Homo sapiens

<400> SEQUENCE: 463
catgtacggt gtggg                                                    15

<210> SEQ ID NO 464
<211> LENGTH: 15
<212> TYPE: DNA
<213> ORGANISM: Homo sapiens

<400> SEQUENCE: 464
catgctcaga acttg                                                    15

<210> SEQ ID NO 465
<211> LENGTH: 15
<212> TYPE: DNA
<213> ORGANISM: Homo sapiens

<400> SEQUENCE: 465
catgggacta aatga                                                    15

<210> SEQ ID NO 466
<211> LENGTH: 15
<212> TYPE: DNA
<213> ORGANISM: Homo sapiens

<400> SEQUENCE: 466
catggcttgg ggatt                                                    15

<210> SEQ ID NO 467
<211> LENGTH: 15
<212> TYPE: DNA
<213> ORGANISM: Homo sapiens

<400> SEQUENCE: 467
catgacccaa ctgcc                                                    15

<210> SEQ ID NO 468
<211> LENGTH: 15
<212> TYPE: DNA
<213> ORGANISM: Homo sapiens

<400> SEQUENCE: 468
catgctgaac ctccc                                                    15

<210> SEQ ID NO 469
<211> LENGTH: 15
<212> TYPE: DNA
```

```
<213> ORGANISM: Homo sapiens

<400> SEQUENCE: 469
catgcaagag tttct                                                 15

<210> SEQ ID NO 470
<211> LENGTH: 15
<212> TYPE: DNA
<213> ORGANISM: Homo sapiens

<400> SEQUENCE: 470
catggtccga gtgca                                                 15

<210> SEQ ID NO 471
<211> LENGTH: 15
<212> TYPE: DNA
<213> ORGANISM: Homo sapiens

<400> SEQUENCE: 471
catgtttggt ttcac                                                 15

<210> SEQ ID NO 472
<211> LENGTH: 15
<212> TYPE: DNA
<213> ORGANISM: Homo sapiens

<400> SEQUENCE: 472
catgcaccta attgg                                                 15

<210> SEQ ID NO 473
<211> LENGTH: 15
<212> TYPE: DNA
<213> ORGANISM: Homo sapiens

<400> SEQUENCE: 473
catgatttga gaagc                                                 15

<210> SEQ ID NO 474
<211> LENGTH: 15
<212> TYPE: DNA
<213> ORGANISM: Homo sapiens

<400> SEQUENCE: 474
catgtgattt cactt                                                 15

<210> SEQ ID NO 475
<211> LENGTH: 15
<212> TYPE: DNA
<213> ORGANISM: Homo sapiens

<400> SEQUENCE: 475
catgttcata cacct                                                 15

<210> SEQ ID NO 476
<211> LENGTH: 15
<212> TYPE: DNA
<213> ORGANISM: Homo sapiens

<400> SEQUENCE: 476
catgccactg cactc                                                 15

<210> SEQ ID NO 477
<211> LENGTH: 15
```

-continued

```
<212> TYPE: DNA
<213> ORGANISM: Homo sapiens

<400> SEQUENCE: 477
catgactaac accct                                                     15

<210> SEQ ID NO 478
<211> LENGTH: 15
<212> TYPE: DNA
<213> ORGANISM: Homo sapiens

<400> SEQUENCE: 478
catgcactac tcacc                                                     15

<210> SEQ ID NO 479
<211> LENGTH: 15
<212> TYPE: DNA
<213> ORGANISM: Homo sapiens

<400> SEQUENCE: 479
catgaaaaca ttctc                                                     15

<210> SEQ ID NO 480
<211> LENGTH: 15
<212> TYPE: DNA
<213> ORGANISM: Homo sapiens

<400> SEQUENCE: 480
catgctcata aggaa                                                     15

<210> SEQ ID NO 481
<211> LENGTH: 15
<212> TYPE: DNA
<213> ORGANISM: Homo sapiens

<400> SEQUENCE: 481
catgtcgaag ccccc                                                     15

<210> SEQ ID NO 482
<211> LENGTH: 15
<212> TYPE: DNA
<213> ORGANISM: Homo sapiens

<400> SEQUENCE: 482
catgacgcag ggaga                                                     15

<210> SEQ ID NO 483
<211> LENGTH: 15
<212> TYPE: DNA
<213> ORGANISM: Homo sapiens

<400> SEQUENCE: 483
catgttggcc aggct                                                     15

<210> SEQ ID NO 484
<211> LENGTH: 15
<212> TYPE: DNA
<213> ORGANISM: Homo sapiens

<400> SEQUENCE: 484
catgttggtg aagga                                                     15

<210> SEQ ID NO 485
```

```
<211> LENGTH: 15
<212> TYPE: DNA
<213> ORGANISM: Homo sapiens

<400> SEQUENCE: 485
catgatcacg ccctc                                                15

<210> SEQ ID NO 486
<211> LENGTH: 15
<212> TYPE: DNA
<213> ORGANISM: Homo sapiens

<400> SEQUENCE: 486
catgtgcctg cacca                                                15

<210> SEQ ID NO 487
<211> LENGTH: 15
<212> TYPE: DNA
<213> ORGANISM: Homo sapiens

<400> SEQUENCE: 487
catgagaccc acaac                                                15

<210> SEQ ID NO 488
<211> LENGTH: 15
<212> TYPE: DNA
<213> ORGANISM: Homo sapiens

<400> SEQUENCE: 488
catgagtttg ttagt                                                15

<210> SEQ ID NO 489
<211> LENGTH: 15
<212> TYPE: DNA
<213> ORGANISM: Homo sapiens

<400> SEQUENCE: 489
catgggaaca aacag                                                15

<210> SEQ ID NO 490
<211> LENGTH: 15
<212> TYPE: DNA
<213> ORGANISM: Homo sapiens

<400> SEQUENCE: 490
catgtggtgt atgca                                                15

<210> SEQ ID NO 491
<211> LENGTH: 15
<212> TYPE: DNA
<213> ORGANISM: Homo sapiens

<400> SEQUENCE: 491
catggaaata cagtt                                                15

<210> SEQ ID NO 492
<211> LENGTH: 15
<212> TYPE: DNA
<213> ORGANISM: Homo sapiens

<400> SEQUENCE: 492
catggtggct cacgc                                                15
```

```
<210> SEQ ID NO 493
<211> LENGTH: 15
<212> TYPE: DNA
<213> ORGANISM: Homo sapiens

<400> SEQUENCE: 493
catggtggtg cacac                                                   15

<210> SEQ ID NO 494
<211> LENGTH: 15
<212> TYPE: DNA
<213> ORGANISM: Homo sapiens

<400> SEQUENCE: 494
catggggttg gcttg                                                   15

<210> SEQ ID NO 495
<211> LENGTH: 15
<212> TYPE: DNA
<213> ORGANISM: Homo sapiens

<400> SEQUENCE: 495
catggtggcg ggtgc                                                   15

<210> SEQ ID NO 496
<211> LENGTH: 15
<212> TYPE: DNA
<213> ORGANISM: Homo sapiens

<400> SEQUENCE: 496
catgtagact agcaa                                                   15

<210> SEQ ID NO 497
<211> LENGTH: 15
<212> TYPE: DNA
<213> ORGANISM: Homo sapiens

<400> SEQUENCE: 497
catggctagg tttat                                                   15

<210> SEQ ID NO 498
<211> LENGTH: 15
<212> TYPE: DNA
<213> ORGANISM: Homo sapiens

<400> SEQUENCE: 498
catgggcttt aggga                                                   15

<210> SEQ ID NO 499
<211> LENGTH: 14
<212> TYPE: DNA
<213> ORGANISM: Homo sapiens

<400> SEQUENCE: 499
catgggggtc aggg                                                    14

<210> SEQ ID NO 500
<211> LENGTH: 15
<212> TYPE: DNA
<213> ORGANISM: Homo sapiens

<400> SEQUENCE: 500
catgattttc taaaa                                                   15
```

```
<210> SEQ ID NO 501
<211> LENGTH: 14
<212> TYPE: DNA
<213> ORGANISM: Homo sapiens

<400> SEQUENCE: 501
catgcacttg ccct                                                    14

<210> SEQ ID NO 502
<211> LENGTH: 15
<212> TYPE: DNA
<213> ORGANISM: Homo sapiens

<400> SEQUENCE: 502
catgcctgct gcagg                                                   15

<210> SEQ ID NO 503
<211> LENGTH: 15
<212> TYPE: DNA
<213> ORGANISM: Homo sapiens

<400> SEQUENCE: 503
catgagaacc ttcca                                                   15

<210> SEQ ID NO 504
<211> LENGTH: 14
<212> TYPE: DNA
<213> ORGANISM: Homo sapiens

<400> SEQUENCE: 504
catgctctgc cctc                                                    14

<210> SEQ ID NO 505
<211> LENGTH: 15
<212> TYPE: DNA
<213> ORGANISM: Homo sapiens

<400> SEQUENCE: 505
catggccatc ccctt                                                   15

<210> SEQ ID NO 506
<211> LENGTH: 15
<212> TYPE: DNA
<213> ORGANISM: Homo sapiens

<400> SEQUENCE: 506
catggcccag cggcc                                                   15

<210> SEQ ID NO 507
<211> LENGTH: 15
<212> TYPE: DNA
<213> ORGANISM: Homo sapiens

<400> SEQUENCE: 507
catgtggcgc gtgtc                                                   15

<210> SEQ ID NO 508
<211> LENGTH: 15
<212> TYPE: DNA
<213> ORGANISM: Homo sapiens

<400> SEQUENCE: 508
catgagggtg ttttc                                                   15
```

```
<210> SEQ ID NO 509
<211> LENGTH: 15
<212> TYPE: DNA
<213> ORGANISM: Homo sapiens

<400> SEQUENCE: 509
catgcctggg aagtg                                                    15

<210> SEQ ID NO 510
<211> LENGTH: 15
<212> TYPE: DNA
<213> ORGANISM: Homo sapiens

<400> SEQUENCE: 510
catgagtctg ctgga                                                    15

<210> SEQ ID NO 511
<211> LENGTH: 15
<212> TYPE: DNA
<213> ORGANISM: Homo sapiens

<400> SEQUENCE: 511
catgcccgcc tcttc                                                    15

<210> SEQ ID NO 512
<211> LENGTH: 15
<212> TYPE: DNA
<213> ORGANISM: Homo sapiens

<400> SEQUENCE: 512
catgaaaaga gtggt                                                    15

<210> SEQ ID NO 513
<211> LENGTH: 15
<212> TYPE: DNA
<213> ORGANISM: Homo sapiens

<400> SEQUENCE: 513
catggccacg tggag                                                    15

<210> SEQ ID NO 514
<211> LENGTH: 14
<212> TYPE: DNA
<213> ORGANISM: Homo sapiens

<400> SEQUENCE: 514
catgaggatg tggg                                                     14

<210> SEQ ID NO 515
<211> LENGTH: 15
<212> TYPE: DNA
<213> ORGANISM: Homo sapiens

<400> SEQUENCE: 515
catgtatagt cctct                                                    15

<210> SEQ ID NO 516
<211> LENGTH: 15
<212> TYPE: DNA
<213> ORGANISM: Homo sapiens

<400> SEQUENCE: 516
```

-continued catgggtcct ctctt					15

<210> SEQ ID NO 517
<211> LENGTH: 15
<212> TYPE: DNA
<213> ORGANISM: Homo sapiens

<400> SEQUENCE: 517
catgatgggc ttgat					15

<210> SEQ ID NO 518
<211> LENGTH: 15
<212> TYPE: DNA
<213> ORGANISM: Homo sapiens

<400> SEQUENCE: 518
catgctgccc cccat					15

<210> SEQ ID NO 519
<211> LENGTH: 15
<212> TYPE: DNA
<213> ORGANISM: Homo sapiens

<400> SEQUENCE: 519
catgttctct acaca					15

<210> SEQ ID NO 520
<211> LENGTH: 15
<212> TYPE: DNA
<213> ORGANISM: Homo sapiens

<400> SEQUENCE: 520
catgaagaag caggg					15

<210> SEQ ID NO 521
<211> LENGTH: 15
<212> TYPE: DNA
<213> ORGANISM: Homo sapiens

<400> SEQUENCE: 521
catgagtagg tggcc					15

<210> SEQ ID NO 522
<211> LENGTH: 15
<212> TYPE: DNA
<213> ORGANISM: Homo sapiens

<400> SEQUENCE: 522
catgacagtg tgtgt					15

<210> SEQ ID NO 523
<211> LENGTH: 15
<212> TYPE: DNA
<213> ORGANISM: Homo sapiens

<400> SEQUENCE: 523
catgggaaaa gtggt					15

<210> SEQ ID NO 524
<211> LENGTH: 14
<212> TYPE: DNA
<213> ORGANISM: Homo sapiens

<400> SEQUENCE: 524

```
catgaagaaa gctc                                                    14

<210> SEQ ID NO 525
<211> LENGTH: 15
<212> TYPE: DNA
<213> ORGANISM: Homo sapiens

<400> SEQUENCE: 525
catgacaccc atcac                                                   15

<210> SEQ ID NO 526
<211> LENGTH: 15
<212> TYPE: DNA
<213> ORGANISM: Homo sapiens

<400> SEQUENCE: 526
catgagatcc caagg                                                   15

<210> SEQ ID NO 527
<211> LENGTH: 15
<212> TYPE: DNA
<213> ORGANISM: Homo sapiens

<400> SEQUENCE: 527
catgaatagt ttccc                                                   15

<210> SEQ ID NO 528
<211> LENGTH: 15
<212> TYPE: DNA
<213> ORGANISM: Homo sapiens

<400> SEQUENCE: 528
catgcagaaa gcatc                                                   15

<210> SEQ ID NO 529
<211> LENGTH: 15
<212> TYPE: DNA
<213> ORGANISM: Homo sapiens

<400> SEQUENCE: 529
catggctttg ctttg                                                   15

<210> SEQ ID NO 530
<211> LENGTH: 15
<212> TYPE: DNA
<213> ORGANISM: Homo sapiens

<400> SEQUENCE: 530
catgtgctgc attga                                                   15

<210> SEQ ID NO 531
<211> LENGTH: 15
<212> TYPE: DNA
<213> ORGANISM: Homo sapiens

<400> SEQUENCE: 531
catgccatcg tcctt                                                   15

<210> SEQ ID NO 532
<211> LENGTH: 15
<212> TYPE: DNA
<213> ORGANISM: Homo sapiens
```

```
<400> SEQUENCE: 532
catggaacag ctcac                                                15

<210> SEQ ID NO 533
<211> LENGTH: 15
<212> TYPE: DNA
<213> ORGANISM: Homo sapiens

<400> SEQUENCE: 533 catgggcta cgtcc                                                 15

<210> SEQ ID NO 534
<211> LENGTH: 15
<212> TYPE: DNA
<213> ORGANISM: Homo sapiens

<400> SEQUENCE: 534
catgcccggc tcctc                                                15

<210> SEQ ID NO 535
<211> LENGTH: 15
<212> TYPE: DNA
<213> ORGANISM: Homo sapiens

<400> SEQUENCE: 535
catgaggtac tacta                                                15

<210> SEQ ID NO 536
<211> LENGTH: 15
<212> TYPE: DNA
<213> ORGANISM: Homo sapiens

<400> SEQUENCE: 536
catgcaaata aatta                                                15

<210> SEQ ID NO 537
<211> LENGTH: 15
<212> TYPE: DNA
<213> ORGANISM: Homo sapiens

<400> SEQUENCE: 537
catgctgtaa aaaaa                                                15

<210> SEQ ID NO 538
<211> LENGTH: 15
<212> TYPE: DNA
<213> ORGANISM: Homo sapiens

<400> SEQUENCE: 538
catggttcaa tccct                                                15

<210> SEQ ID NO 539
<211> LENGTH: 15
<212> TYPE: DNA
<213> ORGANISM: Homo sapiens

<400> SEQUENCE: 539
catgaataaa gcctt                                                15

<210> SEQ ID NO 540
<211> LENGTH: 15
<212> TYPE: DNA
<213> ORGANISM: Homo sapiens
```

<400> SEQUENCE: 540
catgggaagg tttac                    15

<210> SEQ ID NO 541
<211> LENGTH: 15
<212> TYPE: DNA
<213> ORGANISM: Homo sapiens

<400> SEQUENCE: 541
catgggatgg cttat                    15

<210> SEQ ID NO 542
<211> LENGTH: 15
<212> TYPE: DNA
<213> ORGANISM: Homo sapiens

<400> SEQUENCE: 542
catgggtggc ccggg                    15

<210> SEQ ID NO 543
<211> LENGTH: 15
<212> TYPE: DNA
<213> ORGANISM: Homo sapiens

<400> SEQUENCE: 543
catgtactgt acttc                    15

<210> SEQ ID NO 544
<211> LENGTH: 15
<212> TYPE: DNA
<213> ORGANISM: Homo sapiens

<400> SEQUENCE: 544
catgcccttg cactc                    15

<210> SEQ ID NO 545
<211> LENGTH: 15
<212> TYPE: DNA
<213> ORGANISM: Homo sapiens

<400> SEQUENCE: 545
catgcggtgg gacca                    15

<210> SEQ ID NO 546
<211> LENGTH: 15
<212> TYPE: DNA
<213> ORGANISM: Homo sapiens

<400> SEQUENCE: 546
catggccccc aacca                    15

<210> SEQ ID NO 547
<211> LENGTH: 14
<212> TYPE: DNA
<213> ORGANISM: Homo sapiens

<400> SEQUENCE: 547
catggccggc gctc                     14

<210> SEQ ID NO 548
<211> LENGTH: 15
<212> TYPE: DNA

```
<213> ORGANISM: Homo sapiens

<400> SEQUENCE: 548
catgggaggc gctca                                              15

<210> SEQ ID NO 549
<211> LENGTH: 15
<212> TYPE: DNA
<213> ORGANISM: Homo sapiens

<400> SEQUENCE: 549
catgtccccg ttaca                                              15

<210> SEQ ID NO 550
<211> LENGTH: 15
<212> TYPE: DNA
<213> ORGANISM: Homo sapiens

<400> SEQUENCE: 550
catgaaagca aacca                                              15

<210> SEQ ID NO 551
<211> LENGTH: 15
<212> TYPE: DNA
<213> ORGANISM: Homo sapiens

<400> SEQUENCE: 551
catgaaagca gttta                                              15

<210> SEQ ID NO 552
<211> LENGTH: 15
<212> TYPE: DNA
<213> ORGANISM: Homo sapiens

<400> SEQUENCE: 552
catgaaagcg gggct                                              15

<210> SEQ ID NO 553
<211> LENGTH: 15
<212> TYPE: DNA
<213> ORGANISM: Homo sapiens

<400> SEQUENCE: 553
catgaaatcc tgggt                                              15

<210> SEQ ID NO 554
<211> LENGTH: 15
<212> TYPE: DNA
<213> ORGANISM: Homo sapiens

<400> SEQUENCE: 554
catgaaatgg acaac                                              15

<210> SEQ ID NO 555
<211> LENGTH: 15
<212> TYPE: DNA
<213> ORGANISM: Homo sapiens

<400> SEQUENCE: 555
catgaaccag tttgt                                              15

<210> SEQ ID NO 556
<211> LENGTH: 15
```

```
<212> TYPE: DNA
<213> ORGANISM: Homo sapiens

<400> SEQUENCE: 556
catgaactct tgaag                                              15

<210> SEQ ID NO 557
<211> LENGTH: 15
<212> TYPE: DNA
<213> ORGANISM: Homo sapiens

<400> SEQUENCE: 557
catgaactgc ttcaa                                              15

<210> SEQ ID NO 558
<211> LENGTH: 15
<212> TYPE: DNA
<213> ORGANISM: Homo sapiens

<400> SEQUENCE: 558
catgaacttg gccat                                              15

<210> SEQ ID NO 559
<211> LENGTH: 15
<212> TYPE: DNA
<213> ORGANISM: Homo sapiens

<400> SEQUENCE: 559
catgaagatc cccgc                                              15

<210> SEQ ID NO 560
<211> LENGTH: 15
<212> TYPE: DNA
<213> ORGANISM: Homo sapiens

<400> SEQUENCE: 560
catgaaggga gggtc                                              15

<210> SEQ ID NO 561
<211> LENGTH: 15
<212> TYPE: DNA
<213> ORGANISM: Homo sapiens

<400> SEQUENCE: 561
catgaagttg ctatt                                              15

<210> SEQ ID NO 562
<211> LENGTH: 15
<212> TYPE: DNA
<213> ORGANISM: Homo sapiens

<400> SEQUENCE: 562
catgaatgaa aaaaa                                              15

<210> SEQ ID NO 563
<211> LENGTH: 15
<212> TYPE: DNA
<213> ORGANISM: Homo sapiens

<400> SEQUENCE: 563
catgacaaac tgtgg                                              15

<210> SEQ ID NO 564
```

<211> LENGTH: 15
<212> TYPE: DNA
<213> ORGANISM: Homo sapiens

<400> SEQUENCE: 564
catgacaact caata 15

<210> SEQ ID NO 565
<211> LENGTH: 15
<212> TYPE: DNA
<213> ORGANISM: Homo sapiens

<400> SEQUENCE: 565
catgacaccc tgtgc 15

<210> SEQ ID NO 566
<211> LENGTH: 15
<212> TYPE: DNA
<213> ORGANISM: Homo sapiens

<400> SEQUENCE: 566
catgaccatt ggatt 15

<210> SEQ ID NO 567
<211> LENGTH: 15
<212> TYPE: DNA
<213> ORGANISM: Homo sapiens

<400> SEQUENCE: 567
catgaccctt taaca 15

<210> SEQ ID NO 568
<211> LENGTH: 15
<212> TYPE: DNA
<213> ORGANISM: Homo sapiens

<400> SEQUENCE: 568
catgaccgcc gtggt 15

<210> SEQ ID NO 569
<211> LENGTH: 15
<212> TYPE: DNA
<213> ORGANISM: Homo sapiens

<400> SEQUENCE: 569
catgacctgt gacca 15

<210> SEQ ID NO 570
<211> LENGTH: 15
<212> TYPE: DNA
<213> ORGANISM: Homo sapiens

<400> SEQUENCE: 570
catgacgccc tgctc 15

<210> SEQ ID NO 571
<211> LENGTH: 15
<212> TYPE: DNA
<213> ORGANISM: Homo sapiens

<400> SEQUENCE: 571
catgacgtgg tgatg 15

```
<210> SEQ ID NO 572
<211> LENGTH: 15
<212> TYPE: DNA
<213> ORGANISM: Homo sapiens

<400> SEQUENCE: 572
catgactcag cccgg                                                          15

<210> SEQ ID NO 573
<211> LENGTH: 15
<212> TYPE: DNA
<213> ORGANISM: Homo sapiens

<400> SEQUENCE: 573
catgactgag gaaag                                                          15

<210> SEQ ID NO 574
<211> LENGTH: 15
<212> TYPE: DNA
<213> ORGANISM: Homo sapiens

<400> SEQUENCE: 574
catgactgcc cgctg                                                          15

<210> SEQ ID NO 575
<211> LENGTH: 15
<212> TYPE: DNA
<213> ORGANISM: Homo sapiens

<400> SEQUENCE: 575
catgactgta ttttc                                                          15

<210> SEQ ID NO 576
<211> LENGTH: 15
<212> TYPE: DNA
<213> ORGANISM: Homo sapiens

<400> SEQUENCE: 576
catgagcact gcagc                                                          15

<210> SEQ ID NO 577
<211> LENGTH: 15
<212> TYPE: DNA
<213> ORGANISM: Homo sapiens

<400> SEQUENCE: 577
catgagcagg agcgt                                                          15

<210> SEQ ID NO 578
<211> LENGTH: 15
<212> TYPE: DNA
<213> ORGANISM: Homo sapiens

<400> SEQUENCE: 578
catgagctgt attct                                                          15

<210> SEQ ID NO 579
<211> LENGTH: 15
<212> TYPE: DNA
<213> ORGANISM: Homo sapiens

<400> SEQUENCE: 579
catgaggatg acccc                                                          15
```

<210> SEQ ID NO 580
<211> LENGTH: 15
<212> TYPE: DNA
<213> ORGANISM: Homo sapiens

<400> SEQUENCE: 580
catgaggtct tcaat                                                      15

<210> SEQ ID NO 581
<211> LENGTH: 15
<212> TYPE: DNA
<213> ORGANISM: Homo sapiens

<400> SEQUENCE: 581
catgaggtgc ggggg                                                      15

<210> SEQ ID NO 582
<211> LENGTH: 15
<212> TYPE: DNA
<213> ORGANISM: Homo sapiens

<400> SEQUENCE: 582
catgagtatc tggga                                                      15

<210> SEQ ID NO 583
<211> LENGTH: 15
<212> TYPE: DNA
<213> ORGANISM: Homo sapiens

<400> SEQUENCE: 583
catgatactt taatt                                                      15

<210> SEQ ID NO 584
<211> LENGTH: 15
<212> TYPE: DNA
<213> ORGANISM: Homo sapiens

<400> SEQUENCE: 584
catgatcaag aatcc                                                      15

<210> SEQ ID NO 585
<211> LENGTH: 15
<212> TYPE: DNA
<213> ORGANISM: Homo sapiens

<400> SEQUENCE: 585
catgatcaag ggtgt                                                      15

<210> SEQ ID NO 586
<211> LENGTH: 15
<212> TYPE: DNA
<213> ORGANISM: Homo sapiens

<400> SEQUENCE: 586
catgatcaag ttcga                                                      15

<210> SEQ ID NO 587
<211> LENGTH: 15
<212> TYPE: DNA
<213> ORGANISM: Homo sapiens

<400> SEQUENCE: 587
catgatccgg cgcca                                                      15

<210> SEQ ID NO 588
<211> LENGTH: 15
<212> TYPE: DNA
<213> ORGANISM: Homo sapiens

<400> SEQUENCE: 588
catgatgaaa cttcg                                                    15

<210> SEQ ID NO 589
<211> LENGTH: 15
<212> TYPE: DNA
<213> ORGANISM: Homo sapiens

<400> SEQUENCE: 589
catgatgcga aaggc                                                    15

<210> SEQ ID NO 590
<211> LENGTH: 15
<212> TYPE: DNA
<213> ORGANISM: Homo sapiens

<400> SEQUENCE: 590
catgatgtct tcgtt                                                    15

<210> SEQ ID NO 591
<211> LENGTH: 15
<212> TYPE: DNA
<213> ORGANISM: Homo sapiens

<400> SEQUENCE: 591
catgatgtct tttct                                                    15

<210> SEQ ID NO 592
<211> LENGTH: 15
<212> TYPE: DNA
<213> ORGANISM: Homo sapiens

<400> SEQUENCE: 592
catgatgtgt aacga                                                    15

<210> SEQ ID NO 593
<211> LENGTH: 15
<212> TYPE: DNA
<213> ORGANISM: Homo sapiens

<400> SEQUENCE: 593
catgcaactt aaagc                                                    15

<210> SEQ ID NO 594
<211> LENGTH: 15
<212> TYPE: DNA
<213> ORGANISM: Homo sapiens

<400> SEQUENCE: 594
catgcacctg tcctt                                                    15

<210> SEQ ID NO 595
<211> LENGTH: 15
<212> TYPE: DNA
<213> ORGANISM: Homo sapiens

<400> SEQUENCE: 595

```
catgcactca ataaa                                                      15

<210> SEQ ID NO 596
<211> LENGTH: 15
<212> TYPE: DNA
<213> ORGANISM: Homo sapiens

<400> SEQUENCE: 596
catgcagcct ggggc                                                      15

<210> SEQ ID NO 597
<211> LENGTH: 15
<212> TYPE: DNA
<213> ORGANISM: Homo sapiens

<400> SEQUENCE: 597
catgcagcgc gccct                                                      15

<210> SEQ ID NO 598
<211> LENGTH: 15
<212> TYPE: DNA
<213> ORGANISM: Homo sapiens

<400> SEQUENCE: 598
catgcaggtt gtcct                                                      15

<210> SEQ ID NO 599
<211> LENGTH: 15
<212> TYPE: DNA
<213> ORGANISM: Homo sapiens

<400> SEQUENCE: 599
catgcagtct ctcaa                                                      15

<210> SEQ ID NO 600
<211> LENGTH: 15
<212> TYPE: DNA
<213> ORGANISM: Homo sapiens

<400> SEQUENCE: 600
catgcatccc gtgac                                                      15

<210> SEQ ID NO 601
<211> LENGTH: 15
<212> TYPE: DNA
<213> ORGANISM: Homo sapiens

<400> SEQUENCE: 601
catgcattcc tcctt                                                      15

<210> SEQ ID NO 602
<211> LENGTH: 15
<212> TYPE: DNA
<213> ORGANISM: Homo sapiens

<400> SEQUENCE: 602
catgccaccc ccacc                                                      15

<210> SEQ ID NO 603
<211> LENGTH: 15
<212> TYPE: DNA
<213> ORGANISM: Homo sapiens

<400> SEQUENCE: 603
```
catgccagtg gcccg 15

<210> SEQ ID NO 604
<211> LENGTH: 15
<212> TYPE: DNA
<213> ORGANISM: Homo sapiens

<400> SEQUENCE: 604
catgccattt tctgg 15

<210> SEQ ID NO 605
<211> LENGTH: 15
<212> TYPE: DNA
<213> ORGANISM: Homo sapiens

<400> SEQUENCE: 605
catgcccaag ctagc 15

<210> SEQ ID NO 606
<211> LENGTH: 15
<212> TYPE: DNA
<213> ORGANISM: Homo sapiens

<400> SEQUENCE: 606
catgcccatc cgaaa 15

<210> SEQ ID NO 607
<211> LENGTH: 15
<212> TYPE: DNA
<213> ORGANISM: Homo sapiens

<400> SEQUENCE: 607
catgccccct gcaga 15

<210> SEQ ID NO 608
<211> LENGTH: 15
<212> TYPE: DNA
<213> ORGANISM: Homo sapiens

<400> SEQUENCE: 608
catgcccgca tagat 15

<210> SEQ ID NO 609
<211> LENGTH: 15
<212> TYPE: DNA
<213> ORGANISM: Homo sapiens

<400> SEQUENCE: 609
catgccctcc tgggg 15

<210> SEQ ID NO 610
<211> LENGTH: 15
<212> TYPE: DNA
<213> ORGANISM: Homo sapiens

<400> SEQUENCE: 610
catgccggcc ctacc 15

<210> SEQ ID NO 611
<211> LENGTH: 15
<212> TYPE: DNA
<213> ORGANISM: Homo sapiens -continued

<400> SEQUENCE: 611
catgcctggt cccaa                                                    15

<210> SEQ ID NO 612
<211> LENGTH: 15
<212> TYPE: DNA
<213> ORGANISM: Homo sapiens

<400> SEQUENCE: 612
catgcctttg aacag                                                    15

<210> SEQ ID NO 613
<211> LENGTH: 15
<212> TYPE: DNA
<213> ORGANISM: Homo sapiens

<400> SEQUENCE: 613
catgcgccga cgatg                                                    15

<210> SEQ ID NO 614
<211> LENGTH: 15
<212> TYPE: DNA
<213> ORGANISM: Homo sapiens

<400> SEQUENCE: 614
catgctcaac agcaa                                                    15

<210> SEQ ID NO 615
<211> LENGTH: 15
<212> TYPE: DNA
<213> ORGANISM: Homo sapiens

<400> SEQUENCE: 615
catgctcaac ccccc                                                    15

<210> SEQ ID NO 616
<211> LENGTH: 15
<212> TYPE: DNA
<213> ORGANISM: Homo sapiens

<400> SEQUENCE: 616
catgctgaga aactg                                                    15

<210> SEQ ID NO 617
<211> LENGTH: 15
<212> TYPE: DNA
<213> ORGANISM: Homo sapiens

<400> SEQUENCE: 617
catgctgagt ctccc                                                    15

<210> SEQ ID NO 618
<211> LENGTH: 15
<212> TYPE: DNA
<213> ORGANISM: Homo sapiens

<400> SEQUENCE: 618
catgctgcta tacga                                                    15

<210> SEQ ID NO 619
<211> LENGTH: 15
<212> TYPE: DNA
<213> ORGANISM: Homo sapiens

```
<400> SEQUENCE: 619
catgctgctg agtga                                                    15

<210> SEQ ID NO 620
<211> LENGTH: 15
<212> TYPE: DNA
<213> ORGANISM: Homo sapiens

<400> SEQUENCE: 620
catgctggcg ccgat                                                    15

<210> SEQ ID NO 621
<211> LENGTH: 15
<212> TYPE: DNA
<213> ORGANISM: Homo sapiens

<400> SEQUENCE: 621
catgcttcca gctaa                                                    15

<210> SEQ ID NO 622
<211> LENGTH: 15
<212> TYPE: DNA
<213> ORGANISM: Homo sapiens

<400> SEQUENCE: 622
catgcttcct tgcct                                                    15

<210> SEQ ID NO 623
<211> LENGTH: 15
<212> TYPE: DNA
<213> ORGANISM: Homo sapiens

<400> SEQUENCE: 623
catgctttct tccct                                                    15

<210> SEQ ID NO 624
<211> LENGTH: 15
<212> TYPE: DNA
<213> ORGANISM: Homo sapiens

<400> SEQUENCE: 624
catggaaaaa aaaaa                                                    15

<210> SEQ ID NO 625
<211> LENGTH: 15
<212> TYPE: DNA
<213> ORGANISM: Homo sapiens

<400> SEQUENCE: 625
catggaaaca agatg                                                    15

<210> SEQ ID NO 626
<211> LENGTH: 15
<212> TYPE: DNA
<213> ORGANISM: Homo sapiens

<400> SEQUENCE: 626
catggaaata cagtt                                                    15

<210> SEQ ID NO 627
<211> LENGTH: 15
<212> TYPE: DNA
```

<213> ORGANISM: Homo sapiens

<400> SEQUENCE: 627
catggaaatg atgag                                                    15

<210> SEQ ID NO 628
<211> LENGTH: 15
<212> TYPE: DNA
<213> ORGANISM: Homo sapiens

<400> SEQUENCE: 628
catggaagat gtgtg                                                    15

<210> SEQ ID NO 629
<211> LENGTH: 15
<212> TYPE: DNA
<213> ORGANISM: Homo sapiens

<400> SEQUENCE: 629
catggaattt tataa                                                    15

<210> SEQ ID NO 630
<211> LENGTH: 15
<212> TYPE: DNA
<213> ORGANISM: Homo sapiens

<400> SEQUENCE: 630
catggacaaa aaaaa                                                    15

<210> SEQ ID NO 631
<211> LENGTH: 15
<212> TYPE: DNA
<213> ORGANISM: Homo sapiens

<400> SEQUENCE: 631
catggaccac cttta                                                    15

<210> SEQ ID NO 632
<211> LENGTH: 15
<212> TYPE: DNA
<213> ORGANISM: Homo sapiens

<400> SEQUENCE: 632
catggaccag gccct                                                    15

<210> SEQ ID NO 633
<211> LENGTH: 15
<212> TYPE: DNA
<213> ORGANISM: Homo sapiens

<400> SEQUENCE: 633
catggacccc aaggc                                                    15

<210> SEQ ID NO 634
<211> LENGTH: 15
<212> TYPE: DNA
<213> ORGANISM: Homo sapiens

<400> SEQUENCE: 634
catggaccct gccct                                                    15

<210> SEQ ID NO 635
<211> LENGTH: 15

```
<212> TYPE: DNA
<213> ORGANISM: Homo sapiens

<400> SEQUENCE: 635
catggaccta tctct                                                     15

<210> SEQ ID NO 636
<211> LENGTH: 15
<212> TYPE: DNA
<213> ORGANISM: Homo sapiens

<400> SEQUENCE: 636
catggacggc gcagg                                                     15

<210> SEQ ID NO 637
<211> LENGTH: 15
<212> TYPE: DNA
<213> ORGANISM: Homo sapiens

<400> SEQUENCE: 637
catggactct ctgtt                                                     15

<210> SEQ ID NO 638
<211> LENGTH: 15
<212> TYPE: DNA
<213> ORGANISM: Homo sapiens

<400> SEQUENCE: 638
catggagagc tttgc                                                     15

<210> SEQ ID NO 639
<211> LENGTH: 15
<212> TYPE: DNA
<213> ORGANISM: Homo sapiens

<400> SEQUENCE: 639
catggagagt gtctg                                                     15

<210> SEQ ID NO 640
<211> LENGTH: 15
<212> TYPE: DNA
<213> ORGANISM: Homo sapiens

<400> SEQUENCE: 640
catggagcag gatga                                                     15

<210> SEQ ID NO 641
<211> LENGTH: 15
<212> TYPE: DNA
<213> ORGANISM: Homo sapiens

<400> SEQUENCE: 641
catggaggga gttcc                                                     15

<210> SEQ ID NO 642
<211> LENGTH: 15
<212> TYPE: DNA
<213> ORGANISM: Homo sapiens

<400> SEQUENCE: 642
catggagtcc ggagc                                                     15

<210> SEQ ID NO 643
```

```
<211> LENGTH: 15
<212> TYPE: DNA
<213> ORGANISM: Homo sapiens

<400> SEQUENCE: 643
catggagtta tgttg                                                          15

<210> SEQ ID NO 644
<211> LENGTH: 15
<212> TYPE: DNA
<213> ORGANISM: Homo sapiens

<400> SEQUENCE: 644
catggagttc gacct                                                          15

<210> SEQ ID NO 645
<211> LENGTH: 15
<212> TYPE: DNA
<213> ORGANISM: Homo sapiens

<400> SEQUENCE: 645
catggattaa gtgag                                                          15

<210> SEQ ID NO 646
<211> LENGTH: 15
<212> TYPE: DNA
<213> ORGANISM: Homo sapiens

<400> SEQUENCE: 646
catggattga acctc                                                          15

<210> SEQ ID NO 647
<211> LENGTH: 15
<212> TYPE: DNA
<213> ORGANISM: Homo sapiens

<400> SEQUENCE: 647
catggcaaaa aaaaa                                                          15

<210> SEQ ID NO 648
<211> LENGTH: 15
<212> TYPE: DNA
<213> ORGANISM: Homo sapiens

<400> SEQUENCE: 648
catggcattt aaata                                                          15

<210> SEQ ID NO 649
<211> LENGTH: 15
<212> TYPE: DNA
<213> ORGANISM: Homo sapiens

<400> SEQUENCE: 649
catggccaac aacga                                                          15

<210> SEQ ID NO 650
<211> LENGTH: 15
<212> TYPE: DNA
<213> ORGANISM: Homo sapiens

<400> SEQUENCE: 650
catggccccc aataa                                                          15
```

```
<210> SEQ ID NO 651
<211> LENGTH: 15
<212> TYPE: DNA
<213> ORGANISM: Homo sapiens

<400> SEQUENCE: 651
catggccgct acttc                                                      15

<210> SEQ ID NO 652
<211> LENGTH: 15
<212> TYPE: DNA
<213> ORGANISM: Homo sapiens

<400> SEQUENCE: 652
catggccgtc ggagg                                                      15

<210> SEQ ID NO 653
<211> LENGTH: 15
<212> TYPE: DNA
<213> ORGANISM: Homo sapiens

<400> SEQUENCE: 653
catggcctac ccgag                                                      15

<210> SEQ ID NO 654
<211> LENGTH: 15
<212> TYPE: DNA
<213> ORGANISM: Homo sapiens

<400> SEQUENCE: 654
catggcgggg tggag                                                      15

<210> SEQ ID NO 655
<211> LENGTH: 15
<212> TYPE: DNA
<213> ORGANISM: Homo sapiens

<400> SEQUENCE: 655
catggctcag ctgga                                                      15

<210> SEQ ID NO 656
<211> LENGTH: 15
<212> TYPE: DNA
<213> ORGANISM: Homo sapiens

<400> SEQUENCE: 656
catggctttt cagac                                                      15

<210> SEQ ID NO 657
<211> LENGTH: 15
<212> TYPE: DNA
<213> ORGANISM: Homo sapiens

<400> SEQUENCE: 657
catgggaaaa aaaaa                                                      15

<210> SEQ ID NO 658
<211> LENGTH: 15
<212> TYPE: DNA
<213> ORGANISM: Homo sapiens

<400> SEQUENCE: 658
catgggaaaa gtggt                                                      15
```

```
<210> SEQ ID NO 659
<211> LENGTH: 15
<212> TYPE: DNA
<213> ORGANISM: Homo sapiens

<400> SEQUENCE: 659
catgggaagg gaggc                                                    15

<210> SEQ ID NO 660
<211> LENGTH: 15
<212> TYPE: DNA
<213> ORGANISM: Homo sapiens

<400> SEQUENCE: 660
catgggagtc attgt                                                    15

<210> SEQ ID NO 661
<211> LENGTH: 15
<212> TYPE: DNA
<213> ORGANISM: Homo sapiens

<400> SEQUENCE: 661
catgggagtg tgcgt                                                    15

<210> SEQ ID NO 662
<211> LENGTH: 15
<212> TYPE: DNA
<213> ORGANISM: Homo sapiens

<400> SEQUENCE: 662
catgggattg tctgg                                                    15

<210> SEQ ID NO 663
<211> LENGTH: 15
<212> TYPE: DNA
<213> ORGANISM: Homo sapiens

<400> SEQUENCE: 663
catgggcccc tcacc                                                    15

<210> SEQ ID NO 664
<211> LENGTH: 15
<212> TYPE: DNA
<213> ORGANISM: Homo sapiens

<400> SEQUENCE: 664
catgggccct ctgag                                                    15

<210> SEQ ID NO 665
<211> LENGTH: 15
<212> TYPE: DNA
<213> ORGANISM: Homo sapiens

<400> SEQUENCE: 665
catgggctgg tctgg                                                    15

<210> SEQ ID NO 666
<211> LENGTH: 15
<212> TYPE: DNA
<213> ORGANISM: Homo sapiens

<400> SEQUENCE: 666
catggggaag cagat                                                    15
```

<210> SEQ ID NO 667
<211> LENGTH: 15
<212> TYPE: DNA
<213> ORGANISM: Homo sapiens

<400> SEQUENCE: 667
catggggagg ggtgg                                            15

<210> SEQ ID NO 668
<211> LENGTH: 15
<212> TYPE: DNA
<213> ORGANISM: Homo sapiens

<400> SEQUENCE: 668
catggggagg tagca                                            15

<210> SEQ ID NO 669
<211> LENGTH: 15
<212> TYPE: DNA
<213> ORGANISM: Homo sapiens

<400> SEQUENCE: 669
catggggcat ctctt                                            15

<210> SEQ ID NO 670
<211> LENGTH: 15
<212> TYPE: DNA
<213> ORGANISM: Homo sapiens

<400> SEQUENCE: 670
catgggtggg gagat                                            15

<210> SEQ ID NO 671
<211> LENGTH: 15
<212> TYPE: DNA
<213> ORGANISM: Homo sapiens

<400> SEQUENCE: 671
catggtactg tagca                                            15

<210> SEQ ID NO 672
<211> LENGTH: 15
<212> TYPE: DNA
<213> ORGANISM: Homo sapiens

<400> SEQUENCE: 672
catggtactg tggct                                            15

<210> SEQ ID NO 673
<211> LENGTH: 15
<212> TYPE: DNA
<213> ORGANISM: Homo sapiens

<400> SEQUENCE: 673
catggtcaaa atttc                                            15

<210> SEQ ID NO 674
<211> LENGTH: 15
<212> TYPE: DNA
<213> ORGANISM: Homo sapiens

<400> SEQUENCE: 674
catggtctgg ggctt                                    15

<210> SEQ ID NO 675
<211> LENGTH: 15
<212> TYPE: DNA
<213> ORGANISM: Homo sapiens

<400> SEQUENCE: 675
catggtctgt gagag                                    15

<210> SEQ ID NO 676
<211> LENGTH: 15
<212> TYPE: DNA
<213> ORGANISM: Homo sapiens

<400> SEQUENCE: 676
catggtctgt gcagg                                    15

<210> SEQ ID NO 677
<211> LENGTH: 15
<212> TYPE: DNA
<213> ORGANISM: Homo sapiens

<400> SEQUENCE: 677
catggtcttg aagcc                                    15

<210> SEQ ID NO 678
<211> LENGTH: 15
<212> TYPE: DNA
<213> ORGANISM: Homo sapiens

<400> SEQUENCE: 678
catggtgaag gcagt                                    15

<210> SEQ ID NO 679
<211> LENGTH: 15
<212> TYPE: DNA
<213> ORGANISM: Homo sapiens

<400> SEQUENCE: 679
catggtgaat gacgg                                    15

<210> SEQ ID NO 680
<211> LENGTH: 15
<212> TYPE: DNA
<213> ORGANISM: Homo sapiens

<400> SEQUENCE: 680
catggtgcgg aggac                                    15

<210> SEQ ID NO 681
<211> LENGTH: 15
<212> TYPE: DNA
<213> ORGANISM: Homo sapiens

<400> SEQUENCE: 681
catggtgctg gagaa                                    15

<210> SEQ ID NO 682
<211> LENGTH: 15
<212> TYPE: DNA
<213> ORGANISM: Homo sapiens

<400> SEQUENCE: 682

```
catggtggag ggcac                                               15

<210> SEQ ID NO 683
<211> LENGTH: 15
<212> TYPE: DNA
<213> ORGANISM: Homo sapiens

<400> SEQUENCE: 683
catggtggta cagga                                               15

<210> SEQ ID NO 684
<211> LENGTH: 15
<212> TYPE: DNA
<213> ORGANISM: Homo sapiens

<400> SEQUENCE: 684
catggttcac tgcag                                               15

<210> SEQ ID NO 685
<211> LENGTH: 15
<212> TYPE: DNA
<213> ORGANISM: Homo sapiens

<400> SEQUENCE: 685
catggttgtc tttgg                                               15

<210> SEQ ID NO 686
<211> LENGTH: 15
<212> TYPE: DNA
<213> ORGANISM: Homo sapiens

<400> SEQUENCE: 686
catggttgtg gttaa                                               15

<210> SEQ ID NO 687
<211> LENGTH: 15
<212> TYPE: DNA
<213> ORGANISM: Homo sapiens

<400> SEQUENCE: 687
catggtttaa atcga                                               15

<210> SEQ ID NO 688
<211> LENGTH: 15
<212> TYPE: DNA
<213> ORGANISM: Homo sapiens

<400> SEQUENCE: 688
catgtaaggc ttaac                                               15

<210> SEQ ID NO 689
<211> LENGTH: 15
<212> TYPE: DNA
<213> ORGANISM: Homo sapiens

<400> SEQUENCE: 689
catgtaattt tggaa                                               15

<210> SEQ ID NO 690
<211> LENGTH: 15
<212> TYPE: DNA
<213> ORGANISM: Homo sapiens
```

-continued

```
<210> SEQ ID NO 691
<211> LENGTH: 15
<212> TYPE: DNA
<213> ORGANISM: Homo sapiens

<400> SEQUENCE: 691
catgtacatt ttcat                                                    15

<210> SEQ ID NO 692
<211> LENGTH: 15
<212> TYPE: DNA
<213> ORGANISM: Homo sapiens

<400> SEQUENCE: 692
catgtacccc gtaca                                                    15

<210> SEQ ID NO 693
<211> LENGTH: 15
<212> TYPE: DNA
<213> ORGANISM: Homo sapiens

<400> SEQUENCE: 693
catgtaccct tctat                                                    15

<210> SEQ ID NO 694
<211> LENGTH: 15
<212> TYPE: DNA
<213> ORGANISM: Homo sapiens

<400> SEQUENCE: 694
catgtaggaa agtaa                                                    15

<210> SEQ ID NO 695
<211> LENGTH: 15
<212> TYPE: DNA
<213> ORGANISM: Homo sapiens

<400> SEQUENCE: 695
catgtaggtt gtcta                                                    15

<210> SEQ ID NO 696
<211> LENGTH: 15
<212> TYPE: DNA
<213> ORGANISM: Homo sapiens

<400> SEQUENCE: 696
catgtatatt ttctc                                                    15

<210> SEQ ID NO 697
<211> LENGTH: 15
<212> TYPE: DNA
<213> ORGANISM: Homo sapiens

<400> SEQUENCE: 697
catgtatttt ctgcc                                                    15

<210> SEQ ID NO 698
<211> LENGTH: 15
<212> TYPE: DNA
<213> ORGANISM: Homo sapiens
```

<400> SEQUENCE: 690
catgtaattt tggat                                                    15

```
<400> SEQUENCE: 698
catgtcacaa gcaaa                                                    15

<210> SEQ ID NO 699
<211> LENGTH: 15
<212> TYPE: DNA
<213> ORGANISM: Homo sapiens

<400> SEQUENCE: 699
catgtccaaa tcgat                                                    15

<210> SEQ ID NO 700
<211> LENGTH: 15
<212> TYPE: DNA
<213> ORGANISM: Homo sapiens

<400> SEQUENCE: 700
catgtccact ggcct                                                    15

<210> SEQ ID NO 701
<211> LENGTH: 15
<212> TYPE: DNA
<213> ORGANISM: Homo sapiens

<400> SEQUENCE: 701
catgtccatc tgttg                                                    15

<210> SEQ ID NO 702
<211> LENGTH: 15
<212> TYPE: DNA
<213> ORGANISM: Homo sapiens

<400> SEQUENCE: 702
catgtcgtct ttatc                                                    15

<210> SEQ ID NO 703
<211> LENGTH: 15
<212> TYPE: DNA
<213> ORGANISM: Homo sapiens

<400> SEQUENCE: 703
catgtctctg atgct                                                    15

<210> SEQ ID NO 704
<211> LENGTH: 15
<212> TYPE: DNA
<213> ORGANISM: Homo sapiens

<400> SEQUENCE: 704
catgtcttgt aactg                                                    15

<210> SEQ ID NO 705
<211> LENGTH: 15
<212> TYPE: DNA
<213> ORGANISM: Homo sapiens

<400> SEQUENCE: 705
catgtcttgt gcata                                                    15

<210> SEQ ID NO 706
<211> LENGTH: 15
<212> TYPE: DNA
```

-continued

<213> ORGANISM: Homo sapiens

<400> SEQUENCE: 706
catgtgaagt cactg 15

<210> SEQ ID NO 707
<211> LENGTH: 15
<212> TYPE: DNA
<213> ORGANISM: Homo sapiens

<400> SEQUENCE: 707
catgtgaagt tatac 15

<210> SEQ ID NO 708
<211> LENGTH: 15
<212> TYPE: DNA
<213> ORGANISM: Homo sapiens

<400> SEQUENCE: 708
catgtgatgt ctggt 15

<210> SEQ ID NO 709
<211> LENGTH: 15
<212> TYPE: DNA
<213> ORGANISM: Homo sapiens

<400> SEQUENCE: 709
catgtgccat ctgta 15

<210> SEQ ID NO 710
<211> LENGTH: 15
<212> TYPE: DNA
<213> ORGANISM: Homo sapiens

<400> SEQUENCE: 710
catgtgccct caaaa 15

<210> SEQ ID NO 711
<211> LENGTH: 15
<212> TYPE: DNA
<213> ORGANISM: Homo sapiens

<400> SEQUENCE: 711
catgtgccct cagaa 15

<210> SEQ ID NO 712
<211> LENGTH: 15
<212> TYPE: DNA
<213> ORGANISM: Homo sapiens

<400> SEQUENCE: 712
catgtgccct cagga 15

<210> SEQ ID NO 713
<211> LENGTH: 15
<212> TYPE: DNA
<213> ORGANISM: Homo sapiens

<400> SEQUENCE: 713
catgtgccct caggc 15

<210> SEQ ID NO 714
<211> LENGTH: 15

```
<212> TYPE: DNA
<213> ORGANISM: Homo sapiens

<400> SEQUENCE: 714
catgtgcctt acttt                                                      15

<210> SEQ ID NO 715
<211> LENGTH: 15
<212> TYPE: DNA
<213> ORGANISM: Homo sapiens

<400> SEQUENCE: 715
catgtgcgct ggccc                                                      15

<210> SEQ ID NO 716
<211> LENGTH: 15
<212> TYPE: DNA
<213> ORGANISM: Homo sapiens

<400> SEQUENCE: 716
catgtgcttc atctg                                                      15

<210> SEQ ID NO 717
<211> LENGTH: 15
<212> TYPE: DNA
<213> ORGANISM: Homo sapiens

<400> SEQUENCE: 717
catgtggagt ggagg                                                      15

<210> SEQ ID NO 718
<211> LENGTH: 15
<212> TYPE: DNA
<213> ORGANISM: Homo sapiens

<400> SEQUENCE: 718
catgtggccc caggt                                                      15

<210> SEQ ID NO 719
<211> LENGTH: 15
<212> TYPE: DNA
<213> ORGANISM: Homo sapiens

<400> SEQUENCE: 719
catgtgggtg agcca                                                      15

<210> SEQ ID NO 720
<211> LENGTH: 15
<212> TYPE: DNA
<213> ORGANISM: Homo sapiens

<400> SEQUENCE: 720
catgtgtgag cccct                                                      15

<210> SEQ ID NO 721
<211> LENGTH: 15
<212> TYPE: DNA
<213> ORGANISM: Homo sapiens

<400> SEQUENCE: 721
catgtgtgct aaatg                                                      15

<210> SEQ ID NO 722
```

```
<211> LENGTH: 15
<212> TYPE: DNA
<213> ORGANISM: Homo sapiens

<400> SEQUENCE: 722
catgtgtgtg tttgt                                                          15

<210> SEQ ID NO 723
<211> LENGTH: 15
<212> TYPE: DNA
<213> ORGANISM: Homo sapiens

<400> SEQUENCE: 723
catgttatgg atctc                                                          15

<210> SEQ ID NO 724
<211> LENGTH: 15
<212> TYPE: DNA
<213> ORGANISM: Homo sapiens

<400> SEQUENCE: 724
catgttcatt gtaga                                                          15

<210> SEQ ID NO 725
<211> LENGTH: 15
<212> TYPE: DNA
<213> ORGANISM: Homo sapiens

<400> SEQUENCE: 725
catgttctgt gaatc                                                          15

<210> SEQ ID NO 726
<211> LENGTH: 15
<212> TYPE: DNA
<213> ORGANISM: Homo sapiens

<400> SEQUENCE: 726
catgttgccc ccgtg                                                          15

<210> SEQ ID NO 727
<211> LENGTH: 15
<212> TYPE: DNA
<213> ORGANISM: Homo sapiens

<400> SEQUENCE: 727
catgttgctg acttt                                                          15

<210> SEQ ID NO 728
<211> LENGTH: 15
<212> TYPE: DNA
<213> ORGANISM: Homo sapiens

<400> SEQUENCE: 728
catgttggag atctc                                                          15

<210> SEQ ID NO 729
<211> LENGTH: 15
<212> TYPE: DNA
<213> ORGANISM: Homo sapiens

<400> SEQUENCE: 729
catgttgggg tttcc                                                          15
```

```
<210> SEQ ID NO 730
<211> LENGTH: 15
<212> TYPE: DNA
<213> ORGANISM: Homo sapiens

<400> SEQUENCE: 730
catgttggtg aagga                                                15

<210> SEQ ID NO 731
<211> LENGTH: 15
<212> TYPE: DNA
<213> ORGANISM: Homo sapiens

<400> SEQUENCE: 731
catgtttccc tcaaa                                                15

<210> SEQ ID NO 732
<211> LENGTH: 15
<212> TYPE: DNA
<213> ORGANISM: Homo sapiens

<400> SEQUENCE: 732
catgtttcct tcctt                                                15

<210> SEQ ID NO 733
<211> LENGTH: 15
<212> TYPE: DNA
<213> ORGANISM: Homo sapiens

<400> SEQUENCE: 733
catgtttgca ccttt                                                15

<210> SEQ ID NO 734
<211> LENGTH: 14
<212> TYPE: DNA
<213> ORGANISM: Homo sapiens

<400> SEQUENCE: 734
catgtttgtt aaaa                                                 14

<210> SEQ ID NO 735
<211> LENGTH: 15
<212> TYPE: DNA
<213> ORGANISM: Homo sapiens

<400> SEQUENCE: 735
catgtggaaa tgacc                                                15

<210> SEQ ID NO 736
<211> LENGTH: 15
<212> TYPE: DNA
<213> ORGANISM: Homo sapiens

<400> SEQUENCE: 736
catgcacttc aaggg                                                15

<210> SEQ ID NO 737
<211> LENGTH: 15
<212> TYPE: DNA
<213> ORGANISM: Homo sapiens

<400> SEQUENCE: 737
catgatgtga agagw                                                15
```

<210> SEQ ID NO 738
<211> LENGTH: 15
<212> TYPE: DNA
<213> ORGANISM: Homo sapiens

<400> SEQUENCE: 738
catggcccaa ggacc                                                15

<210> SEQ ID NO 739
<211> LENGTH: 15
<212> TYPE: DNA
<213> ORGANISM: Homo sapiens

<400> SEQUENCE: 739
catgatcttg ttact                                                15

<210> SEQ ID NO 740
<211> LENGTH: 15
<212> TYPE: DNA
<213> ORGANISM: Homo sapiens

<400> SEQUENCE: 740
catggtgcgc tgagc                                                15

<210> SEQ ID NO 741
<211> LENGTH: 15
<212> TYPE: DNA
<213> ORGANISM: Homo sapiens

<400> SEQUENCE: 741
catgacaggc tacgg                                                15

<210> SEQ ID NO 742
<211> LENGTH: 15
<212> TYPE: DNA
<213> ORGANISM: Homo sapiens

<400> SEQUENCE: 742
catggtgtgt ttgta                                                15

<210> SEQ ID NO 743
<211> LENGTH: 15
<212> TYPE: DNA
<213> ORGANISM: Homo sapiens

<400> SEQUENCE: 743
catggatttc tcagc                                                15

<210> SEQ ID NO 744
<211> LENGTH: 15
<212> TYPE: DNA
<213> ORGANISM: Homo sapiens

<400> SEQUENCE: 744
catgaccatt ctgct                                                15

<210> SEQ ID NO 745
<211> LENGTH: 15
<212> TYPE: DNA
<213> ORGANISM: Homo sapiens

<400> SEQUENCE: 745
catgtccttc tccac                                                15

```
<210> SEQ ID NO 746
<211> LENGTH: 15
<212> TYPE: DNA
<213> ORGANISM: Homo sapiens

<400> SEQUENCE: 746
catgcttctg tgtay                                              15

<210> SEQ ID NO 747
<211> LENGTH: 15
<212> TYPE: DNA
<213> ORGANISM: Homo sapiens

<400> SEQUENCE: 747
catgatgtaa aaaat                                              15

<210> SEQ ID NO 748
<211> LENGTH: 15
<212> TYPE: DNA
<213> ORGANISM: Homo sapiens

<400> SEQUENCE: 748
catgggcaga ggacc                                              15

<210> SEQ ID NO 749
<211> LENGTH: 15
<212> TYPE: DNA
<213> ORGANISM: Homo sapiens

<400> SEQUENCE: 749
catgaatatt gagaa                                              15

<210> SEQ ID NO 750
<211> LENGTH: 15
<212> TYPE: DNA
<213> ORGANISM: Homo sapiens

<400> SEQUENCE: 750
catgtttttg ataaa                                              15

<210> SEQ ID NO 751
<211> LENGTH: 15
<212> TYPE: DNA
<213> ORGANISM: Homo sapiens

<400> SEQUENCE: 751
catgcagctg gccat                                              15

<210> SEQ ID NO 752
<211> LENGTH: 15
<212> TYPE: DNA
<213> ORGANISM: Homo sapiens

<400> SEQUENCE: 752
catggttcac attag                                              15

<210> SEQ ID NO 753
<211> LENGTH: 15
<212> TYPE: DNA
<213> ORGANISM: Homo sapiens

<400> SEQUENCE: 753
```
catgaaaaga aactt 15

<210> SEQ ID NO 754
<211> LENGTH: 15
<212> TYPE: DNA
<213> ORGANISM: Homo sapiens

<400> SEQUENCE: 754
catgaatgca ggcag 15

<210> SEQ ID NO 755
<211> LENGTH: 15
<212> TYPE: DNA
<213> ORGANISM: Homo sapiens

<400> SEQUENCE: 755
catgtgaaat aaaac 15

<210> SEQ ID NO 756
<211> LENGTH: 15
<212> TYPE: DNA
<213> ORGANISM: Homo sapiens

<400> SEQUENCE: 756 catgtttatgg gatct 15

<210> SEQ ID NO 757
<211> LENGTH: 15
<212> TYPE: DNA
<213> ORGANISM: Homo sapiens

<400> SEQUENCE: 757
catgcaataa atgtt 15

<210> SEQ ID NO 758
<211> LENGTH: 15
<212> TYPE: DNA
<213> ORGANISM: Homo sapiens

<400> SEQUENCE: 758
catgagcctt tgttg 15

<210> SEQ ID NO 759
<211> LENGTH: 15
<212> TYPE: DNA
<213> ORGANISM: Homo sapiens

<400> SEQUENCE: 759
catgacctgt atccc 15

<210> SEQ ID NO 760
<211> LENGTH: 15
<212> TYPE: DNA
<213> ORGANISM: Homo sapiens

<400> SEQUENCE: 760
catgttcaat aaaaa 15

<210> SEQ ID NO 761
<211> LENGTH: 15
<212> TYPE: DNA
<213> ORGANISM: Homo sapiens

<400> SEQUENCE: 761

```
catgcgaccc cacgc                                                   15

<210> SEQ ID NO 762
<211> LENGTH: 15
<212> TYPE: DNA
<213> ORGANISM: Homo sapiens

<400> SEQUENCE: 762
catgcagatc tttgt                                                   15

<210> SEQ ID NO 763
<211> LENGTH: 15
<212> TYPE: DNA
<213> ORGANISM: Homo sapiens

<400> SEQUENCE: 763
catgctggcg agcgc                                                   15

<210> SEQ ID NO 764
<211> LENGTH: 15
<212> TYPE: DNA
<213> ORGANISM: Homo sapiens

<400> SEQUENCE: 764
catgattggc ttaaa                                                   15

<210> SEQ ID NO 765
<211> LENGTH: 15
<212> TYPE: DNA
<213> ORGANISM: Homo sapiens

<400> SEQUENCE: 765
catggtggtg gacac                                                   15

<210> SEQ ID NO 766
<211> LENGTH: 15
<212> TYPE: DNA
<213> ORGANISM: Homo sapiens

<400> SEQUENCE: 766
catgtcctgc cccat                                                   15

<210> SEQ ID NO 767
<211> LENGTH: 15
<212> TYPE: DNA
<213> ORGANISM: Homo sapiens

<400> SEQUENCE: 767
catgactggg tctat                                                   15

<210> SEQ ID NO 768
<211> LENGTH: 15
<212> TYPE: DNA
<213> ORGANISM: Homo sapiens

<400> SEQUENCE: 768
catgaagaag ataga                                                   15

<210> SEQ ID NO 769
<211> LENGTH: 15
<212> TYPE: DNA
<213> ORGANISM: Homo sapiens
```

<400> SEQUENCE: 769
catgacatca tcgat                                                              15

<210> SEQ ID NO 770
<211> LENGTH: 15
<212> TYPE: DNA
<213> ORGANISM: Homo sapiens

<400> SEQUENCE: 770
catgctgttg gtgat                                                              15

<210> SEQ ID NO 771
<211> LENGTH: 15
<212> TYPE: DNA
<213> ORGANISM: Homo sapiens

<400> SEQUENCE: 771
catgattatt tttct                                                              15

<210> SEQ ID NO 772
<211> LENGTH: 15
<212> TYPE: DNA
<213> ORGANISM: Homo sapiens

<400> SEQUENCE: 772
catggctttt aagga                                                              15

<210> SEQ ID NO 773
<211> LENGTH: 15
<212> TYPE: DNA
<213> ORGANISM: Homo sapiens

<400> SEQUENCE: 773
catgggcaag aagaa                                                              15

<210> SEQ ID NO 774
<211> LENGTH: 15
<212> TYPE: DNA
<213> ORGANISM: Homo sapiens

<400> SEQUENCE: 774
catgctcttc gagaa                                                              15

<210> SEQ ID NO 775
<211> LENGTH: 15
<212> TYPE: DNA
<213> ORGANISM: Homo sapiens

<400> SEQUENCE: 775
catgctgttg attgc                                                              15

<210> SEQ ID NO 776
<211> LENGTH: 15
<212> TYPE: DNA
<213> ORGANISM: Homo sapiens

<400> SEQUENCE: 776
catgctgggt taata                                                              15

<210> SEQ ID NO 777
<211> LENGTH: 15
<212> TYPE: DNA
<213> ORGANISM: Homo sapiens

```
<400> SEQUENCE: 777
catgatggct ggtat                                              15

<210> SEQ ID NO 778
<211> LENGTH: 15
<212> TYPE: DNA
<213> ORGANISM: Homo sapiens

<400> SEQUENCE: 778
catggatgct gccaa                                              15

<210> SEQ ID NO 779
<211> LENGTH: 15
<212> TYPE: DNA
<213> ORGANISM: Homo sapiens

<400> SEQUENCE: 779
catgccttcg agatc                                              15

<210> SEQ ID NO 780
<211> LENGTH: 15
<212> TYPE: DNA
<213> ORGANISM: Homo sapiens

<400> SEQUENCE: 780
catgctcctc acctg                                              15

<210> SEQ ID NO 781
<211> LENGTH: 15
<212> TYPE: DNA
<213> ORGANISM: Homo sapiens

<400> SEQUENCE: 781
catgtgtgtt gagag                                              15

<210> SEQ ID NO 782
<211> LENGTH: 15
<212> TYPE: DNA
<213> ORGANISM: Homo sapiens

<400> SEQUENCE: 782
catgttacca tatca                                              15

<210> SEQ ID NO 783
<211> LENGTH: 15
<212> TYPE: DNA
<213> ORGANISM: Homo sapiens

<400> SEQUENCE: 783
catggcctgc tgggc                                              15

<210> SEQ ID NO 784
<211> LENGTH: 15
<212> TYPE: DNA
<213> ORGANISM: Homo sapiens

<400> SEQUENCE: 784
catgcctcgg aaaat                                              15

<210> SEQ ID NO 785
<211> LENGTH: 15
<212> TYPE: DNA
```

```
<213> ORGANISM: Homo sapiens

<400> SEQUENCE: 785
catgtacaag aggaa                                                      15

<210> SEQ ID NO 786
<211> LENGTH: 15
<212> TYPE: DNA
<213> ORGANISM: Homo sapiens

<400> SEQUENCE: 786
catgaacgac ctcgt                                                      15

<210> SEQ ID NO 787
<211> LENGTH: 15
<212> TYPE: DNA
<213> ORGANISM: Homo sapiens

<400> SEQUENCE: 787
catgccctgc cttgt                                                      15

<210> SEQ ID NO 788
<211> LENGTH: 15
<212> TYPE: DNA
<213> ORGANISM: Homo sapiens

<400> SEQUENCE: 788
catgcccagg gagaa                                                      15

<210> SEQ ID NO 789
<211> LENGTH: 15
<212> TYPE: DNA
<213> ORGANISM: Homo sapiens

<400> SEQUENCE: 789
catgagcacc tccag                                                      15

<210> SEQ ID NO 790
<211> LENGTH: 15
<212> TYPE: DNA
<213> ORGANISM: Homo sapiens

<400> SEQUENCE: 790
catgcgccgg aacac                                                      15

<210> SEQ ID NO 791
<211> LENGTH: 15
<212> TYPE: DNA
<213> ORGANISM: Homo sapiens

<400> SEQUENCE: 791
catgctaaaa aaaaa                                                      15

<210> SEQ ID NO 792
<211> LENGTH: 15
<212> TYPE: DNA
<213> ORGANISM: Homo sapiens

<400> SEQUENCE: 792
catgggctga tgtgg                                                      15

<210> SEQ ID NO 793
<211> LENGTH: 15
```

```
<212> TYPE: DNA
<213> ORGANISM: Homo sapiens

<400> SEQUENCE: 793
catgattctc cagta                                                     15

<210> SEQ ID NO 794
<211> LENGTH: 15
<212> TYPE: DNA
<213> ORGANISM: Homo sapiens

<400> SEQUENCE: 794
catggaaaaa tggtt                                                     15

<210> SEQ ID NO 795
<211> LENGTH: 15
<212> TYPE: DNA
<213> ORGANISM: Homo sapiens

<400> SEQUENCE: 795
catgcagctc actga                                                     15

<210> SEQ ID NO 796
<211> LENGTH: 15
<212> TYPE: DNA
<213> ORGANISM: Homo sapiens

<400> SEQUENCE: 796
catgataatt ctttg                                                     15

<210> SEQ ID NO 797
<211> LENGTH: 15
<212> TYPE: DNA
<213> ORGANISM: Homo sapiens

<400> SEQUENCE: 797
catgaatcct gtgga                                                     15

<210> SEQ ID NO 798
<211> LENGTH: 15
<212> TYPE: DNA
<213> ORGANISM: Homo sapiens

<400> SEQUENCE: 798
catgaatagg tccaa                                                     15

<210> SEQ ID NO 799
<211> LENGTH: 15
<212> TYPE: DNA
<213> ORGANISM: Homo sapiens

<400> SEQUENCE: 799
catgaaaaaa aaaan                                                     15

<210> SEQ ID NO 800
<211> LENGTH: 15
<212> TYPE: DNA
<213> ORGANISM: Homo sapiens

<400> SEQUENCE: 800
catgccagaa cagac                                                     15

<210> SEQ ID NO 801
```

<211> LENGTH: 15
<212> TYPE: DNA
<213> ORGANISM: Homo sapiens

<400> SEQUENCE: 801
catgaaggtg gagga                                              15

<210> SEQ ID NO 802
<211> LENGTH: 15
<212> TYPE: DNA
<213> ORGANISM: Homo sapiens

<400> SEQUENCE: 802
catgcctagc tggat                                              15

<210> SEQ ID NO 803
<211> LENGTH: 15
<212> TYPE: DNA
<213> ORGANISM: Homo sapiens

<400> SEQUENCE: 803
catggaacac atcca                                              15

<210> SEQ ID NO 804
<211> LENGTH: 15
<212> TYPE: DNA
<213> ORGANISM: Homo sapiens

<400> SEQUENCE: 804
catgaaggag atggg                                              15

<210> SEQ ID NO 805
<211> LENGTH: 15
<212> TYPE: DNA
<213> ORGANISM: Homo sapiens

<400> SEQUENCE: 805
catgaggcta cggaa                                              15

<210> SEQ ID NO 806
<211> LENGTH: 15
<212> TYPE: DNA
<213> ORGANISM: Homo sapiens

<400> SEQUENCE: 806
catgaggtcc tagcc                                              15

<210> SEQ ID NO 807
<211> LENGTH: 15
<212> TYPE: DNA
<213> ORGANISM: Homo sapiens

<400> SEQUENCE: 807
catgtggtgt tgagg                                              15

<210> SEQ ID NO 808
<211> LENGTH: 15
<212> TYPE: DNA
<213> ORGANISM: Homo sapiens

<400> SEQUENCE: 808
catgctcaac atctc                                              15

```
<210> SEQ ID NO 809
<211> LENGTH: 15
<212> TYPE: DNA
<213> ORGANISM: Homo sapiens

<400> SEQUENCE: 809
catggtgtta accag                                                         15

<210> SEQ ID NO 810
<211> LENGTH: 15
<212> TYPE: DNA
<213> ORGANISM: Homo sapiens

<400> SEQUENCE: 810
catgagggct tccaa                                                         15

<210> SEQ ID NO 811
<211> LENGTH: 15
<212> TYPE: DNA
<213> ORGANISM: Homo sapiens

<400> SEQUENCE: 811
catgggattt ggcct                                                         15

<210> SEQ ID NO 812
<211> LENGTH: 15
<212> TYPE: DNA
<213> ORGANISM: Homo sapiens

<400> SEQUENCE: 812
catgattaac aaagc                                                         15

<210> SEQ ID NO 813
<211> LENGTH: 15
<212> TYPE: DNA
<213> ORGANISM: Homo sapiens

<400> SEQUENCE: 813
catgtgtacc tgtaa                                                         15

<210> SEQ ID NO 814
<211> LENGTH: 15
<212> TYPE: DNA
<213> ORGANISM: Homo sapiens

<400> SEQUENCE: 814
catgtggccc caccc                                                         15

<210> SEQ ID NO 815
<211> LENGTH: 15
<212> TYPE: DNA
<213> ORGANISM: Homo sapiens

<400> SEQUENCE: 815
catgtaataa aggtg                                                         15

<210> SEQ ID NO 816
<211> LENGTH: 15
<212> TYPE: DNA
<213> ORGANISM: Homo sapiens

<400> SEQUENCE: 816
catggcataa taggt                                                         15
```

```
<210> SEQ ID NO 817
<211> LENGTH: 15
<212> TYPE: DNA
<213> ORGANISM: Homo sapiens

<400> SEQUENCE: 817
catgtaccat caata                                                  15

<210> SEQ ID NO 818
<211> LENGTH: 15
<212> TYPE: DNA
<213> ORGANISM: Homo sapiens

<400> SEQUENCE: 818
catgatttgt cccag                                                  15

<210> SEQ ID NO 819
<211> LENGTH: 15
<212> TYPE: DNA
<213> ORGANISM: Homo sapiens

<400> SEQUENCE: 819
catggaggga gtttc                                                  15

<210> SEQ ID NO 820
<211> LENGTH: 15
<212> TYPE: DNA
<213> ORGANISM: Homo sapiens

<400> SEQUENCE: 820
catgcgccgc cggct                                                  15

<210> SEQ ID NO 821
<211> LENGTH: 15
<212> TYPE: DNA
<213> ORGANISM: Homo sapiens

<400> SEQUENCE: 821
catggtgaaa cccan                                                  15

<210> SEQ ID NO 822
<211> LENGTH: 15
<212> TYPE: DNA
<213> ORGANISM: Homo sapiens

<400> SEQUENCE: 822
catgaagaca gtggc                                                  15

<210> SEQ ID NO 823
<211> LENGTH: 15
<212> TYPE: DNA
<213> ORGANISM: Homo sapiens

<400> SEQUENCE: 823
catgccccag ccagt                                                  15

<210> SEQ ID NO 824
<211> LENGTH: 15
<212> TYPE: DNA
<213> ORGANISM: Homo sapiens

<400> SEQUENCE: 824
catgtgggca aagcc                                                  15
```

<210> SEQ ID NO 825
<211> LENGTH: 15
<212> TYPE: DNA
<213> ORGANISM: Homo sapiens

<400> SEQUENCE: 825
catgtgaggg aataa                                                    15

<210> SEQ ID NO 826
<211> LENGTH: 15
<212> TYPE: DNA
<213> ORGANISM: Homo sapiens

<400> SEQUENCE: 826
catggacgac acgag                                                    15

<210> SEQ ID NO 827
<211> LENGTH: 15
<212> TYPE: DNA
<213> ORGANISM: Homo sapiens

<400> SEQUENCE: 827
catgaacgcg gccaa                                                    15

<210> SEQ ID NO 828
<211> LENGTH: 15
<212> TYPE: DNA
<213> ORGANISM: Homo sapiens

<400> SEQUENCE: 828
catgtgcacg ttttc                                                    15

<210> SEQ ID NO 829
<211> LENGTH: 15
<212> TYPE: DNA
<213> ORGANISM: Homo sapiens

<400> SEQUENCE: 829
catgcacaaa cggta                                                    15

<210> SEQ ID NO 830
<211> LENGTH: 15
<212> TYPE: DNA
<213> ORGANISM: Homo sapiens

<400> SEQUENCE: 830
catgggagtg gacat                                                    15

<210> SEQ ID NO 831
<211> LENGTH: 15
<212> TYPE: DNA
<213> ORGANISM: Homo sapiens

<400> SEQUENCE: 831
catggccgag gaagg                                                    15

<210> SEQ ID NO 832
<211> LENGTH: 15
<212> TYPE: DNA
<213> ORGANISM: Homo sapiens

<400> SEQUENCE: 832

-continued catggggaa atcgc 15

<210> SEQ ID NO 833
<211> LENGTH: 15
<212> TYPE: DNA
<213> ORGANISM: Homo sapiens

<400> SEQUENCE: 833
catggcagcc atccg 15

<210> SEQ ID NO 834
<211> LENGTH: 15
<212> TYPE: DNA
<213> ORGANISM: Homo sapiens

<400> SEQUENCE: 834
catgtaagga gctga 15

<210> SEQ ID NO 835
<211> LENGTH: 15
<212> TYPE: DNA
<213> ORGANISM: Homo sapiens

<400> SEQUENCE: 835
catgggcaag cccca 15

<210> SEQ ID NO 836
<211> LENGTH: 15
<212> TYPE: DNA
<213> ORGANISM: Homo sapiens

<400> SEQUENCE: 836
catggttccc tggcc 15

<210> SEQ ID NO 837
<211> LENGTH: 15
<212> TYPE: DNA
<213> ORGANISM: Homo sapiens

<400> SEQUENCE: 837
catgccgtcc aaggg 15

<210> SEQ ID NO 838
<211> LENGTH: 15
<212> TYPE: DNA
<213> ORGANISM: Homo sapiens

<400> SEQUENCE: 838
catgttggtc ctctg 15

<210> SEQ ID NO 839
<211> LENGTH: 15
<212> TYPE: DNA
<213> ORGANISM: Homo sapiens

<400> SEQUENCE: 839
catgcaaacc atcca 15

<210> SEQ ID NO 840
<211> LENGTH: 15
<212> TYPE: DNA
<213> ORGANISM: Homo sapiens

<400> SEQUENCE: 840

```
catgagctct ccctg                                                    15

<210> SEQ ID NO 841
<211> LENGTH: 15
<212> TYPE: DNA
<213> ORGANISM: Homo sapiens

<400> SEQUENCE: 841
catgaggtca ggagw                                                    15

<210> SEQ ID NO 842
<211> LENGTH: 15
<212> TYPE: DNA
<213> ORGANISM: Homo sapiens

<400> SEQUENCE: 842
catggggctg gggtc                                                    15

<210> SEQ ID NO 843
<211> LENGTH: 15
<212> TYPE: DNA
<213> ORGANISM: Homo sapiens

<400> SEQUENCE: 843
catgacgttc tcttc                                                    15

<210> SEQ ID NO 844
<211> LENGTH: 15
<212> TYPE: DNA
<213> ORGANISM: Homo sapiens

<400> SEQUENCE: 844
catgtctcca taccc                                                    15

<210> SEQ ID NO 845
<211> LENGTH: 15
<212> TYPE: DNA
<213> ORGANISM: Homo sapiens

<400> SEQUENCE: 845
catggactgc gtgcc                                                    15

<210> SEQ ID NO 846
<211> LENGTH: 15
<212> TYPE: DNA
<213> ORGANISM: Homo sapiens

<400> SEQUENCE: 846
catgcttaat cctga                                                    15

<210> SEQ ID NO 847
<211> LENGTH: 15
<212> TYPE: DNA
<213> ORGANISM: Homo sapiens

<400> SEQUENCE: 847
catgggttgg caggg                                                    15

<210> SEQ ID NO 848
<211> LENGTH: 15
<212> TYPE: DNA
<213> ORGANISM: Homo sapiens
```

```
<400> SEQUENCE: 848
catggccctc tgcca                                                    15

<210> SEQ ID NO 849
<211> LENGTH: 15
<212> TYPE: DNA
<213> ORGANISM: Homo sapiens

<400> SEQUENCE: 849
catgaacaga agcaa                                                    15

<210> SEQ ID NO 850
<211> LENGTH: 15
<212> TYPE: DNA
<213> ORGANISM: Homo sapiens

<400> SEQUENCE: 850
catgctgccg agctc                                                    15

<210> SEQ ID NO 851
<211> LENGTH: 15
<212> TYPE: DNA
<213> ORGANISM: Homo sapiens

<400> SEQUENCE: 851
catgttcctc gggca                                                    15

<210> SEQ ID NO 852
<211> LENGTH: 15
<212> TYPE: DNA
<213> ORGANISM: Homo sapiens

<400> SEQUENCE: 852
catgaactaa tacta                                                    15

<210> SEQ ID NO 853
<211> LENGTH: 15
<212> TYPE: DNA
<213> ORGANISM: Homo sapiens

<400> SEQUENCE: 853
catgtagata atggc                                                    15

<210> SEQ ID NO 854
<211> LENGTH: 15
<212> TYPE: DNA
<213> ORGANISM: Homo sapiens

<400> SEQUENCE: 854
catggccaca ccccm                                                    15

<210> SEQ ID NO 855
<211> LENGTH: 15
<212> TYPE: DNA
<213> ORGANISM: Homo sapiens

<400> SEQUENCE: 855
catggaaccc tggga                                                    15

<210> SEQ ID NO 856
<211> LENGTH: 15
<212> TYPE: DNA
<213> ORGANISM: Homo sapiens
```

```
<400> SEQUENCE: 856
catgaactaa aaaaa                                               15

<210> SEQ ID NO 857
<211> LENGTH: 15
<212> TYPE: DNA
<213> ORGANISM: Homo sapiens

<400> SEQUENCE: 857
catggaaatg taaga                                               15

<210> SEQ ID NO 858
<211> LENGTH: 15
<212> TYPE: DNA
<213> ORGANISM: Homo sapiens

<400> SEQUENCE: 858
catgactcca aaaaa                                               15

<210> SEQ ID NO 859
<211> LENGTH: 15
<212> TYPE: DNA
<213> ORGANISM: Homo sapiens

<400> SEQUENCE: 859
catggttcgt gccaa                                               15

<210> SEQ ID NO 860
<211> LENGTH: 15
<212> TYPE: DNA
<213> ORGANISM: Homo sapiens

<400> SEQUENCE: 860
catgttacct ccttc                                               15

<210> SEQ ID NO 861
<211> LENGTH: 15
<212> TYPE: DNA
<213> ORGANISM: Homo sapiens

<400> SEQUENCE: 861
catggcacaa gaaga                                               15

<210> SEQ ID NO 862
<211> LENGTH: 15
<212> TYPE: DNA
<213> ORGANISM: Homo sapiens

<400> SEQUENCE: 862
catgccctgg gttct                                               15

<210> SEQ ID NO 863
<211> LENGTH: 15
<212> TYPE: DNA
<213> ORGANISM: Homo sapiens

<400> SEQUENCE: 863
catggcctgt atgag                                               15

<210> SEQ ID NO 864
<211> LENGTH: 15
<212> TYPE: DNA
```

-continued

<213> ORGANISM: Homo sapiens

<400> SEQUENCE: 864
catgcccgtc cggaa                                    15

<210> SEQ ID NO 865
<211> LENGTH: 15
<212> TYPE: DNA
<213> ORGANISM: Homo sapiens

<400> SEQUENCE: 865
catgaggaaa gctgc                                    15

<210> SEQ ID NO 866
<211> LENGTH: 15
<212> TYPE: DNA
<213> ORGANISM: Homo sapiens

<400> SEQUENCE: 866
catgtcagat ctttg                                    15

<210> SEQ ID NO 867
<211> LENGTH: 15
<212> TYPE: DNA
<213> ORGANISM: Homo sapiens

<400> SEQUENCE: 867
catgccagga ggaat                                    15

<210> SEQ ID NO 868
<211> LENGTH: 15
<212> TYPE: DNA
<213> ORGANISM: Homo sapiens

<400> SEQUENCE: 868
catgtcaccc acacc                                    15

<210> SEQ ID NO 869
<211> LENGTH: 15
<212> TYPE: DNA
<213> ORGANISM: Homo sapiens

<400> SEQUENCE: 869
catggtgttg cacaa                                    15

<210> SEQ ID NO 870
<211> LENGTH: 15
<212> TYPE: DNA
<213> ORGANISM: Homo sapiens

<400> SEQUENCE: 870
catggccgtg tccgc                                    15

<210> SEQ ID NO 871
<211> LENGTH: 27
<212> TYPE: DNA
<213> ORGANISM: Homo sapiens

<400> SEQUENCE: 871
tccggcgcgc cgtttccca gtcacga                        27